(12) United States Patent
Wu et al.

(10) Patent No.: US 12,102,626 B2
(45) Date of Patent: Oct. 1, 2024

(54) (PYRIDIN-2-YL)AMINE DERIVATIVES AS TGF-BETA R1 (ALK5) INHIBITORS FOR THE TREATMENT OF CANCER

(71) Applicant: Nexys Therapeutics, Inc., San Diego, CA (US)

(72) Inventors: Tom Yao-Hsiang Wu, San Diego, CA (US); Qihui Jin, San Diego, CA (US)

(73) Assignee: Nexys Therapeutics, Inc., San Diego, CA (US)

( * ) Notice: Subject to any disclaimer, the term of this patent is extended or adjusted under 35 U.S.C. 154(b) by 615 days.

(21) Appl. No.: 17/299,696

(22) PCT Filed: Dec. 17, 2019

(86) PCT No.: PCT/US2019/066993
§ 371 (c)(1),
(2) Date: Jun. 3, 2021

(87) PCT Pub. No.: WO2020/139636
PCT Pub. Date: Jul. 2, 2020

(65) Prior Publication Data
US 2022/0054465 A1 Feb. 24, 2022

Related U.S. Application Data

(60) Provisional application No. 62/785,616, filed on Dec. 27, 2018.

(51) Int. Cl.
| | |
|---|---|
| *A61K 31/444* | (2006.01) |
| *A61K 31/4709* | (2006.01) |
| *A61P 35/00* | (2006.01) |
| *C07D 401/12* | (2006.01) |
| *C07D 401/14* | (2006.01) |
| *C07D 405/14* | (2006.01) |

(52) U.S. Cl.
CPC ........ *A61K 31/444* (2013.01); *A61K 31/4709* (2013.01); *A61P 35/00* (2018.01); *C07D 401/12* (2013.01); *C07D 401/14* (2013.01); *C07D 405/14* (2013.01)

(58) Field of Classification Search
CPC .............. A61K 31/444; A61K 31/4709; A61K 31/4439; A61P 35/00; A61P 43/00; C07D 401/12; C07D 401/14; C07D 405/14; C07D 213/74
See application file for complete search history.

(56) References Cited

FOREIGN PATENT DOCUMENTS

| CN | 112707902 A | 4/2021 |
|---|---|---|
| WO | 2009022171 A1 | 2/2009 |
| WO | 2015157093 A1 | 10/2015 |
| WO | 2016057278 A1 | 4/2016 |
| WO | 2017015425 A1 | 1/2017 |
| WO | 2020103817 A1 | 5/2020 |
| WO | 2020258006 A1 | 12/2020 |

OTHER PUBLICATIONS

Herbertz, Stephan, et al. "Clinical Development of Galunisertib (LY2157299 Monohydrate), a Small Molecule Inhibitor of Transforming Growth Factor-Beta Signaling Pathway." Drug Design, Development and Therapy, vol. 9, Aug. 2015, pp. 4479-4499. PubMed Central, https://doi.org/10.2147/DDDT.S86621. (Year: 2015).*
EP19839715.0_Communication to Rule 161(1) and 162 (EPC), dated Aug. 12, 2021, 3 pages.
EP19839715.0_Response to Communication to Rules 161(2) and 162 EPC, dated Feb. 18, 2022, 211 pages.
EP19839715.0_Communication Pursuant to Article 94(3) EPC, dated Feb. 15, 2023, 3 pages.
IN202117026711_First Examination Report, dated Jan. 19, 2023, 6 pages.
EA202191619_First Office Action (EN), dated Jul. 29, 2022, 3 pages.

(Continued)

*Primary Examiner* — Clinton A Brooks
*Assistant Examiner* — Kyle Nottingham

(57) ABSTRACT

The present invention relates to pharmaceutical compounds, compositions and methods, especially as they are related to compositions and methods for the treatment and/or prevention of a proliferation disorder associated with TGFβR1 activity, such as a cancer or fibrosis. The invention provides compounds of Formula (I) and Formula (II) as further described herein having an acidic moiety that enhances tissue specificity for targeted tissues and organs. The invention includes pharmaceutical compositions, pharmaceutical combinations, and methods of use of these compounds for treating conditions including cancer or fibrosis.

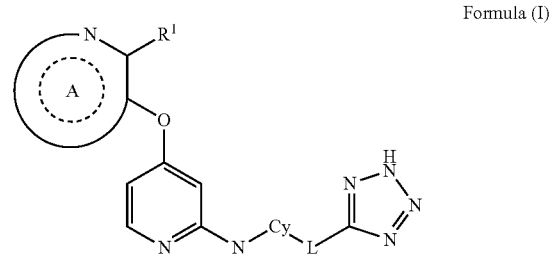

Formula (I)

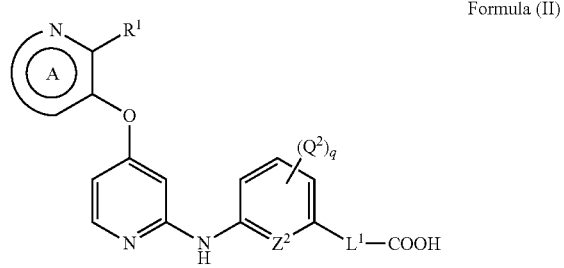

Formula (II)

19 Claims, No Drawings

(56) References Cited

OTHER PUBLICATIONS

EA202191619_Response to 1st Exam Report, dated Sep. 10, 2022, 14 pages.
EA202191619_Notice of readiness to grant (EN), Sep. 30, 2022, 1 page.
EA202191619_Response to the Notice of Readiness to Grant, Feb. 7, 2023, 13 pages.
EA202191619_Decision on Grant, Mar. 10, 2023, 3 pages.
GCC201938916_First Examination-Report, dated Apr. 28, 2021, 6 pages.
GCC201938916_Response to first Exam Report, Sep. 2, 2021, 1 page.
Tu, et al., "Medicinal Chemistry Design Principles for Liver Targeting Through OATP Transporters", Current Topics in Medicinal Chemistry, 2013, 13, 857-866.
Stauber, et al., "Nonclinical Safety Evaluation of a Transforming Growth Factor β Receptor I Inhibitor in Fischer 344 Rats and Beagle Dogs", J. Clin Pract., 2014, vol. 4, Issue 3, 1-10.
Tauriello, et al., "TGFβ drives immune evasion in genetically reconstituted colon cancer metastasis", Nature, 2018, vol. 554, 538-543.
Mariathasan, et al., "TGFβ attenuates tumour response to PD-L1 blockade by contributing to exclusion of T cells", Nature, 2018, vol. 554, 544-548.
International Search Report mailed on Jun. 12, 2020, 5 pages.
International Preliminary Report on Patentability issued by the International Bureau on behalf of the International Search Authority on Jun. 16, 2021, 9 pages.
CN201980086920.0_Dec. 12, 2023_1st Exam Report with EN translation (14 pages).
CN201980086920.0_Mar. 26, 2024_Resp 1st Exam Report with EN translation (18 pages).
CN201980086920.0_Apr. 8, 2024_2nd Exam Report with EN translation (23 pages).
EP19839715.0_Apr. 24, 2023_Resp to Communication Pursuant to Art. 94(3) EPC dated Feb. 18, 2022 (17 pages).
EP19839715.0_Aug. 25, 2023_Communication Under Rule 71(3) EPC (163 pages).
EP19839715.0_Jan. 11, 2024_Decision to Grant a European patent pursuant to Art. 97(1) EPC (2 pages).
GC201941553_Mar. 16, 2023_Examination Report (4 pages).
GC201941553_Oct. 23, 2023_Response to Examination Report (202 pages).
IL284266_Jul. 11, 2023_Notice of Acceptance & claims (8 pages).
IN202117026711_Apr. 28, 2023_Response to First Exam Report (32 pages).
IN202117026711_Sep. 19, 2023_Post Hearing Written Submission (30 pages).
JP2021-536757_Nov. 17, 2023_1st Exam Report w EN translation (22 pages).
JP2021-536757_Apr. 12, 2024_Resp 1st Exam Report w EN translation (25 pages).
MXa2021007738_Mar. 12, 2024_First Examination Report w EN translation (8 pages).
Nozaki, Masakatsu, et al., Medical Chemistry, first edition, 1995, pp. 98-99, Japan, Kagakudojin.
TW108147526_Sep. 4, 2023_office action with EN translation and claims (19 pages).
TW108147526_Apr. 4, 2024_response to First Office Action w. EN translation and claims (27 pages).

* cited by examiner

(PYRIDIN-2-YL)AMINE DERIVATIVES AS TGF-BETA R1 (ALK5) INHIBITORS FOR THE TREATMENT OF CANCER

CROSS-REFERENCE TO RELATED APPLICATIONS

This application is a U.S. National Phase filing of International Patent Application Serial No. PCT/US2019/066993, entitled "INHIBITORS OF TGF-BETA R1 (ALK5) USEFUL TO TREAT CELL PROLIFERATION DISORDERS," having an international filing date of Dec. 17, 2019, which claims priority to U.S. Provisional Application No. 62/785,616, filed Dec. 27, 2018; the contents of each of these applications are incorporated herein by reference in their entireties for all purposes.

FIELD OF THE INVENTION

The field of this invention is compounds, pharmaceutical compositions and methods, especially as they are related to compositions and methods for the treatment of a cell proliferation disorder such as fibrosis or cancer, particularly in tissues and organs where the compounds of the invention tend to accumulate in relatively high concentrations due to their pharmacokinetic properties.

BACKGROUND OF THE INVENTION

The present invention relates to novel aryloxypyridinyl compounds having an acidic moiety, which inhibit activity of transforming growth factor beta receptor 1 (TGFβR1), and tend, due to the acidic moiety, to have limited systemic distribution and thus limit exposure of off-target tissues to the inhibitor. The compounds are must useful to treat conditions such as cancer and fibrosis that occur in the digestive tract and in the first-pass metabolism tissues (liver, kidneys). The invention provides pharmaceutical compositions comprising the compounds, and methods of using the compounds to treat cancer, preferably colon cancer, hepatocellular carcinoma (HCC), renal cancer, pancreatic cancer, myelodysplastic syndrome (MDS), and gastric cancer, and/or fibrosis, preferably liver fibrosis and chronic kidney disease.

Transforming growth factor beta (TGF-beta or TGFβ) is a multi-functionalcytokine which binds to the heteromeric complexes of TGF-beta type I and type II serine/threonine kinase receptors and activates the TGF-beta receptor complex, which phosphorylates and activates SMAD2 and SMAD3, which then associate with SMAD4 and migrate into the nucleus and regulate expression of different target genes. Key players of TGF-beta receptor signal transduction pathway include TGFβ1, TGFβ2, TGFβ3, TGFβR1, TGFβR2, SMADs, SnoN, SARA, SKI, DAB, TRAP, TAKI, SMIF, E2F4, E2F5, RBL1, RBL2, RBI, TFDP1, TFDP2, SMURF1, SMURF2, P300, CBP, and JUN. The SMAD mediated TGF-beta receptor pathway regulates various cellular and Signaling via the TGF pathway has been associated with cancer and tumor progression in several indications (Elliott et. al. (2005) J Clin Oncol 23:2078; Levy et. al. (2006) Cytokine & Growth Factor Rev 17:41-58). There are several types of cancer where TGF ligands produced by the tumor or by the stroma in the tumor microenvironment may participate in tumor progression.

TGF-β1 has been associated with angiogenesis, metastasis and poor prognosis in human prostate and advanced gastric cancer (Wikstrom, P., et al. (1998) Prostate 37: 19-29; Saito, H. et al. (1999) Cancer 86: 1455-1462). In breast cancer, poor prognosis is associated with elevated TGF-β (Dickson, et al. (1987) Proc. Natl. Acad. Sci. USA 84:837-841; Kasid, et al. (1987) Cancer Res. 47:5733-5738; Daly, et al. (1990) J. Cell Biochem. 43:199-211; Barrett-Lee, et al. (1990) Br. J Cancer 61:612-617; King, et al. (1989) J. Steroid Biochem. 34:133-138; Welch, et al. (1990) Proc. Natl. Acad. Sci. USA 87:7678-7682; Walker, et al. (1992) Eur. J. Cancer 238:641-644) and induction of TGF-β1 by tamoxifen treatment (Butta, et al. (1992) Cancer Res. 52:4261-4264) has been associated with failure of tamoxifen treatment for breast cancer (Thompson, et al. (1991) Br. J. Cancer 63:609-614). Anti TGFβ1 antibodies inhibit the growth of MDA-231 human breast cancer cells in athymic mice (Arteaga, et al. (1993) J. Clin. Invest. 92:2569-2576), a treatment which is correlated with an increase in spleen natural killer cell activity. CHO cells transfected with latent TGFβ1 also showed decreased NK activity and increased tumor growth in nude mice (Wallick, et al. (1990) J. Exp. Med. 172:1777-1784). Thus, TGF-β secreted by breast tumors may cause an endocrine immune suppression. High plasma concentrations of TGFβ1 have been shown to indicate poor prognosis for advanced breast cancer patients (Anscher, et al. (1993) N. Engl. J. Med. 328:1592-1598). Patients with high circulating TGF before high dose chemotherapy and autologous bone marrow transplantation are at high risk for hepatic veno-occlusive disease (15-50% of all patients with a mortality rate up to 50%) and idiopathic interstitial pneumonitis (40-60% of all patients). The implication of these findings is 1) that elevated plasma levels of TGFβ can be used to identify at risk patients and 2) that reduction of TGFβ signaling could decrease the morbidity and mortality of these common treatments for breast cancer patients.

Recent publications have also suggested that TGFβ signaling may be important in driving resistance of tumors to standard of care therapies, including chemotherapies and receptor tyrosine kinases (WO2012138783). Specifically, in colon cancer, a specific gene expression signature has been shown to isolate a group of patients who are resistant to common first line treatments. These tumor cells regain sensitivity to therapy when the TGFβ pathway is blocked with a TGFβRI specific small molecule inhibitor (Huang, et. al. (2012) Cell 151:937-950; Sadanandamet. al. (2013) Nat Med 19:619-625; Vermeulen et. al. (2013) Nat Ned 19:614-618; Roepman et. al. (2014) 134:552-562).

Myleodysplastic syndromes (MDS) are disorders of the hematopoietic system in the myeloid compartment and are characterized by ineffective production of myeloid cells. MDS is linked to alterations of the TGFβ pathway represented by reduced SMAD7 levels. SMAD7 is an inhibitory SMAD which functions to inhibit TGFβ mediated SMAD signaling and is downstream of ligand activated signaling through TGFβRI and TGFβRII. Overexpression of SMAD7 is thus thought to lead to over-activation of TGFβ signaling in MDS, and this phenotype can be reversed by treating with a TGFβRI small molecule inhibitor (Zhou et. al. (2011) Cancer Res. 71:955-963). Similarly, in glioblastoma (GBM), TGFβ ligand levels are elevated and related to disease progression. An antisense oligonucleotide therapeutic, AP1002, has been shown to be potentially active in a subset of GBM patients (Bogdahn et. al. (2011). Curr Phann Biotechnol). In melanoma, TGFβ pathway signaling activation has also been linked to resistance to BRAF and MEK inhibitors (Sun et. al. (2014) Nature. 508:118-122).

Many malignant cells secrete transforming growth factor-β (TGF-β), a potent immunosuppressant, suggesting that TGFβ production may represent a significant tumor escape mechanism from host immunosurveillance (Flavell et. al. (2010) Nat Rev Immunol 10:554-567; Kast et. al. (1999) Leukemia 13:1188-1199). Establishment of a leukocyte subpopulation with disrupted TGFβ signaling in the tumor-bearing host offers a potential means for immunotherapy of cancer alone or in combination with one or more other immunotherapies, for example in combination with one or more PD-1 inhibitor such as nivolumab, pembrolizumab, PD-L1 inhibitors, cancer vaccines, and bispecific immune engaging molecules such as IMCgp100. TGFβ ligand produced by lymphocytes has been shown preclinically to antagonize tumor immune surveillance (Donkor et. al. (2012) Development. Oncoimmunology 1:162-171, Donkor et. al. (2011) Cytokine Immunity 35:123-134); disrupting this axis preclinically has been shown to provide anti-tumor benefit in murine models and in vitro (Zhong et. al. (2010) Cancer Res 16:1191-1205; Petrausch et. al. (2009) J Immunol 183:3682-3689); Wakefield et. al. (2013) Nat. Rev Cancer 13:328-341). A bispecific fusion protein binding both TGFβ and PD-L1 also exhibited synergistic antitumor activity compared to separate binding agents. Lan, et al., *Sci. Transl. Med. Vol.* 10, 17 Jan. 2018. A transgenic animal model with disrupted TGFβ signaling in T cells is capable of eradicating a normally lethal TGFβ over expressing lymphoma tumor, EL4 (Gorelik and Flavell, (2001) Nature Medicine 7(10): 1118-1122). Down regulation of TGF secretion in tumor cells results in restoration of immunogenicity in the host, while T-cell insensitivity to TGFβ results in accelerated differentiation and autoimmunity, elements of which may be required in order to combat self-antigen-expressing tumors in a tolerized host. The immunosuppressive effects of TGFβ have also been implicated in a subpopulation of HIV patients with lower than predicted immune response based on their CD4/CD8 T cell counts (Garba, et al. J. Immunology (2002) 168: 2247-2254). A TGFβ neutralizing antibody was capable of reversing the effect in culture, indicating that TGFβ signaling inhibitors may have utility in reversing the immune suppression present in this subset of HIV patients.

During the earliest stages of carcinogenesis, TGFβ1 can act as a potent tumor suppressor and may mediate the actions of some chemopreventive agents. However, at some point during the development and progression of malignant neoplasms, tumor cells appear to escape from TGFβ-dependent growth inhibition in parallel with the appearance of bioactive TGFβ in the microenvironment. The dualtumor suppression/tumor promotion roles of TGFβ have been most clearly elucidated in a transgenic system overexpressing TGFβ in keratinocytes. While the transgenics were more resistant to formation of benign skin lesions, the rate of metastatic conversion in the transgenics was dramatically increased (Cui, et al (1996) Cell 86(4):531-42).

The production of TGFβ by malignant cells in primary tumors appears to increase with advancing stages of tumor progression. Studies in many of the major epithelial cancers suggest that the increased production of TGFβ by human cancers occurs as a relatively late event during tumor progression. Further, this tumor-associated TGFβ provides the tumor cells with a selective advantage and promotes tumor progression. The effects of TGFβ on cell/cell and cell/stroma interactions result in a greater propensity for invasion and metastasis. Tumor-associated TGF may allow tumor cells to escape from immune surveillance since it is a potent inhibitor of the clonal expansion of activated lymphocytes. TGFβ has also been shown to inhibit the production of angiostatin.

Cancer therapeutic modalities such as radiation therapy and chemotherapy induce the production of activated TGFβ in the tumor, thereby selecting outgrowth of malignant cells that are resistant to TGFβ grow inhibitory effects. Thus, these anticancer treatments increase the risk and hasten the development of tumors with enhanced growth and invasiveness. In this situation, agents targeting TGFβ-mediated signal transduction might be a very effective therapeutic strategy. The resistance of tumor cells to TGFβ has been shown to negate much of the cytotoxic effects of radiation therapy and chemotherapy and the treatment-dependent activation of TGFβ in the stroma may even be detrimental as it can make the microenvironment more conducive to tumor progression and contribute to tissue damage leading to fibrosis. The development of TGFβ signal transduction inhibitors is likely to benefit the treatment of progressed cancer when used alone or in combination with other therapies.

Additionally, it is known in the art that TGFβ signaling is involved in fibrotic conditions such as liver fibrosis and chronic kidney disease. See for example, Ueha S, et. al. 2012. Front Immunol. 3:71. Cellular and molecular mechanisms of chronic inflammation-associated organ fibrosis; Bottinger et. al.. 2002. J Amer Soc Nephrol. 13:2600. TGFβ Signaling in Renal Disease; Trachtman H., et al. 2011. Kidney International 79:1236. A phase 1, single-dose study of fresolimumab, an anti-TGFβ antibody, in treatment-resistant primary focal segmental glomerulosclerosis; and Rosenbloom J, et. al. 2010. Narrative review: fibrotic diseases: cellular and molecular mechanisms and novel therapies. Ann Intern Med 152: 159-166.

Small molecule inhibitors of TGFβR1 are known in the art for the treatment of cancer and/or fibrosis. See for example, WO2012/002680, WO2009/022171, WO2004/048382, WO2002/094833, and WO2016/057278. Unfortunately, the known classes of inhibitors have not resulted in any drugs reaching regulatory approval (although at least one, galunisertib, remains under investigation), likely because of the diverse bioactivities of TGFβR1, which can produce toxic responses at in vivo concentrations similar to those needed for therapeutic efficacy.

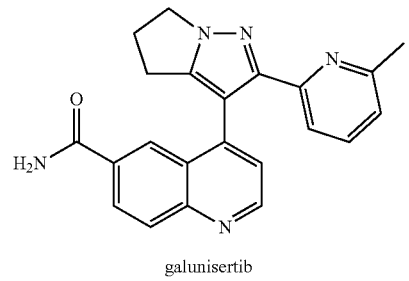 [SMILES: Cc1cccc(-c2nn3c(c2-c2ccnc4ccc(C(N)=O)cc24)CCC3)n1]

galunisertib

There remains a need for new small-molecule inhibitors of TGFβR1 useful for the treatment of cell proliferation disorders like cancer and fibrosis, and particularly for inhibitors having pharmacokinetic properties that can provide higher concentrations in organs or tissues to be treated and lower effective concentratons in other tissues, whereby toxic effects in non-target tissues may be reduced. For example, small-molecule inhibitors could be administered orally to treat cancers in the digestive system, where they may interact directly with targeted tissues without need for systemic distribution. Similarly, these compounds may possess pharmacokinetic properties causing them to preferentially concentrate in target organs such as liver or kidneys, enabling them to be used to treat cancers in those organs, while the compounds may still be excreted relatively quickly before they fully enter systemic circulation, and thus do not produce high systemic drug concentrations that tend to produce toxicity elsewhere, e.g. in cardiac tissues.

The invention provides compounds that inhibit TGFβR1, also known as Alk5, and comprise an acidic moiety in a region of the structure where it does not interfere with binding to the target site. The compounds of the invention may be effective even if present only intermittently; thus long residence times (long in vivo half-life) and maintaining drug levels above a minimum inhibitory concentration (MIC) are not necessarily needed to achieve therapeutic efficacy, particularly when the compounds of the invention are used in combination with an additional anti-cancer therapeutic agent, including a PD-1 or PD-L1 inhibitor. These compounds are thus useful to treat cancers and fibrosis conditions in targeted tissues such as liver, kidney, and gastrointestinal system, while presenting reduced toxicity in non-targeted organs or tissues.

Without being bound by theory, the acidic moiety in compounds of Formula (I) and Formula (II) tends to reduce concentration of the drug in many tissues or promote relatively rapid excretion, while producing locally effective concentrations in e.g., the colon, small intestine, liver and/or kidneys, thus increasing the therapeutic index relative to non-acidic inhibitors of TGFβR1 for use in these organs. The increase in therapeutic index in these tissues is particularly advantageous for oral administration. The acidic compounds are also believed to be transported actively via transport polypeptides (e.g., OATP1, OATP2) into the tissues of the liver and kidneys, thus producing localized concentrations in those organs even when the compounds enter systemic circulation. In addition, since cancer of the colon often metastasizes to the liver; the compounds of the invention are also expected to inhibit metastasis by presenting locally high concentrations in both colon and liver tissues. The compounds of the invention are thus especially useful to treat colon cancer, hepatocellular carcinoma (HCC), renal cancer, liver cancer, and gastric cancer, as well as fibrosis in the digestive system and first-pass metabolic systems, particularly liver fibrosis and kidney fibrosis conditions.

SUMMARY OF THE INVENTION

In one aspect, the present disclosure provides a heterocyclic compound having a structure according to Formula I:

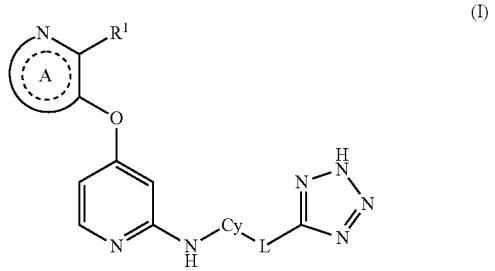

(I)

wherein:
Ring A is a 5-6 membered heteroaromatic ring optionally containing an additional nitrogen atom as a ring member, optionally further substituted by one or two groups independently selected from halo, $C_1$-$C_4$ alkyl, $C_1$-$C_4$ haloalkyl, $C_1$-$C_4$ alkoxy, $C_1$-$C_4$ haloalkoxy, phenyl, pyridinyl, and $C_3$-$C_6$ cycloalkyl, or fused to an additional phenyl or pyridinyl ring;

$R^1$ is selected from H, halo, CN, $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, 5-6 membered heterocyclyl containing N, O or S as a ring member, phenyl, and 5-6 membered heteroaryl containing one or two nitrogen atoms as ring members,
wherein said $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, phenyl, and 5-6 membered heteroaryl are each optionally substituted with one or two groups selected from $R^2$;
$R^2$ is independently selected at each occurrence from halo, —OH, $C_1$-$C_4$ alkyl, $C_1$-$C_4$ haloalkyl, $C_1$-$C_4$ alkoxy, $C_1$-$C_4$ haloalkoxy, and $C_3$-$C_6$ cycloalkyl;

Cy is a ring selected from $C_3$-$C_6$ cycloalkyl, phenyl, and 5-6 membered heteroaryl containing one or two nitrogen atoms as ring members, and is optionally further substituted with one or two groups selected from halo, $C_1$-$C_4$ alkyl, $C_1$-$C_4$ haloalkyl, $C_1$-$C_4$ alkoxy, and $C_1$-$C_4$ haloalkoxy;

L is a divalent linker selected from a bond, $CR_2$, —$(CR_2)_{2-4}$—, —O—$(CR_2)_{1-3}$—, and —$(CR_2)_m$—X—$(CR_2)_n$—,
wherein R is independently selected at each occurrence from H, F, and $C_1$-$C_4$ alkyl; or two R groups on the same carbon can be taken together with the carbon to which they are attached to form a 3-6 membered cycloalkyl ring or 3-6 membered cyclic ether;
m is 0, 1, or 2;
n is 0, 1 or 2; and
X is a 5-membered heteroaromatic ring containing one to four heteroatoms selected from N, O and S as ring members;
or a pharmaceutically acceptable salt thereof.

In another aspect, the invention provides compounds of Formula (II):

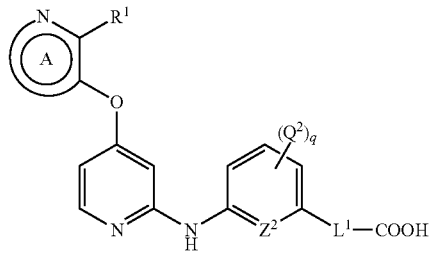

(II)

wherein:
Ring A is a 5 or 6 membered heteroaromatic ring optionally containing an additional nitrogen atom as a ring member and optionally fused to a phenyl or pyridinyl ring, and Ring A is optionally substituted by one or two groups independently selected from halo, $C_1$-$C_4$ alkyl, $C_1$-$C_4$ haloalkyl, $C_1$-$C_4$ alkoxy, $C_1$-$C_4$ haloalkoxy, phenyl, pyridinyl, and $C_3$-$C_6$ cycloalkyl;
$R^1$ is selected from CN, $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, 5-6 membered heterocyclyl containing N, O or S as a ring member, phenyl, and 5-6 membered heteroaryl containing one or two nitrogen atoms as ring members,
wherein said $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, 5-6 membered heterocyclyl, phenyl, and 5-6 membered heteroaryl are each optionally substituted with one or two groups selected from $Q^1$;
$Q^1$ is independently selected at each occurrence from halo, —OH, $C_1$-$C_4$ alkyl, $C_1$-$C_4$ haloalkyl, $C_1$-$C_4$ alkoxy, $C_1$-$C_4$ haloalkoxy, and $C_3$-$C_6$ cycloalkyl;
$L^1$ is a divalent linker selected from —C($R^9$)$_2$—, —(C($R^{10}$)$_2$)$_{2-4}$—, —O—(C($R^{10}$)$_2$)$_{1-3}$—, and —(C($R^{10}$)$_2$)$_m$—X—(C($R^{10}$)$_2$)$_n$—;
each $R^9$ is independently $C_1$-$C_2$ alkyl, or two $R^9$ can be taken together with the carbon atom to which both are attached to form a 3-6 membered cycloalkyl ring or 3-6 membered cyclic ether;
$R^{10}$ is independently selected at each occurrence from H, F, and $C_1$-$C_4$ alkyl; or two $R^{10}$ groups on the same carbon can be taken together with the carbon to which they are attached to form a 3-6 membered cycloalkyl ring or 3-6 membered cyclic ether;
m is 0, 1, or 2;
n is 0, 1 or 2;
X is a pyrazolyl, triazolyl, or tetrazolyl ring;
$Z^2$ is selected from CH, C$Q^2$, and N; and
q is 0 or 1;
$Q^2$ is selected from halo, $C_1$-$C_4$ alkyl, $C_1$-$C_4$ haloalkyl, $C_1$-$C_4$ alkoxy, and $C_1$-$C_4$ haloalkoxy;
or a pharmaceutically acceptable salt thereof.

Other aspects of the invention relate to pharmaceutical compositions comprising a compound of Formula (I) or Formula (II). In other aspects, the invention provides methods of using the compounds and compositions of the invention for treating conditions such as cancer, as further disclosed herein. Additional aspects of the invention are disclosed herein.

While depicted as a specific tautomer, it is understood that the compounds of Formula (I) and Formula (II) include other tautomers, particularly in the tetrazole ring moiety of compounds of Formula (I).

The compounds described herein can be used for many suitable purposes. In some embodiments, the compound described above can be used in therapy, particularly therapy for treatment of cellular proliferative disorders such as cancer and fibrosis disorders, particularly disorders of the gastrointestinal system or first-pass metabolic system, including ones described herein.

In still another aspect, the present disclosure provides a pharmaceutical composition comprising a compound of Formula (I) or Formula (II) or any of the sub-formulae described herein, admixed with at least one pharmaceutically acceptable carrier or excipient.

In yet another aspect, the present disclosure provides a method for treating and/or preventing a cellular proliferation disorder, such as a cancer or fibrosis, which comprises administering to a subject in need thereof an effective amount of a compound of Formula (I) or Formula (II) or any of the sub-formulae described herein, or a pharmaceutical composition containing at least one compound of Formula (I) or Formula (II) or any of the sub-formulae described herein. While suitable for treating many cellular proliferative conditions, the compounds are especially indicated for use to treat cancers associated with excessive activity of TGFβR1, also known as Alk5, particularly for cancers of the liver, kidneys and gastrointestinal system, where their physicochemical properties promote higher localized concentrations in these organs with reduced exposure in other tissues where toxic effects tend to appear.

In yet another aspect, the present disclosure provides a use of a compound of Formula (I) or Formula (II) or any of the sub-formulae described herein for the manufacture of a medicament. The acidic compounds of the invention are particularly useful for manufacture of a medicament for use to treat cancers associated with excessive activity of TGFβR1, also known as Alk5, particularly for cancers of the liver, kidneys and gastrointestinal system.

In yet another aspect, the present disclosure provides a combination for treating and/or preventing a cell proliferation disorder in a subject, which combination comprises an effective amount of Formula (I) or Formula (II) or any of the sub-formulae described herein, or a pharmaceutically acceptable salt thereof, and an effective amount of a second prophylactic or therapeutic agent for treating and/or preventing a cellular proliferation disorder, such as a cancer or fibrosis in a subject, preferably a subject having been diagnosed as in need of treatment for such disorder. Suitable second therapeutic agents for use in combination with the compounds of the invention include small molecule and antibody therapeutics useful to treat the same conditions to be treated with the compounds of Formula (I) or Formula (II) and subformula thereof. Chemotherapeutic agents for use in such combinations include 5-fluorouracil, leucovorin, oxaliplatin, capecitabine, irinotecan, regorafenib, trifluridine, tipiracil, a drug that targets VEGF such as bevacizumab, ziv-aflibercept, or ramucirumab, or a drug that targets EGFR such as cetuximab or panitumumab.

In one aspect, the combination of the invention comprises a compound of Formula (I) or Formula (II) or any subformula thereof, in combination with an immunooncology therapeutic agent, such as a PD-1 or PD-L1 inhibitor, or other known checkpoint inhibitors, that help the body's own immune system recognize and combat cancer cells. The checkpoint inhibitors assist the subject's immune system in recognizing and attacking abnormal cells, such as cancerous cells, and can significantly boost the efficacy of chemotherapies such as the compounds disclosed herein. Suitable checkpoint inhibitors include biologics as well as small-molecule therapeutics; examples of these include ipilimumab, nivolumab, atezolizumab, avelumab, pembrolizumab, tislelizumab, and durvalumab.

In yet another aspect, the present disclosure provides a method for treating and/or preventing a proliferation disorder, cancer, or fibrosis in a subject, which methods comprises administering to a subject in need thereof an effective amount of a combination described above that contains a compound of Formula (I) or Formula (II) or any of the sub-formulae described herein. The acidic compounds of the invention are particularly useful for treating cancers associated with excessive activity of TGFβR1, also known as Alk5, particularly for cancers of the liver, kidneys and gastrointestinal system.

In yet another aspect, the present disclosure provides for a method for inhibiting an activity of TGFβR1, which comprises administering to a subject in need thereof, or contacting a cell that possesses such activity, with an effective amount of Formula (I) or Formula (II) or any of the sub-formulae described herein, or a pharmaceutical composition a combination containing such compound.

Other aspects and embodiments of the invention are described in or will be apparent from the detailed description and examples below.

DETAILED DESCRIPTION

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein, "a" or "an" means "at least one" or "one or more".

As used herein, the term "subject" refers to an animal. In certain aspects, the animal is a mammal. A subject also refers to for example, primates (e.g., humans), cows, sheep, goats, horses, dogs, cats, rabbits, rats, mice, fish, birds and the like. In certain embodiments, the subject is a human. A "patient" as used herein refers to a human subject.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both.

In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

"Optionally substituted" means the group referred to can be unsubstituted or can be substituted at one or more positions by any one or any combination of the radicals suitable for substitution on that group, or those specified. The number, placement and selection of substituents is understood to encompass only those substitutions that a skilled chemist would expect to be reasonably stable; thus 'oxo' would not be a substituent on an aryl or heteroaryl ring, for example, and a single carbon atom would not have three hydroxy or amino substituents.

"Halo" or "halogen", as used herein, may be fluorine, chlorine, bromine or iodine.

"$C_1$-$C_6$ alkyl", or "$C_{1-6}$ alkyl" as used herein, denotes straight chain or branched alkyl having 1-6 carbon atoms. If a different number of carbon atoms is specified, such as $C_4$ or $C_3$, then the definition is to be amended accordingly, such as "$C_1$-$C_4$ alkyl" will represent methyl, ethyl, propyl, isopropyl, butyl, isobutyl, sec-butyl and tert-butyl.

"$C_1$-$C_6$ alkoxy", or "$C_{1-6}$ alkoxy" as used herein, denotes straight chain or branched alkoxy having 1-6 carbon atoms. If a different number of carbon atoms is specified, such as $C_4$ or $C_3$, then the definition is to be amended accordingly, such as "$C_1$-$C_4$ alkoxy" will represent methoxy, ethoxy, propoxy, isopropoxy, butoxy, isobutoxy, sec-butoxy and tert-butoxy.

"$C_1$-$C_4$ haloalkyl" or "$C_{1-4}$haloalkyl" as used herein, denotes straight chain or branched alkyl having 1-4 carbon atoms wherein at least one hydrogen has been replaced with a halogen. The number of halogen replacements can be from one up to the number of hydrogen atoms on the unsubstituted alkyl group. If a different number of carbon atoms is specified, such as $C_6$ or $C_3$, then the definition is to be amended accordingly. Thus "$C_1$-$C_4$ haloalkyl" will represent methyl, ethyl, propyl, isopropyl, butyl, isobutyl, sec-butyl and tert-butyl that have at least one hydrogen substituted with halogen, such as where the halogen is fluorine: $CF_3CF_2$—, $(CF_3)_2CH$—, $CH_3$—$CF_2$—, $CF_3CF_2$—, $CF_3$, $CF_2H$—, $CF_3CF_2CHCF_3$ or $CF_3CF_2CF_2CF_2$—.

"$C_3$-$C_8$ cycloalkyl" as used herein refers to a saturated monocyclic hydrocarbon ring of 3 to 8 carbon atoms. Examples of such groups include cyclopropyl, cyclobutyl, cyclopentyl and cyclohexyl. If a different number of carbon atoms is specified, such as $C_3$-$C_6$, then the definition is to be amended accordingly.

"3-6 membered cyclic ether" as used herein refers to a 3-6 membered saturated heterocyclic ring containing one oxygen atom as a ring member, including oxirane, oxetane, tetrahydrofuran, and tetrahydropyran. These 3-6 membered cyclic ethers can be substituted with groups suitable as substituents on other heterocyclic ring moieties.

"4- to 8-Membered heterocyclyl", "5- to 6-membered heterocyclyl", "3- to 10-membered heterocyclyl", "3- to 14-membered heterocyclyl", "4- to 14-membered heterocyclyl" and "5- to 14-membered heterocyclyl", refers, respectively, to 4- to 8-membered, 5- to 6-membered, 3- to 10-membered, 3- to 14-membered, 4- to 14-membered and 5- to 14-membered heterocyclic rings; unless otherwise specified, such rings contain 1 to 7, 1 to 5, or 1 to 3 heteroatoms selected from the group consisting of nitrogen, oxygen and sulphur as ring members, and the rings may be saturated, or partially saturated but not aromatic. The heterocyclic group can be attached at a heteroatom or a carbon atom. The term "heterocyclyl" includes single ring groups, fused ring groups and bridged groups. Examples of such heterocyclyl include, but are not limited to pyrrolidine, piperidine, piperazine, pyrrolidine, pyrrolidinone, morpholine, tetrahydrofuran, tetrahydrothiophene, tetrahydrothiopyran, tetrahydropyran, 1,4-dioxane, 1,4-oxathiane, 8-azabicyclo[3.2.1]octane, 3,8-diazabicyclo[3.2.1]octane, 3-Oxa-8-aza-bicyclo[3.2.1]octane, 8-Oxa-3-aza-bicyclo[3.2.1]octane, 2-Oxa-5-aza-bicyclo[2.2.1]heptane, 2,5-Diazabicyclo[2.2.1]heptane, azetidine, ethylenedioxo, oxetane or thiazole. Preferred heterocycles or heterocyclic groups are 5-membered saturated rings containing one heteroatom selected from N, O and S, and 6-membered saturated rings containing one or two heteroatoms that are not adjacent, and are selected from N, O and S.

A "cyclic ether" as used herein refers to a heterocyclic ring comprising at least one oxygen atom as a ring member. Generally, the term refers to a heterocyclic ring containing exactly one oxygen atom as a ring member. Particular examples of cyclic ethers include oxetane or oxetanyl, tetrahydrofuranyl, tetrahydropyranyl, and the like. The cyclic ethers may be substituted by one or more groups suitable as substituents on heterocyclic rings.

"Heteroaryl" is a completely unsaturated (aromatic) ring. The term "heteroaryl" refers to a 5-14 membered monocyclic- or bicyclic- or tricyclic-aromatic ring system, having 1 to 8 heteroatoms selected from N, O or S. Typically, the heteroaryl is a 5-10 membered ring or ring system (e.g., 5-7 membered monocyclic group or an 8-10 membered bicyclic group), often a 5-6 membered ring. Typical heteroaryl groups include furan, isothiazole, thiadiazole, oxadiazole, indazole, indole, quinoline, 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-(1,2,4-triazolyl), 4- or 5-(1,2, 3-triazolyl), tetrazolyl, triazine, pyrimidine, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "hydroxy" or "hydroxyl" refers to the group —OH.

The term "alkyl" as used herein refers to saturated hydrocarbon groups in a straight, branched, or cyclic configuration or any combination thereof, and particularly contemplated alkyl groups include those having ten or less carbon atoms, especially 1-6 carbon atoms, and lower alkyl groups having 1-4 carbon atoms. Exemplary alkyl groups are methyl, ethyl, propyl, isopropyl, butyl, sec-butyl, tertiary butyl, pentyl, isopentyl, hexyl, cyclopropylmethyl, etc.

Alkyl groups can be unsubstituted, or they can be substituted to the extent that such substitution makes sense chemically. Typical substituents include, but are not limited to, halo, =O, =N—CN, =N—$OR^a$, =$NR^a$, —$OR^a$, —$NR^a{}_2$, —$SR^a$, —$SO_2R^a$, —$SO_2NR^a{}_2$, —$NR^aSO_2R^a$, —$NR^a$-$CONR^a{}_2$, —$NR^aCOOR^a$, —$NR^aCOR^a$, —CN, —$COOR^a$, —$CONR^a{}_2$, —$OOCR^a$, —$COR^a$, and —$NO_2$, wherein each $R^a$ is independently H, $C_1$-$C_8$ alkyl, $C_2$-$C_8$ heteroalkyl, $C_3$-$C_8$ heterocyclyl, $C_4$-$C_{10}$ heterocyclyclalkyl, $C_1$-$C_8$ acyl, $C_2$-$C_8$ heteroacyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, or $C_5$-$C_{10}$ heteroaryl, and each $R^a$ is optionally substituted with halo, =O, =N—CN, =N—$OR^b$, =$NR^b$, $OR^b$, $NR^b{}_2$, $SR^b$, $SO_2R^b$, $SO_2NR^b{}_2$, $NR^bSO_2R^b$, $NR^bCONR^b{}_2$, $NR^bCOOR^b$, $NR^bCOR^b$, CN, $COOR^b$, $CONR^b{}_2$, $OOCR^b$, $COR^b$, and $NO_2$, wherein each $R^b$ is independently H, $C_1$-$C_8$ alkyl, $C_2$-$C_8$ heteroalkyl, $C_3$-$C_8$ heterocyclyl, $C_4$-$C_{10}$ heterocyclyclalkyl, $C_1$-$C_8$ acyl, $C_2$-$C_8$ heteroacyl, $C_2$-$C_8$ alkenyl, $C_6$-$C_{10}$ aryl, or $C_5$-$C_{10}$ heteroaryl. Alkyl, alkenyl and alkynyl groups can also be substituted by $C_1$-$C_8$ acyl, $C_2$-$C_8$ heteroacyl, $C_6$-$C_{10}$ aryl or $C_5$-$C_{10}$ heteroaryl, each of which can be substituted by the substituents that are appropriate for the particular group. Where a substituent group contains two $R^a$ or $R^b$ groups on the same or adjacent atoms (e.g., —$NR^b{}_2$, or $NR^b$—C(O) $R^b$), the two $R^a$ or $R^b$ groups can optionally be taken together with the atoms in the substituent group to which are attached to form a ring having 5-8 ring members, which can be substituted as allowed for the $R^a$ or $R^b$ itself, and can contain an additional heteroatom (N, O or S) as a ring member.

The term "alkenyl" as used herein refers to an alkyl as defined above having at least two carbon atoms and at least one carbon-carbon double bond. Thus, particularly contemplated alkenyl groups include straight, branched, or cyclic alkenyl groups having two to ten carbon atoms (e.g., ethenyl, propenyl, butenyl, pentenyl, etc.) or 5-10 atoms for cyclic alkenyl groups. Alkenyl groups are optionally substituted by groups suitable for alkyl groups as set forth herein.

Similarly, the term "alkynyl" as used herein refers to an alkyl or alkenyl as defined above and having at least two (preferably three) carbon atoms and at least one carbon-carbon triple bond. Especially contemplated alkynyls include straight, branched, or cyclic alkynes having two to ten total carbon atoms (e.g., ethynyl, propynyl, butynyl, cyclopropylethynyl, etc.). Alkynyl groups are optionally substituted by groups suitable for alkyl groups as set forth herein.

The term "cycloalkyl" as used herein refers to a cyclic alkane (i.e., in which a chain of carbon atoms of a hydrocarbon forms a ring), preferably including three to eight carbon atoms. Thus, exemplary cycloalkanes include cyclopropyl, cyclobutyl, cyclopentyl, cyclohexyl, cycloheptyl, and cyclooctyl. Cycloalkyls also include one or two double bonds, which form the "cycloalkenyl" groups. Cycloalkyl groups are optionally substituted by groups suitable for alkyl groups as set forth herein.

The term "aryl" or "aromatic moiety" as used herein refers to an aromatic ring system, which may further include one or more non-carbon atoms. These are typically 5-6 membered isolated rings, or 8-10 membered bicyclic groups, and can be substituted. Thus, contemplated aryl groups include (e.g., phenyl, naphthyl, etc.) and pyridyl. Further contemplated aryl groups may be fused (i.e., covalently bound with 2 atoms on the first aromatic ring) with one or two 5- or 6-membered aryl or heterocyclic group, and are thus termed "fused aryl" or "fused aromatic".

Aromatic groups containing one or more heteroatoms (typically N, O or S) as ring members can be referred to as heteroaryl or heteroaromatic groups. Typical heteroaromatic groups include monocyclic 5-6 membered aromatic groups such as pyridyl, pyrimidyl, pyrazinyl, thienyl, furanyl, pyrrolyl, pyrazolyl, thiazolyl, oxazolyl, isothiazolyl, isoxazolyl, and imidazolyl and the fused bicyclic moieties formed by fusing one of these monocyclic groups with a phenyl ring or with any of the heteroaromatic monocyclic groups to form an 8-10 membered bicyclic group such as indolyl, benzimidazolyl, indazolyl, benzotriazolyl, isoquinolyl, quinolyl, benzothiazolyl, benzofuranyl, pyrazolopyridyl, pyrazolopyrimidyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferred heteroaryl groups are 5-6 membered rings.

As also used herein, the terms "heterocycle", "cycloheteroalkyl", and "heterocyclic moieties" are used interchangeably herein and refer to any compound in which a plurality of atoms form a ring via a plurality of covalent bonds, wherein the ring includes at least one atom other than a carbon atom as a ring member. Particularly contemplated heterocyclic rings include 5- and 6-membered rings with nitrogen, sulfur, or oxygen as the non-carbon atom (e.g., imidazole, pyrrole, triazole, dihydropyrimidine, indole, pyridine, thiazole, tetrazole etc.).

Typically these rings contain 0-1 oxygen or sulfur atoms, at least one and typically 2-3 carbon atoms, and up to four nitrogen atoms as ring members. Further contemplated heterocycles may be fused (i.e., covalently bound with two atoms on the first heterocyclic ring) to one or two carbocyclic rings or heterocycles, and are thus termed "fused heterocycle" or "fused heterocyclic ring" or "fused heterocyclic moieties" as used herein. Where the ring is aromatic, these can be referred to herein as 'heteroaryl' or heteroaromatic groups.

Heterocyclic groups that are not aromatic can be substituted with groups suitable for alkyl group substituents, as set forth above.

Aryl and heteroaryl groups can be substituted where permitted. Suitable substituents include, but are not limited to, halo, —OR$^a$, —NR$^a_2$, —SR$^a$, —SO$_2$R$^a$, —SO$_2$NR$^a_2$, —NR$^a$SO$_2$R$^a$, —NR$^a$CONR$^a_2$, —NR$^a$COOR$^a$, —NR$^a$COR$^a$, —CN, —COOR$^a$, —CONR$^a_2$, —OOCR$^a$, —COR$^a$, and —NO$_2$, wherein each R$^a$ is independently H, C$_1$-C$_8$ alkyl, C$_2$-C$_8$ heteroalkyl, C$_3$-C$_8$ heterocyclyl, C$_4$-C$_{10}$ heterocyclylalkyl, C$_1$-C$_8$ acyl, C$_2$-C$_8$ heteroacyl, C$_2$-C$_8$ alkenyl, C$_2$-C$_8$ heteroalkenyl, C$_2$-C$_8$ alkynyl, C$_2$-C$_8$ heteroalkynyl, C$_6$-C$_{10}$ aryl, or C$_5$-C$_{10}$ heteroaryl, and each R$^a$ is optionally substituted with halo, =O, =N—CN, =N—OR$^b$, =NR$^b$, OR$^b$, NR$^b_2$, SR$^b$, SO$_2$R$^b$, SO$_2$NR$^b_2$, NR$^b$SO$_2$R$^b$, NR$^b$CONR$^b_2$, NR$^b$COOR$^b$, NR$^b$COR$^b$, CN, COOR$^b$, CONR$^b_2$, OOCR$^b$, COR$^b$, and NO$_2$, wherein each R$^b$ is independently H, C$_1$-C$_8$ alkyl, C$_2$-C$_8$ heteroalkyl, C$_3$-C$_8$ heterocyclyl, C$_4$-C$_{10}$ heterocyclylalkyl, C$_1$-C$_8$ acyl, C$_2$-C$_8$ heteroacyl, C$_2$-C$_8$ alkenyl, C$_6$-C$_{10}$ aryl, or C$_5$-C$_{10}$ heteroaryl. Alkyl, alkenyl and alkynyl groups can also be substituted by C$_1$-C$_8$ acyl, C$_2$-C$_8$ heteroacyl, C$_6$-C$_{10}$ aryl or C$_5$-C$_{10}$ heteroaryl, each of which can be substituted by the substituents that are appropriate for the particular group. Where a substituent group contains two R$^a$ or R$^b$ groups on the same or adjacent atoms (e.g., —NR$^b_2$, or NR$^b$—C(O) R$^b$), the two R$^a$ or R$^b$ groups can optionally be taken together with the atoms in the substituent group to which are attached to form a ring having 5-8 ring members, which can be substituted as allowed for the R$^a$ or R$^b$ itself, and can contain an additional heteroatom (N, O or S) as a ring member.

The term "alkoxy" as used herein refers to a hydrocarbon group connected through an oxygen atom, e.g., —O-Hc, wherein the hydrocarbon portion He may have any number of carbon atoms, typically 1-10 carbon atoms, may further include a double or triple bond and may include one or two oxygen, sulfur or nitrogen atoms in the alkyl chains, and can be substituted with aryl, heteroaryl, cycloalkyl, and/or heterocyclyl groups. For example, suitable alkoxy groups include methoxy, ethoxy, propyloxy, isopropoxy, methoxyethoxy, benzyloxy, allyloxy, and the like. Similarly, the term "alkylthio" refers to alkylsulfides of the general formula —S-Hc, wherein the hydrocarbon portion He is as described for alkoxy groups. For example, contemplated alkylthio groups include methylthio, ethylthio, isopropylthio, methoxyethylthio, benzylthio, allylthio, and the like.

The term 'amino' as used herein refers to the group —NH$_2$. The term "alkylamino" refers to amino groups where one or both hydrogen atoms are replaced by a hydrocarbon group He as described above, wherein the amino nitrogen "N" can be substituted by one or two He groups as set forth for alkoxy groups described above. Exemplary alkylamino groups include methylamino, dimethylamino, ethylamino, diethylamino, etc. Also, the term "substituted amino" refers to amino groups where one or both hydrogen atoms are replaced by a hydrocarbon group He as described above, wherein the amino nitrogen "N" can be substituted by one or two He groups as set forth for alkoxy groups described above.

The term 'acyl' as used herein refers to a group of the formula —C(=O)—D, where D represents an alkyl, alkenyl, alkynyl, cycloalkyl, aryl, heteroaryl, or heterocycle as described above. Typical examples are groups wherein D is a C$_1$-C$_{10}$ alkyl, C$_2$-C$_{10}$ alkenyl or alkynyl, or phenyl, each of which is optionally substituted. In some embodiments, D can be H, Me, Et, isopropyl, propyl, butyl, C$_1$-C$_4$ alkyl substituted with —OH, —OMe, or NH$_2$, phenyl, halophenyl, alkylphenyl, and the like.

The term "aryloxy" as used herein refers to an aryl group connecting to an oxygen atom, wherein the aryl group may be further substituted. For example, suitable aryloxy groups include phenyloxy, etc. Similarly, the term "arylthio" as used herein refers to an aryl group connecting to a sulfur atom, wherein the aryl group may be further substituted. For example, suitable arylthio groups include phenylthio, etc.

The hydrocarbon portion of each alkoxy, alkylthio, alkylamino, and aryloxy, etc. can be substituted as appropriate for the relevant hydrocarbon moiety.

The following enumerated embodiments are representative of some aspects of the invention:

1. A compound of Formula (I):

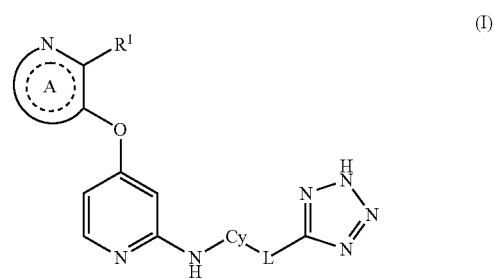

wherein:
Ring A is a 5-6 membered heteroaromatic ring optionally containing an additional nitrogen atom as a ring member, optionally fused to an additional phenyl or pyridinyl ring, and optionally further substituted by one or two groups independently selected from halo, C$_1$-C$_4$ alkyl, C$_1$-C$_4$ haloalkyl, C$_1$-C$_4$ alkoxy, C$_1$-C$_4$ haloalkoxy, phenyl, pyridinyl, and C$_3$-C$_6$ cycloalkyl;

R$^1$ is selected from H, halo, CN, C$_1$-C$_4$ alkyl, C$_1$-C$_4$ haloalkyl, C$_1$-C$_4$ alkoxy, C$_1$-C$_4$ haloalkoxy, C$_3$-C$_6$ cycloalkyl, 5-6 membered heterocyclyl containing N, O or S as a ring member, phenyl, and 5-6 membered heteroaryl containing one or two nitrogen atoms as ring members,
wherein said C$_1$-C$_4$ alkyl, C$_1$-C$_4$ haloalkyl, C$_1$-C$_4$ alkoxy, C$_1$-C$_4$ haloalkoxy, C$_3$-C$_6$ cycloalkyl, phenyl, and 5-6 membered heteroaryl are each optionally substituted with one or two groups selected from R$^2$;

R$^2$ is independently selected at each occurrence from halo, —OH, C$_1$-C$_4$ alkyl, C$_1$-C$_4$ haloalkyl, C$_1$-C$_4$ alkoxy, C$_1$-C$_4$ haloalkoxy, and C$_3$-C$_6$ cycloalkyl;

Cy is a ring selected from C$_3$-C$_6$ cycloalkyl, phenyl, and 5-6 membered heteroaryl containing one or two nitrogen atoms as ring members, and is optionally further substituted with one or two groups selected from halo, C$_1$-C$_4$ alkyl, C$_1$-C$_4$ haloalkyl, C$_1$-C$_4$ alkoxy, and C$_1$-C$_4$ haloalkoxy;

L is a divalent linker selected from a bond, CR$_2$, —(CR$_2$)$_{2-4}$—, —O—(CR$_2$)$_{1-3}$—, and —(CR$_2$)$_m$—X—(CR$_2$)$_n$—,
wherein R is independently selected at each occurrence from H, F, and C$_1$-C$_4$ alkyl; or two R groups on the same carbon can be taken together with the carbon to which they are attached to form a 3-6 membered cycloalkyl ring or 3-6 membered cyclic ether;

m is 0, 1, or 2;

n is 0, 1 or 2; and

X is a 5-membered heteroaromatic ring containing one to four heteroatoms selected from N, O and S as ring members;

or a pharmaceutically acceptable salt thereof.

2. The compound of embodiment 1, wherein $R^1$ is selected from $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, 5-6 membered heterocyclyl containing N, O or S as a ring member, phenyl, and 5-6 membered heteroaryl containing one or two nitrogen atoms as ring members, wherein said $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, 5-6 membered heterocyclyl containing N, O or S as a ring member, phenyl, and 5-6 membered heteroaryl are each optionally substituted with one or two groups selected from $R^2$;

or a pharmaceutically acceptable salt thereof.

3. The compound of embodiment 1 or 2, wherein $R^1$ is methyl, phenyl, or 2-pyridinyl; or a pharmaceutically acceptable salt thereof.

4. The compound of any one of embodiments 1-3, wherein Cy is a ring selected from phenyl and pyridinyl, and is optionally further substituted with a group selected from halo, $C_1$-$C_4$ alkyl, $C_1$-$C_4$ haloalkyl, $C_1$-$C_4$ alkoxy, and $C_1$-$C_4$ haloalkoxy; or a pharmaceutically acceptable salt thereof.

5. The compound of embodiment 4, which is of the formula

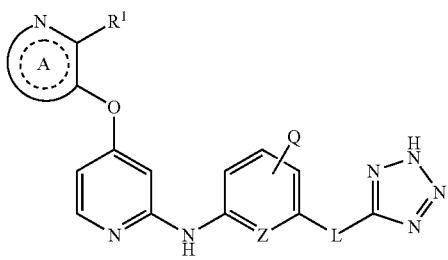

wherein Z is CH or N, and Q is selected from H, Me, $CF_3$, OMe and halo;

or a pharmaceutically acceptable salt thereof.

6. The compound of any one of the preceding embodiments, wherein L is a divalent linker selected from $CR_2$, —$(CR_2)_{2-4}$—, —O—$(CR_2)_{1-3}$—, and —$(CR_2)_m$—X—$(CR_2)_n$—;

or a pharmaceutically acceptable salt thereof.

7. The compound of embodiment 6, wherein R is independently selected at each occurrence from H, F and Me;

or a pharmaceutically acceptable salt thereof.

8. The compound of embodiment 6, wherein L is selected from $CH_2$, —$CH_2CH_2$—, $C(Me)_2$, —CHMe-, —$OCH_2$—, —$CH_2CF_2$—, —$CF_2CH_2$—, —$CMe_2CH_2$—, and —$CH_2CMe_2$-;

or a pharmaceutically acceptable salt thereof.

9. The compound of any one of the preceding embodiments, which is a compound of formula (Ia):

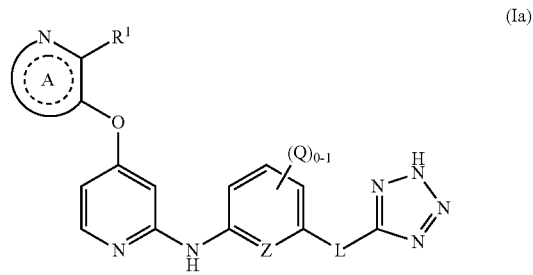

(Ia)

wherein Q is independently selected at each occurrence from halo, $C_1$-$C_4$ alkyl, $C_1$-$C_4$ haloalkyl, and $C_1$-$C_4$ alkoxy; and Z is CH, CQ or N;

or a pharmaceutically acceptable salt thereof.

10. The compound of any one of the preceding embodiments, wherein Ring A is pyridinyl or pyrazolyl, and is optionally substituted by one or two groups independently selected from halo, $C_1$-$C_4$ alkyl, $C_1$-$C_4$ haloalkyl, $C_1$-$C_4$ alkoxy, $C_1$-$C_4$ haloalkoxy, and $C_3$-$C_6$ cycloalkyl;

or a pharmaceutically acceptable salt thereof.

11. The compound of embodiment 1, wherein $R^1$ is pyridinyl, phenyl, methyl, tetrahydrofuranyl, or tetrahydropyranyl, and is optionally substituted with one or two groups selected from $R^2$;

or a pharmaceutically acceptable salt thereof. Preferably, $R^1$ is 2-pyridinyl, methyl or phenyl in these embodiments.

12. The compound of any one of embodiments 1-10, which is a compound of formula (Ib):

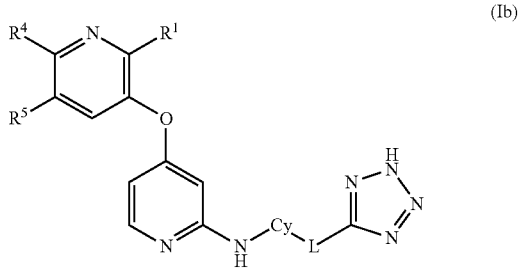

(Ib)

wherein $R^4$ and $R^5$ are independently selected from H, halo, $C_1$-$C_4$ alkyl, $C_1$-$C_4$ haloalkyl, $C_1$-$C_4$ alkoxy, $C_1$-$C_4$ haloalkoxy, phenyl and pyridinyl; or $R^4$ and $R^5$ can be taken together with the carbon atoms to which they are attached to form a phenyl ring fused to the pyridinyl ring to which $R^4$ and $R^5$ are attached;

or a pharmaceutically acceptable salt thereof.

13. The compound of any one of embodiments 1-10, which is a compound of formula (Ic):

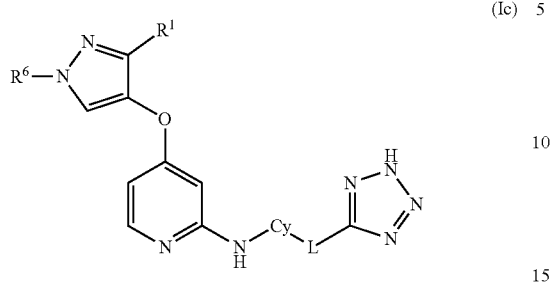

wherein $R^6$ is selected from $C_1$-$C_4$ alkyl, $C_1$-$C_4$ haloalkyl, and $C_3$-$C_6$ cycloalkyl;
or a pharmaceutically acceptable salt thereof.

14. The compound of embodiment 13, wherein $R^6$ is selected from methyl, ethyl, isopropyl, and cyclopropyl; or a pharmaceutically acceptable salt thereof.

15. The compound of any one of the preceding embodiments, wherein L is [Cy]—(CR$_2$)$_m$—X—(CR$_2$)$_n$—, where [Cy] indicates where L is attached to the group Cy;
m is 1 or 2;
n is 0, 1 or 2; and
X is a tetrazolyl ring;
or a pharmaceutically acceptable salt thereof.

16. The compound of any one of embodiments 1-15, wherein L is CH$_2$, C(Me)$_2$, —OCH$_2$-[T], —CH$_2$CH$_2$—, —C(Me)$_2$CH$_2$-[T], —CH$_2$C(Me)$_2$-[T], or —CF$_2$CH$_2$-[T], wherein [T] indicates which end of L is attached to the tetrazole ring in Formula (I); or a pharmaceutically acceptable salt thereof.

17. The compound of embodiment 1, wherein the compound is selected from the compounds of Examples 12-33, 44-65, 67, and 175-216; or a pharmaceutically acceptable salt thereof.

18. A compound of Formula (II):

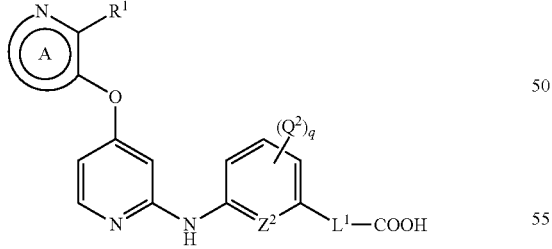

wherein:
Ring A is a 5 or 6 membered heteroaromatic ring optionally containing an additional nitrogen atom as a ring member and optionally fused to a phenyl or pyridinyl ring, and Ring A is optionally substituted by one or two groups independently selected from halo, $C_1$-$C_4$ alkyl, $C_1$-$C_4$ haloalkyl, $C_1$-$C_4$ alkoxy, $C_1$-$C_4$ haloalkoxy, phenyl, pyridinyl, and $C_3$-$C_6$ cycloalkyl;

$R^1$ is selected from CN, $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, 5-6 membered heterocyclyl containing N, O or S as a ring member, phenyl, and 5-6 membered heteroaryl containing one or two nitrogen atoms as ring members,
wherein said $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, 5-6 membered heterocyclyl, phenyl, and 5-6 membered heteroaryl are each optionally substituted with one or two groups selected from $Q^1$;

$Q^1$ is independently selected at each occurrence from halo, —OH, $C_1$-$C_4$ alkyl, $C_1$-$C_4$ haloalkyl, $C_1$-$C_4$ alkoxy, $C_1$-$C_4$ haloalkoxy, and $C_3$-$C_6$ cycloalkyl;

$L^1$ is a divalent linker selected from —C(R$^9$)$_2$—, —(C(R$^{10}$)$_2$)$_{2-4}$—, —O—(C(R$^{10}$)$_2$)$_{1-3}$—, and —(C(R$^{10}$)$_2$)$_m$—X—C(R$^{10}$)$_2$)$_n$—;

each $R^9$ is independently $C_1$-$C_2$ alkyl, or two $R^9$ can be taken together with the carbon atom to which both are attached to form a 3-6 membered cycloalkyl ring or 3-6 membered cyclic ether;

$R^{10}$ is independently selected at each occurrence from H, F, and $C_1$-$C_4$ alkyl; or two $R^{10}$ groups on the same carbon can be taken together with the carbon to which they are attached to form a 3-6 membered cycloalkyl ring or 3-6 membered cyclic ether;

m is 0, 1, or 2;

n is 0, 1 or 2;

X is a pyrazolyl, triazolyl, or tetrazolyl ring;

$Z^2$ is selected from CH, CQ$^2$, and N; and q is 0 or 1;

$Q^2$ is selected from halo, $C_1$-$C_4$ alkyl, $C_1$-$C_4$ haloalkyl, $C_1$-$C_4$ alkoxy, and $C_1$-$C_4$ haloalkoxy;
or a pharmaceutically acceptable salt thereof.

19. The compound of embodiment 18, wherein the compound is of Formula (IIa):

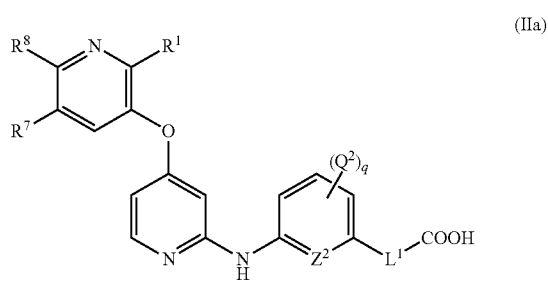

$R^7$ and $R^8$ are independently selected from H, halo, $C_1$-$C_4$ alkyl, $C_1$-$C_4$ haloalkyl, $C_1$-$C_4$ alkoxy, $C_1$-$C_4$ haloalkoxy, phenyl and pyridinyl; or $R^7$ and $R^8$ can be taken together with the carbon atoms to which they are attached to form a phenyl ring fused to the pyridinyl ring to which $R^7$ and $R^8$ are attached;
or a pharmaceutically acceptable salt thereof.

20. The compound of embodiment 18 or 19, wherein the compound is of Formula (IIb):

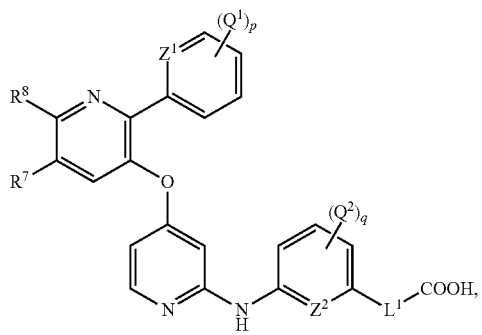

wherein $Z^1$ is selected from CH and N;
p is 0, 1 or 2; and
each $Q^1$ is independently selected from halo, $C_1$-$C_4$ alkyl, $C_1$-$C_4$ haloalkyl, $C_1$-$C_4$ alkoxy, and $C_1$-$C_4$ haloalkoxy;
or a pharmaceutically acceptable salt thereof.

21. The compound of any one of embodiments 18-20, wherein $L^1$ is $C(Me)_2$, —$OCH_2$—[C], —$CH_2CH_2$—, —$C(Me)_2CH_2$—[C], —$CH_2C(Me)_2$-[C], or —$CF_2CH_2$—[C], wherein [C] indicates which end of L is attached to the carboxylic acid in Formula (II) or (IIa) or IIb);
or a pharmaceutically acceptable salt thereof.

22. The compound of any one of embodiments 18-20, wherein $L^1$ is —$(CR^{10}_2)_m$—X—$(CR^{10}_2)_n$—, where m is 1 and n is 1; or a pharmaceutically acceptable salt thereof.

23. The compound of any one of embodiments 19-22, wherein $R^7$ and $R^8$ are each independently selected from H and Me; or a pharmaceutically acceptable salt thereof.

24. The compound of any one of embodiments 19-23, wherein $Z^2$ is CH or N; or a pharmaceutically acceptable salt thereof.

25. The compound of any one of embodiments 18-24, wherein $Z^2$ is CH; or a pharmaceutically acceptable salt thereof.

26. The compound of embodiment 18, which is selected from the compounds of Examples 1, 4-7, 10-11, 34-37, 39-41, 43, 66, 68, 70-110, 115-116, 118-174, and 217; or a pharmaceutically acceptable salt thereof.

27. A compound that is selected from the compounds of Examples 1-217; or a pharmaceutically acceptable salt thereof.

28. A pharmaceutical composition comprising a compound of any of the preceding embodiments admixed with at least one pharmaceutically acceptable carrier or excipient.

29. A method to treat cancer or fibrosis, which comprises administering to a subject in need thereof an effective amount of a compound of any one of embodiments 1-27, or a pharmaceutical composition of embodiment 28.

30. The method of embodiment 29, which is a method to treat colon cancer, hepatocellular carcinoma (HCC), renal cancer, liver cancer, gastric cancer, or fibrosis in the liver or kidney.

31. A compound according to any one of embodiments 1-27 for use in therapy.

32. Use of a compound according to any one of embodiments 1-27 for the manufacture of a medicament.

33. A pharmaceutical combination comprising an effective amount of a compound according to any one of embodiments 1-27 and an additional therapeutic agent.

A further set of embodiments of the invention include these:

1A. A compound of Formula (II):

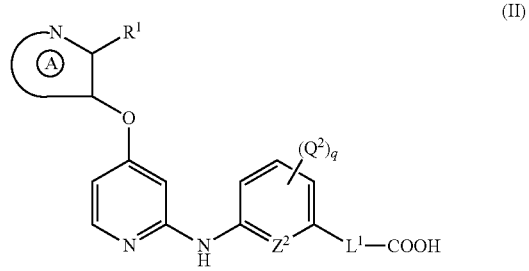

wherein:
Ring A is a 5 or 6 membered heteroaromatic ring optionally containing an additional nitrogen atom as a ring member and optionally fused to a phenyl or pyridinyl ring, and Ring A is optionally substituted by one or two groups independently selected from halo, $C_1$-$C_4$ alkyl, $C_1$-$C_4$ haloalkyl, $C_1$-$C_4$ alkoxy, $C_1$-$C_4$ haloalkoxy, phenyl, pyridinyl, a 4-6 membered cyclic ether, and $C_3$-$C_6$ cycloalkyl;
$R^1$ is selected from CN, $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, 5-6 membered heterocyclyl containing N, O or S as a ring member, phenyl, and 5-6 membered heteroaryl containing one or two nitrogen atoms as ring members,
wherein said $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, 5-6 membered heterocyclyl, phenyl, and 5-6 membered heteroaryl are
each optionally substituted with one or two groups selected from $Q^1$;
$Q^1$ is independently selected at each occurrence from halo, CN, —OH, $C_1$-$C_4$ alkyl, $C_1$-$C_4$ haloalkyl, $C_1$-$C_4$ alkoxy, $C_1$-$C_4$ haloalkoxy, and $C_3$-$C_6$ cycloalkyl;
$L^1$ is a divalent linker selected from —$C(R^9)_2$—, —$(CR^{10}_2)_{2-4}$—, —O—$(C(R^{10})_2)_{1-3}$—, and —$(C(R^{10})_2)_m$—X—$C(R^{10})_2)_n$—;
each $R^9$ is independently $C_1$-$C_2$ alkyl or halo, or two $R^9$ can be taken together with the carbon atom to which both are attached to form a 3-6 membered cycloalkyl ring or 3-6 membered cyclic ether;
$R^{10}$ is independently selected at each occurrence from H, F, and $C_1$-$C_4$ alkyl; or two $R^{10}$ groups on the same carbon can be taken together with the carbon to which they are attached to form a 3-6 membered cycloalkyl ring or 3-6 membered cyclic ether;
m is 0, 1, or 2;
n is 0, 1 or 2;
X is a pyrazolyl, triazolyl, or tetrazolyl ring;
$Z^2$ is selected from CH, $CQ^2$, and N; and
q is 0 or 1;
$Q^2$ is selected from halo, $C_1$-$C_4$ alkyl, $C_1$-$C_4$ haloalkyl, $C_1$-$C_4$ alkoxy, and $C_1$-$C_4$ haloalkoxy;
or a pharmaceutically acceptable salt thereof.

In examples of Embodiment 1A, Ring A is pyridinyl or pyrazolyl.

2A. The compound of embodiment 1A, wherein the compound is of Formula (IIa):

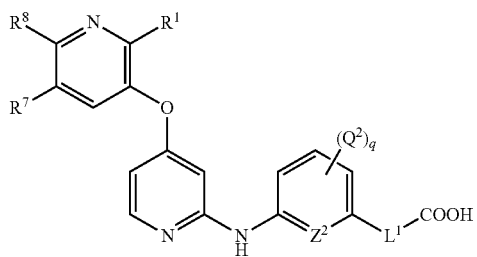

(IIa)

wherein:

$R^7$ and $R^8$ are independently selected from H, halo, $C_1$-$C_4$ alkyl, $C_1$-$C_4$ haloalkyl, $C_1$-$C_4$ alkoxy, $C_1$-$C_4$ haloalkoxy, phenyl and pyridinyl; or $R^7$ and $R^8$ can be taken together with the carbon atoms to which they are attached to form a phenyl ring fused to the pyridinyl ring to which $R^7$ and $R^8$ are attached;

or a pharmaceutically acceptable salt thereof.

Preferably in this Embodiment 2A, $R^7$ and $R^8$ are each independently selected from H, halo, and $C_1$-$C_4$ alkyl. In one example of Embodiment 2A, $R^1$ is selected from methyl, phenyl, pyridinyl and tetrahydropyranyl.

3A. The compound of embodiment 1A or 2A, wherein the compound is of Formula (IIb):

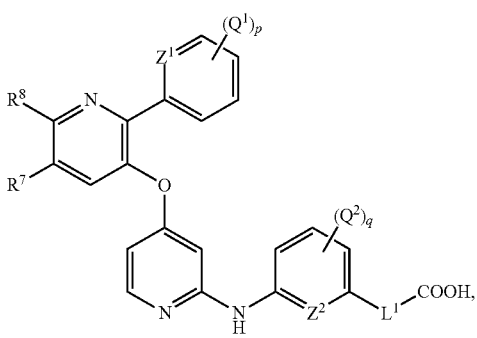

(IIb)

wherein $Z^1$ is selected from CH and N;

p is 0, 1 or 2; and each $Q^1$ is independently selected from halo, $C_1$-$C_4$ alkyl, $C_1$-$C_4$ haloalkyl, $C_1$-$C_4$ alkoxy, and $C_1$-$C_4$ haloalkoxy;

or a pharmaceutically acceptable salt thereof.

Preferably in Embodiment 3A, $R^7$ and $R^8$ are each independently selected from H, halo, and $C_1$-$C_4$ alkyl.

4A. The compound of embodiment 1A or 2A, wherein $R^1$ is selected from CN, $C_1$-$C_4$ alkyl, $C_1$-$C_4$ haloalkyl, $C_3$-$C_6$ cycloalkyl, and 5-6 membered heterocyclyl containing N, O or S as a ring member; or a pharmaceutically acceptable salt thereof.

5A. The compound of embodiment 1A, wherein the compound is of Formula (IIc):

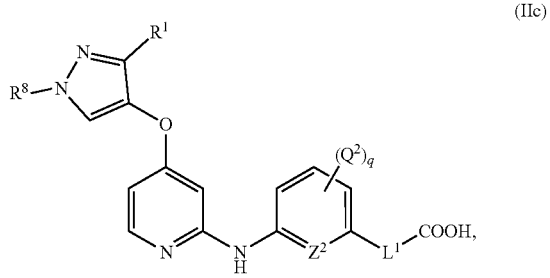

(IIc)

wherein $R^6$ is selected from $C_1$-$C_4$ alkyl, $C_1$-$C_4$ haloalkyl, and $C_3$-$C_6$ cycloalkyl;

or a pharmaceutically acceptable salt thereof.

In one example of Embodiment 5A, $R^1$ is selected from methyl, phenyl, pyridinyl and tetrahydropyranyl.

6A. The compound of any one of embodiments 1A-5A, wherein $L^1$ is $C(Me)_2$, —$OCH_2$—[C], —$CH_2CH_2$—, —$C(Me)_2CH_2$—[C], —$CH_2C(Me)_2$-[C], or —$CF_2CH_2$—[C], wherein [C] indicates which end of L is attached to the carboxylic acid in Formula (II) or (IIa) or (IIb);

or a pharmaceutically acceptable salt thereof.

7A. The compound of any one of embodiments A 1-5A, wherein $L^1$ is —$(CR^{10}_2)_m$—X—$(CR^{10}_2)_n$—, where m is 1 and n is 1; or a pharmaceutically acceptable salt thereof.

8A. The compound of any one of embodiments 1AA-4, wherein $R^7$ and $R^8$ are each independently selected from H, Me and Et; or a pharmaceutically acceptable salt thereof.

9A. The compound of any one of embodiments 1A-8A, wherein $Z^2$ is CH or N; or a pharmaceutically acceptable salt thereof.

10A. The compound of embodiment 9A, wherein $Z^2$ is CH; or a pharmaceutically acceptable salt thereof.

11A. The compound of embodiment 10A, wherein $R^1$ is Me and $L^1$ is —$C(Me)_2$-, or a pharmaceutically acceptable salt thereof.

12A. The compound of embodiment 1A, which is selected from the compounds of Examples 1, 4-7, 10-11, 34-37, 39-41, 43, 66, 68, 70-110, 115-116, 118-174, and 217; or a pharmaceutically acceptable salt thereof.

13A. A compound of Formula (I):

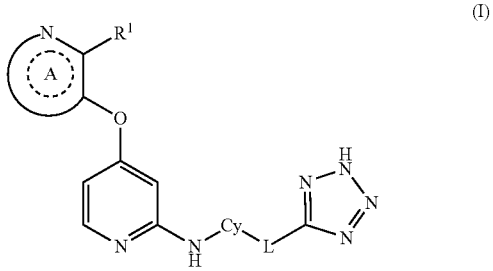

(I)

wherein:

Ring A is a 5 or 6 membered heteroaromatic ring optionally containing an additional nitrogen atom as a ring member and is optionally fused to a phenyl or pyridinyl ring, and Ring A is optionally substituted by one or two groups independently selected from halo, $C_1$-$C_4$ alkyl, $C_1$-$C_4$ haloalkyl, $C_1$-$C_4$ alkoxy, $C_1$-$C_4$ haloalkoxy, phenyl, pyridinyl, a 4-6 membered cyclic ether, and $C_3$-$C_6$ cycloalkyl;

$R^1$ is selected from H, halo, CN, $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, 5-6 membered heterocyclyl containing N, O or S as a ring member, phenyl, and 5-6 membered heteroaryl containing one or two nitrogen atoms as ring members, wherein said $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, phenyl, 5-6 membered heterocyclyl, and 5-6 membered heteroaryl are each optionally substituted with one or two groups selected from $R^2$;

$R^2$ is independently selected at each occurrence from halo, CN, —OH, $C_1$-$C_4$ alkyl, $C_1$-$C_4$ haloalkyl, $C_1$-$C_4$ alkoxy, $C_1$-$C_4$ haloalkoxy, and $C_3$-$C_6$ cycloalkyl;

Cy is a ring selected from $C_3$-$C_6$ cycloalkyl, phenyl, and 5-6 membered heteroaryl containing one or two nitrogen atoms as ring members, and is optionally further substituted with one or two groups selected from halo, $C_1$-$C_4$ alkyl, $C_1$-$C_4$ haloalkyl, $C_1$-$C_4$ alkoxy, and $C_1$-$C_4$ haloalkoxy;

L is a divalent linker selected from a bond, $CR_2$, —$(CR_2)_{2-4}$—, —O—$(CR_2)_{1-3}$—, and —$(CR_2)_m$—X—$(CR_2)_n$—, wherein R is independently selected at each occurrence from H, F, and $C_1$-$C_4$ alkyl; or two R groups on the same carbon can be taken together with the carbon to which they are attached to form a 3-6 membered cycloalkyl ring or 3-6 membered cyclic ether;

m is 0, 1, or 2;

n is 0, 1 or 2; and

X is a 5-membered heteroaromatic ring containing one to four heteroatoms selected from N, O and S as ring members;

or a pharmaceutically acceptable salt thereof.

Frequently in Embodiment 13A, $R^1$ is methyl, phenyl, pyridinyl or tetrahydropyranyl. Preferably, Ring A is pyridinyl or pyrazolyl. Also preferably, Cy is a phenyl or pyridinyl ring, and in some embodiments the —NH and -L groups shown in Formula (I) are in a meta (1,3-disubstituted) orientation.

14A. The compound of embodiment 13A, wherein $R^1$ is selected from $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, 5-6 membered heterocyclyl containing N, O or S as a ring member, phenyl, and 5-6 membered heteroaryl containing one or two nitrogen atoms as ring members, wherein said $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, 5-6 membered heterocyclyl containing N, O or S as a ring member, phenyl, and 5-6 membered heteroaryl are each optionally substituted with one or two groups selected from $R^2$;

or a pharmaceutically acceptable salt thereof.

15A. The compound of embodiment 13A or 14A, wherein $R^1$ is methyl, phenyl, or 2-pyridinyl; or a pharmaceutically acceptable salt thereof.

16A. The compound of any one of embodiments 13A-15A, wherein Cy is a ring selected from phenyl and pyridinyl, and is optionally further substituted with a group selected from halo, $C_1$-$C_4$ alkyl, $C_1$-$C_4$ haloalkyl, $C_1$-$C_4$ alkoxy, and $C_1$-$C_4$ haloalkoxy;

or a pharmaceutically acceptable salt thereof.

17A. The compound of embodiments 16A, which is of the formula

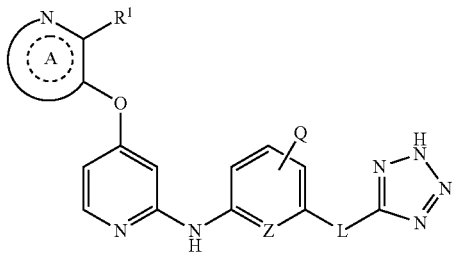

wherein Z is CH or N, and Q is selected from H, Me, $CF_3$, OMe and halo;

or a pharmaceutically acceptable salt thereof.

In a preferred example of embodiment 17A, Ring A is pyridinyl or pyrazolyl. In many examples of such compounds, $R^1$ is selected from methyl, phenyl and 2-pyridinyl.

18A. The compound of any one of embodiments 13A-17A, wherein L is a divalent linker selected from $CR_2$, —$(CR_2)_{2-4}$—, —O—$(CR_2)_{1-3}$—, and —$(CR_2)_m$—X—$(CR_2)_n$—;

or a pharmaceutically acceptable salt thereof.

19A. The compound of embodiment 18A, wherein R is independently selected at each occurrence from H, F and Me;

or a pharmaceutically acceptable salt thereof.

20A. The compound of embodiment 19A, wherein L is selected from $CH_2$, —$CH_2CH_2$—, $C(Me)_2$, —CHMe-, —$OCH_2$—, —$CH_2CF_2$—, —$CF_2CH_2$—, —$CMe_2CH_2$—, and —$CH_2CMe_2$-;

or a pharmaceutically acceptable salt thereof.

21A. The compound of any one of embodiments 13A-20A, which is a compound of formula (Ia):

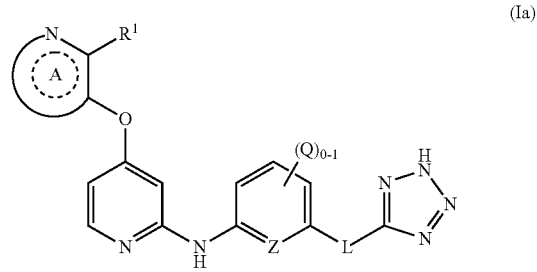

(Ia)

wherein Q is independently selected at each occurrence from halo, $C_1$-$C_4$ alkyl, $C_1$-$C_4$ haloalkyl, and $C_1$-$C_4$ alkoxy; and Z is CH, CQ or N;

or a pharmaceutically acceptable salt thereof.

In preferred embodiments of the compounds of Embodiment 21A, Ring A is a pyrazolyl or pyridinyl ring, and frequently $R^1$ is selected from methyl, phenyl and pyridinyl.

22A. The compound of any one of embodiments 13A-21A, wherein Ring A is pyridinyl or pyrazolyl, and is optionally substituted by one or two groups independently selected from halo, $C_1$-$C_4$ alkyl, $C_1$-$C_4$ haloalkyl, $C_1$-$C_4$ alkoxy, $C_1$-$C_4$ haloalkoxy, and $C_3$-$C_6$ cycloalkyl;

or a pharmaceutically acceptable salt thereof.

23A. The compound of embodiment 13A, wherein $R^1$ is pyridinyl, phenyl, tetrahydrofuranyl, or tetrahydropyranyl, and is optionally substituted with one or two groups selected from $R^2$;
or a pharmaceutically acceptable salt thereof.

Preferably, when $R^1$ is pyridinyl, it is an optionally substituted 2-pyridinyl group, having the ring N of the pyridine adjacent (ortho) to the Ring A.

24A. The compound of any one of embodiments 13A-23A, which is a compound of formula (Ib):

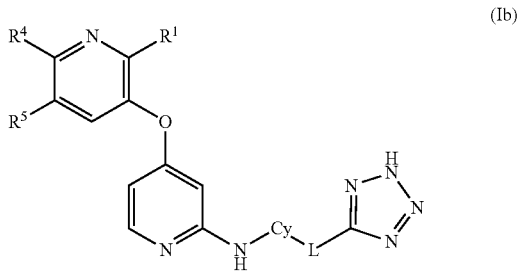

(Ib)

wherein $R^4$ and $R^5$ are independently selected from H, halo, $C_1$-$C_4$ alkyl, $C_1$-$C_4$ haloalkyl, $C_1$-$C_4$ alkoxy, $C_1$-$C_4$ haloalkoxy, phenyl and pyridinyl; or $R^4$ and $R^5$ can be taken together with the carbon atoms to which they are attached to form a phenyl ring fused to the pyridinyl ring to which $R^4$ and $R^5$ are attached;
or a pharmaceutically acceptable salt thereof.

In preferred embodiments of the compounds of Embodiment 24A, $R^4$ and $R^5$ are independently selected from H, halo, methyl, ethyl, and cyclopropyl. In these embodiments, preferably, $R^4$ is not H.

25A. The compound of any one of embodiments 13A-23A, which is a compound of formula (Ic):

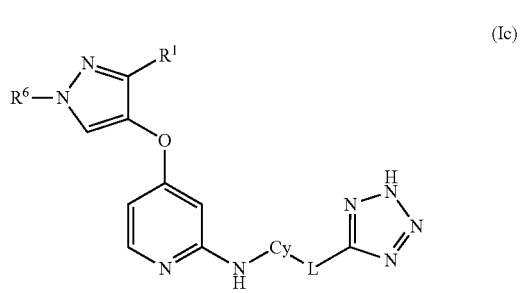

(Ic)

wherein $R^6$ is selected from $C_1$-$C_4$ alkyl, $C_1$-$C_4$ haloalkyl, and $C_3$-$C_6$ cycloalkyl;
or a pharmaceutically acceptable salt thereof.

In compounds of Embodiment 25A, $R^1$ is preferably methyl, phenyl or pyridinyl.

26A. The compound of embodiment 25A, wherein $R^6$ is selected from methyl, ethyl, isopropyl, and cyclopropyl; or a pharmaceutically acceptable salt thereof.

27A. The compound of any one of embodiments 13A-26A, wherein L is [Cy]-$(CR_2)_m$—X—$(CR_2)_n$—, where [Cy] indicates where L is attached to the group Cy;
m is 1 or 2;
n is 0, 1 or 2; and
X is a tetrazolyl ring;
or a pharmaceutically acceptable salt thereof.

28A. The compound of any one of embodiments 13A-27A, wherein L is $CH_2$, $C(Me)_2$, —$OCH_2$-[T], —$CH_2CH_2$—, —$C(Me)_2CH_2$-[T], —$CH_2C(Me)_2$-[T], or —$CF_2CH_2$-[T], wherein [T] indicates which end of L is attached to the tetrazole ring in Formula (I);
or a pharmaceutically acceptable salt thereof.

29A. The compound of embodiment 13A, wherein the compound is selected from the compounds of Examples 12-33, 44-65, 67 and 175-216;
or a pharmaceutically acceptable salt thereof.

30A. A compound selected from the compounds of numbered Examples 1-217; or a pharmaceutically acceptable salt thereof.

31A. A pharmaceutical composition comprising a compound of any of the Embodiments 1A-30A admixed with at least one pharmaceutically acceptable carrier or excipient.

32A. A method to treat cancer or fibrosis, which comprises administering to a subject in need thereof an effective amount of a compound of any one of embodiments 1A-30A, or a pharmaceutical composition of embodiment 31A.

33A. The method of embodiment 32A, which is a method to treat colon cancer, hepatocellular carcinoma (HCC), renal cancer, liver cancer, gastric cancer, or fibrosis in the liver or kidney.

34A. A compound according to any one of embodiments 1A-30A for use in therapy.

35A. Use of a compound according to any one of embodiments 1A-30A for the manufacture of a medicament.

36A. A pharmaceutical combination comprising an effective amount of a compound according to any one of embodiments 1A-30A and an additional therapeutic agent.

37A. A pharmaceutical composition comprising the pharmaceutical combination of embodiment 36A admixed with at least one pharmaceutically acceptable excipient.

38A. A method to treat cancer or fibrosis in a subject in need thereof, which comprising administering an effective amount of the pharmaceutical composition according to embodiment 37A.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

It should further be recognized that all of the above-defined groups may further be substituted with one or more substituents, which may in turn be substituted with hydroxy, amino, cyano, $C_1$-$C_4$ alkyl, halo, or $C_1$-$C_4$ haloalkyl. For example, a hydrogen atom in an alkyl or aryl can be replaced by an amino, halo or $C_1$-$C_4$ haloalkyl or alkyl group.

It is understood that in all substituted groups defined above, compounds arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "an optical isomer" or "a stereoisomer" refers to any of the various stereoisomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms except where otherwise specified. Optically active (R)- and (S)-isomers may be prepared using chiral synthons or chiral reagents, or resolved using conventional techniques. If the compound contains a di- or tri-substituted double bond, the substituent may be E or Z configuration. If the compound contains a disubstituted cycloalkyl, the cycloalkyl substituents may have a cis- or trans-configuration. All tautomeric forms are also intended to be included.

Any resulting mixtures of isomers can be separated on the basis of the physicochemical differences of the constituents, into the pure or substantially pure geometric or optical isomers or diastereomers, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyltartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral stationary phase, for example.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

As used herein, the terms "salt" or "salts" refers to an acid addition or base addition salt of a compound of the present invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamie.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

The compounds and compositions described herein can be administered to a subject in need of treatment for a cell proliferation disorder such as cancer or fibrosis, particularly cancers that occur in the gastrointestinal system and in the first-pass metabolic system organs and tissues.

The subject for treatment with compounds and pharmaceutical compositions of the invention is typically a mammal diagnosed as being in need of treatment for one or more of such proliferative disorders, and frequently the subject is a human. Typically, the subject is a patient diagnosed with a cancer associated with excessive activity of TGFβR1, also known as Alk5, particularly for cancers of the liver, kidneys and gastrointestinal system. The methods comprise administering an effective amount of at least one compound of the invention; optionally the compound may be administered in combination with one or more additional therapeutic agents, particularly therapeutic agents known to be useful for treating the cancer or proliferative disorder afflicting the particular subject.

Compounds of the invention may be used in the treatment of states, disorders or diseases as described herein, or for the manufacture of pharmaceutical compositions for use in the treatment of these diseases. The invention provides methods of use of compounds of the present invention in the treatment of these diseases or for preparation of pharmaceutical compositions having compounds of the present invention for the treatment of these diseases.

The term "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of a compound of Formula (I) or Formular (II), or any subgenus thereof described herein as active ingredient in combination with a pharmaceutically acceptable excipient, and optionally two or more pharmaceutically acceptable excipients.

The phrase "pharmaceutically acceptable excipient" is understood by those of skill in the art, and includes a pharmaceutically acceptable material, composition or vehicle, suitable for administering compounds of the present invention to mammals. The excipients include liquid or solid filler, diluent, carrier, solvent or encapsulating material, involved in carrying or transporting the subject agent from one organ, or portion of the body, to another organ, or portion of the body, or in making the drug product more easily formulated, tableted, stored, used, or administered. Each excipient must be "acceptable" in the sense of being compatible with the other ingredients of the formulation and not injurious to the patient. Some examples of materials which can serve as pharmaceutically acceptable excipients include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Typically, pharmaceutically acceptable excipients are sterilized and/or substantially pyrogen-free.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, inhalation, topical, transdermal, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier or excipient and, optionally, one or more accessory ingredients. In general, the formulations are prepared by uniformly and intimately bringing into association a compound of the present invention with liquid excipient, or finely divided solid excipient, or both, and then, if necessary, shaping the product.

Formulations of the invention suitable for oral administration may be in the form of capsules, cachets, pills, tablets, lozenges (using a flavored base, for example, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable excipients, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable excipient, and with any preservatives, buffers, or propellants that may be required.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable carriers such as sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, glycol ethers, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Intravenous infusion is sometimes a preferred method of delivery for compounds of the invention. Infusion may be used to deliver a single daily dose or multiple doses. In some embodiments, a compound of the invention is administered by infusion over an interval between 15 minutes and 4 hours, typically between 0.5 and 3 hours. Such infusion may be used once per day, twice per day or up to three times per day.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated effects, will range from about 0.0001 to about 100 mg per kilogram of body weight per day, more preferably from about 0.01 to about 50 mg per kg per day, and still more preferably from about 1.0 to about 100 mg per kg per day. An effective amount is an amount that achieves a desired or observable therapeutic effect.

If desired, the effective daily dose of the active compound may be administered as two, three, four, five, six or more sub-doses administered separately at appropriate intervals throughout the day, optionally, in unit dosage forms. Compounds delivered orally or by inhalation, are commonly administered in one to four doses per day. Compounds delivered by injection are typically administered once per day, or once every other day. Compounds delivered by infusion are typically administered in one to three doses per day.

While it is possible for a compound of the present invention to be administered alone, it is preferable to administer the compound as a pharmaceutical composition such as those described herein.

Pharmaceutical Compositions, Combinations, and Other Related Uses

In still another aspect, the present disclosure provides for a pharmaceutical composition comprising a compound of Formula (I) or Formula (II) or any of the subformulae thereof described herein, admixed with at least one pharmaceutically acceptable carrier or excipient.

The above described compounds can be used for any suitable purpose. For example, the present compounds can be used in therapy and/or testing.

In yet another aspect, the present disclosure provides for a method for treating and/or preventing a proliferation disorder, such as a cancer or a tumor. The compounds, compositions and methods are particularly useful for cancers associated with excessive activity of TGFβR1, also known as Alk5, particularly for cancers of the liver, kidneys and gastrointestinal system.

In yet another aspect, the present disclosure provides for a use of a compound described above for the manufacture of a medicament.

In yet another aspect, the present disclosure provides for a combination for treating and/or preventing a proliferation disorder, which combination comprises an effective amount of a compound of Formula (I) or Formula (II) or any of the subformulae thereof disclosed herein, or a pharmaceutically acceptable salt thereof, and an effective amount of a second prophylactic or therapeutic agent for treating and/or preventing a proliferation disorder, a cancer, or a tumor or fibrosis, particularly for treatment of colon cancer, hepatocellular carcinoma (HCC), renal cancer, liver cancer, and gastric cancer, as well as fibrosis in the digestive system and first-pass metabolic systems, particularly liver fibrosis and kidney fibrosis conditions.

In yet another aspect, the present disclosure provides for a method for inhibiting an activity of TGFβR1 in a subject, which comprises administering to the subject an effective amount of a compound of Formula (I) or Formula (II) as described herein.

In another aspect, the invention provides a method to inhibit activity of TGFβR1 in a tissue or cell, which comprises contacting the tissue or cell with an effective amount of a compound of Formula (I) or Formula (II) as described herein.

In some embodiments, the compound is any of the compounds of the numbered Examples disclosed herein.

Formulations

Any suitable formulation of the compounds described herein can be prepared. See generally, Remington's Pharmaceutical Sciences, (2000) Hoover, J. E. editor, 20 th edition, Lippincott Williams and Wilkins Publishing Company, Easton, Pa., pages 780-857. A formulation is selected to be suitable for an appropriate route of administration. In cases where compounds are sufficiently acidic to form stable nontoxic base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art, for example, by a sufficiently basic compound such as an amine with a suitable acid, affording a physiologically acceptable anion. Alkali metal (e.g., sodium, potassium or lithium) or alkaline earth metal (e.g., calcium) salts, as well as amine salts of carboxylic acids and tetrazoles also are made.

Where contemplated compounds are administered in a pharmacological composition, it is contemplated that the compounds can be formulated in admixture with a pharmaceutically acceptable excipient and/or carrier. For example, contemplated compounds can be administered orally as neutral compounds or as pharmaceutically acceptable salts, or intravenously in a physiological saline solution. Conventional buffers such as phosphates, bicarbonates or citrates can be used for this purpose. Of course, one of ordinary skill in the art may modify the formulations within the teachings of the specification to provide numerous formulations for a particular route of administration. In particular, contemplated compounds may be modified to render them more soluble in water or other vehicle, which for example, may be easily accomplished with minor modifications (salt formulation, esterification, etc.) that are well within the ordinary skill in the art. It is also well within the ordinary skill of the art to select or modify the route of administration and dosage regimen of a particular compound in order to manage the pharmacokinetics of the present compounds for maximum beneficial effect in a patient.

The compounds having formula I-II as described herein are generally soluble in organic solvents such as chloroform, dichloromethane, ethyl acetate, ethanol, methanol, isopropanol, acetonitrile, glycerol, N,N-dimethylformamide, N,N-dimetheylaceatmide, dimethylsulfoxide, etc. In one embodiment, the present invention provides formulations prepared by mixing a compound having formula I-II with a pharmaceutically acceptable excipient. In one aspect, the formulation may be prepared using a method comprising: a) dissolving a described compound in a water-soluble organic solvent, a non-ionic solvent, a water-soluble lipid, a vitamin such as tocopherol, a fatty acid, a fatty acid ester, or a combination thereof, to provide a solution; and b) adding saline or a buffer containing 1-10% carbohydrate solution. In one example, the carbohydrate comprises dextrose. The pharmaceutical compositions obtained using the present methods are stable and useful for animal and clinical applications.

Illustrative examples of water soluble organic solvents for use in the present methods include and are not limited to polyethylene glycol (PEG), alcohols, acetonitrile, N-methyl-2-pyrrolidone, N,N-dimethylformamide, N,N-dimethylacetamide, dimethyl sulfoxide, or a combination thereof. Examples of alcohols include but are not limited to methanol, ethanol, isopropanol, glycerol, or propylene glycol.

Illustrative examples of water soluble non-ionic surfactants for use in the present methods include and are not limited to CREMOPHOR© EL, polyethylene glycol modified CREMOPHOR© (polyoxyethyleneglyceroltriricinoleat 35), hydrogenated CREMOPHOR© RH40, hydrogenated CREMOPHOR© RH60, PEG-succinate, polysorbate 20, polysorbate 80, SOLUTOL©HS (polyethylene glycol 660 12-hydroxystearate), sorbitan monooleate, poloxamer, LABRAFIL©(ethoxylated persic oil), LABRASOL© (capryl-caproyl macrogol-8-glyceride), GELUCIRE©(glycerol ester), SOFTIGEN©(PEG 6 caprylic glyceride), glycerin, glycol-polysorbate, or a combination thereof.

Illustrative examples of water soluble lipids for use in the present methods include but are not limited to vegetable oils, triglycerides, plant oils, or a combination thereof. Examples of lipid oils include but are not limited to castor oil, polyoxyl castor oil, corn oil, olive oil, cottonseed oil, peanut oil, peppermint oil, safflower oil, sesame oil, soybean oil, hydrogenated vegetable oil, hydrogenated soybean oil, a triglyceride of coconut oil, palm seed oil, and hydrogenated forms thereof, or a combination thereof.

Illustrative examples of fatty acids and fatty acid esters for use in the present methods include but are not limited to oleic acid, monoglycerides, diglycerides, a mono- or di-fatty acid ester of PEG, or a combination thereof.

One of ordinary skill in the art may modify the formulations within the teachings of the specification to provide numerous formulations for a particular route of administration. In particular, the compounds may be modified to render them more soluble in water or other vehicle. It is also well within the ordinary skill of the art to modify the route of administration and dosage regimen of a particular compound in order to manage the pharmacokinetics of the present compounds for maximum beneficial effect in a patient.

Drug Combinations

The methods of the embodiments comprise administering an effective amount of at least one exemplary compound of the present disclosure; optionally the compound may be administered in combination with one or more additional therapeutic agents, particularly therapeutic agents known to be useful for treating the condition or disease afflicting the subject.

The additional active ingredients may be administered in a separate pharmaceutical composition from at least one exemplary compound of the present disclosure or may be included with at least one exemplary compound of the present disclosure in a single pharmaceutical composition. The additional active ingredients may be administered simultaneously with, prior to, or after administration of at least one exemplary compound of the present disclosure.

Methods of Using the Exemplary Compounds and Pharmaceutical Compositions Thereof The present invention also provides pharmaceutical compositions for the treatment and/or prevention of a proliferation disorder or cancer such as those disclosed herein, comprising any compound having formula I or II, or any of the compounds of Examples 1-110 herein.

To practice the method of the present invention, compounds having formula and pharmaceutical compositions thereof may be administered orally, parenterally, by inhalation, topically, rectally, nasally, buccally, vaginally, via an implanted reservoir, or other drug administration methods. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, such as a sterile injectable aqueous or oleaginous suspension, may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed include mannitol, water, Ringer's solution and isotonic sodium chloride solution. Suitable carriers and other pharmaceutical excipient are typically sterile.

In addition, sterile, fixed oils are conventionally employed as a solvent or suspending medium (e.g., synthetic mono- or diglycerides). Fatty acids, such as oleic acid and its glyceride derivatives, are useful in the preparation of injectables, as are pharmaceutically acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Various emulsifying agents or bioavailability enhancers which are commonly used in the manufacture of pharmaceutically acceptable solid, liquid, or other dosage forms can also be used for the purpose of formulation.

A composition for oral administration may be any orally acceptable dosage form including, but not limited to, tablets, capsules, emulsions and aqueous suspensions, dispersions and solutions. In the case of tablets for oral use, commonly used carriers include lactose and corn starch. Lubricating agents, such as magnesium stearate, can also be added. For oral administration in a capsule form, useful diluents include lactose and dried corn starch. When aqueous suspensions or emulsions are administered orally, the active ingredient can be suspended or dissolved in an oily phase combined with emulsifying or suspending agents. If needed, certain sweetening, flavoring, or coloring agents can be added. A nasal aerosol or inhalation compositions can be prepared according to techniques well-known in the art of pharmaceutical formulation and can be prepared as solutions in, for example saline, employing suitable preservatives (for example, benzyl alcohol), absorption promoters to enhance bioavailability, and/or other solubilizing or dispersing agents known in the art.

In addition, the compounds having formula I or Formula (II) or any of the subformulae thereof, may be administered alone or in combination with other therapeutic agents, e.g., anticancer agents, for the treatment of a subject in need of treatment. Combination therapies according to the present invention comprise the administration of at least one exemplary compound of Formula (I) or Formula (II) or any subformulae thereof as disclosed herein and at least one additional pharmaceutically active ingredient. The compound of the invention and additional pharmaceutically active agents may be administered separately or together. The amounts of the compound of the invention and of the additional pharmaceutically active agent(s) and the relative timings of administration will be selected in order to achieve the desired combined therapeutic effect.

The compounds as described herein may be synthesized by the general synthetic routes below, specific examples of which are described in more detail in the Examples.

Within the scope of this text, only a readily removable group that is not a constituent of the particular desired end product of the compounds of the present invention is designated a "protecting group," unless the context indicates otherwise. The protection of functional groups by such protecting groups, the protecting groups themselves, and their cleavage reactions are described for example in standard reference works, such as e.g., Science of Synthesis: Houben-Weyl Methods of Molecular Transformation. Georg Thieme Verlag, Stuttgart, Germany. 2005. 41627 pp. (URL: science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (Chemistry of Carbohydrates: Monosaccharides and Derivatives), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g., by enzymatic cleavage).

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethyl hexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralisation of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g., using chromatographic methods, distribution methods, (re-) crystallization, and the like.

The process steps to synthesize the compounds of the invention can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g., in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described in Science of Synthesis: Houben-Weyl Methods of Molecular Transformation, Georg Thieme Verlag, Stuttgart, Germany, 2005.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

In accordance with the foregoing the present invention provides in a yet further aspect:

A pharmaceutical combination comprising a) a first agent which is a compound of the invention, e.g. a compound of Formula (I) or Formula (II) or any subformulae thereof, and b) a co-agent, e.g. an additional pharmaceutically active agent as defined above.

A method as defined above comprising co-administration, e.g. concomitantly or in sequence, of a therapeutically effective amount of a compound of the invention, e.g. a compound of formula I or formula (II) or any subformulae thereof, and a co-agent, e.g. an additional therapeutic agent as defined above.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time. Fixed combinations are also within the scope of the present invention. The administration of a pharmaceutical combination of the invention results in a beneficial effect, e.g. a synergistic therapeutic effect, compared to a monotherapy applying only one of its pharmaceutically active ingredients.

Each component of a combination according to this invention may be administered separately, together, or in any combination thereof.

The compound of the invention and any additional agent may be formulated in separate dosage forms. Alternatively, to decrease the number of dosage forms administered to a patient, the compound of the invention and any additional agent may be formulated together in any combination. For example, the compound of the invention inhibitor may be formulated in one dosage form and the additional agent may be formulated together in another dosage form. Any separate dosage forms may be administered at the same time or different times.

Alternatively, a composition of this invention comprises an additional agent as described herein. Each component may be present in individual compositions, combination compositions, or in a single composition.

| | ABBREVIATIONS |
|---|---|
| Ac | acetyl |
| ACN | Acetonitrile |
| AcOEt/EtOAc | Ethyl acetate |
| AcOH | acetic acid |
| aq | aqueous |
| Ar | aryl |
| Bn | benzyl |
| Bu | butyl (nBu = n-butyl, tBu = tert-butyl) |
| CDI | Carbonyldiimidazole |
| $CH_3CN$ | Acetonitrile |
| DBU | 1,8-Diazabicyclo[5.4.0]-undec-7-ene |
| $Boc_2O$ | di-tert-butyl dicarbonate |
| DCE | 1,2-Dichloroethane |
| DCM | Dichloromethane |
| DiBAl-H | Diisobutylaluminum Hydride |
| DIPEA | N-Ethyldiisopropylamine |
| DMA | N,N-dimethylacetamide |
| DMAP | Dimethylaminopyridine |
| DMF | N,N'-Dimethylformamide |
| DMSO | Dimethylsulfoxide |
| EI | Electrospray ionisation |
| $Et_2O$ | Diethylether |
| $Et_3N$ | Triethylamine |
| Ether | Diethylether |

ABBREVIATIONS

| | |
|---|---|
| EtOAc or EA | Ethylacetate |
| EtOH | Ethanol |
| FC | Flash Chromatography |
| h | hour(s) |
| HATU | O-(7-Azabenzotriazole-1-yl)-N,N,N'N'-tetramethyluronium hexafluorophosphate |
| HBTU | O-(Benzotriazol-1-yl)-N,N,N',N'-tetramethyluronium hexafluorophosphate |
| HCl | Hydrochloric acid |
| HMPA | Hexamethylphosphoramide |
| HOBt | 1-Hydroxybenzotriazole |
| HPLC | High Performance Liquid Chromatography |
| $H_2O$ | Water |
| L | liter(s) |
| LC-MS | Liquid Chromatography Mass Spectrometry |
| LiHMDS | Lithium bis(trimethylsilyl)amide |
| mCPBA | meta-chloroperoxybenzoic acid |
| $MgSO_4$ | Magnesium Sulfate |
| Me | methyl |
| MeI | Iodomethane |
| MeOH | Methanol |
| mg | milligram |
| min | minute(s) |
| mL | milliliter |
| MS | Mass Spectrometry |
| $NaHCO_3$ | Sodium Bicarbonate |
| $Na_2SO_4$ | Sodium Sulfate |
| $NH_2OH$ | hydroxylamine |
| Pd/C | palladium on charcoal |
| $Pd(OH)_2$ | palladium hydroxide |
| PE | petroleum ether |
| PG | protecting group |
| Ph | phenyl |
| $Ph_3P$ | triphenyl phosphine |
| Prep | Preparative |
| Rf | ratio of fronts |
| RP | reverse phase |
| Rt | Retention time |
| r.t. | Room temperature |
| RT | Room temperature |
| $SiO_2$ | Silica gel |
| $SOCl_2$ | Thionyl Chloride |
| TBAF | Tetrabutylammonium fluoride |
| TBDMS | t-Butyldimethylsilyl |
| TEA | Triethylamine |
| TFA | Trifluoroacetic acid |
| THF | Tetrahydrofuran |
| TLC | Thin Layer Chromatography |
| TsCl | toluene sulfonyl chloride |

The compounds of the invention can be produced by organic synthesis methods known to one of ordinary skill in the art with reference to the following reaction schemes and examples. General methods for synthesis of compounds of Formula (I) and Formula (II) are provided in Schemes 1-3 below.

General Synthetic Procedures

Compounds of the present invention are prepared from commonly available compounds using procedures known to those skilled in the art in view of the examples and schemes provided herein.

Scheme 1.

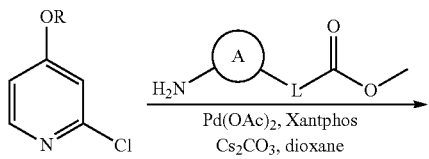

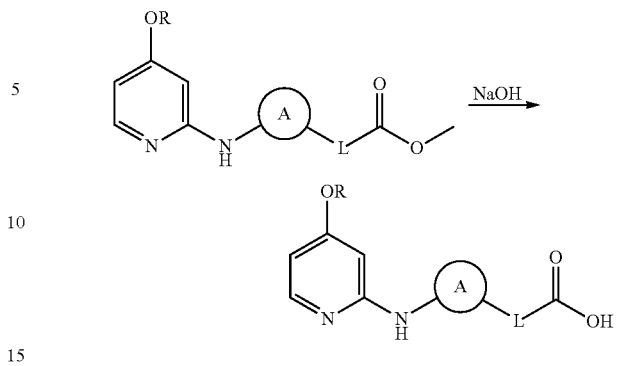

In Scheme 1, Ring A, substituted by an amino group and linked with an ester, is coupled to a chloropyridine. The ester can be hydrolyzed to provide a free carboxylic acid. Depending on the choice of R, the product can be a compound of Formula (I) or Formula (II) or a precursor to such compounds. Ring A corresponds to, e.g., the group Cy in compounds of Formula (I), or to a phenyl/pyridinyl ring in compounds of Formula (II).

Scheme 2.

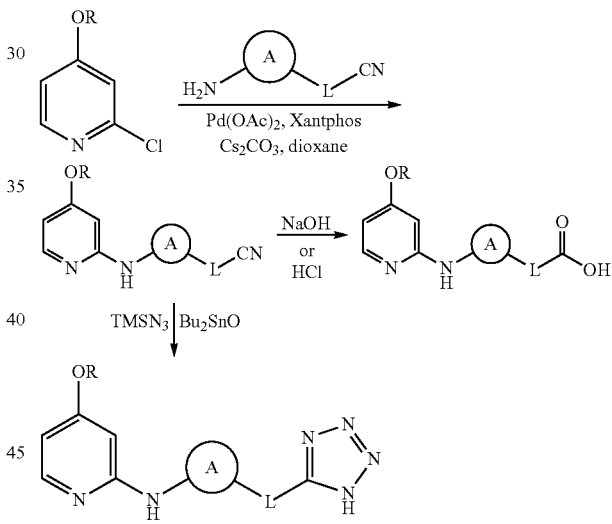

In Scheme 2, Ring A has an amino group and is linked with a nitrile; after coupling with the chloropyridine, the nitrile can be converted into a carboxylate group by hydrolysis, or it can be converted with trimethylsilyl azide to an acidic tetrazole group. Again, depending on the choice of R, the product can be a compound of Formula (I) or Formula (II) or a precursor to such compounds.

Scheme 3.

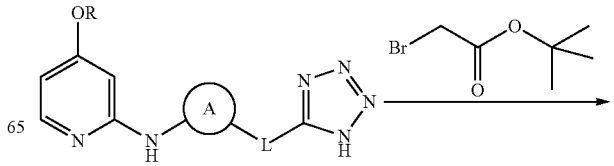

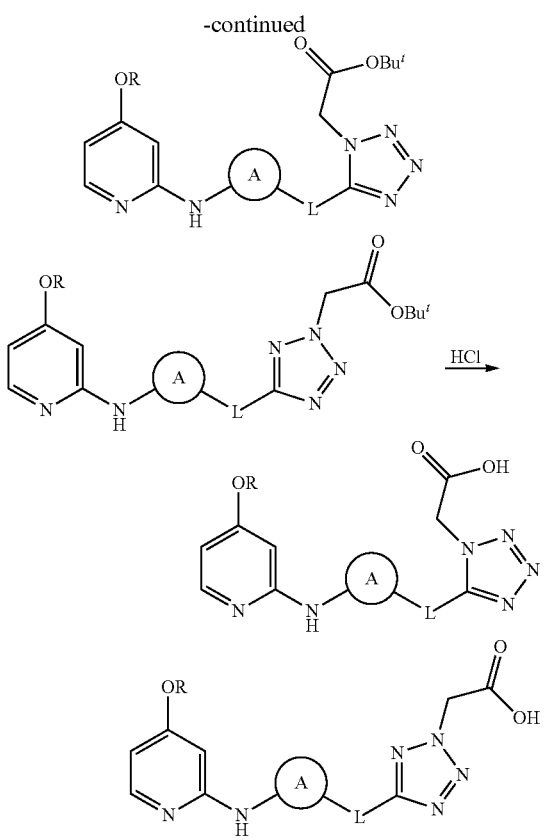

In Scheme 3, a tetrazole product of Scheme 2 is alkylated with t-butyl bromoacetate to provide two isomeric carboxymethyl tetrazole products. Again, depending on the choice of R, the product can be a compound of Formula (I) or Formula (II), or a precursor to such compounds.

Using these and known alternative starting materials, the skilled person can prepare a wide variety of compounds of Formula (I) or Formula (II) having either a carboxylate or tetrazole as an acidic group.

Intermediates

Intermediate A1: 3-((2-chloropyridin-4-yl)oxy)-5,6-dimethyl-2,2'-bipyridine

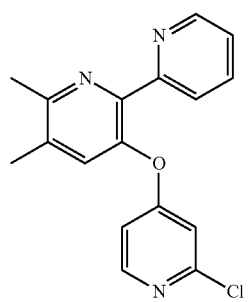 [SMILES: Cc1cc(Oc2ccnc(Cl)c2)c(-c2ccccn2)nc1C]

The compound was prepared following the procedure published in WO2005080377.

Step 1: (4,5-dimethylfuran-2-yl)(pyridin-2-yl)methanone

Under Ar, to a solution of 2,3-dimethylfuran (1.0 eq) in Et$_2$O (0.65 M) was added dropwise n-BuLi (1.6 M, 1.3 eq) at 0° C. The mixture was stirred at 40° C. for 1.5 h and then cooled to −78° C. A solution of picolinonitrile (1.0 eq) in Et$_2$O (2 M) was added dropwise thereto. The resulting mixture was stirred at r.t. for 1.5 h before quenched with ice. The pH value of the mixture was adjusted to around 5 with 2N HCl. The mixture was extracted with DCM. The combined DCM layer was washed with water and dried over Na$_2$SO$_4$. The organic solvent was removed, and the residue was purified by flash chromatography on silica gel (eluent: petroleum ether/EtOAc 10:1) to give the title product as a yellow solid. LC-MS (m/z): [M+1]$^+$=202; $^1$H NMR (400 MHz, CDCl$_3$) δ 8.70 (d, J=5.2 Hz, 1H), 8.13 (d, J=7.6 Hz, 1H), 7.86 (t, J=7.6 Hz, 1H), 7.82 (s, 1H), 7.46 (dd, J=7.6, 5.2 Hz, 1H), 2.38 (s, 3H), 2.04 (s, 3H).

Step 2: 5,6-dimethyl-[2,2'-bipyridin]-3-ol

A mixture of above product (1.0 eq) in MeOH (0.033 M) and 28% NH$_3$·H$_2$O (10 mL) was sealed in a tube, and stirred at 170° C. for 8 h. The mixture was cooled to r.t, concentrated and purified by flash chromatography on silica gel (eluent: petroleum ether/EtOAc 20:1) to give the title compound as a yellow solid. LC-MS (m/z): [M+1]$^+$=201; $^1$H NMR (400 MHz, CDCl$_3$) δ 13.86 (s, 1H), 8.58 (d, J=8.0 Hz, 1H), 8.47 (d, J=4.4 Hz, 1H), 7.86 (td, J=8.0, 1.6 Hz, 1H), 7.28-7.25 (m, 1H), 7.08 (s, 1H), 2.47 (s, 3H), 2.28 (s, 3H).

Step 3: 3-((2-chloropyridin-4-yl)oxy)-5,6-dimethyl-2,2'-bipyridine

A mixture of above product (1.0 eq), 2,4-dichloropyridine (2.0 eq), Cs$_2$CO$_3$ (2.0 eq) in DMSO (0.09 M) was stirred at 180° C. for 5 h. The mixture was cooled to r.t. The mixture was quenched by water and extracted with EtOAc. The solvent was removed under reduced pressure.

The residue was purified by flash chromatography on silica gel (eluent: petroleum ether/EtOAc 2:1) to give the title compound as a yellow solid. LC-MS (m/z): [M+1]$^+$=312; $^1$H NMR (400 MHz, CDCl$_3$) δ 8.57 (ddd, J=4.8, 2.0, 1.2 Hz, 1H), 8.13 (d, J=6.0 Hz, 1H), 7.84 (dt, J=7.6, 1.2 Hz, 1H), 7.70 (td, J=7.6, 1.6 Hz, 1H), 7.27 (d, J=6.0 Hz, 1H), 7.20 (ddd, J=7.6, 4.8, 1.2 Hz, 1H), 6.73 (d, J=2.0 Hz, 1H), 6.70 (dd, J=6.0, 2.0 Hz, 1H), 2.63 (s, 3H), 2.38 (s, 3H).

Intermediate A2: 3-((2-chloropyridin-4-yl)oxy)-2,6-dimethylpyridine

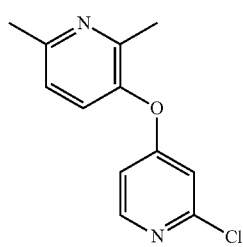 [SMILES: Cc1ccc(Oc2ccnc(Cl)c2)c(C)n1]

The compound was prepared following the procedure published in WO2009022171. A mixture of 2,6-dimethylpyridin-3-ol (1.0 eq), 2,4-dichloropyridine (1.5 eq) and Cs$_2$CO$_3$ (2.0 eq) in DMSO (0.5 M) was stirred at 150° C. for 3 h. The reaction was monitored by TLC. The solution was cooled down to r.t and extracted with EA/H$_2$O, washed with brine, dried over Na$_2$SO$_4$. The organic phase was concentrated. The residue was purified by flash chromatography on silica gel (petroleum ether/EtOAc 9:1) to give the title compound as a white solid. LC-MS (m/z): [M+H]$^+$=235.3; $^1$H NMR (400 MHz, CDCl$_3$) δ 8.24 (d, J=5.6 Hz, 1H), 7.24 (d, J=8.0 Hz, 1H), 7.09 (d, J=8.0 Hz, 1H), 6.74-6.71 (m, 2H), 2.58 (s, 3H), 2.38 (s, 3H).

Intermediate A3: 3-((2-chloropyridin-4-yl)oxy)-6-methyl-2,2'-bipyridine

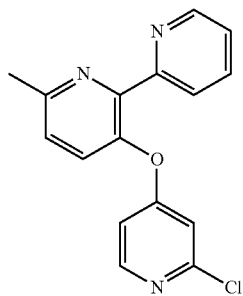

The compound was prepared following the procedure published in WO2009022171.

Step 1: 3-((2-chloropyridin-4-yl)oxy)-2-iodo-6-methylpyridine

A mixture of 2-iodo-6-methylpyridin-3-ol (1.05 eq), 2,4-dichloropyridine (1.0 eq), Cs$_2$CO$_3$ (2.0 eq) in DMF (0.22 M) was stirred at 100° C. for 16 h. The reaction was monitored by LC-MS. The reaction mixture was cooled down to RT, filtered and washed with EtOAC. The filtrate was washed with brine, and then dried over Na$_2$SO$_4$. The organic phase was concentrated under reduced pressure. The residue was purified by flash chromatography on silica gel (petroleum ether/EtOAC 8:1) to give the product as a white solid. LC-MS (m/z): [M+H]$^+$=347; $^1$H NMR (400 MHz, CDCl$_3$) δ 8.21 (d, J=5.6 Hz, 1H), 7.25 (d, J=8.0 Hz, 1H), 7.18 (d, J=8.0 Hz, 1H), 6.71 (d, J=2.4 Hz, 1H), 6.69 (dd, J=5.6, 2.4 Hz, 1H), 2.54 (s, 3H).

Step 2: 3-((2-chloropyridin-4-yl)oxy)-6-methyl-2,2'-bipyridine

A mixture of 3-((2-chloropyridin-4-yl)oxy)-2-iodo-6-methylpyridine (1.0 eq), pyridin-2-ylzinc(II) bromide (0.5M in THF, 1.2 eq), Pd(PPh$_3$)$_4$ (0.1 eq) in DMA (0.43 M) was stirred at 120° C. for 16h under Ar. The reaction was monitored by LC-MS. The mixture solution was cooled down to r.t and diluted with EtOAC. The mixture was washed with brine, and then dried over Na$_2$SO$_4$. The organic phase was concentrated under reduced pressure. The residue was purified by flash chromatography on silica gel (100% EtOAc) to give the title compound as a yellow oil. LC-MS (m/z): [M+H]$^+$=298.

The following compounds were prepared according to the procedure described for Intermediate A3.

| Intermediate | Structure | LCMS [M + 1]$^+$ and/or $^1$H NMR |
|---|---|---|
| A4 | 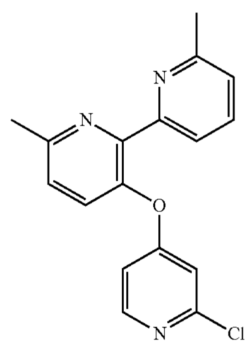 [SMILES: Cc1cccc(-c2nc(C)ccc2Oc2ccnc(Cl)c2)n1] | LCMS (m/z): [M + 1]$^+$ = 312 |
| A5 | 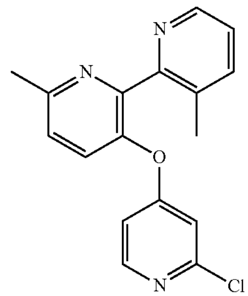 [SMILES: Cc1ccc(Oc2ccnc(Cl)c2)c(-c2ncccc2C)n1] | LCMS (m/z): [M + 1]$^+$ = 312 |

Intermediate A6: 3-((2-chloropyridin-4-yl)oxy)-6-methyl-2-phenylpyridine

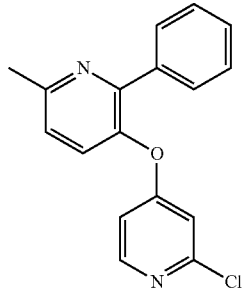

The compound was prepared following the procedure published in WO2009022171.

A mixture of 3-((2-chloropyridin-4-yl)oxy)-2-iodo-6-methylpyridine (1.0 eq), phenyl boronic acid (1.2 eq), Pd(dppf)Cl$_2$ (0.1 eq) and Na$_2$CO$_3$ (2.0 eq) in dioxane/H$_2$O (5:1, 0.25 M) was stirred at 100° C. for 3h. The reaction was monitored by LC-MS. The mixture solution was cooled down to r.t and was diluted with EtOAc. The mixture was washed with brine, and then dried over Na$_2$SO$_4$. The organic phase was concentrated under reduced pressure. The residue was purified by flash chromatography on silica gel (100% EtOAc) to give the title compound as a yellow oil. LC-MS (m/z): [M+H]$^+$=297; $^1$H NMR (400 MHz, CDCl$_3$) δ 8.06 (d, J=6.0 Hz, 1H), 7.68 (dd, J=8.0, 1.6 Hz, 2H), 7.31-7.24 (m, 4H), 7.13 (d, J=8.0 Hz, 1H), 6.64 (d, J=2.4 Hz, 1H), 6.59 (dd, J=6.0, 2.4 Hz, 1H), 2.59 (s, 3H).

The following compounds were prepared according to the procedure described for Intermediate A6.

| Intermediate | Structure | LCMS [M + 1]$^+$ and/or $^1$H NMR |
|---|---|---|
| A7 | 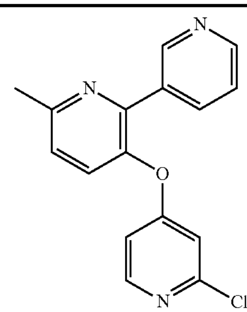 | LCMS (m/z): [M + 1]$^+$ = 298 |
| A8 | 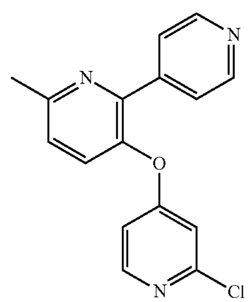 [SMILES: Cc1ccc(Oc2ccnc(Cl)c2)c(-c2ccccc2)n1] | LCMS (m/z): [M + 1]$^+$ = 298 |
| A9 | 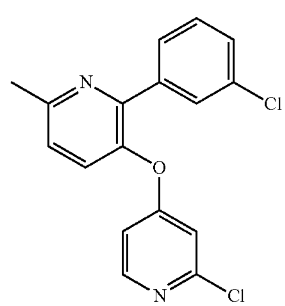 [SMILES: Cc1ccc(Oc2ccnc(Cl)c2)c(-c2cccc(Cl)c2)n1] | LCMS (m/z): [M + 1]$^+$ = 331.3 |

| Intermediate | Structure | LCMS [M + 1]⁺ and/or ¹H NMR |
|---|---|---|
| A10 | 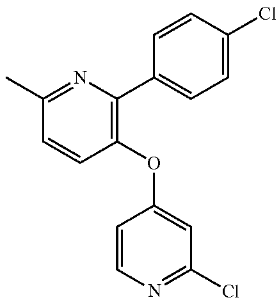 [SMILES: Cc1ccc(Oc2ccnc(Cl)c2)c(-c2ccc(Cl)cc2)n1] | LCMS (m/z): [M + 1]⁺ = 331 |
| A11 | 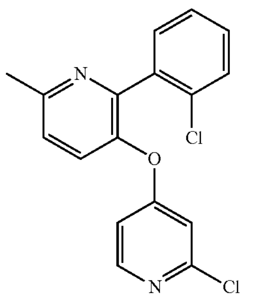 [SMILES: Cc1ccc(Oc2ccnc(Cl)c2)c(-c2ccccc2Cl)n1] | LCMS (m/z): [M + 1]⁺ = 331 |

Intermediate A12: 2-chloro-4-((1-cyclopropyl-3-(tetrahydro-2H-pyran-4-yl)-1H-pyrazol-4-yl)oxy)pyridine

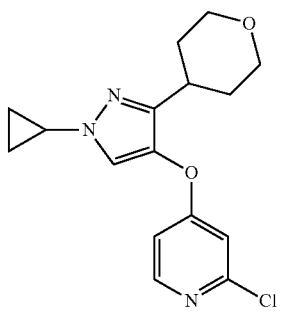 [SMILES: Clc1cc(Oc2cn(C3CC3)nc2C2CCOCC2)ccn1]

The compound was prepared following the procedure in WO2016057278.

Step 1: 2-((2-chloropyridin-4-yl)oxy)-1-(tetrahydro-2H-pyran-4-yl)ethan-1-one A mixture of 2-bromo-1-(tetrahydro-2H-pyran-4-yl)ethan-1-one (1.0 eq), 2-chloropyridin-4-ol (1.0 eq) and K₂CO₃ (1.5 eq) in acetone (0.12 M) was stirred for 16h at RT. The reaction was monitored by TLC. Then the solid was filtered off and the filtrate was concentrated under reduced pressure to give the title compound as a brown oil.

Step 2: 2-chloro-4-((3-(tetrahydro-2H-pyran-4-yl)-1H-pyrazol-4-yl)oxy)pyridine A solution of 2-((2-chloropyridin-4-yl)oxy)-1-(tetrahydro-2H-pyran-4-yl)ethan-1-one (1.0 eq) in DMF-DMA (0.37 M) was stirred at 100° C. for 2 h. The mixture was concentrated under reduced pressure. The residue was dissolved in AcOH (50 mL) at 0° C., was treated with NH₂NH₂·H₂O (80% wt, 3.0 eq). The resulting mixture was stirred at rt for 16 h. The reaction was monitored by LCMS. Then the mixture was diluted with water and extracted with EtOAc. The organic layer was washed with brine, dried over Na₂SO₄, concentrated under reduced pressure to give the title compound as a brown oil. LC-MS (m/z): [M+H]⁺=280.

Step 3: 2-chloro-4-((1-cyclopropyl-3-(tetrahydro-2H-pyran-4-yl)-1H-pyrazol-4-yl)oxy)pyridine A mixture of pyridine (1.1 eq) and Cu(OAc)₂ (1.1 eq) in DCE (0.37 M) was stirred at 75° C. for 0.5 h. The mixture was cooled to rt, and a solution of above product (1.0 eq) in DCE (0.1 M) was added, followed by cyclopropylboronic acid (2.0 eq) and Na₂CO₃ (2.0 eq). The resulting mixture was stirred at 75° C. for 16 h under oxygen atmosphere. The reaction was monitored by LCMS. The solid was filtered off, and the filtrate was concentrated. The residue was purified by flash chromatography on silica gel (eluent: petroleum ether/EtOAc 10:1 to 2:1) to give title compound as a brown oil. LC-MS (m/z): [M+H]⁺=320.

Intermediate A13: 3-((2-chloropyridin-4-yl)oxy)-6-methylpicolinonitrile

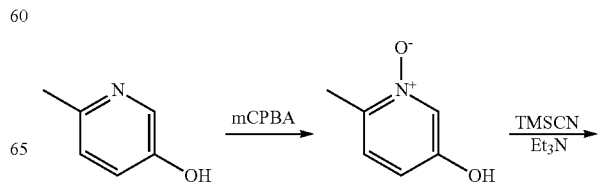

-continued

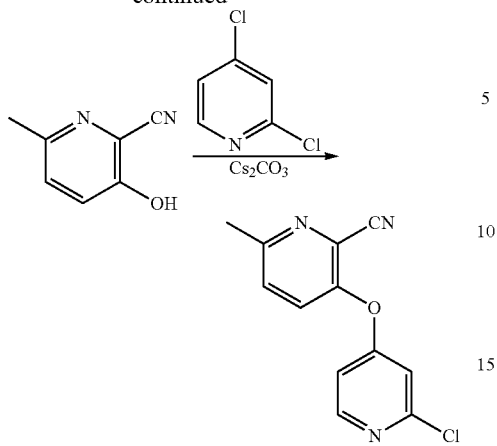

Step 1: 5-hydroxy-2-methylpyridine 1-oxide

To a solution of 6-methylpyridin-3-ol (1.0 eq) in DCM (0.5 M) was added m-CPBA (1.2 eq). The mixture was stirred at rt for 16 h. The reaction was monitored by LC-MS. The solid was filtered off and the filtrate was concentrated under reduced pressure. The residue was dissolved in hot EtOH, then cooled to rt and treated with Et$_2$O. The precipitated solid was collected by filtration, dried to give the title compound as a yellow solid. LC-MS (m/z): [M+H]$^+$=126.

Step 2: 3-hydroxy-6-methylpicolinonitrile

A mixture of above product (1.0 eq), TMSCN (3.5 eq) and TEA (2.5 eq) in MeCN (3.0 mL) was sealed into a tube reactor. The mixture was stirred at 150° C. for 2.5 h in a microwave. The reaction was monitored by LC-MS. The mixture was concentrated under reduced pressure to give the title compound as a black oil, which was used directly in the next step without further purification. LC-MS (m/z): [M+H]$^+$=135; $^1$H NMR (400 MHz, DMSO) δ 11.34 (s, 1H), 7.40 (d, J=8.8 Hz, 1H), 7.36 (d, J=8.8 Hz, 1H), 2.33 (s, 3H).

Step 3: 3-((2-chloropyridin-4-yl)oxy)-6-methylpicolinonitrile

A mixture of above product (1.0 eq), 2,4-dichloropyridine (1.5 eq) and Cs$_2$CO$_3$ (2.0 eq) in DMSO (0.37 M) was stirred at 120° C. for 16 h. The reaction was monitored by LC-MS. Then the mixture was diluted with water and extracted with EtOAc. The organic layer was concentrated under reduced pressure. The residue was purified by flash chromatography on silica gel (eluent: petroleum ether/EtOAc 10:1 to 3:1) to give the title compound as a yellow solid. LC-MS (m/z): [M+H]$^+$=246.

Intermediate A14: 3-((2-chloropyridin-4-yl)oxy)-6-methyl-2-(trifluoromethyl)pyridine

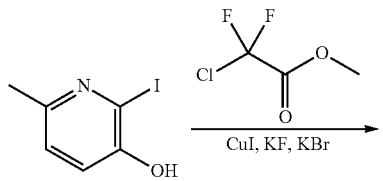

-continued

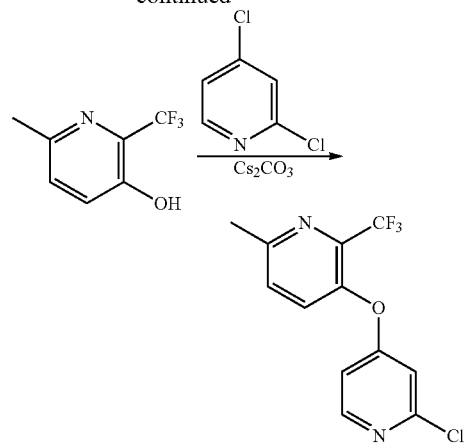

Step 1: 6-methyl-2-(trifluoromethyl)pyridin-3-ol

A mixture of 2-iodo-6-methylpyridin-3-ol (1.0 eq), methyl 2-chloro-2,2-difluoroacetate (3.0 eq), CuI (1.5 eq), KF (2 eq), KBr (2.0 eq) in DMF (0.2 M) was stirred at 110° C. for 16 h under Ar. The reaction was monitored by LC-MS. After the reaction was complete, the reaction mixture was filtered, and the filtrate was concentrated under reduced pressure. The residue was purified by flash chromatrography on silica gel (eluent: petroleum ether/EtOAc 1:0 to 50:1) to give the title compound as a yellow solid. LCMS (m/z): [M+H]$^+$=178.4.

Step 2: 3-((2-chloropyridin-4-yl)oxy)-6-methyl-2-(trifluoromethyl)pyridine

A mixture of 6-methyl-2-(trifluoromethyl)pyridin-3-ol (1.0 eq), 2,4-dichloropyridine (2.0 eq), Cs$_2$CO$_3$ (2.0 eq) in DMSO (0.1 M) was stirred at 140° C. for 3 h. The reaction mixture was cooled to r.t., treated with water and extracted with EtOAc. The solvent was removed under reduced pressure, and the residue was purified by flash chromatography on silica gel (eluent: petroleum ether/EtOAc 2:1) to give the title compound as a yellow oil. LC-MS (m/z): [M+1]$^+$=289.

Intermediate A15: 3-((2-chloropyridin-4-yl)oxy)-2-ethyl-6-methylpyridine

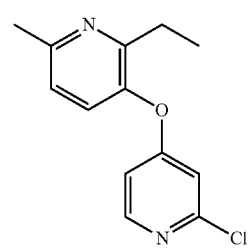 [SMILES: CCc1nc(C)ccc1Oc1ccnc(Cl)c1]

A mixture of 2-ethyl-6-methylpyridin-3-ol (1.0 eq), 2,4-dichloropyridine (1.0 eq), Cs$_2$CO$_3$ (2.0 eq) in DMF (1.5 M) was stirred at 110° C. for 16h. The reaction was monitored by LCMS. The mixture was filtered and washed with water, extracted with EtOAc. The organic layer was washed with brine, and dried over Na$_2$SO$_4$. The crude product was purified by flash chromatography on silica gel (petroleum ether/EtOAc 20:1) to give the title compound as a colorless oil. LC-MS (m/z): [M+H]⁺=249; 1H NMR (400 MHz, DMSO-d6) δ 8.30 (d, J=5.6 Hz, 1H), 7.53 (d, J=8.0 Hz, 1H), 7.23 (d, J=8.0 Hz, 1H), 7.01 (d, J=2.0 Hz, 1H), 6.91 (dd, J=5.6, 2.4 Hz, 1H), 2.60 (q, J=7.6 Hz, 2H), 2.50 (s, 3H), 1.13 (t, J=7.6 Hz, 3H).

Intermediate A16: 3-((2-chloropyridin-4-yl)oxy)-6-ethyl-2-methylpyridine

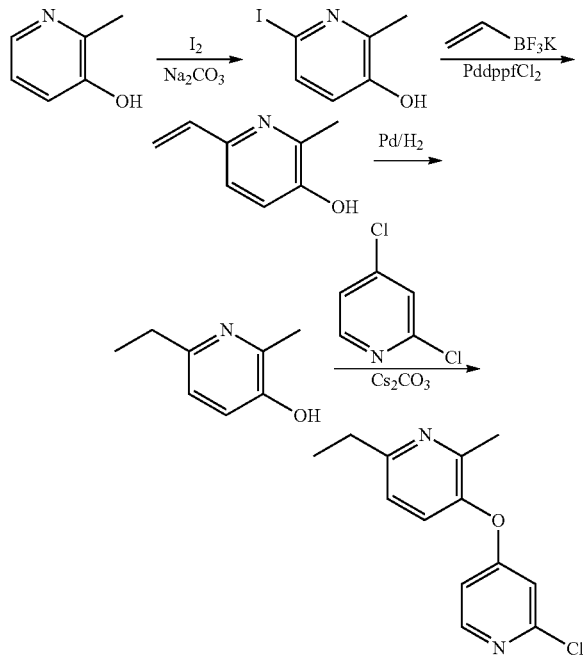

Step 1: 6-iodo-2-methylpyridin-3-ol

A mixture of 2-methylpyridin-3-ol (1.0 eq), I2 (1.0 eq), Na$_2$CO$_3$ (2.2 eq) in H$_2$O (0.46 M) was stirred at r.t. for 1h under Ar. The reaction was monitored by LCMS. The solution was adjusted to pH 6 with HCl (2N). The solid precipitated was filtered, washed with water (10 mL×2), and dried to give a yellow solid. The solid was dissolved in EtOAc at 80° C., and petroleum ether (70 ml) was added. The mixture was cooled to room temperature. The crystallized solid was filtered and dried to get the title compound as a yellow solid.

Step 2: 2-methyl-6-vinylpyridine-3-ol

A mixture of 6-iodo-2-methylpyridin-3-ol (1.0 eq), potassium trifluoro(vinyl)borate (1.0 eq), Pd(dppf)Cl$_2$ (0.1 eq), K$_2$CO$_3$ (3.0 eq) in 1,4-dioxane-water (20:1, 0.85 M) was stirred at 100° C. for 16h under Ar. The reaction was monitored by LCMS. The reaction mixture was filtered, and the filtrate was concentrated under reduced pressure. The residue was purified by flash chromatography on silica gel to give the title compound as a yellow oil.

Step 3: 6-ethyl-2-methylpyridin-3-ol

To a solution of 2-methyl-6-vinylpyridine-3-ol (1.0 eq) in MeOH (0.35 M) was added Pd/C (10% wt, 0.02 eq). The reaction mixture was stirred at RT for 16h under H$_2$. The reaction was monitored by LCMS. The solid was filtered off, and the filtrate was concentrated to give the title compound as a yellow oil.

Step 4: 3-((2-chloropyridin-4-yl)oxy)-6-ethyl-2-methylpyridine

A mixture of 6-ethyl-2-methylpyridin-3-ol (1.0 eq), 2,4-dichloropyridine (1.0 eq), Cs$_2$CO$_3$ (2.0 eq) in DMF (0.58 M) was stirred at 100° C. for 16h. The reaction was monitored by LCMS. The mixture was filtered and washed with water (15 ml), extracted with EtOAc (15 ml×3). The organic layer was washed with brine (10 ml×2), and then dried over Na$_2$SO$_4$. The crude product was purified by flash chromatography on silica gel (petroleum ether/EtOAc 20:1) to give the title compound as a yellow oil. LC-MS (m/z): [M+H]⁺=249.1; 1H NMR (400 MHz, DMSO-d6) δ 8.30 (d, J=5.6 Hz, 1H), 7.55 (d, J=8.4 Hz, 1H), 7.24 (d, J=8.4 Hz, 1H), 7.00 (d, J=2.0 Hz, 1H), 6.90 (dd, J=5.6, 2.4 Hz, 1H), 2.76 (q, J=7.6 Hz, 2H), 2.29 (s, 3H), 1.25 (t, J=7.6 Hz, 3H).

Alternative route for preparation of 6-ethyl-2-methylpyridin-3-ol

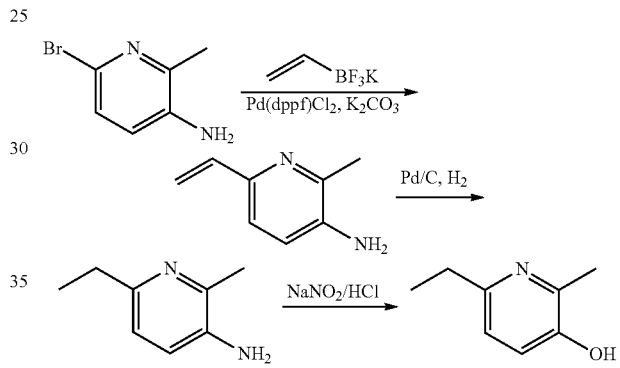

Step 1: 2-methyl-6-vinylpyridin-3-amine

A mixture of 6-bromo-2-methylpyridin-3-amine (1.0 eq), C$_2$H$_3$BF$_3$K (1.2 eq), K$_2$CO$_3$ (3.0 eq) and Pd(dppf)Cl$_2$ (0.05 eq) in 1,4-dioxane:H$_2$O (4:1, 0.27 M) was stirred under Ar at 100° C. for 16 h. The reaction mixture was cooled to RT, and diluted with water and EtOAc. The organic layer was separated, and the aqueous layer was extracted with EtOAc. The combined organic layer was dried over Na$_2$SO$_4$, filtered and concentrated. The residue was purified by flash chromatography on silica gel (eluent: petroleum ether/EtOAc=10:1~1:1) to give the title compound as a yellow solid. LC-MS (m/z): [M+H]⁺=135.

Step 2: 6-ethyl-2-methylpyridin-3-amine

A mixture of 2-methyl-6-vinylpyridin-3-amine (1.0 eq) and Pd/C (10%, 0.01 eq) in MeOH (2.1 M) was stirred under H$_2$ at r.t for 2 h. The solid was filtered off, and the filtrate was concentrated to give the title compound as a white solid.

Step 3: 6-ethyl-2-methylpyridin-3-ol

At 0° C., to a solution of 6-ethyl-2-methylpyridin-3-amine (1.0 eq) in aq. HCl (1.0 N, 5 eq) was added dropwise a solution of NaNO$_2$ (1.5 eq) in H$_2$O (3.1 M). The reaction mixture was stirred at 0° C. for 1 h, and then heated at 70°

C. for 16 h. The reaction mixture was cooled to RT, washed with EtOAc two times. The aqueous layer was concentrated, and the pH was adjusted ~7 with 3.0 M aq. NaOH solution. The solvent was fully evaporated under reduced pressure, and the residue was dissolved in DCM/MeOH (v/v=8:1). The solid was filtered off, and the filtrated was concentrated to give the title compound as a brown solid. LC-MS (m/z): $[M+H]^+=138$.

Intermediate A17: 3-((2-chloropyridin-4-yl)oxy)-2-methylquinoline

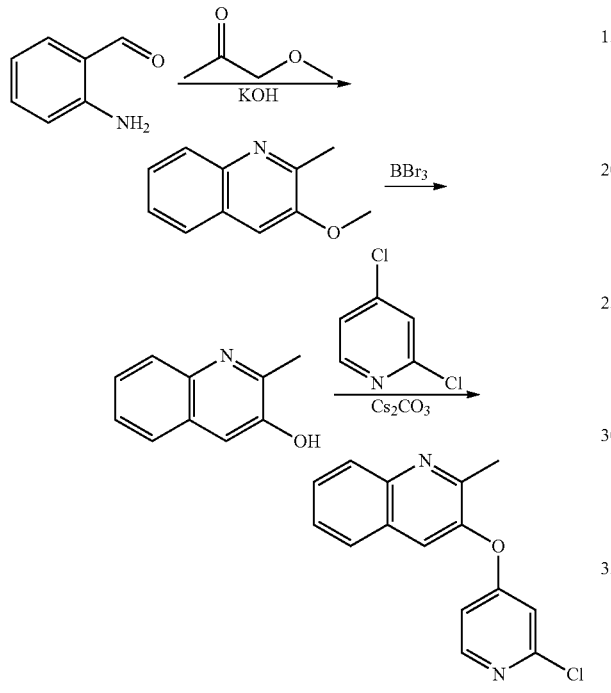

Step 1: 3-methoxy-2-methylquinoline

A mixture of 2-aminobenzaldehyde (1.0 eq), 1-methoxypropan-2-one (1.4 eq), KOH (1 eq) in EtOH-water (5:1, 0.34 M) was heated at 85° C. for 1h. The mixture was cooled to r.t. and worked up. The crude product was purified by flash chromatrography on silica gel (petroleum ether/EtOAc 15:1) to give the title compound as a yellow oil.

Step 2: 2-methylquinolin-3-ol

A solution of 3-methoxy-2-methylquinoline (5.7 g, 32.95 mmol, 1.0 eq) in DCM (0.33 M) was cooled to −20° C. BBr$_3$ (3.0 eq) was added slowly under Ar, and the resulting mixture was stirred at r.t overnight. The reaction was monitored by LC-MS and TLC. Upon completion, the reaction mixture was cooled to below 0° C., quenched with saturated aqueous NaHCO$_3$ solution and extracted with DCM/MeOH. The organic layer was concentrated under reduced pressure to give the title compound as a yellow solid.

Step 3: 3-((2-chloropyridin-4-yl)oxy)-2-methylquinoline

A mixture of 2-methylquinolin-3-ol (1.0 eq), 2,4-dichloropyridine (1.2 eq), Cs$_2$CO$_3$ (3.0 eq) in DMSO (0.16 M) was stirred at 150° C. for 3h under N$_2$. The reaction was monitored by TLC. The mixture was cooled to rt, treated with water, extracted with EtOAc, and then dried over Na$_2$SO$_4$. The crude product was purified by flash chromatography on silica gel (petroleum ether/EtOAc 4:1) to give the title compound as a yellow oil. $^1$H NMR (400 MHz, CDCl$_3$) δ 8.29 (d, J=5.6 Hz, 1H), 8.10 (d, J=8.4 Hz, 1H), 7.75-7.71 (m, 1H), 7.56 (t, J=7.2 Hz, 1H), 6.84 (d, J=2.0 Hz, 1H), 6.82 (dd, J=5.6, 2.0 Hz, 1H), 2.61 (s, 3H).

Intermediate A18: 3-((2-chloropyridin-4-yl)oxy)-5-ethyl-6-methyl-2,2'-bipyridine

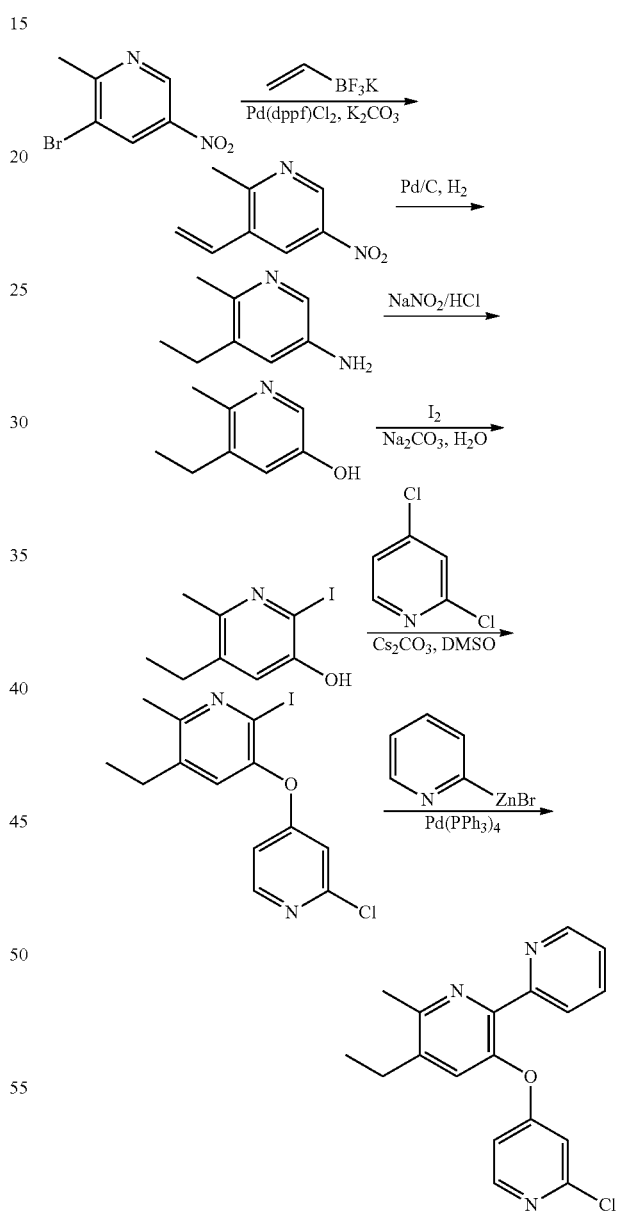

Step 1: 2-methyl-5-nitro-3-vinylpyridine

Under Ar atmosphere, a mixture of 3-bromo-2-methyl-5-nitropyridine (1.0 eq), potassium trifluoro(vinyl)borate (1.0 eq), K$_2$CO$_3$ (2.0 eq) and Pd(dppf)Cl$_2$ (0.1 eq) in dioxane/

H₂O (v/v=4:1, 0.5 M) was stirred at 100° C. for 16 h. The mixture was filtered through a pad of celite. The filtrate was diluted with EtOAc, washed with water, brine, and the organic layer was dried over Na₂SO₄. The crude product was purified by flash chromatography on silicon gel to give the title compound. LC-MS (m/z): [M+H]⁺=165.3.

Step 2: 5-ethyl-6-methylpyridin-3-amine

A mixture of 2-methyl-5-nitro-3-vinylpyridine (1.0 eq) and Pd/C (10%, 0.01 eq) in MeOH (0.3 M) was stirred under H₂ at r.t for 16 h. The solid was filtered off, and the filtrate was concentrated under the reduced pressure to give the title compound. LC-MS (m/z): [M+H]⁺=137.2.

Step 3: 5-ethyl-6-methylpyridin-3-ol

At 0° C., to a stirring solution of 5-ethyl-6-methylpyridin-3-amine (1.0 eq) in 1.0 N aq. HCl (0.7 M) was added dropwise a solution of NaNO₂ (1.0 eq) in H₂O (7 M). The reaction mixture was stirred at 0° C. for 0.5 h, and then heated at 70° C. for another 2 h. The resulting mixture was stirred at r.t for 16 h, and neutralized with NaHCO₃ to pH ~8 with NaHCO₃, and then extracted with EtOAc. The organic layer was washed with brine, and then dried over Na₂SO₄. The title compound was obtained upon removal of the solvent. LC-MS (m/z): [M+H]⁺=138.2.

Step 4: 5-ethyl-2-iodo-6-methylpyridin-3-ol

A mixture of 5-ethyl-6-methylpyridin-3-ol (1.9 g, 13.8 mmol, 1.0 eq), 12 (3.52 g, 13.8 mmol, 1.0 eq) and Na₂CO₃ (3.23 g, 30.5 mmol, 2.2 eq) in H₂O (50 mL) was stirred at r.t for 2 h. The reaction mixture was extracted with EtOAc, and the combined organic layer was concentrated under the reduced pressure. The crude product was purified by flash chromatography on silica gel (eluent: petroleum ether/EtOAc=10:1 to 5:1) to give the title compound. LC-MS (m/z): [M+H]⁺=264.2.

Step 5: 3-((2-chloropyridin-4-yl)oxy)-5-ethyl-2-iodo-6-methylpyridine

A mixture of 5-ethyl-2-iodo-6-methylpyridin-3-ol (1.0 eq), 2,4-dichloropyridine (1.05 eq) and Cs₂CO₃ (2.0 eq) in DMF (0.2 M) was stirred for 16 h at 100° C. under Ar atmosphere. The mixture was diluted with EtOAc, washed with brine for 10 times, and then dried over Na₂SO₄. The crude product was purified by flash chromatography on silica gel (eluent: petroleum ether/EtOAc=50:1 to 10:1) to give the title compound). LC-MS (m/z): [M+H]⁺=375.0.

Step 6: 3-((2-chloropyridin-4-yl)oxy)-5-ethyl-6-methyl-2,2'-bipyridine

To a mixture of 3-((2-chloropyridin-4-yl)oxy)-5-ethyl-2-iodo-6-methylpyridine (1.0 eq) and Pd(dppf)Cl₂ (0.1 eq) in DMA (0.4 M) was added pyridin-2-ylzinc(II) bromide (0.5M in THF, 1.2 eq). The reaction mixture was stirred at 120° C. for 16 h under Ar. The mixture was filtered through a pad of celite, and the filtrate was concentrated. The residue was diluted with EtOAc, washed with brine, and then dried over Na₂SO₄. The crude product was purified by flash chromatography on silica gel to give the title compound. LC-MS (m/z): [M+H]⁺=326.2.

The following intermediate was prepared according to the procedure descried in Intermediate A18.

| Intermediate | Structure | LCMS [M + 1]⁺ and/or ¹H NMR |
|---|---|---|
| A19 | 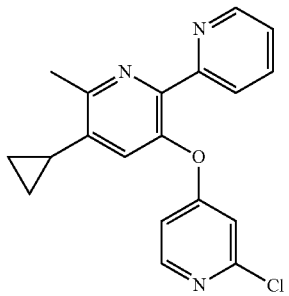 [SMILES: Cc1nc(-c2ccccn2)c(Oc2ccnc(Cl)c2)cc1C1CC1] | LCMS (m/z): [M + 1]⁺ = 338.2 |

Intermediate A20: 3-((2-chloropyridin-4-yl)oxy)-5-isopropyl-6-methyl-2,2'-bipyridine

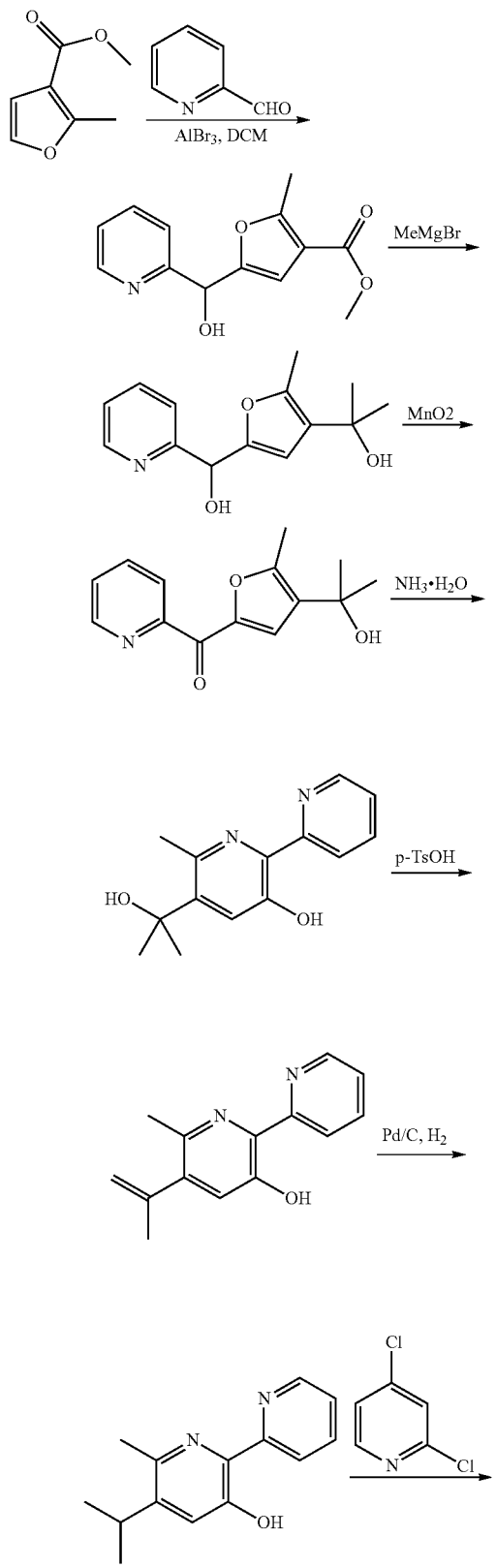

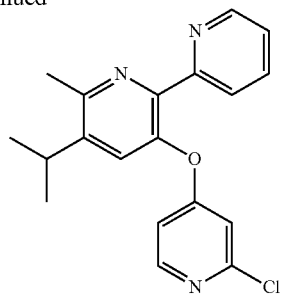

Step 1: methyl 5-(hydroxy(pyridin-2-yl)methyl)-2-methylfuran-3-carboxylate

At 0° C., to a suspension of AlBr$_3$ (1.0 eq) in dry DCM (0.2 M) was s added picolinaldehyde (1.0 eq), and the resulting mixture was stirred at 0° C. for 30 min under Ar before a solution of methyl 2-methylfuran-3-carboxylate (1.0 eq) in DCM (0.1 M) was added dropwise. The resulting suspension was stirred at r.t. for 16 h, and then quenched with sat. NaHCO$_3$ aqueous solution. The mixture was partitioned between DCM/water, and the organic layer was separated and dried over Na$_2$SO$_4$. The crude product was purified by flash chromatography on silica gel (eluent petroleum ether/EtOAc from 100:1 to 2:1) to give the title compound. LC-MS (m/z): [M+H]$^+$=248.1.

Step 2: 2-(5-(hydroxy(pyridin-2-yl)methyl)-2-methylfuran-3-yl)propan-2-ol

To a solution of methyl 5-(hydroxy(pyridin-2-yl)methyl)-2-methylfuran-3-carboxylate (1.0 eq) in THF (0.12 M) was added CH$_3$MgBr (4.0 eq). The resulting mixture was stirred at r.t. for 2h under Ar before quenched with sat. NaHCO$_3$. The mixture was partitioned between EtOAc/water. The organic layer was separated and dried over Na$_2$SO$_4$. Upon removal of solvent the title compound was obtained and used in the next step without further purification. LC-MS (m/z): [M+H]$^+$=248.1.

Step 3: (4-(2-hydroxypropan-2-yl)-5-methylfuran-2-yl)(pyridin-2-yl)methanone To a solution of 2-(5-(hydroxy(pyridin-2-yl)methyl)-2-methylfuran-3-yl)propan-2-ol (1.0 eq) in DCM (0.25 M) was added MnO$_2$ (3.0 eq), and the resulting mixture was stirred overnight at r.t. The mixture was filtered through a pad of celite, and the filtrate was concentrated and purified by flash chromatography on silica gel (eluent petroleum ether/EtOAc from 100:1 to 2:1) to give the title compound as a light-yellow solid. LC-MS (m/z): [M+H]$^+$=246.1.

Step 4: 5-(2-hydroxypropan-2-yl)-6-methyl-[2,2'-bipyridin]-3-ol

A solution of (4-(2-hydroxypropan-2-yl)-5-methylfuran-2-yl)(pyridin-2-yl)methanone (1.0 eq) in NH$_3$·H$_2$O/MeOH (1:1, 0.15 M) in a sealed tube was stirred for 8 h at 170° C. The solvents were removed, and the residue was lyophilized to give the title as a light yellow solid. LC-MS (m/z): [M+H]$^+$=245.2.

Step 5: 6-methyl-5-(prop-1-en-2-yl)-[2,2'-bipyridin]-3-ol

A mixture of 5-(2-hydroxypropan-2-yl)-6-methyl-[2,2'-bipyridin]-3-ol (370 mg, 1.51 mmol, 1.0 eq), p-TsOH (317 mg, 1.67 mmol, 1.1 eq) in toluene was refluxed at 135° C. for 16 h. After the reaction was completed, the mixture was concentrated to give the title compound. LC-MS (m/z): [M+H]$^+$=227.3.

Step 6: 5-isopropyl-6-methyl-[2,2'-bipyridin]-3-ol

A mixture of 6-methyl-5-(prop-1-en-2-yl)-[2,2'-bipyridin]-3-ol (343 mg, 1.52 mmol, 1.0 eq) and Pd/C (10%, 0.06 eq) in THF/MeOH (5:1, 0.025 M) was stirred under H$_2$ at r.t. for 5 h. The solid was filtered off, and the filtrate was concentrated to give the title compound. LC-MS (m/z): [M+H]$^+$=229.1.

Step 7: 3-((2-chloropyridin-4-yl)oxy)-5-isopropyl-6-methyl-2,2'-bipyridine

A mixture of 5-isopropyl-6-methyl-[2,2'-bipyridin]-3-ol (1.0 eq), 2,4-dichloropyridine (2.0 eq), Cs$_2$CO$_3$ (2.0 eq) in DMSO (0.1 M) was stirred at 150° C. for 6 h. The mixture was cooled down to rt, and quenched with water. The crude product was purified by flash chromatography on silica gel (eluent MeOH/DCM 0 to 5%) to give the title compound as a light yellow solid. LC-MS (m/z): [M+H]$^+$=340.1.

Intermediate A21: 3-((2-chloropyridin-4-yl)oxy)-6-ethyl-2,2'-bipyridine

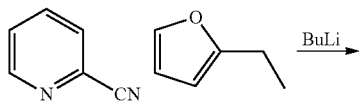

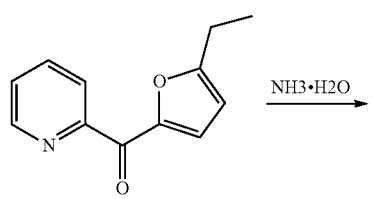

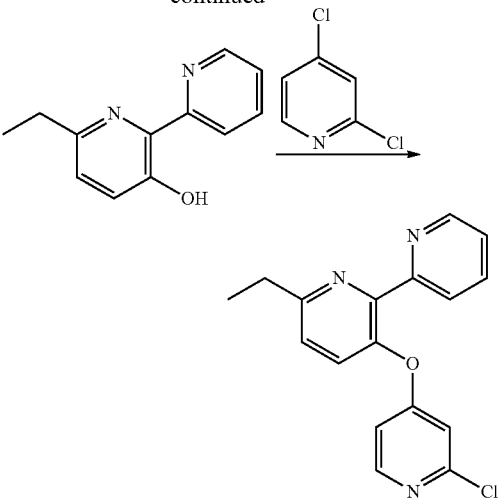

The compound was prepared by following the procedure described in Intermediate A1.

Step 1: (5-ethylfuran-2-yl)(pyridin-2-yl)methanone

At 0° C., to a stirring solution of 2-ethylfuran (2.0 g, 20.8 mmol, 1.0 eq) in Et$_2$O (80 mL) was added dropwise n-BuLi (2.5 M, 10.8 mL, 27.1 mmol, 1.3 eq). The mixture was stirred at 40° C. for 1.5 h, then cooled to −78° C. A solution of picolinonitrile (2.4 g, 22.9 mmol, 1.1 eq) in Et$_2$O (20 mL) was added dropwise to the above mixture. The resulting mixture was stirred at r.t for 1.5 h. The reaction was monitored by LC-MS. The reaction mixture was quenched with ice-water. The pH value of the mixture was adjusted to ~5 by 2N HCl. The aqueous layer was extracted with DCM. The organic layer was washed with water and dried over Na$_2$SO$_4$, filtered and concentrated. The residue was purified by FCC (eluent: PE/EA=10:1) to give compound 3 (1.25 g, 30%) as a yellow solid. LC-MS (m/z): [M+1]$^+$=202.2.

Step 2: 6-ethyl-[2,2'-bipyridin]-3-ol

A mixture of (5-ethylfuran-2-yl)(pyridin-2-yl)methanone (1.25 g, 4.97 mmol, 1.0 eq), MeOH (10 mL) and NH$_3$H$_2$O (10 mL) placed in a sealed tube was heated at 170° C. for 8 h. The mixture was allowed to cool to r.t., and the solvents were removed to give the title compound as a yellow solid, which was used directly to next step without further purification. LC-MS (m/z): [M+1]$^+$=201.2

Step 3: 3-((2-chloropyridin-4-yl)oxy)-6-ethyl-2,2'-bipyridine

A mixture of 6-ethyl-[2,2'-bipyridin]-3-ol (1.0 eq), 2,4-dichloropyridine (1.05 eq) and Cs$_2$CO$_3$ (2.0 eq) in DMF (0.4 M) was stirred at 100° C. for 16 h under Ar. The reaction was monitored by LC-MS. The mixture was quenched by water and extracted with EA. The organic layer was dried over Na$_2$SO$_4$, concentrated. The residue was purified by FCC (eluent: PE/EA=2:1) to give the title compound as a yellow solid. LC-MS (m/z): [M+1]$^+$=312.1.

The following intermediates were prepared according to the procedure descried in Intermediate A21.

| Intermediate | Structure | LCMS [M + 1]+ and/or 1H NMR |
|---|---|---|
| A22 | 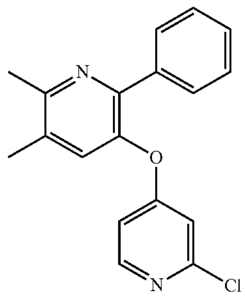 [SMILES: Cc1cc(Oc2ccnc(Cl)c2)c(-c2ccccc2)nc1C] | LCMS (m/z): [M + 1]+ = 311.1 |
| A45 | 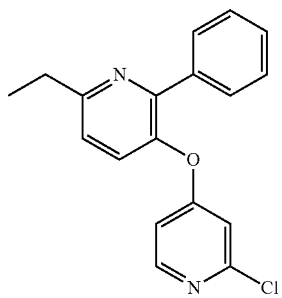 [SMILES: CCc1ccc(Oc2ccnc(Cl)c2)c(-c2ccccc2)n1] | LCMS (m/z): [M + 1]+ = 311.1 |

Intermediate A23: 3-((2-chloropyridin-4-yl)oxy)-6-ethyl-5-methyl-2,2'-bipyridine

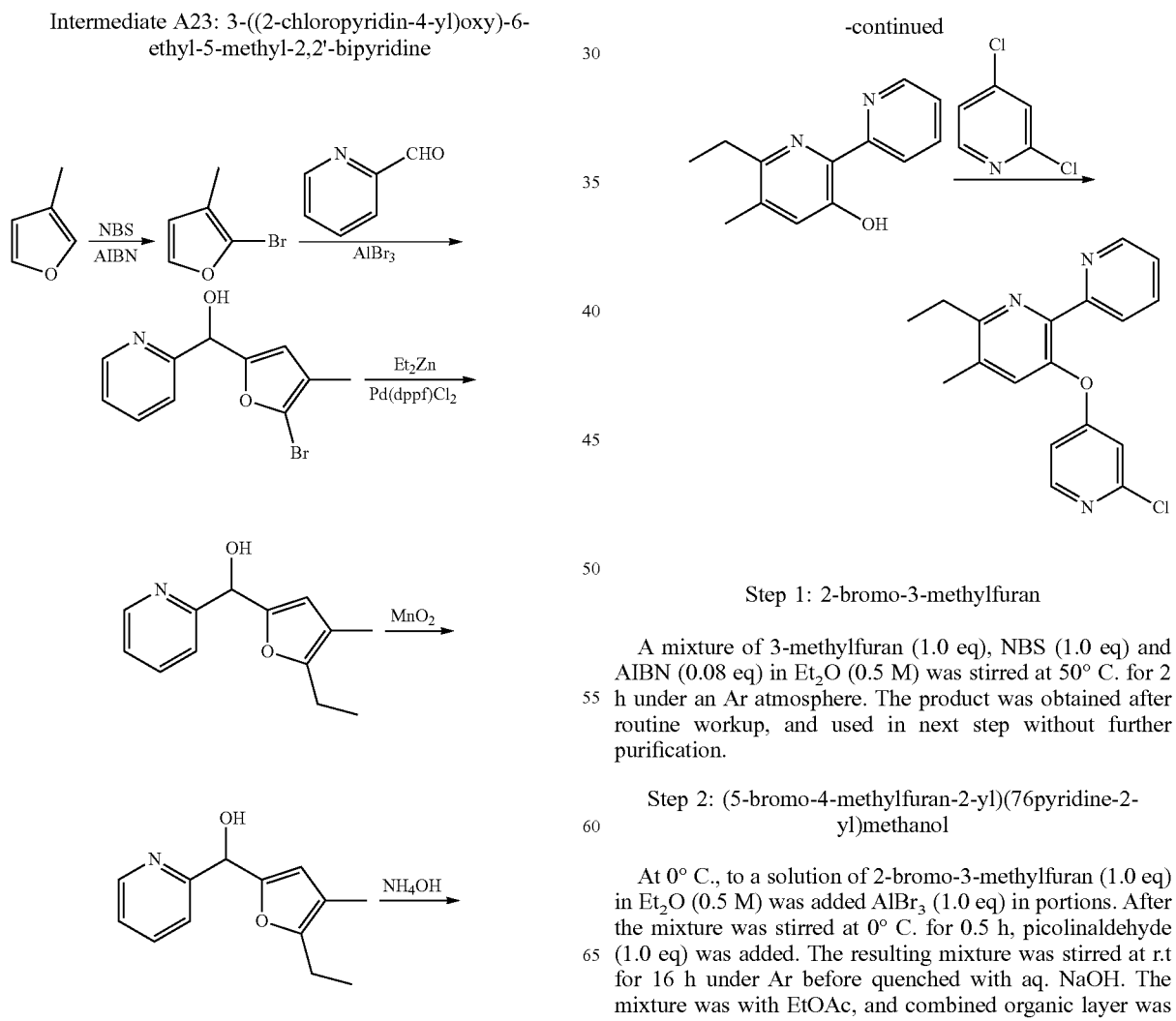

Step 1: 2-bromo-3-methylfuran

A mixture of 3-methylfuran (1.0 eq), NBS (1.0 eq) and AIBN (0.08 eq) in Et$_2$O (0.5 M) was stirred at 50° C. for 2 h under an Ar atmosphere. The product was obtained after routine workup, and used in next step without further purification.

Step 2: (5-bromo-4-methylfuran-2-yl)(76pyridine-2-yl)methanol

At 0° C., to a solution of 2-bromo-3-methylfuran (1.0 eq) in Et$_2$O (0.5 M) was added AlBr$_3$ (1.0 eq) in portions. After the mixture was stirred at 0° C. for 0.5 h, picolinaldehyde (1.0 eq) was added. The resulting mixture was stirred at r.t for 16 h under Ar before quenched with aq. NaOH. The mixture was with EtOAc, and combined organic layer was washed with brine and then dried over Na₂SO₄. The crude product was purified by flash chromatography on silica gel (eluent: petroleum ether/EtOAc=20:1-5:1) to give the title compound as a yellow oil. LC-MS (m/z): [M+H]+: 268.

Step 3: (5-ethyl-4-methylfuran-2-yl)(pyridin-2-yl)methanol

At 0° C., to a mixture of (5-bromo-4-methylfuran-2-yl)(pyridin-2-yl)methanol (1.0 eq) and Pd(dppf)Cl₂ (0.05 eq) in THF (0.25 M) was added dropwise Et₂Zn (3.0 eq). The mixture was stirred at 70° C. for 16 h under Ar. The mixture was poured into ice-water, and filtered through a pad of celite. The filtrate was extracted with EtOAc, and the combined organic layer was dried over Na₂SO₄. The crude product was purified by flash chromatography on silica gel (eluent: petroleum ether/EtOAc=20:1-5:1) to give the title compound as a yellow oil. LC-MS (m/z): [M+H]+: 218.

Step 4: (5-ethyl-4-methylfuran-2-yl)(pyridin-2-yl)methanone

A mixture of (5-ethyl-4-methylfuran-2-yl)(pyridin-2-yl)methanol (1.0 eq) and MnO₂ (5.0 eq) in THF (0.2 M) was stirred at 50° C. for 16 h. The mixture was filtered through a pad of celite, and the filtrate was concentrated to give the title compound as a yellow oil. LC-MS (m/z): [M+H]+: 216.

Step 5: 6-ethyl-5-methyl-[2,2'-bipyridin]-3-ol

A mixture of (5-ethyl-4-methylfuran-2-yl)(pyridin-2-yl)methanone (1.0 eq) and NH₃·H₂O/MeOH (1:1, 0.2 M) in a sealed tube was heated at 170° C. for 8 h. The solvents were removed to give the title compound which was used in next step without further purification. LC-MS (m/z): [M+H]+: 215.

Step 6: 3-((2-chloropyridin-4-yl)oxy)-6-ethyl-5-methyl-2,2'-bipyridine

A mixture of 6-ethyl-5-methyl-[2,2'-bipyridin]-3-ol (1.0 eq), 2,4-dichloropyridine (1.5 eq) and Cs₂CO₃ (2.0 eq) in DMF (0.5 M) was stirred at 100° C. for 16 h under Ar. The mixture was cooled to rt, diluted with water and extracted with EtOAc. The combined organic layers was washed with brine, and then dried over Na₂SO₄. The crude product was purified by flash chromatography on silica gel (eluent: petroleum ether/EtOAc=10:1-1:1) to give the title compound as yellow solid. LC-MS (m/z): [M+H]+: 326.

Alternative route for preparation of (5-ethyl-4-methylfuran-2-yl)(pyridin-2-yl)methanone:

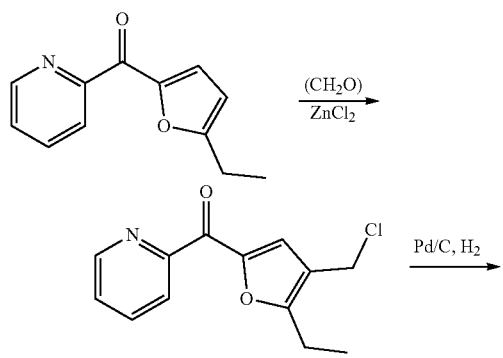

Step 1: (4-(chloromethyl)-5-ethylfuran-2-yl)(pyridin-2-yl)methanone

A mixture of (5-ethylfuran-2-yl)(pyridin-2-yl)methanone (1.0 eq), (HCHO)ₙ (4.0 eq), ZnCl₂ (4.0 eq) and HCl/dioxane (10 eq) in DCE (0.22 M) was stirred at 50° C. for 16 h under Ar. Most of solvent was removed, and the residue was adjusted pH to ~8 with 1.0 M aq. NaOH. The mixture was diluted with DCM. The organic layer was separated, and the aqueous layer was extracted with DCM. The combined organic layer was washed with brine, and then dried over Na₂SO₄. The crude product was purified by flash chromatography on silica gel (eluent: petroleum ether/EtOAc=20:1-5:1) to give the title compound as a brown oil. LC-MS (m/z): [M+H]⁺=250.

Step 2: (5-ethyl-4-methylfuran-2-yl)(pyridin-2-yl)methanone

A mixture of (4-(chloromethyl)-5-ethylfuran-2-yl)(pyridin-2-yl)methanone (1.0 eq), Pd/C (10%, 0.03 eq) and TEA (2.0 eq) in EtOAc (0.2 M) was stirred under H₂ at r.t for 2.5 h. The solid was filtered off, and the filtrate was concentrated. The residue was purified by flash chromatography on silica gel (eluent: petroleum ether/EtOAc=10:1-5:1) to give the title compound as a yellow solid. LC-MS (m/z): [M+H]⁺=216.

Intermediate A24: 3-((2-chloropyridin-4-yl)oxy)-5,6-dimethyl-2-(tetrahydro-2H-pyran-4-yl)pyridine

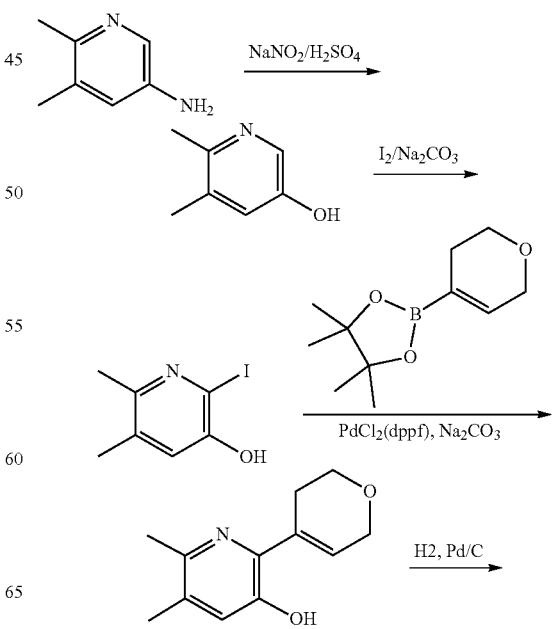

67

-continued

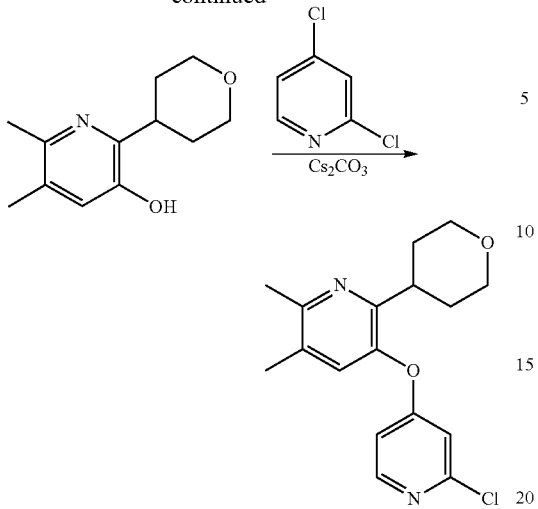

Step 1: 5,6-dimethylpyridin-3-ol

At 0° C., to a mixture of 5,6-dimethylpyridin-3-amine (1.0 eq) in 2M H$_2$SO$_4$ (0.33 M) was added dropwise a solution of NaNO$_2$ (1.0 eq) in H$_2$O. The mixture was stirred for 30 min at r.t, 2h at 70° C., and then 16 h at rt. The mixture was diluted with EtOAc/H$_2$O. The organic layer was separated and dried over Na$_2$SO$_4$. The solvent was removed to give the title compound, which was used in next step without further purification. LC-MS (m/z): [M+H]$^+$=124.4.

Step 2: 2-iodo-5,6-dimethylpyridin-3-ol

To a mixture of 5,6-dimethylpyridin-3-ol (1.0 eq), Na$_2$CO$_3$ (2.0 eq) in H$_2$O/THF (1:4, 0.15 M) was added I2 (1.1 eq) in portions, and the mixture was stirred at r.t for 0.5 h. The mixture was diluted with DCM/H$_2$O, and the organic layer was separated and dried over Na$_2$SO$_4$. The crude product was purified by flash chromatography on silica gel (eluent: petroleum ether/EtOAc=2:1) to give the title compound as a yellow solid. LC-MS (m/z): [M+H]$^+$=250.0.

Step 3: 2-(3,6-dihydro-2H-pyran-4-yl)-5,6-dimethylpyridin-3-ol

A mixture of 2-iodo-5,6-dimethylpyridin-3-ol (1.0 eq), 2-(3,6-dihydro-2H-pyran-4-yl)-4,4,5,5-tetramethyl-1,3,2-dioxaborolane (1.5 eq), PdCl$_2$(dppf)(0.1 eq) and Na$_2$CO$_3$ (2.0 eq) in dioxane/H$_2$O (10:1, 0.2 M) was stirred at 100° C. for 16 h under Ar. The mixture was diluted with DCM/H$_2$O, and the organic layer was separated and dried over Na$_2$SO$_4$. The crude product was purified by flash chromatography on silica gel (eluent: petroleum ether/EtOAc=3:1) to give the title compound as a white solid. LC-MS (m/z): [M+H]$^+$=206.4.

Step 4: 5,6-dimethyl-2-(tetrahydro-2H-pyran-4-yl)pyridin-3-ol

A mixture of 2-(3,6-dihydro-2H-pyran-4-yl)-5,6-dimethylpyridin-3-ol (1.0 eq), Pd/C (20% wt, 0.05 eq) in MeOH (0.1 M) was stirred under H$_2$ at r.t for 2 h. The solid was filtered off, and the filtrate was concentrated to give the title compound as a white solid. LC-MS (m/z): [M+H]$^+$=208.4.

68

Step 5: 3-((2-chloropyridin-4-yl)oxy)-5,6-dimethyl-2-(tetrahydro-2H-pyran-4-yl)pyridine A mixture of, 6-dimethyl-2-(tetrahydro-2H-pyran-4-yl) pyridin-3-ol (1.0 eq), 2,4-dichloropyridine (1.1 eq), Cs$_2$CO$_3$ (2.0 eq) in DMSO (0.1 M) was stirred at 130° C. for 2 h under Ar. The mixture was cooled to rt, and diluted with EtOA and water. The organic layer was separated and dried over Na$_2$SO$_4$. The crude product was purified by prepare TLC (eluent: petroleum ether/EtOAc=3:1) to give the title compound as a colorless oil. LC-MS (m/z): [M+H]$^+$=319.3.

Intermediate A25: 3-((2-chloropyridin-4-yl)oxy)-6-methyl-2-(tetrahydro-2H-pyran-4-yl)pyridine

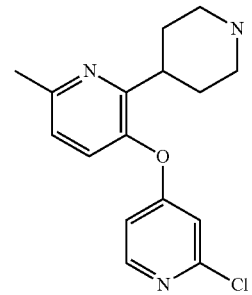 [SMILES: Cc1ccc(Oc2ccnc(Cl)c2)c(C2CCNCC2)n1]

This compound was prepared by following the procedure described in Intermediate A24. LCMS (m/z): [M+1]$^+$=305.

Intermediate A26: 3-chloro-5-((2-chloropyridin-4-yl)oxy)-2,6-dimethylpyridine

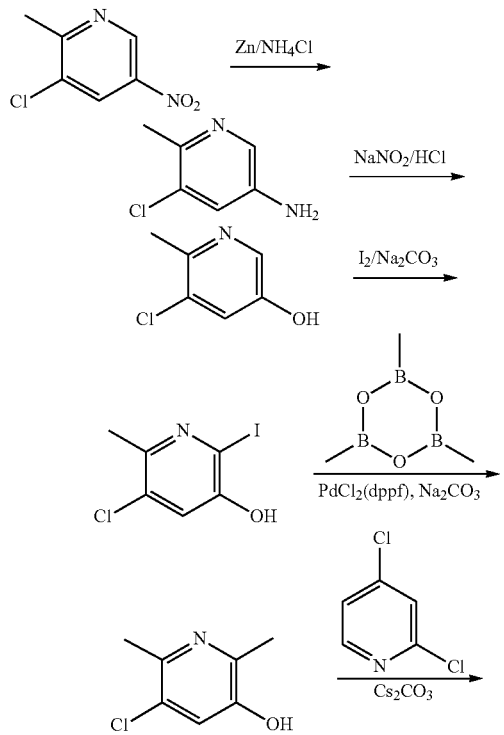

-continued

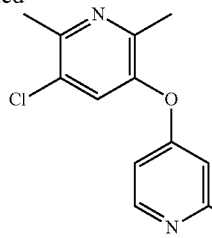

Step 1: 5-chloro-6-methylpyridin-3-amine

To a mixture of 3-chloro-2-methyl-5-nitropyridine (1.0 eq) in MeOH/H$_2$O (1:1, 0.6 M) was added Zn powder (10 eq) and NH$_4$Cl (10 eq), and the reaction mixture was stirred at r.t for 16 h. The reaction mixture was filtered through a pad of celite, and the solid cake was washed with EtOAc. The organic layer was separated, and the aqueous layer was extracted with EtOAc. The combined organic layers was washed with brine, and then dried over Na$_2$SO$_4$. The crude product was purified by flash chromatography on silica gel (eluent: petroleum ether/EtOAc=5:1) to give the title compound as a yellow oil. LC-MS (m/z): [M+H]$^+$=143.1.

Step 2: 5-chloro-6-methylpyridin-3-ol

At 0° C., to a solution of 5-chloro-6-methylpyridin-3-amine (1.0 eq) in 1M HCl (0.56 M) was added dropwise a solution of NaNO$_2$ (1.1 eq) in water (3.0 M), and the reaction mixture was stirred at 0° C. for 2 h, then heated to 70° C. for 16 h. The reaction was quenched with sat. aq. Na$_2$CO$_3$ (20 mL), and the mixture was extracted with EtOAc. The combined organic layer was dried over anhydrous Na$_2$SO$_4$. The crude product was purified by flash chromatography on silica gel (eluent: DCM/MeOH=30:1) to give the title compound as a white solid. LC-MS (m/z): [M+H]$^+$=144.1.

Step 3: 5-chloro-2-iodo-6-methylpyridin-3-ol

At 0° C., to a mixture of 5-chloro-6-methylpyridin-3-ol (1.0 eq), Na$_2$CO$_3$ (2.0 eq) in water (1.0 M) was added I2 (1.0 eq), and the the mixture was stirred at r.t for 16 h. The mixture was extracted with EtOA, and the combined organic layers was dried over Na$_2$SO$_4$. The crude product was purified by flash chromatography on silica gel (eluent: petroleum ether/EtOAc=5:1) to give the title compound as a white solid. LC-MS (m/z): [M+H]$^+$=270.0.

Step 4: 5-chloro-2,6-dimethylpyridin-3-ol

A mixture of 5-chloro-2-iodo-6-methylpyridin-3-ol (1.0 eq), trimethylboroxine (1.1 eq), Pd(dppf)Cl$_2$ (0.05 eq) and K$_2$CO$_3$ (2.5 eq) in dioxane (0.2 M) was stirred at 100° C. for 16 h under an Ar atmosphere. The reaction was quenched with aq. NH$_4$Cl (10 mL), and the mixture was filtered through a pad of celite. The filtrate was extracted with EtOAc, and the combined organic layers was dried over anhydrous Na$_2$SO$_4$. The crude product was purified by flash chromatography on silica gel (eluent: petroleum ether/EtOAc=10:1) to give the the title compound as a white solid. LC-MS (m/z): [M+H]$^+$=158.1.

Step 5: 3-chloro-5-((2-chloropyridin-4-yl)oxy)-2,6-dimethylpyridine

To a solution of 5-chloro-2,6-dimethylpyridin-3-ol (1.0 eq) in DMF (0.07 M) was added 2,4-dichloropyridine (1.1 eq) and Cs$_2$CO$_3$ (2.5 eq). After stirred under Ar at 100° C. for 16 h, the reaction mixture was quenched with ice-water (10 mL), and extracted with EtOAc. The combined organic layers was washed with brine, and then dried over anhydrous Na$_2$SO$_4$. The crude product was purified by prepare TLC (eluent: petroleum ether/EtOAc=6:1) to give the title compound as a white solid. LC-MS (m/z): [M+H]$^+$=269.0.

Intermediate A27: 3-((2-chloropyridin-4-yl)oxy)-2,5,6-trimethylpyridine

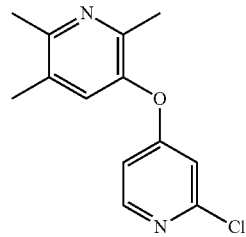 [SMILES: Cc1cc(Oc2ccnc(Cl)c2)c(C)nc1C]

This compound was prepared by following the procedure described in Intermediate A26. LCMS (m/z): [M+1]$^+$=249.1.

The following intermediates were prepared according to the procedure described in Intermediate A6.

| Intermediate | Structure | LCMS [M + 1]$^+$ and/or $^1$H NMR |
|---|---|---|
| A28 | 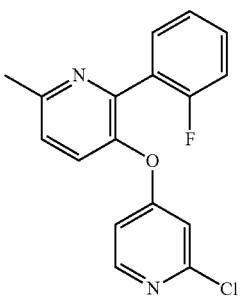 [SMILES: Cc1ccc(Oc2ccnc(Cl)c2)c(-c2ccccc2F)n1] | LCMS (m/z): [M + 1]$^+$ = 315 |

-continued

| Intermediate | Structure | LCMS [M + 1]+ and/or 1H NMR |
|---|---|---|
| A29 | 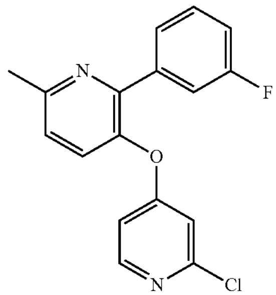 [SMILES: Cc1ccc(Oc2ccnc(Cl)c2)c(-c2cccc(F)c2)n1] | LCMS (m/z): [M + 1]+ = 315 |
| A30 | 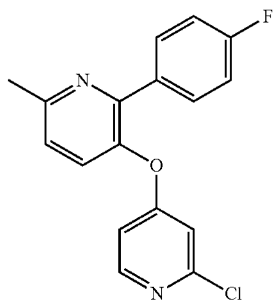 [SMILES: Cc1ccc(Oc2ccnc(Cl)c2)c(-c2ccc(F)cc2)n1] | LCMS (m/z): [M + 1]+ = 315.3 |
| A31 | 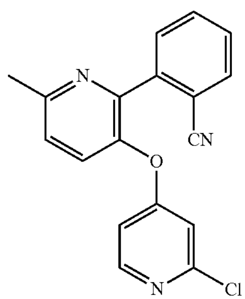 [SMILES: Cc1ccc(Oc2ccnc(Cl)c2)c(-c2ccccc2C#N)n1] | LCMS (m/z): [M + 1]+ = 322 |
| A32 | 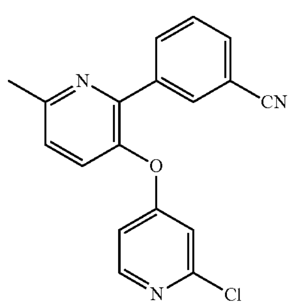 [SMILES: Cc1ccc(Oc2ccnc(Cl)c2)c(-c2cccc(C#N)c2)n1] | LCMS (m/z): [M + 1]+ = 322 |
| A33 | 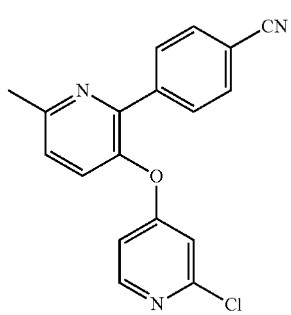 [SMILES: Cc1ccc(Oc2ccnc(Cl)c2)c(-c2ccc(C#N)cc2)n1] | LCMS (m/z): [M + 1]+ = 322 |

-continued
| Intermediate | Structure | LCMS [M + 1]+ and/or 1H NMR |
|---|---|---|
| A34 | 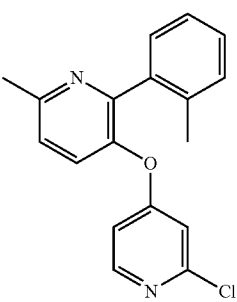 [SMILES: Cc1ccc(Oc2ccnc(Cl)c2)c(-c2ccccc2C)n1] | LCMS (m/z): [M + 1]+ = 311 |
| A35 | 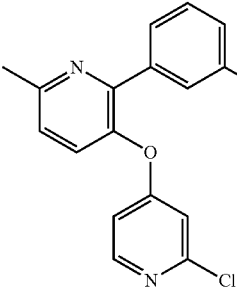 | LCMS (m/z): [M + 1]+ = 311 |
| A36 | 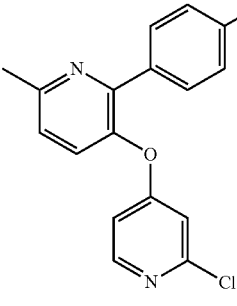 | LCMS (m/z): [M + 1]+ = 311 |
| A37 | 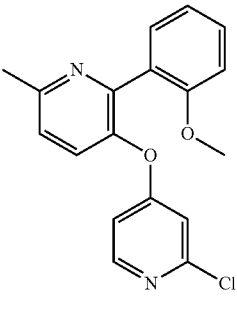 | LCMS (m/z): [M + 1]+ = 327 |
| A38 | 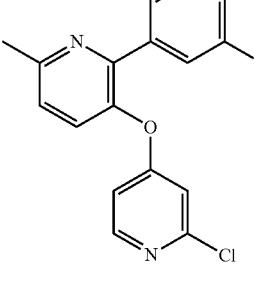 | LCMS (m/z): [M + 1]+ = 327.3 |

| Intermediate | Structure | LCMS [M + 1]⁺ and/or ¹H NMR |
|---|---|---|
| A39 | 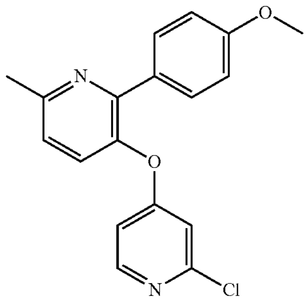 | LCMS (m/z): [M + 1]⁺ = 327.3 |
| A40 | 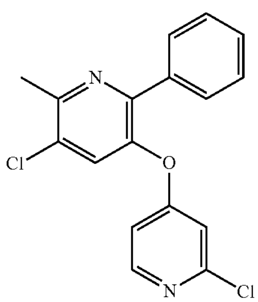 [SMILES: Cc1nc(-c2ccccc2)c(Oc2ccnc(Cl)c2)cc1Cl] | LCMS (m/z): [M + 1]⁺ = 331.0 |

Intermediate A41: 3-((2-chloropyridin-4-yl)oxy)-5-cyclopropyl-6-methyl-2-phenylpyridine

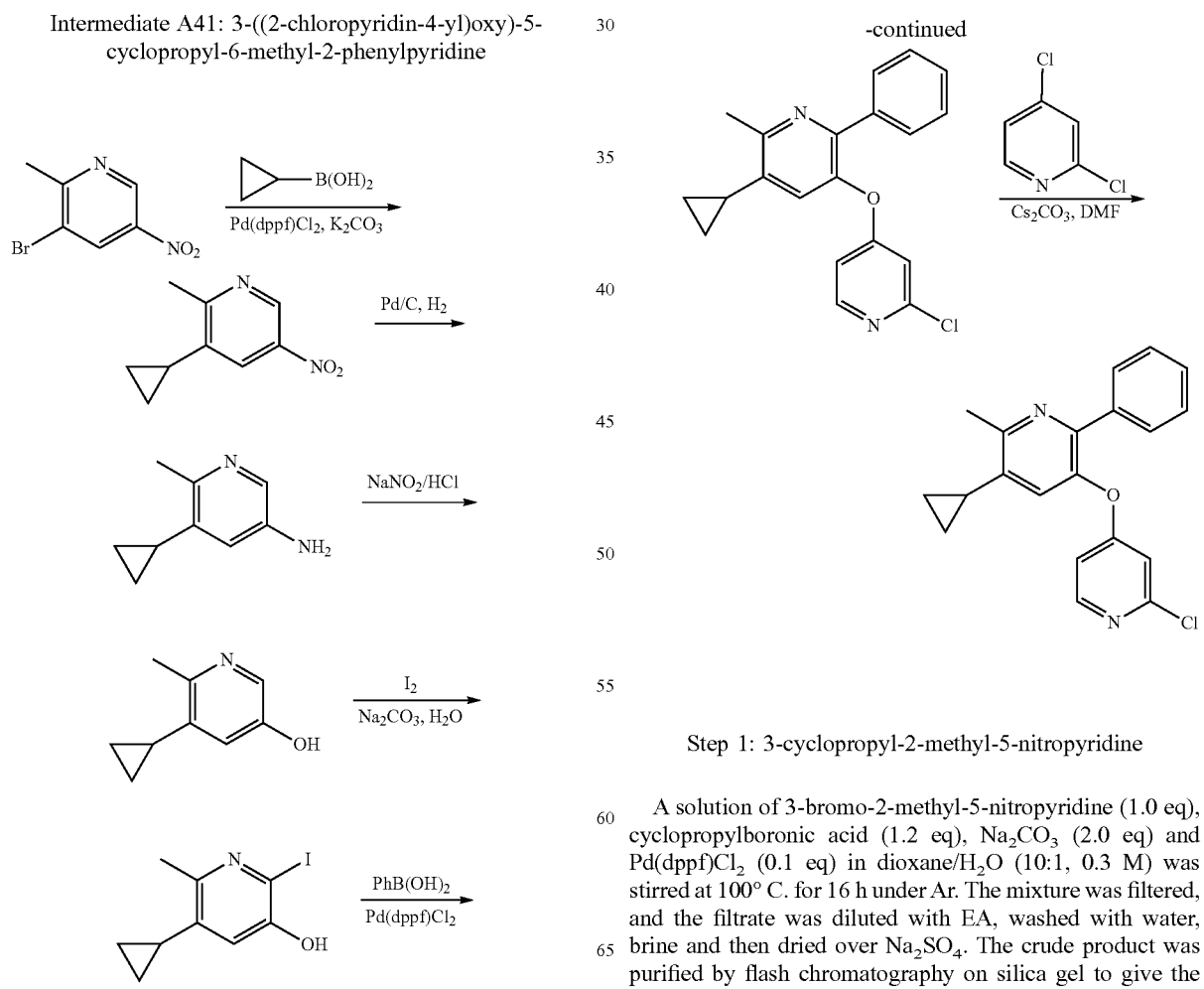

Step 1: 3-cyclopropyl-2-methyl-5-nitropyridine

A solution of 3-bromo-2-methyl-5-nitropyridine (1.0 eq), cyclopropylboronic acid (1.2 eq), Na₂CO₃ (2.0 eq) and Pd(dppf)Cl₂ (0.1 eq) in dioxane/H₂O (10:1, 0.3 M) was stirred at 100° C. for 16 h under Ar. The mixture was filtered, and the filtrate was diluted with EA, washed with water, brine and then dried over Na₂SO₄. The crude product was purified by flash chromatography on silica gel to give the title compound. LCMS (m/z): [M+H]⁺=179.2.

Step 2: 5-cyclopropyl-6-methylpyridin-3-amine

A mixture of 3-cyclopropyl-2-methyl-5-nitropyridine (1.0 eq), Pd/C (10% wt, 0.1 eq) in MeOH (0.3 M) was stirred under H$_2$ at r.t for 16 h. The solid was filtered off, and the filtrate was concentrated under reduced pressure to give the title compound. LCMS (m/z): [M+H]$^+$=149.2.

Step 3: 5-cyclopropyl-6-methylpyridin-3-ol

At 0° C., to a stirring solution of 5-cyclopropyl-6-methylpyridin-3-amine (1.0 eq) in 1N aq. HCl (0.3 M) was added dropwise a solution of NaNO$_2$ (1.0 eq) in H$_2$O (2.7 M). The mixture was stirred at for 0.5 h at 0° C., 2h at 70° C., and 16 h at RT. The mixture was adjusted pH to ~8 with NaHCO$_3$, and then extracted with EtOAc. The combined organic layer was dried over Na$_2$SO$_4$. The title compound was obtained upon removal of solvent. LCMS (m/z): [M+H]$^+$=150.4.

Step 4: 5-cyclopropyl-2-iodo-6-methylpyridin-3-ol

A mixture of 5-cyclopropyl-6-methylpyridin-3-ol (1.0 eq), I2 (1.0 eq), Na$_2$CO$_3$ (2.2 eq) in H$_2$O (0.25 M) was stirred at r.t for 2 h. The mixture was extracted with EA, and the combined organic layer was dried over Na$_2$SO$_4$. The crude product was purified by flash chromatography on silica gel (eluent: petroleum ether/EtOAc=10:1 to 5:1) to give the title compound. LCMS (m/z): [M+H]$^+$=276.1.

Step 5: 3-((2-chloropyridin-4-yl)oxy)-5-cyclopropyl-6-methyl-2-phenylpyridine A solution of 5-cyclopropyl-2-iodo-6-methylpyridin-3-ol (1.0 eq), phenylboronic acid (1.2 eq), Na$_2$CO$_3$ (2.0 eq) and Pd(dppf)Cl$_2$ (0.1 eq) in dioxane/H$_2$O (10:1, 0.1 M) was stirred at 100° C. for 16 h under Ar. The mixture was filtered, the filtrate was diluted with EA, washed with water, brine, and then dried over Na$_2$SO$_4$. The crude product was purified by flash chromatography on silica gel to give the title compound. LCMS (m/z): [M+H]$^+$=226.3.

Step 6: 3-((2-chloropyridin-4-yl)oxy)-5-cyclopropyl-6-methyl-2-phenylpyridine A mixture of 3-((2-chloropyridin-4-yl)oxy)-5-cyclopropyl-6-methyl-2-phenylpyridine (1.0 eq), 2,4-dichloropyridine (1.05 eq) and Cs$_2$CO$_3$ (2.0 eq) in DMF (0.1 M) was stirred at 100° C. for 16 h under Ar. The mixture was diluted with EA and brine. The organic layer was separated and dried over Na$_2$SO$_4$. The crude product was purified by flash chromatography on silica gel (eluent: petroleum ether/EtOAc=50:1 to 5:1) to give the title compound. LCMS (m/z): [M+H]$^+$=337.1.

Intermediate A42: 3-((2-chloropyridin-4-yl)oxy)-5-ethyl-6-methyl-2-phenylpyridine

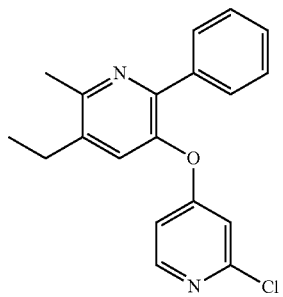 [SMILES: CCc1cc(Oc2ccnc(Cl)c2)c(-c2ccccc2)nc1C]

This compound was prepared by following the procedure described in Intermediate A41. LCMS (m/z): [M+H]$^+$=325.1.

Intermediate A43: 3-((2-chloropyridin-4-yl)oxy)-5-isopropyl-6-methyl-2-phenylpyridine

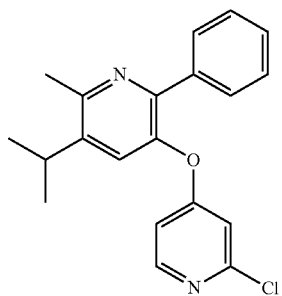 [SMILES: Cc1nc(-c2ccccc2)c(Oc2ccnc(Cl)c2)cc1C(C)C]

This compound was prepared by following the procedure described in Intermediate A20 by minor modification.

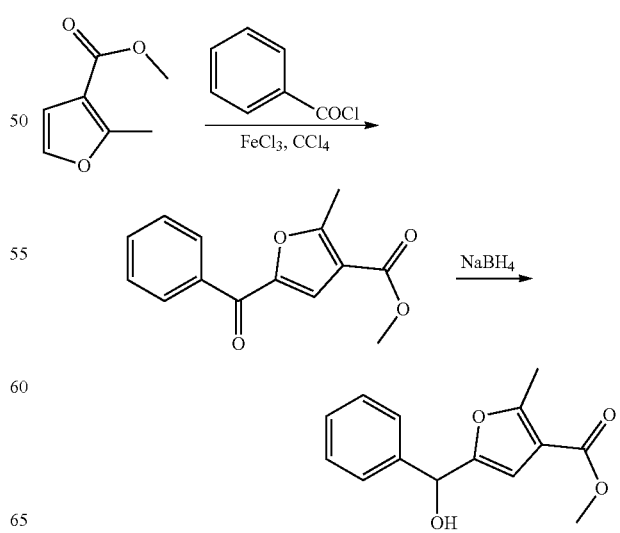

Step 1: methyl 5-benzoyl-2-methylfuran-3-carboxylate

To a suspension of FeCl$_3$ (0.013 eq) in CCl$_4$ (4.5 M) was added benzoyl chloride (1.05 eq), followed by methyl 2-methylfuran-3-carboxylate (6.0 g, 42.8 mmol, 1.0 eq). The mixture was stirred at 80° C. for 1h, and then partitioned between DCM/water. The organic layer was separated, and dried over Na$_2$SO$_4$. The crude product was purified by flash chromatography on silica gel (petroleum ether/EtOAc=1:0 to 10:1) to give the title compound as a yellow oil.

Step 2: methyl 5-(hydroxy(phenyl)methyl)-2-methylfuran-3-carboxylate

At 0° C., to a solution of methyl 5-benzoyl-2-methylfuran-3-carboxylate (1.0 eq) in MeOH (1.0 M) was added NaBH$_4$ (2.0 eq) portionwise, and the mixture was stirred for 2h 0° C. The reaction was quenched with sat. NH$_4$Cl, and the mixture was extracted with EtOAc. The combined organic layers were dried over Na$_2$SO$_4$. The crude product was purified by flash chromatography on silica gel (petroleum ether/EtOAc=1:0 to 5:1) to give the title compound as a yellow oil.

The rest of steps followed the procedure described in Intermediate A20 (steps 2-7). The crude product was purified by flash chromatography on silica gel(eluent MeOH/DCM=0 to 5%) to give the Intermediate A43 as a light-yellow solid. LCMS (m/z): [M+H]$^+$=339.3.

Intermediate A44: 2-(5-((2-chloropyridin-4-yl)oxy)-2-methyl-6-phenylpyridin-3-yl)propan-2-ol

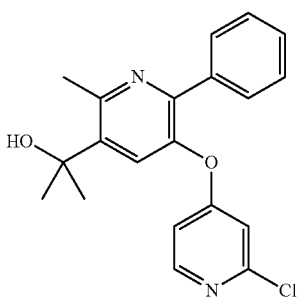 [SMILES: Cc1nc(-c2ccccc2)c(Oc2ccnc(Cl)c2)cc1C(C)(C)O]

This compound was prepared by following the procedure described in Intermediate A43. The crude product was purified by flash chromatography on silica gel (eluent: MeOH/DCM=0 to 5%) to give the title compound as a light-yellow solid. LCMS (m/z): [M+H]$^+$=355.

Intermediate A45: 3-((2-chloropyridin-4-yl)oxy)-6-ethyl-2-phenylpyridine

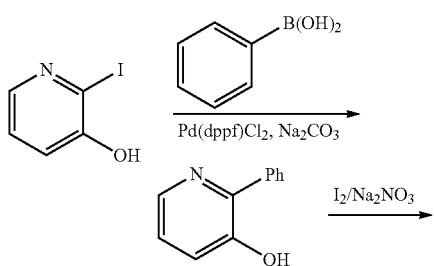

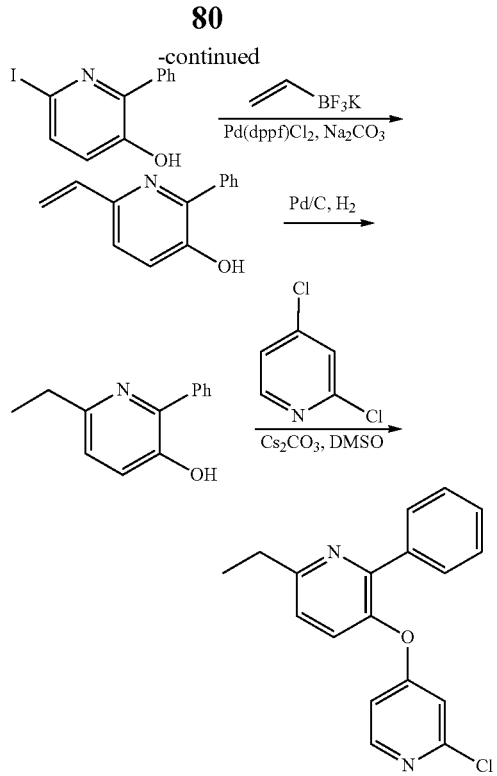

Step 1: 2-phenylpyridin-3-ol

A mixture of 2-iodopyridin-3-ol (1.0 eq), phenylboronic acid (1.1 eq), PdCl$_2$(dppf) (0.1 eq) and Na$_2$CO$_3$ (2.0 eq) in dioxane/H$_2$O (10:1, 0.2 M) was stirred at 90° C. for 16 h under an Ar atmosphere. The mixture was diluted with DCM. The organic layer was separated, and dried over Na$_2$SO$_4$. The crude product was purified by flash chromatography on silica gel (eluent: petroleum ether/EtOAc=3:1) to give the title compound as a yellow solid. LCMS (m/z): [M+H]$^+$=172.2.

Step 2: 6-iodo-2-phenylpyridin-3-ol

To a mixture of 2-phenylpyridin-3-ol (1.0 eq) and Na$_2$CO$_3$ (2.0 eq) in THF/H$_2$O (4:1, 0.15 M) was added I2 (1.1 eq) in portions, and the mixture was stirred at r.t for 0.5 h before diluted with DCM. The organic layer was separated, washed with brine, and then dried over Na$_2$SO$_4$. The crude product was purified by flash chromatography on silica gel (eluent: petroleum ether/EtOAc=4:1) to give the title compound as a yellow solid. LCMS (m/z): [M+H]$^+$=297.9.

Step 3: 2-phenyl-6-vinylpyridin-3-ol

A mixture of 6-iodo-2-phenylpyridin-3-ol (1.0 eq), CH$_2$CHBF$_3$K (1.5 eq), K$_2$CO$_3$ (2.0 eq) and PdCl$_2$(dppf)(0.1 eq) in dioxane/H$_2$O (4:1, 0.1 M) was stirred at 95° C. for 16 h under an Ar atmosphere. The mixture was diluted with DCM, and the organic layer was separated, and then dried over Na$_2$SO$_4$. The crude product was purified by flash chromatography on silica gel (eluent: petroleum ether/EtOAc=3:1) to give the title compound as a yellow solid. LCMS (m/z): [M+H]$^+$=198.0.

Step 4: 6-ethyl-2-phenylpyridin-3-ol

A mixture of 2-phenyl-6-vinylpyridin-3-ol (1.0 eq) and Pd/C (10% wt, 0.02 eq) in MeOH (0.06 M) was stirred under $H_2$ at r.t for 1 h. The solid was filtered off, and the filtrate was concentrated to give the title compound as a white solid. LCMS (m/z): [M+H]=200.0.

Step 5: 3-((2-chloropyridin-4-yl)oxy)-6-ethyl-2-phenylpyridine

A mixture of 6-ethyl-2-phenylpyridin-3-ol (1.0 eq), 2,4-dichloropyridine (2.0 eq) and $Cs_2CO_3$ (2.0 eq) in DMSO (0.1 M) was stirred at 130° C. for 2 h under Ar. The mixture was diluted with EtOAc and water. The organic layer was separated, and dried over $Na_2SO_4$. The crude product was purified by prepare TLC (eluent: petroleum ether/EtOAc=4:1) to give the title compound as a colorless oil. LCMS (m/z): [M+H]$^+$=311.1.

The following intermediates were prepared according to the procedure described in Intermediate A45.

| Intermediate | Structure | LCMS (m/z) [M + 1]$^+$ and/or $^1$H NMR |
|---|---|---|
| A46 | 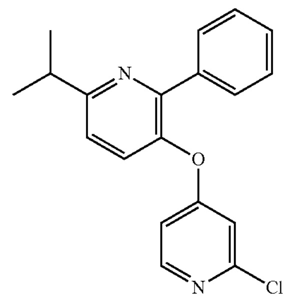 | LCMS (m/z): [M + 1]$^+$ = 315 |
| A47 | 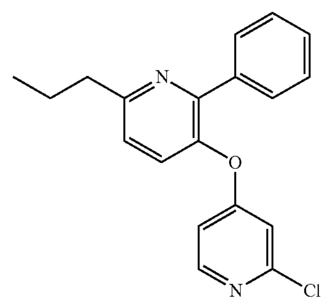 | LCMS (m/z): [M + 1]$^+$ = 315 |
| A48 | 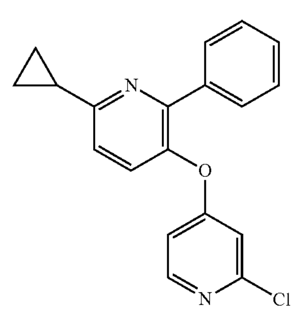 [SMILES: Clc1cc(Oc2ccc(C3CC3)nc2-c2ccccc2)ccn1] | LCMS (m/z): [M + 1]$^+$ = 315.3 |

Intermediate A49: 3-((2-chloropyridin-4-yl)oxy)-6-ethyl-2,5-dimethylpyridine

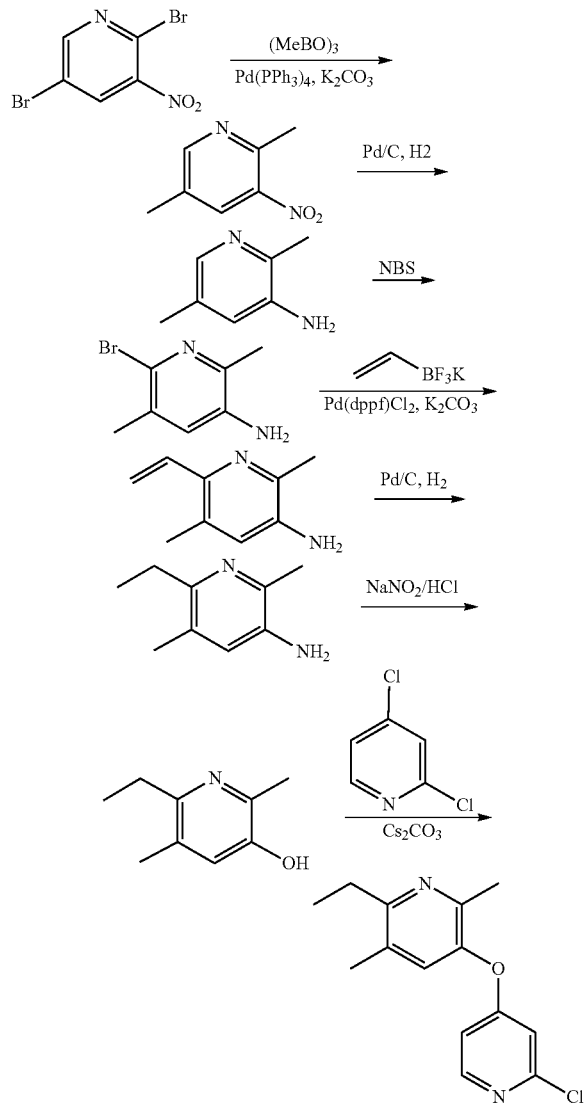

Step 1: 2,5-dimethyl-3-nitropyridine

A mixture of 2,5-dibromo-3-nitropyridine (1.0 eq), trimethylboroxine (3.0 eq), Pd(dppf)Cl$_2$ (0.04 eq) and K$_2$CO$_3$ (6.0 eq) in dioxane (0.25 M) was stirred at 100° C. for 16 h under an Ar atmosphere. The mixture was worked up, and the cured product was purified by flash chromatography on silica gel (eluent: petroleum ether/EtOAc=5:1) to give the title compound as a yellow oil. LCMS (m/z): [M+H]$^+$=153.

Step 2: 2,5-dimethylpyridin-3-amine

A mixture of 2,5-dimethyl-3-nitropyridine (1.0 eq), 10 percent Pd/C (10% wt, 0.01 eq) in MeOH (0.3 M) was stirred under H$_2$ for 16 h AT RT. The solid was filtered off, and the filtrate was concentrated to give the title compound as a yellow solid. LCMS (m/z): [M+H]$^+$=123.

Step 3: 6-bromo-2,5-dimethylpyridin-3-amine

At 0° C., to a stirring solution of 2,5-dimethylpyridin-3-amine (1.0 eq) in MeCN (0.4 M) was added NBS (1.0 eq) in portions under Ar. The mixture was stirred at 0° C. for 1 h, and then quenched with water. Acetonitril was removed, and the aqueous layer was extracted with EtOAc. The combined organic layer was washed with brine, and then dried over Na$_2$SO$_4$. The title compound was obtained upon removal of solvent. LCMS (m/z): [M+H]$^+$=201.

Step 4: 2,5-dimethyl-6-vinylpyridin-3-amine

A mixture of 6-bromo-2,5-dimethylpyridin-3-amine (1.0 eq), potassium trifluoro(vinyl)borate (1.2 eq), Pd(dppf)Cl$_2$ (0.05 eq) and K$_2$CO$_3$ (3.0 eq) in dioxane/water (14:1, 0.27 M) was stirred at 100° C. for 16 h under Ar. The mixture was worked up, and the crude product was purified by flash chromatography on silica gel (eluent: petroleum ether/EtOAc=5:1) to give the title compound as a yellow solid. LCMS (m/z): [M+H]$^+$=150.

Step 5: 6-ethyl-2,5-dimethylpyridin-3-amine

A mixture of 2,5-dimethyl-6-vinylpyridin-3-amine (1.0 eq), Pd/C (10% wt, 0.01 eq) in MeOH (0.32 M) was stirred under H$_2$ at r.t for 16 h. The solid was filtered off, and the filtrate was concentrated to give the title compound as a yellow solid. LCMS (m/z): [M+H]$^+$=151.

Step 6: 6-ethyl-2,5-dimethylpyridin-3-ol

At 0° C., to a solution of 6-ethyl-2,5-dimethylpyridin-3-amine (1.0 eq) in 1N HCl (0.16 M) was added dropwise a solution of NaNO$_2$ (1.0 eq) in H$_2$O (2.4 M). The mixture was stirred at 0° C. for 1 h, then heated to 70° C. for 16 h. After adjusted pH to ~8 with 1.0 M aq. NaOH, the mixture was concentrated, and the residue was dissolved in DCM/MeOH (v/v=10/1). The solid was filtered off, and the filtrate was concentrated to give the title compound as a yellow solid. LCMS (m/z): [M+H]$^+$=152.

Step 7: 3-((2-chloropyridin-4-yl)oxy)-6-ethyl-2,5-dimethylpyridine

A mixture of 6-ethyl-2,5-dimethylpyridin-3-ol (1.0 eq), 2,4-dichloropyridine (1.0 eq) and Cs$_2$CO$_3$ (2.0 eq) in DMF (0.25 M) was stirred at 100° C. for 16 h under Ar, and then he mixture was diluted with water and EtOAc. The organic layer separated, and the aqueous layer was extracted with EtOAc. The combined organic layers were washed with brine, and then dried over Na$_2$SO$_4$. The crude product was purified by flash chromatography on silica gel (eluent: petroleum ether/EtOAc=2:1) to give the title compound as a yellow oil. LCMS (m/z): [M+H]$^+$=263.

Intermediate A50: 3-chloro-5-((2-chloropyridin-4-yl)oxy)-2-ethyl-6-methylpyridine

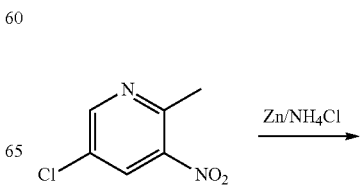

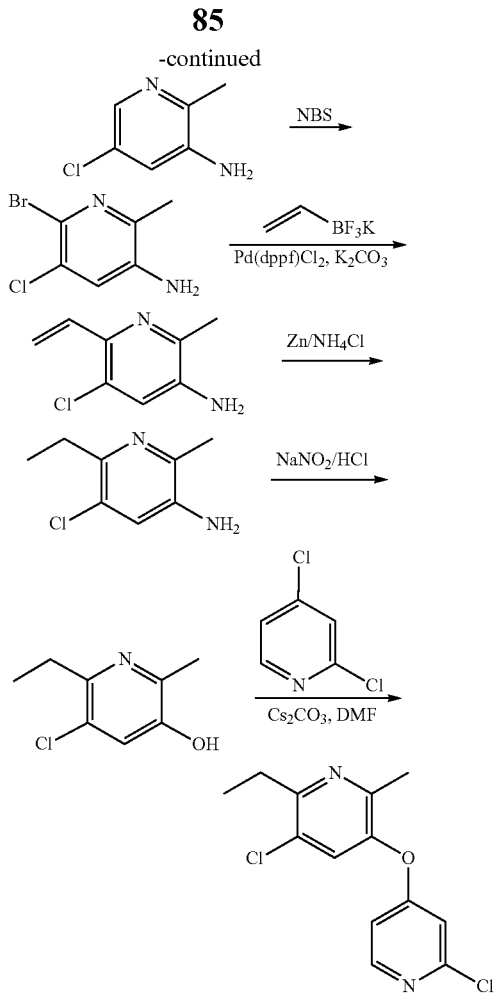

Step 1: 5-chloro-2-methylpyridin-3-amine

To a solution of 5-chloro-2-methyl-3-nitropyridine (30.0 g, 0.17 mol, 1.0 eq) in EtOH/sat. aqueous NH$_4$Cl (1:4, 0.7 M) was added Zn powder (4.0 eq). The reaction mixture was stirred for 16 h at r.t. before filtered through a pad of celite. The filtrate was extracted with EtOAc, and the combined organic layers was dried over anhydrous Na$_2$SO$_4$. The crude product was purified by flash chromatography on silica gel (eluent: DCM/MeOH=100:1) to give the title compound as a white solid. LCMS (m/z): [M+H]$^+$=142.0.

Step 2: 6-bromo-5-chloro-2-methylpyridin-3-amine

At 0° C., to a solution of 5-chloro-2-methylpyridin-3-amine (1.0 eq) in acetonitrile (0.5 M) was added NBS (1.0 eq) portionwise. The reaction mixture was stirred at 0° C. for 2 h, and then quenched with Ice-water (100 mL). Part of solvent was removed under reduced pressure, and the residue was extracted with EtOAc. The combined organic layers was dried over anhydrous Na$_2$SO$_4$. The crude product was purified by flash chromatography on silica gel (eluent: petroleum ether/EtOAc=5:1) to give the title compound as a white solid. LCMS (m/z): [M+H]$^+$=221.0.

Step 3: 5-chloro-2-methyl-6-vinylpyridin-3-amine

A mixture of 6-bromo-5-chloro-2-methylpyridin-3-amine (1.0 eq), potassium trifluoro(vinyl)borate (1.2 eq), Pd(dppf)Cl$_2$ (0.05 eq) and K$_2$CO$_3$ (2.5 eq) in dioxane/water (5:1, 0.4 M) was stirred at 80° C. for 2 h under an atmosphere. The mixture was filtered through a pad of celite, and the filtrate was extracted with EtOAc. The combined organic layers was dried over Na$_2$SO$_4$. The crude product was purified by flash chromatography on silica gel (eluent: petroleum ether/EtOAc=8:1) to give the title compound as a colorless oil. LCMS (m/z): [M+H]$^+$=169.0.

Step 4: 5-chloro-6-ethyl-2-methylpyridin-3-amine

To a solution of 5-chloro-2-methyl-6-vinylpyridin-3-amine (1.0 eq) and sat. aq. NH$_4$Cl/EtOH (2:1, 0.5 M) was added Zn powder (5.0 eq). The reaction mixture was stirred at 50° C. for 16 h. The mixture was filtered through a pad of celite, and the filtrate was extracted with EtOAc. The combined organic layers was dried over anhydrous Na$_2$SO$_4$. The crude product was purified by flash chromatography on silica gel (eluent: 100% DCM) to give the title compound as a colorless oil. LCMS (m/z): [M+H]$^+$=171.0.

Step 5: 5-chloro-6-ethyl-2-methylpyridin-3-ol

At 0° C., to a solution of 5-chloro-6-ethyl-2-methylpyridin-3-amine (1.0 eq) in 1N aq. HCl (0.25 M) was added dropwise a solution of NaNO$_2$ (1.5 eq) in water (3.0 M), and the mixture was stirred for 2 h at 0° C., and then 16h at 70° C. Saturated aq. NaHCO$_3$ was added, and the resulting mixture was extracted with DCM. The combined organic layer was dried over anhydrous Na$_2$SO$_4$. The crude product was purified by flash chromatography on silica gel (eluent: DCM/MeOH=100:1) to give the title compound as a white solid. LCMS (m/z): [M+H]$^+$=172.0.

Step 6: 3-chloro-5-((2-chloropyridin-4-yl)oxy)-2-ethyl-6-methylpyridine

To a solution of 5-chloro-6-ethyl-2-methylpyridin-3-ol (1.0 eq) in DMF (0.4 M) was added 2,4-dichloropyridine (1.2 eq) and Cs$_2$CO$_3$ (2.5 eq). The reaction mixture was stirred at 100° C. for 16 h under an Ar atmosphere, and cooled to rt. Ice-water (100 mL) was added, and the resulting mixture was extracted with EtOAc. The combined organic layer was washed with brine, and then dried over Na$_2$SO$_4$. The crude product was purified by prepare TLC (eluent: petroleum ether/EtOAc=10:1) to give the title compound as a white solid. LCMS (m/z): [M+H]$^+$=283.1; $^1$H NMR (400 MHz, CDCl$_3$) δ 8.27 (d, J=5.6 Hz, 1H), 7.34 (s, 1H), 6.77 (d, J=2.0 Hz, 1H), 6.74 (dd, J=6.0, 2.4 Hz, 1H), 2.96 (q, J=7.6 Hz, 2H), 2.37 (s, 3H), 1.32 (t, J=7.2 Hz, 3H).

The following intermediates were prepared according to the procedure described in Intermediate A12.

| Intermediate | Structure | LCMS [M + 1]⁺ and/or ¹H NMR |
|---|---|---|
| A51 | 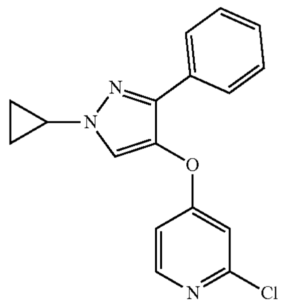 [SMILES: Clc1cc(Oc2cn(C3CC3)nc2-c2ccccc2)ccn1] | LCMS (m/z): [M + 1]⁺ = 312.2; ¹H NMR (400 MHz, CDCl₃) δ 8.20 (d, J = 6.0 Hz, 1H), 7.74-7.70 (m, 2H), 7.45 (s, 1H), 7.35-7.24 (m, 3H), 6.92 (d, J = 2.0 Hz, 1H), 6.86 (dd, J = 5.6, 2.4 Hz, 1H), 3.69-3.64 (m, 1H), 1.26-1.20 (m, 2H), 1.12-1.07 (m, 2H). |
| A52 | 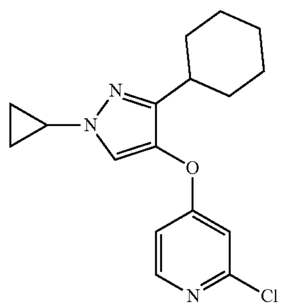 [SMILES: Clc1cc(Oc2cn(C3CC3)nc2C2CCCCC2)ccn1] | LCMS (m/z): [M + 1]⁺ = 318.2 |
| A53 | 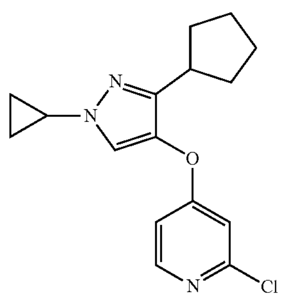 [SMILES: Clc1cc(Oc2cn(C3CC3)nc2C2CCCC2)ccn1] | LCMS (m/z): [M + 1]⁺ = 304 |
| A54 | 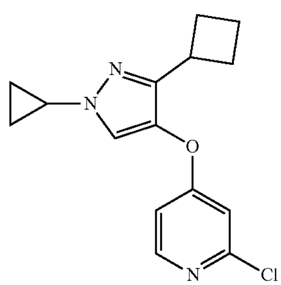 [SMILES: Clc1cc(Oc2cn(C3CC3)nc2C2CCC2)ccn1] | LCMS (m/z): [M + 1]⁺ = 290 |
| A55 | 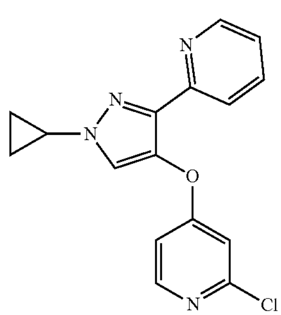 [SMILES: Clc1cc(Oc2cn(C3CC3)nc2-c2ccccn2)ccn1] | LCMS (m/z): [M + 1]⁺ = 313 |

Intermediate A56: 2-chloro-4-((1-cyclobutyl-3-phenyl-1H-pyrazol-4-yl)oxy)pyridine

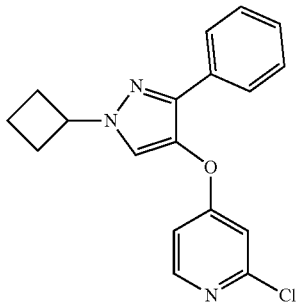 [SMILES: Clc1cc(Oc2cn(C3CCC3)nc2-c2ccccc2)ccn1]

A mixture of 2-chloro-4-((3-phenyl-1H-pyrazol-4-yl)oxy)pyridine (1.0 eq), bromocyclobutane (2.0 eq) and $K_2CO_3$ (2.0 eq) in dioxane (0.35 M) was stirred at 80° C. for 16 h. The reaction mixture cooled to RT, and diluted with EtOAc. The organic layer was separated, and dried over $Na_2SO_4$. The crude product was purified by flash chromatography on silica gel (eluent: petroleum ether/EtOAc=5:1-1:1) to give the title compound as a yellow solid. LC-MS (m/z): $[M+H]^+$=326.

The following intermediates were prepared according to the procedure described in Intermediate A56.

| Intermediate | Structure | LCMS [M + 1]$^+$ and/or $^1$H NMR |
|---|---|---|
| A57 | 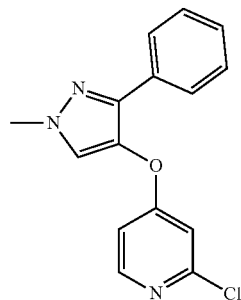 [SMILES: Cn1cc(Oc2ccnc(Cl)c2)c(-c2ccccc2)n1] | LCMS (m/z): [M + 1]$^+$ = 286.1 |
| A58 | 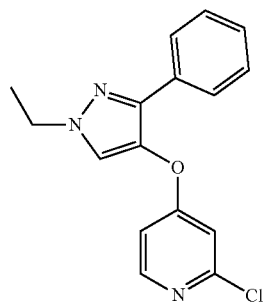 [SMILES: CCn1cc(Oc2ccnc(Cl)c2)c(-c2ccccc2)n1] | LCMS (m/z): [M + 1]$^+$ = 300.1 |
| A59 | 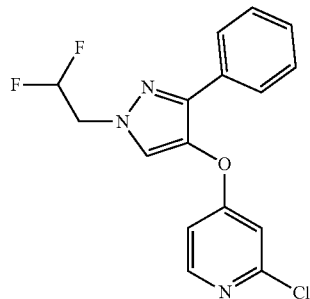 [SMILES: FC(F)Cn1cc(Oc2ccnc(Cl)c2)c(-c2ccccc2)n1] | LCMS (m/z): [M + 1]$^+$ = 336.1 |

-continued
| Intermediate | Structure | LCMS [M + 1]+ and/or 1H NMR |
|---|---|---|
| A60 | 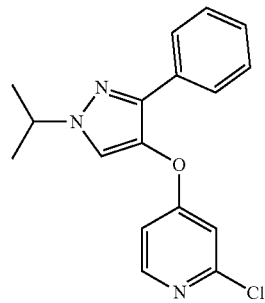 [SMILES: CC(C)n1cc(Oc2ccnc(Cl)c2)c(-c2ccccc2)n1] | LCMS (m/z): [M + 1]+ = 314.2 |
| A61 | 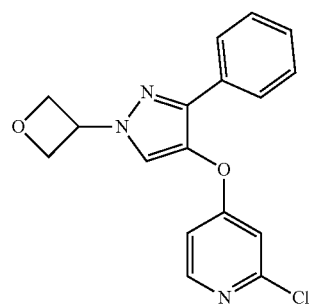 [SMILES: Clc1cc(Oc2cn(C3COC3)nc2-c2ccccc2)ccn1] | LCMS (m/z): [M + 1]+ = 328 |
| A62 | 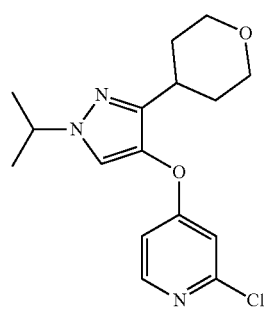 [SMILES: CC(C)n1cc(Oc2ccnc(Cl)c2)c(C2CCOCC2)n1] | LCMS (m/z): [M + 1]+ = 322.1 |
| A63 | 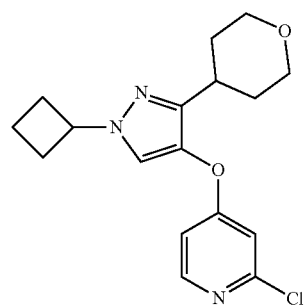 [SMILES: Clc1cc(Oc2cn(C3CCC3)nc2C2CCOCC2)ccn1] | LCMS (m/z): [M + 1]+ = 334 |

Intermediate A64: 2-chloro-4-((1-(difluoromethyl)-3-phenyl-1H-pyrazol-4-yl)oxy)pyridine

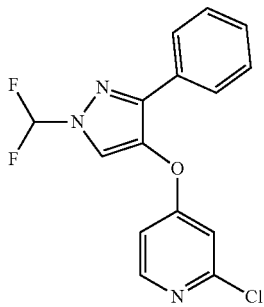 [SMILES: FC(F)n1cc(Oc2ccnc(Cl)c2)c(-c2ccccc2)n1]

A mixture of 2-chloro-4-((3-phenyl-1H-pyrazol-4-yl)oxy)pyridine (1.0 eq), diethyl (bromodifluoromethyl)phosphonite (10 eq), KF (2.0 eq) and NaI (1.0 eq) in MeCN (0.2 M) was stirred at 80° C. overnight under an Ar atmosphere. The mixture was filtered through a pad of celite, and the filtrate was concentrated. The residue was purified by flash chromatography on silica gel (eluent: petroleum ether/EtOAc=5:1) to give the title compound as a yellow oil. LCMS (m/z): $[M+1]^+$=322.1.

Intermediate A65: 3-((2-chloropyridin-4-yl)oxy)-2-methyl-6-phenylpyridine

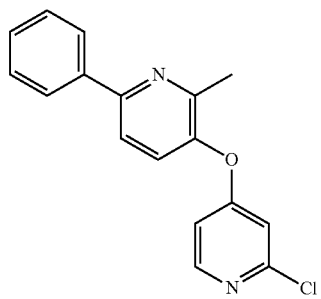 [SMILES: Cc1nc(-c2ccccc2)ccc1Oc1ccnc(Cl)c1]

Step 1: 2-methyl-6-phenylpyridin-3-ol

A mixture of 6-iodo-2-methylpyridin-3-ol (step 1 of Intermediate A16, 1.0 eq), phenylboronic acid (1.05 eq), Pd(dppf)Cl$_2$ (0.1 eq) and K$_2$CO$_3$ (3.0 eq) in dioxane/H$_2$O (8:1, 0.61 M) was stirred at 115° C. for 16h under Ar. The mixture was filtered, and the filtrate was concentrated. The reside was purified by flash chromatography on silica gel (petroleum ether:EtOAc=10:1) to give the title compound as a white solid.

Step 2: 3-((2-chloropyridin-4-yl)oxy)-2-methyl-6-phenylpyridine

A mixture of 2-methyl-6-phenylpyridin-3-ol (1.0 eq), 2,4-dichloropyridine (1.0 eq) and Cs$_2$CO$_3$ (2.0 eq) in DMF (0.36 M) was stirred at 115° C. for 16h under Ar. The mixture was filtered, and the filtrate was treated with water, extracted with EtOAc. The combined organic layer was dried over Na$_2$SO$_4$. The crude product was purified by flash chromatography on silica gel (petroleum ether:EtOAc=20:1) to give the title compound as a colorless oil.

Intermediate A66: 3-((2-chloropyridin-4-yl)oxy)-6-methyl-2-(1-methyl-1H-pyrazol-4-yl)pyridine

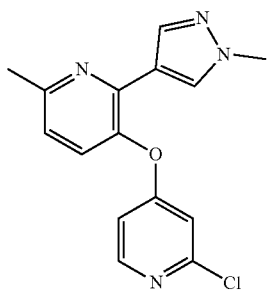

A mixture of 3-((2-chloropyridin-4-yl)oxy)-2-iodo-6-methylpyridine (Step 1 of Intermediate A3, 500 mg, 1.45 mmol, 1.0 eq), (1-methyl-1H-pyrazol-4-yl)boronic acid (1.2 eq), Pd(dppf)Cl$_2$ (0.1 eq), Na$_2$CO$_3$ (2.0 eq) in dioxane/H$_2$O (10:1, 0.13 M) was stirred overnight at 100° C. under Ar. The solid was filtered off, and the filtrate was diluted with EtOAc, washed with water, brine, and then dried over Na$_2$SO$_4$. The crude product was purified by flash chromatography on silica gel to give the title compound. LC-MS (m/z): $[M+H]^+$=301.1.

Intermediate B1: methyl 3-(3-aminophenyl)propanoate

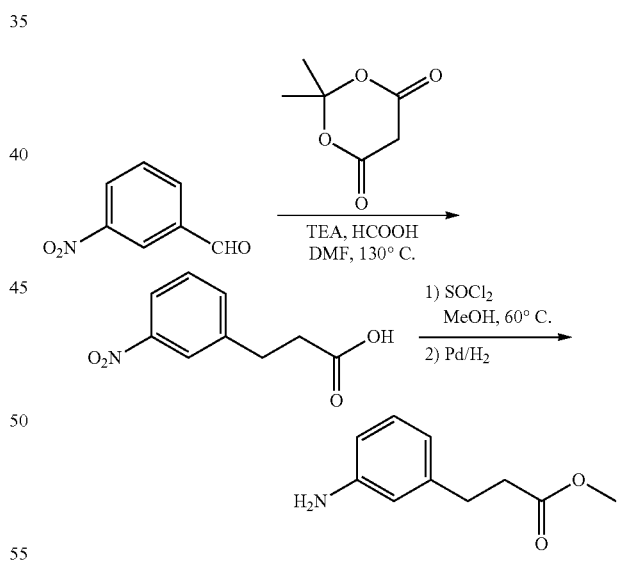

Step 1: 3-(3-nitrophenyl)propanoic acid

At RT, TEA (1.4 eq) was added dropwise to a stirring HCOOH (3.5 eq). The resulting reagent was added to a solution of 3-nitrobenzaldehyde (1.0 eq), 2,2-dimethyl-1,3-dioxane-4,6-dione (1.0 eq) in DMF (2.5 M). The reaction mixture was heated at 130° C. for 3 h. The solution was cooled down to r.t., diluted with H$_2$O (200 mL), adjusted pH to 9 with sat. aq NaHCO$_3$, and washed with EtOAc (2×50 mL). The aqueous phase was acidified to pH to 2 with conc.

HCl. The solid precipitated was collected by filtration, washed with H$_2$O, and dried in vacuum to give the title compound as a yellow solid. LC-MS (m/z): [2M−1]$^−$=389.

Step 2: methyl 3-(3-nitrophenyl)propanoate

To a solution of above product (1.0 eq) in MeOH (0.74 M) was added SOCl$_2$ (2.0 eq) at RT. The resulting mixture was stirred at 60° C. for 2 h. Then the mixture was cooled down to r.t, concentrated under reduced pressure. The residue was diluted with H$_2$O (150 mL), and extracted with EtOAc (2×50 mL). The organic phase was washed with sat. aq NaHCO$_3$ (2×20 mL), dried over Na$_2$SO$_4$, concentrated under reduced pressure. The residue was purified by flash chromatography on silica gel (eluent: petroleum ether/EtOAc 10:1) to give the title compound as a white solid.

Step 3: methyl 3-(3-aminophenyl)propanoate

To a stirring solution of above product (1.0 eq) in MeOH (0.5 M) was added Pd/C (10% wt), and the mixture was stirred under H$_2$ for 16 h at RT. The solid was filtered off, and filtrate was concentrated. The residue was dissolved in DCM (30 mL), and treated with 4.0 M HCl/dioxane (9 mL). The mixture was concentrated, and the residue was triturated with Et$_2$O (30 mL). The solid was collected by filtration, and then dissolved in H$_2$O (100 mL). The solution was adjusted to pH about 9 with sat. aq NaHCO$_3$ and extracted with DCM (2×50 mL). The DCM layer was dried over Na$_2$SO$_4$, concentrated under reduced pressure to give the title compound as a slightly yellow oil. LC-MS (m/z): [M+1]$^+$=180.

Intermediate B2: 3-(3-aminophenyl)propanenitrile

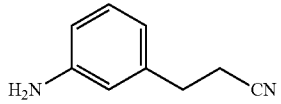 [SMILES: N#CCCc1cccc(N)c1]

Step 1: 3-(3-nitrophenyl)propanamide

To a solution of 3-(3-nitrophenyl)propanoic acid (1.0 eq) in DCM (0.25 M) was added HATU (1.2 eq), the mixture was stirred at rt for 30 min, then NH$_4$Cl (1.5 eq) and DIEA (3.0 eq) were added. The mixture was stirred at rt for 4 h then quenched with H$_2$O (50 mL). The aqueous was extracted with DCM (3×30 mL). The combined organic layer was dried over Na$_2$SO$_4$, concentrated to give the title compound as a yellow oil, which was used directly for the next step without further purification. LC-MS (m/z): [M+1]$^+$=195.

Step 2: 3-(3-nitrophenyl)propanenitrile

A mixture of 3-(3-nitrophenyl)propanamide (1.0 eq) and (CNCl)$_3$ (1.5 eq) in DMF (0.25 mM) was stirred at rt for 2 h. The reaction mixture was quenched with H$_2$O (200 mL) and extracted with EA (3×50 mL). The combined organic layer was washed with brine (60 mL) and then dried over Na$_2$SO$_4$. The solvent was removed, and the residue was purified by flash chromatography on silica gel (petroleum ether/EtOAc 4:1 to 2:1) to give the title compound as a white solid. LC-MS (m/z): [M+1]$^+$=177; $^1$H NMR (400 MHz, CDCl$_3$) δ 8.16 (d, J=8.4 Hz, 1H), 8.12 (s, 1H), 7.62 (d, J=7.6 Hz, 1H), 7.55 (t, J=8.0 Hz, 1H), 5.01 (s, 2H), 3.09 (t, J=7.2 Hz, 2H), 2.72 (t, J=7.2 Hz, 2H).

Step 3: 3-(3-aminophenyl)propanenitrile

A mixture of 3-(3-nitrophenyl)propanenitrile (1.0 eq), Zn (5.0 eq) in MeOH/NH$_4$C$_1$ (1:1, 0.4 M) was stirred at 80° C. for 16 h. The reaction was monitored by TLC. The reaction mixture was cooled to r.t and filtered. The filtrate was extracted with EA. The combined organic layer was washed with brine and dried over Na$_2$SO$_4$. The solvent was removed to give the title product as a yellow oil. LC-MS (m/z): [M+1]$^+$=147; $^1$H NMR (400 MHz, DMSO) δ 6.95 (dd, J=8.4, 7.2 Hz, 1H), 6.44 (d, J=0.8 Hz, 1H), 6.43-6.39 (m, 2H), 5.01 (s, 2H), 2.73-2.68 (m, 4H).

Intermediate B3: methyl 3-(4-aminophenyl)propanoate

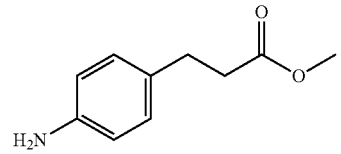

The compound was obtained following the procedure described in Intermediate B1. $^1$H NMR (400 MHz, CDCl$_3$) δ 6.98 (d, J=8.4 Hz, 2H), 6.62 (d, J=8.4 Hz, 2H), 3.66 (s, 3H), 2.84 (t, J=7.6 Hz, 2H), 2.57 (t, J=7.6 Hz, 2H).

Intermediate B4: 3-(4-aminophenyl)propanenitrile

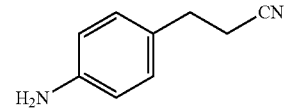 [SMILES: N#CCCc1ccc(N)cc1]

Step 1: 3-(4-nitrophenyl)propanamide

To a solution of 3-(4-nitrophenyl)propanoic acid (1.0 eq) in DCM (0.4 M) was added HATU (1.2 eq) and stirred at rt for 30 min, then NH$_4$Cl (1.5 eq) and DIEA (3.0 eq) were added. The mixture was stirred at rt for 4 h before quenched with H$_2$O (50 mL). The aqueous layer was extracted with DCM (3×30 mL) and dried over Na$_2$SO$_4$. The solvent was removed to give the title compound as a yellow oil, which was used directly to next step without further purification.

Step 2: 3-(4-nitrophenyl)propanenitrile

A mixture of 3-(4-nitrophenyl)propanamide (1.0 eq) and (CNCl)$_3$ (1.5 eq) in DMF (0.25 mM) was stirred at rt for 2 h. The solution was quenched with H$_2$O. The aqueous layer was extracted with EA (3×50 mL). The combined organic layer was washed with brine (60 mL) and dried over Na$_2$SO$_4$. The crude product was purified by flash chromatography on silica gel (eluent: petroleum ether/EtOAc 4:1 to 2:1) to give the title compound as a yellow solid. $^1$H NMR (400 MHz, DMSO) δ 8.21 (d, J=8.8 Hz, 2H), 7.60 (d, J=8.8 Hz, 2H), 3.05 (t, J=7.2 Hz, 2H), 2.90 (t, J=7.2 Hz, 2H).

Step 3: 3-(4-aminophenyl)propanenitrile

To a solution of 3-(4-nitrophenyl)propanenitrile (1.0 eq) in MeOH (0.4 M) was added Pd/C (0.1 eq). The mixture was stirred at rt for 3 h under $H_2$. The solid was filtered off, and the filtrate was concentrated to give the title compound as a yellow oil. LC-MS (m/z): $[M+1]^+=147$. $^1H$ NMR (400 MHz, DMSO) δ 6.92 (d, J=8.4 Hz, 2H), 6.51 (d, J=8.4 Hz, 2H), 4.94 (s, 2H), 2.68 (s, 4H).

Intermediate B5:
2-(3-aminophenyl)-2-methylpropanenitrile

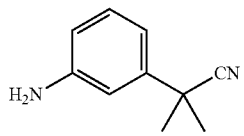

Step 1: 2-methyl-2-(3-nitrophenyl)propanenitrile

To a solution of 2-(3-nitrophenyl)acetonitrile (1.0 eq) in DMF (0.3 M) was added t-BuOK (3.0 eq) in portions at 0° C. The mixture was stirred at 0° C. for 15 min and MeI (5.0 eq) was added dropwise. Then the mixture was stirred at r.t for 2 h. The reaction was monitored by TLC. The mixture solution was quenched with $NH_4Cl$ (aq, 50 mL), extracted with EtOAc (100 mL). The organic phase was washed with brine, dried over $Na_2SO_4$. The organic phase was concentrated. The residue was purified by flash chromatography on silica gel (petroleum ether/EtOAc 8:1) to give the title compound as a yellow solid. $^1H$ NMR (400 MHz, $CDCl_3$) δ 8.24 (t, J=2.0 Hz, 1H), 8.14 (ddd, J=8.0, 2.0, 1.2 Hz, 1H), 7.82 (ddd, J=8.0, 2.0, 1.2 Hz, 1H), 7.54 (t, J=8.0 Hz, 1H), 3.74 (s, 2H), 2.83 (t, J=7.2 Hz, 2H), 2.57 (t, J=7.2 Hz, 2H).

Step 2: 2-(3-aminophenyl)-2-methylpropanenitrile

A mixture of above product (1.0 eq), Zn (5.0 eq), $NH_4Cl$ (10.0 eq) in MeOH—$H_2O$ (2:1, 0.15 mM) was stirred at 80° C. for 16 h. The reaction was monitored by LC-MS. The mixture solution was filtered, washed with EtOAc (10 mL). The filtrate was extracted with EtOAc (50 mL), and the organic layer was washed with brine, dried with $Na_2SO_4$, concentrated to give the residue. The residue was purified by flash chromatography on silica gel (petroleum ether/EtOAc 5:1) to give the title product as a yellow oil. LC-MS (m/z): $[M+H]^+=161$. $^1H$ NMR (400 MHz, $CDCl_3$) δ 7.08 (t, J=8.0 Hz, 1H), 6.76-6.72 (m, 2H), 6.57-6.53 (m, 1H), 3.38 (s, 2H), 1.61 (s, 6H).

Intermediate B6:
3-(3-amino-4-fluorophenyl)propanenitrile

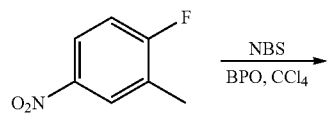

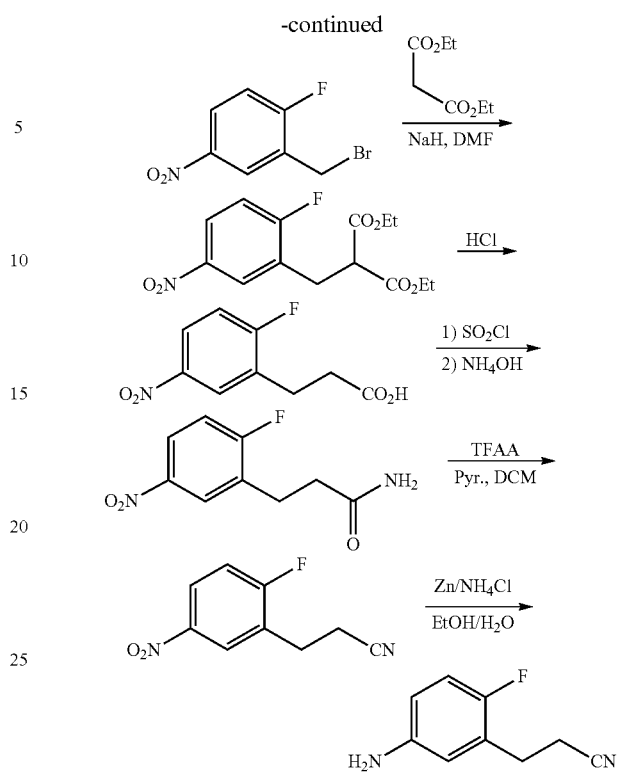

Step 1: 2-(bromomethyl)-1-fluoro-4-nitrobenzene

A mixture of 1-fluoro-2-methyl-4-nitrobenzene (1.0 eq), NBS (1.1 eq) and BPO (benzoyl peroxide, 0.1 eq) in $CCl_4$ (0.86 M) was stirred at 95° C. for 16 h under Ar. The reaction was monitored by TLC. Then the mixture was filtered. The filtrate was concentrated under reduced pressure. The residue was purified by flash chromatrography on silica gel (eluent: petroleum ether/EtOAc 1:0 to 50:1) to give the title compound as a white solid.

Step 2: diethyl 2-(2-fluoro-5-nitrobenzyl)malonate

At 0° C., to a stirring solution NaH (60% in oil, 1.0 eq) in DMF (0.22 M) was added a solution of diethylmalonate (2.0 eq) in DMF (2 M). The mixture was stirred at 0° C. for 0.5 h, and then 2-(bromomethyl)-1-fluoro-4-nitrobenzene (1.0 eq) in DMF (0.34 M) was added dropwise to the above mixture and stirred for another 0.5 h. The reaction was monitored by TLC. The resulting mixture was diluted with ice-water and extracted with EtOAc. The organic layer was washed with brine, and then dried over $Na_2SO_4$. The solvent was removed under reduced pressure to give the title compound as an oil.

Step 3: 2-(2-fluoro-5-nitrophenyl)propanoic acid

A mixture of diethyl 2-(2-fluoro-5-nitrobenzyl)malonate (1.0 eq) in 6N aq. HCl (31 eq, 0.19 M) was heated at 120° C. for 16 h. The reaction was monitored by LC-MS. The reaction mixture was cooled to RT, diluted with water and extracted with EtOAc. The organic layer was washed with brine, and then dried over $Na_2SO_4$. The solvent was removed under reduced pressure, and the residue was purified by flash chromatography on silica gel (eluent: petroleum ether/EtOAC 3:1) to give the title compound. $^1$H NMR (400 MHz, CDCl$_3$) δ 8.20-8.12 (m, 2H), 7.26-7.16 (m, 1H), 3.07 (t, J=7.6 Hz, 2H), 2.75 (t, J=7.6 Hz, 2H).

Step 4: 2-(2-fluoro-5-nitrophenyl)propanamide

A mixture of 2-(2-fluoro-5-nitrophenyl)propanoic acid (1.0 eq), SOCl$_2$ (2.0 eq) and cat. DMF (1 drop) in tolene (0.42 M) was stirred at 85° C. for 1 h. The reaction was monitored by TLC. The mixture was concentrated under reduced pressure. The residue was retaken in Et$_2$O (0.8 M), and was added dropwise to a stirring solution of NH$_3$H$_2$O (30 mL) at 0° C. The resulting mixture was stirred at 0° C. for 0.5 h. The reaction was monitored by LC-MS to the completion. The reaction mixture was extracted with EtOAc. The organic layer was dried over Na$_2$SO$_4$, concentrated under reduced pressure to give the title compound.

Step 5: 2-(2-fluoro-5-nitrophenyl)propanenitrile

At 0° C., to a solution of of 2-(2-fluoro-5-nitrophenyl) propanamide (1.0 eq) and pyridine (2.5 eq) in DCM (0.39 M) was added dropwise of TFAA (2.5 eq). The resulting mixture was stirred at 0° C. for 0.5 h. TLC indicated that the reaction was completed. The mixture was washed with 1.0 M aq. HCl, brine, and then dried over Na$_2$SO$_4$. The solvent was removed under reduced pressure to give the title compound.

Step 6: 2-(5-amino-2-fluorophenyl)propanenitrile

A mixture of 2-(2-fluoro-5-nitrophenyl)propanenitrile (1.0 eq), Zn (5.0 eq) and NH$_4$Cl (10 eq) in EtOH/H$_2$O (v/v=5:1, 0.5M) was stirred at 80° C. for 0.5h. The mixture was filtered. The filtrate was diluted with water and extracted with EtOAc. The organic layer was dried over Na$_2$SO$_4$, concentrated under reduced pressure to give the title compound. LCMS (m/z): [M+H]$^+$=165; $^1$H NMR (400 MHz, CDCl$_3$) δ 6.82-8.87 (m, 2H), 6.52-6.56 (m, 2H), 2.90 (t, J=7.6 Hz, 2H), 2.62 (t, J=7.2 Hz, 2H).

The following compounds were prepared according to the procedure described in Intermediate B6.

Intermediate B10: methyl 3-(5-amino-2-fluorophenyl)propanoate

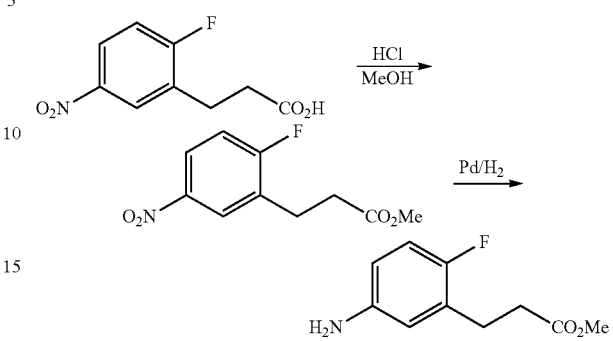

Step 1: methyl 3-(2-fluoro-5-nitrophenyl)propanoate

To a solution of 3-(2-fluoro-5-nitrophenyl)propanoic acid (1.0 eq) in 2.5 M HCl/MeOH (6.7 eq 0.37 M) was stirred at rt for 1 h. The reaction was monitored by TLC. The reaction mixture was concentrated under reduced pressure to give the title compound.

Step 2: methyl 3-(5-amino-2-fluorophenyl)propanoate

To a solution of mixture of methyl 3-(2-fluoro-5-nitrophenyl)propanoate (1.0 eq) in MeOH (0.35 M) was added Pd/C (10% wt, 0.02 eq). The reaction mixture was stirred under hydrogent at rt for 3 h. The reaction was monitored by TLC. The solid was filtered off, and the filtrate was concentrated under reduced pressure to give the title compound as a brown oil. LC-MS (m/z): [M+H]$^+$=198.3; $^1$H NMR (400 MHz, CDCl$_3$) δ 6.77 (t, J=7.6 Hz, 1H), 6.53-6.61 (m, 2H), 3.64 (s, 3H), 2.83 (t, J=7.6 Hz, 2H), 2.58 (t, J=8.0 Hz, 2H).

The following compounds were prepared according to the procedure described in Intermediate B10.

| Intermediate | Structure | LCMS and/or $^1$HNMR |
|---|---|---|
| B7 | ![F, H2N, CN structure] | $^1$H NMR (400 MHz, CDCl$_3$) δ 6.93 (dd, J = 10.8, 8.0 Hz, 1H), 6.64 (dd, J = 8.4, 2.4 Hz, 1H), 6.53 (ddd, J = 8.4, 4.4, 2.4 Hz, 1H), 3.74 (s, 2H), 2.83 (t, J = 7.2 Hz, 2H), 2.57 (t, J = 7.2 Hz, 2H). |
| B8 | ![H2N, F, CN structure] | LCMS (m/z): [M + H]$^+$ = 165<br>$^1$H NMR (400 MHz, DMSO) δ 6.81 (t, J = 7.7 Hz, 1H), 6.66 (td, J = 8.7 Hz, 1.6 Hz, 1H), 6.51-6.41 (m, 1H), 5.12 (s, 2H), 2.86-2.80 (m, 2H), 2.79-2.74 (m, 2H). |
| B9 | ![Cl, H2N, CN structure] | $^1$H NMR (400 MHz, CDCl$_3$) δ 8.137-8.143 (m, 1H), 8.05-8.08 (m, 1H), 7.52 (d, J = 8.0 Hz, 1H), 3.14 (t, J = 7.2 Hz, 2H), 2.69 (t, J = 7.2 Hz, 2H). |

| Intermediate | Structure | LCMS and/or ¹H NMR |
|---|---|---|
| B11 | F-phenyl with H₂N and CH₂CH₂C(O)OCH₃ | LCMS (m/z): [M + 1]⁺ = 198; ¹H NMR (400 MHz, DMSO-d6) δ 6.85 (dd, J = 11.6, 8.4 Hz, 1H), 6.58 (dd, J = 8.8, 2.0 Hz, 1H), 6.33 (ddd, J = 8.4, 4.4, 2.0 Hz, 1H), 5.02 (s, 2H), 3.58 (s, 3H), 2.68 (t, J = 7.6 Hz, 2H), 2.54 (t, J = 7.6 Hz, 2H) |
| B12 | H₂N, F-phenyl with CH₂CH₂C(O)OCH₃ | LCMS (m/z): [M + H]⁺ = 198; ¹H NMR (400 MHz, DMSO) δ 6.76 (t, J = 7.7 Hz, 1H), 6.62 (t, J = 8.3 Hz, 1H), 6.39 (t, J = 6.5 Hz, 1H), 5.04 (s, 2H), 3.59 (s, 3H), 2.80 (t, J = 7.6 Hz, 2H), 2.58 (t, J = 7.7 Hz, 2H). |
| B13 | Cl-phenyl with H₂N and CH₂CH₂C(O)OCH₃ | LCMS (m/z): [M + 1]⁺ = 214.1 |

Intermediate B14: 3-(6-amino pyridin-2-yl)propanenitrile

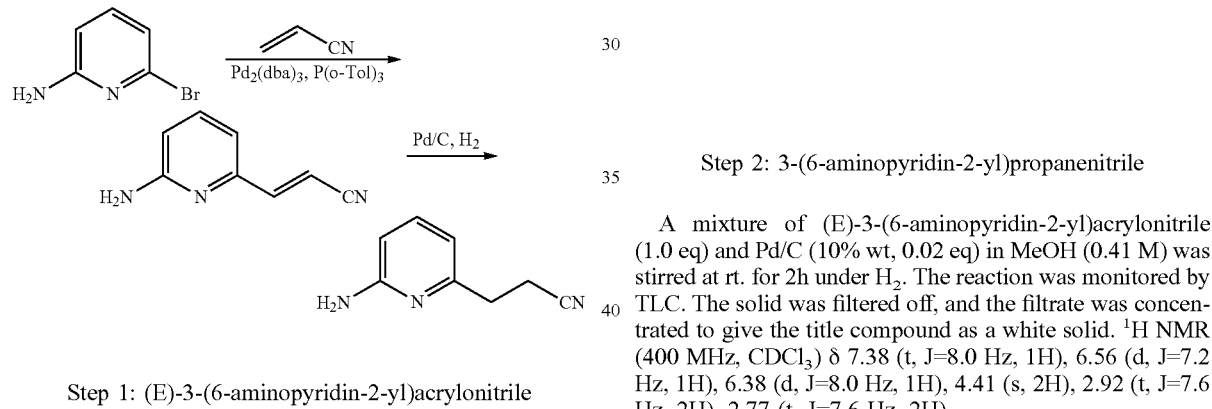

Step 1: (E)-3-(6-aminopyridin-2-yl)acrylonitrile

A mixture of 6-bromopyridin-2-amine (1.0 eq), acrylonitrile (3.0 eq), Pd₂(dba)₃ (0.1 eq), tri-o-tolylphosphine (0.3 eq) in DMF (0.57 M) was heated at 140° C. overnight. The mixture was cooled to rt. The crude product was purified by flash chromatography on silica gel (petroleum ether/EtOAc 1:1) to give title compound as a yellow solid.

Step 2: 3-(6-aminopyridin-2-yl)propanenitrile

A mixture of (E)-3-(6-aminopyridin-2-yl)acrylonitrile (1.0 eq) and Pd/C (10% wt, 0.02 eq) in MeOH (0.41 M) was stirred at rt. for 2h under H₂. The reaction was monitored by TLC. The solid was filtered off, and the filtrate was concentrated to give the title compound as a white solid. ¹H NMR (400 MHz, CDCl₃) δ 7.38 (t, J=8.0 Hz, 1H), 6.56 (d, J=7.2 Hz, 1H), 6.38 (d, J=8.0 Hz, 1H), 4.41 (s, 2H), 2.92 (t, J=7.6 Hz, 2H), 2.77 (t, J=7.6 Hz, 2H).

The following intermediates were prepared according to the procedure described in intermediate B14.

| Intermediate | Structure | LCMS and/or ¹H NMR |
|---|---|---|
| B15 | 2-aminopyridine-4-yl-CH₂CH₂CN | ¹H NMR (400 MHz, CDCl₃) δ 8.02 (d, J = 5.2 Hz, 1H), 6.52 (d, J = 5.2 Hz, 1H), 6.37 (s, 1H), 4.49 (s, 2H), 2.83 (t, J = 7.6 Hz, 2H), 2.61 (t, J = 7.6 Hz, 2H). |
| B16 | 5-amino-3-pyridinyl-CH₂CH₂CN | ¹H NMR (400 MHz, CDCl₃) δ 8.01 (d, J = 2.8 Hz, 1H), 7.89 (d, J = 1.6 Hz, 1H), 6.87 (t, J = 2.4 Hz, 1H), 3.79 (s, 2H), 2.87 (t, J = 7.6 Hz, 2H), 2.61 (t, J = 7.2 Hz, 2H). |

Intermediate B17: methyl 3-(6-aminopyridin-2-yl)propanoate

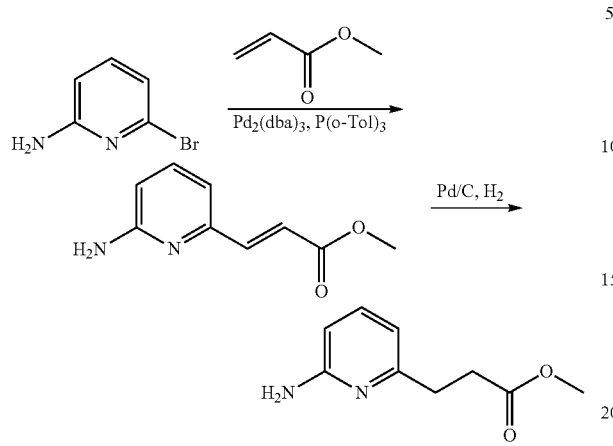

Step 1: methyl (E)-3-(6-aminopyridin-2-yl)acrylate

A mixture of 6-bromopyridin-2-amine (3.0 g, 17.34 mmol, 1.0 eq), methyl acrylate (4.5 mL, 52.02 mmol, 3.0 eq), Pd$_2$(dba)$_3$ (0.1 eq), tri-o-tolylphosphine (0.3 eq) in DMF (0.58 M) was heated at 140° C. overnight. The mixture was cooled to rt, and the solvent was removed under reduced pressure. The residue was purified by flash chromatography on silica gel (petroleum ether/EtOAc 2:1) to give the title compound as a yellow solid.

Step 2: methyl 3-(6-aminopyridin-2-yl)propanoate

A mixture of methyl (E)-3-(6-aminopyridin-2-yl)acrylate (1.0 eq) and Pd/C (10% wt, 0.02 eq) in MeOH (0.36 M) was stirred at rt. for 4h under H$_2$. The reaction was monitored by TLC. The solid was filtered off, and the filtrate was concentrated to give the title compound as a yellow oil. $^1$H NMR (400 MHz, CDCl$_3$) δ 7.33 (t, J=7.6 Hz, 1H), 6.52 (d, J=7.2 Hz, 1H), 6.32 (d, J=8.0 Hz, 1H), 4.36 (s, 2H), 3.67 (s, 3H), 2.93 (t, J=7.2 Hz, 2H), 2.73 (t, J=7.2 Hz, 2H).

The following intermediates were prepared according to the procedure described in intermediate B17.

Intermediate B20: ethyl 3-(4-aminopyridin-2-yl)propanoate

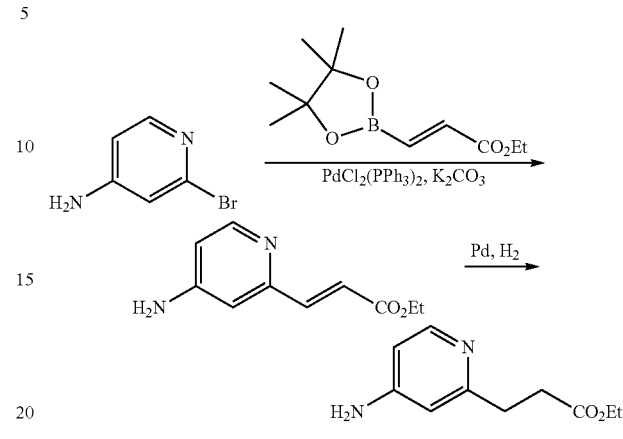

Step 1: ethyl (E)-3-(4-aminopyridin-2-yl)acrylate

A mixture of 2-bromopyridin-4-amine (842 mg, 4.86 mmol, 1.0 eq), ethyl (E)-3-(4,4,5,5-tetramethyl-1,3,2-dioxaborolan-2-yl)acrylate (0.95 eq), Pd(PPh$_3$)$_2$Cl$_2$ (0.1 eq), K$_2$CO$_3$ (2.5 eq) in dioxane/H$_2$O (5:1, 0.4 M) was heated at 95° C. for 16h. The reaction mixture was cooled to rt, and the solvent was removed under reduced pressure. The residue was purified by flash chromatography on silica gel (petroleum ether/EtOAc 1:4) to give the title compound as a yellow solid.

Step 2: ethyl 3-(4-aminopyridin-2-yl)propanoate

A mixture of ethyl (E)-3-(4-aminopyridin-2-yl)acrylate (1.0 eq) and Pd/C (0.02 eq) in MeOH (0.3 M) was stirred at rt. for 2h under H$_2$. The reaction was monitored by TLC. The solid was filtered off, and the filtrate was concentrated under reduced pressure to give the title compound as a brown oil. $^1$H NMR (400 MHz, CDCl$_3$) δ 8.13 (d, J=5.6 Hz, 1H), 6.43 (d, J=2.0 Hz, 1H), 6.38-6.36 (m, 1H), 3.66 (s, 3H), 2.96 (t, J=7.6 Hz, 2H), 2.75 (t, J=7.6 Hz, 2H).

| Intermediate | Structure | LCMS and/or $^1$H NMR |
| --- | --- | --- |
| B18 | ![structure] | $^1$H NMR (400 MHz, CDCl$_3$) δ 7.97 (d, J = 5.2 Hz, 1H), 6.50 (d, J = 5.2 Hz, 1H), 6.34 (s, 1H), 4.38 (s, 2H), 3.68 (s, 3H), 2.83 (t, J = 7.2 Hz, 2H), 2.61 (t, J = 7.6 Hz, 2H). |
| B19 | ![structure] | $^1$H NMR (400 MHz, CDCl$_3$) δ 7.94 (d, J = 2.4 Hz, 1H), 7.88 (d, J = 2.0 Hz, 1H), 6.32 (t, J = 2.4 Hz, 1H), 3.67 (s, 3H), 2.86 (t, J = 7.2 Hz, 2H), 2.61 (t, J = 7.6 Hz, 2H). |

Intermediate B21:
3-(5-amino-2-methylphenyl)propanenitrile

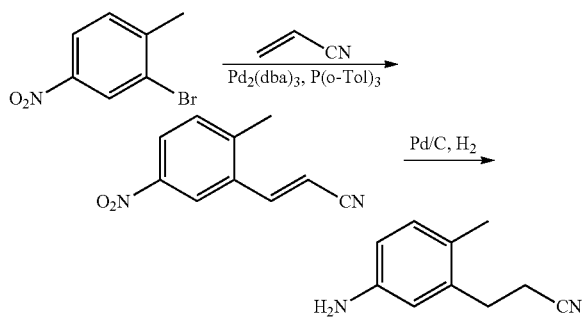

Step 1: (E)-3-(2-methyl-5-nitrophenyl)acrylonitrile

A mixture of 2-bromo-1-methyl-4-nitrobenzene (1.0 eq), acrylonitrile (1.5 eq), Pd$_2$(dba)$_3$ (0.1 eq), P(o-Tol)$_3$ (0.2 eq) and TEA (3.0 eq) in DMF (2.3 M) was stirred at 120° C. for 16 h under Ar. The reaction was monitored by TLC. The reaction mixture was diluted with water and extracted with EtOAc. The organic layer was dried over Na$_2$SO$_4$, concentrated under reduced pressure. The residue was purified by flash chromatography on silica gel (eluent petroleum ether/ EtOAc 20:1 to 5:1) to give the title compound as a brown solid.

Step 2: 3-(5-amino-2-methylphenyl)propanenitrile

To a solution of (E)-3-(2-methyl-5-nitrophenyl)acrylonitrile (1.0 eq) in MeOH (0.15 M) was added Pd/C (10% wt, 0.02 eq). The reaction mixture was stirred at rt for 16 h under H$_2$. The reaction was monitored by LC-MS. The solid was filtered off, and the filtrate was concentrated under reduced pressure to give the title compound as a brown solid. LCMS (m/z): [M+H]$^+$=161; $^1$H NMR (400 MHz, CDCl$_3$) δ 6.96 (d, J=8.8 Hz, 1H), 6.55-6.52 (m, 2H), 3.57 (br s, 2H), 2.88 (t, J=7.6 Hz, 2H), 2.55 (t, J=8.0 Hz, 2H), 2.20 (s, 3H).

The following intermediates were prepared according to the procedure described in Intermediate B21.

| Intermediate | Structure | LCMS and/or $^1$H NMR |
|---|---|---|
| B22 | (structure) | $^1$H NMR (400 MHz, CDCl$_3$) δ 7.00 (d, J = 7.2 Hz, 1H), 6.55 (d, J = 8.8 Hz, 1H), 6.53(s, 1H), 3.62 (s, 2H), 2.84 (t, J = 7.6 Hz, J = 7.2 Hz, 2H), 2.57 (t, J = 7.2 Hz, J = 7.6 Hz, 2H), 2.14 (s, 3H). |
| B23 | (structure) | LC-MS(m/z): [M + H]$^+$ = 161; $^1$H NMR (400 MHz, CDCl$_3$) δ 6.42-6.35(m, 3H), 3.63(br, 2H), 2.82(t, J-7.6 Hz, 2H), 2.57(t, J = 7.6 Hz, 2H), 2.24(s, 3H). |
| B24 | (structure) | LC-MS (m/z): [M + 1]$^+$ = 161; $^1$H NMR (400 MHz, CDCl$_3$) δ 6.99(t, J = 8.0 Hz, 1H), 6.62(d, J = 7.6 Hz, 2H), 3.64(br, 2H), 2.97(t, J = 7.6 Hz, 2H), 2.54(t, J = 7.6 Hz, 2H), 2.10(s, 3H). |
| B25 | (structure) | LC-MS (m/z): [M + 1]$^+$ = 215. |

Intermediate B26: methyl 1-(3-aminophenyl)cyclopropane-1-carboxylate

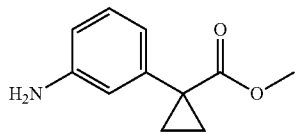

Step 1: 1-(3-nitrophenyl)cyclopropane-1-carbonitrile

To a mixture of 2-(3-nitrophenyl)acetonitrile (2.0 g, 12.33 mmol, 1.0 eq), 1,2-dibromoethane (3.47 g, 18.50 mmol, 1.5 eq), Et₃NBnCl (562 mg, 2.47 mmol, 0.2 eq) in toluene (1.2 M) was added aqueous NaOH solution (50% wt, 10 eq). The reaction mixture was stirred at 35° C. for 16 h. The reaction was monitored by TLC and H NMR. The mixture was diluted with water and extracted with EtOAc. The organic layer was washed with 1.0 M aq. HCl, brine, and then dried over Na₂SO₄. Upon removal of solvent the title compound 3 (700 mg, 30%) was obtained as brown solid.

Step 2: 1-(3-nitrophenyl)cyclopropane-1-carboxylic acid

To a solution of 1-(3-nitrophenyl)cyclopropane (600 mg, 3.19 mmol, 1.0 eq) in conc·HCl (10 mL) was stirred at 120° C. for 4 h. The reaction was monitored by LCMS. The mixture was diluted with water and extracted with DCM. The organic layer was washed with aq. NaHCO₃, and then dried over Na₂SO₄. The solid was filtered off, and the filtrate was concentrated under reduced pressure to give the title compound as black solid. LC-MS (m/z): [M−H]⁻=206; ¹H NMR (400 MHz, CDCl₃) δ 6.96 (d, J=8.8 Hz, 1H), 6.55-6.52 (m, 2H), 3.57 (br s, 2H), 2.88 (t, J=7.6 Hz, 2H), 2.55 (t, J=8.0 Hz, 2H), 2.20 (s, 3H).

Step 3: 1-(3-aminophenyl)cyclopropane-1-carboxylic acid

To a solution of 1-(3-nitrophenyl)cyclopropane-1-carboxylic acid (1.0 eq) in MeOH (0.24 M) was added Pd/C (20% wt, 0.1 eq). The mixture was stirred at 35° C. for 3 h under H₂. The reaction was monitored by TLC. The solid was filtered off, and the filtrate was concentrated under reduced pressure to give the title compound as a brown solid.

Step 4: methyl 1-(3-aminophenyl)cyclopropane-1-carboxylate

To a solution of 1-(3-aminophenyl)cyclopropane-1-carboxylic acid (428 mg, 2.41 mmol, 1.0 eq) in 2.5 M HCl/MeOH (1.0 eq, 0.24 M) was stirred at 50° C. for 3 h. The reaction was monitored by TLC and LC-MS until completion. The mixture was concentrated under reduced pressure, and the residue was dissolved in DCM, washed with aq. NaHCO₃. The organic layer was dried over Na₂SO₄. The crude product was purified by flash chromatography on silica gel (eluent: DCM/MeOH 1:0 to 20:1) to give the title compound as a white solid. LC-MS (m/z): [M+H]⁺=192.

Intermediate B27: methyl 2-(3-aminophenyl)-2-methylpropanoate

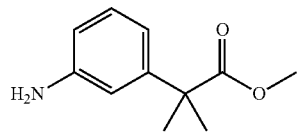

Step 1: methyl 2-methyl-2-(3-nitrophenyl)propanoate

To a solution of methyl 2-(3-nitrophenyl)acetate (1.0 eq) in DMF (0.14 M) was added t-BuOK (3.0 eq) in portions at 0° C. The mixture was stirred for 10 min at the same temperature. MeI (5.0 eq) was introduced into the mixture and the temperature was kept below 5° C. The reaction mixture was quenched with water after stirred for 2h at room temperature. The resulting solution was extracted with Et₂O. The organic layers were combined and concentrated, and the residue was purified by flash chromatography on silica gel (petroleum ether/EtOAc 20:1-15:1) to give the title compound as a light yellow oil.

Step 2: methyl 2-(3-aminophenyl)-2-methylpropanoate

To a solution of methyl 2-methyl-2-(3-nitrophenyl)propanoate (1.0 eq) in MeOH/H₂O (1:1, 0.12 M) was added NH₄Cl (10 eq) and Zn (5.0 eq). The reaction was heated at 80° C. for 2 h. The reaction was monitored by TLC. The solid was filtered off, and the filtrate was concentrated and extracted with DCM. The organic layers were combined, dried and purified by flash chromatography on silica gel (petroleum ether/EtOAc 15:1-8:1) to give the title compound. ¹H NMR (400 MHz, CDCl₃) δ 7.11 (t, J=8.0 Hz, 1H), 6.72 (d, J=8.0 Hz, 1H), 6.65 (t, J=1.6 Hz, 1H), 6.57 (dd, J=8.0, 1.6 Hz, 1H), 3.65 (s, 3H), 1.48 (s, 6H).

Intermediate B28: 3-(3-amino-5-methoxyphenyl)propanenitrile

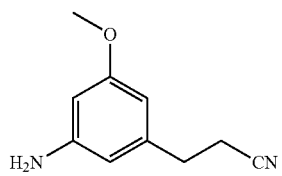

The intermediate was prepared following the procedure described in Intermediate B2. LCMS (m/z): [M+H]⁺=177; ¹H NMR (400 MHz, CDCl₃) δ 6.18-6.13 (m, 3H), 3.76 (s, 3H), 3.69 (s, 2H, NH₂), 2.82 (t, J=7.6, 2H), 2.58 (t, J=7.6 Hz, 2H).

Intermediate B29:
3-(3-amino-5-fluorophenyl)propanenitrile

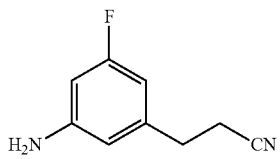 [SMILES: N#CCCc1cc(N)cc(F)c1]

The intermediate was prepared following the procedure described in Intermediate B2. LCMS (m/z): [M+1]⁺=165.2; ¹H NMR (400 MHz, CDCl₃) δ 6.32-6.26 (m, 3H), 3.80 (br s, 2H), 2.83 (t, J=7.6 Hz, 2H), 2.59 (t, J=7.6 Hz, 2H).

Intermediate B30:
3-(3-amino-5-chlorophenyl)propanenitrile

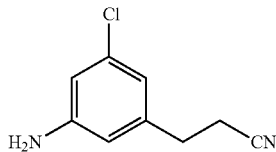 [SMILES: N#CCCc1cc(N)cc(Cl)c1]

The intermediate was prepared following the procedure described in Intermediate B6. LCMS (m/z): [M+1]⁺=181.1.

Intermediate B31:
3-(3-aminophenyl)-2,2-dimethylpropanenitrile

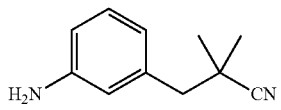

Step 1: 1-(bromomethyl)-3-nitrobenzene

A solution of 1-methyl-3-nitrobenzene (1 eq), NBS (1.05 eq) and AIBN (0.03 eq) in CCl₄ was heated at 95° C. for 16h. The reaction was monitored with TLC to completion. The solid was filtered off, and the filtrate was concentrated to give the crude product which was purified by flash chromatography on silica gel (petroleum ether as eluent) to give the title compound.

Step 2: 2,2-dimethyl-3-(3-nitrophenyl)propanenitrile

At −78° C., to a solution of LDA (1.1 eq) in THF was added a solution of isobutyronitrile (1.0 eq) in THF, and the resulting solution was stirred for 30 min at −78° C. A solution of 1-(bromomethyl)-3-nitrobenzene (1.0 eq) in THF was then added, and the reaction mixture was allowed to warm up to RT in 3h. Upon completion, the reaction was quenched with sat. NH₄C₁ solution and extracted with EtOAc. The combined organic layer was dried over Na₂SO₄, concentrated and purified by flash chromatography on silica gel (100% petroleum ether) to give the title compound.

Step 3: 3-(3-aminophenyl)-2,2-dimethylpropanenitrile

A mixture of 2,2-dimethyl-3-(3-nitrophenyl)propanenitrile (1.0 eq) and palladium on carbon (0.03 eq) in MeOH was stirred under H₂ (balloon) at r.t. for 16h. The solid was filtered off, and the filtrate was concentrated to give the title compound. LCMS (m/z): [M+H]⁺=175; ¹H NMR (400 MHz, CDCl₃) δ 7.11 (t, J=7.2 Hz, 1H), 6.65-6.61 (m, 3H), 3.67 (br s, 2H), 2.72 (s, 2H), 1.34 (s, 6H).

Intermediate B32: 3-(3-amino-5-methylphenyl)-2,2-dimethylpropanenitrile

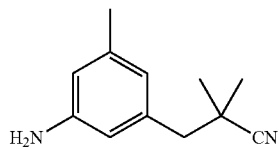

The intermediate was prepared following the procedure described in Intermediate B31. LCMS (m/z): [M+1]⁺=189.3; ¹H NMR (400 MHz, CDCl₃) δ 6.46 (s, 1H), 6.44 (s, 1H), 6.42 (s, 1H), 3.61 (br s, 2H), 2.68 (s, 2H), 2.25 (s, 3H), 1.34 (s, 6H).

Intermediate B33:
3-(3-aminobenzyl)oxetane-3-carbonitrile

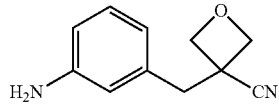 [SMILES: N#CC1(Cc2cccc(N)c2)COC1]

The intermediate was prepared by following the procedure described in Intermediate B31. The last step of reduction of nitro to amine was used Zn/NH₄Cl instead of Pd/C/H₂ method. LCMS (m/z): [M+1]⁺=189.2.

Intermediate B34: methyl 3-(3-aminophenyl)-3-methylbutanoate

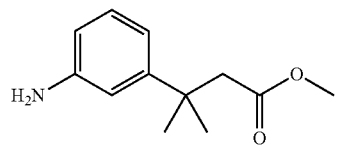

Step 1: 3-(4-bromophenyl)-3-methylbutanoic acid

A mixture of 3-methylbut-2-enoic acid (1 eq), AlCl₃ (2 eq) in bromobenzene (4 eq) was stirred at 65° C. for 1 h. The mixture was quenched with aq. NaOH, and washed with EtOAc (3×50 mL). The aqueous phase was neutralized with citric acid solution and extracted with EtOAc (3×50 mL). The organic layer was washed with brine, dried over NaSO₄, and concentrated in vacuum to give the title compound as a yellow solid. LCMS (m/z): [M−H]−=255.

Step 2: 3-(4-bromo-3-nitrophenyl)-3-methylbutanoic acid

A mixture of 3-(4-bromophenyl)-3-methylbutanoic acid (1.6 eq) and KNO$_3$ (1.0 eq) in concentrated H$_2$SO$_4$ (1.2 M) was stirred at −30° C. for 5 min. The mixture was quenched with water and extracted with EtOAc (2×50 mL). The combined organic layers were washed with brine, concentrated. The crude product was purified by flash chromatography on silica gel (eluent: petroleum ether/EtOAc=5/1 to 2/1) to give the title compound as a yellow solid. LCMS (m/z): [M−H]$^-$=300.

Step 3: 3-(3-aminophenyl)-3-methylbutanoic acid

A mixture of 3-(4-bromo-3-nitrophenyl)-3-methylbutanoic acid (1 eq) and Pd/C (10%, 0.03 eq.) in MeOH (0.3 M) was stirred at r.t for 16 h. The solid was filtered off, and the filtrate was concentrated to give the title compound as a yellow oil LCMS (m/z): [M+H]$^+$=194.

Step 4: methyl 3-(3-aminophenyl)-3-methylbutanoate

A solution of 3-(3-aminophenyl)-3-methylbutanoic acid (1.55 mmol) in 1 M HCl/MeOH (0.16 M) was stirred at r.t for 1 h, and the solvent was removed under reduced pressure to give the title compound as a yellow solid. LCMS (m/z): [M+H]$^+$=208.

Intermediate B35: 3-(3-aminophenyl)-3-methylbutanenitrile

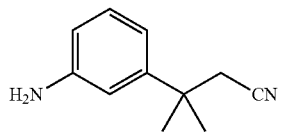

Step 1: 3-(4-bromo-3-nitrophenyl)-3-methylbutanamide

To a solution of 3-(4-bromo-3-nitrophenyl)-3-methylbutanoic acid (1.0 eq) in THF (0.25 M) were added HATU (1.3 eq), DIEA (2.0 eq) and NH$_4$Cl (2.0 eq). The mixture was stirred at r.t for 16 h. The mixture was quenched with water, extracted with EA (2×30 mL). The combined organic layer was washed with brine, dried over Na$_2$SO$_4$, concentrated in vacuum to give the title compound as a yellow oil. LC-MS (m/z): [M+H]$^+$=301.0.

Step 2: 3-(4-bromo-3-nitrophenyl)-3-methylbutanenitrile

To a solution of 3-(4-bromo-3-nitrophenyl)-3-methylbutanamide (1.0 eq) in DMF (0.66 M) was added (CNCl)$_3$ (1.2 eq), and the resulting mixture was stirred at r.t for 16 h. The mixture was quenched with aq. NH$_4$Cl, and extracted with EA (3×20 mL). The crude product was purified by flash chromatography on silica gel (eluent: petroleum ether/EtOAc=5:1 to 1:1) to give the title compound as a yellow oil.

Step 3: 3-(3-aminophenyl)-3-methylbutanenitrile

To a solution of 3-(4-bromo-3-nitrophenyl)-3-methylbutanenitrile (1.0 eq) in MeOH (0.4 M) was added 10 percent Pd/C (10% wt, 0.03 eq). The mixture was stirred under H$_2$ at r.t for 16 h. The solid was filtered off, and filtrate was concentrated in vacuum to give the title compound as a yellow oil. LC-MS (m/z): [M+H]$^+$=175.1.

Intermediate B36: 2-(3-amino-5-methylphenyl)acetonitrile

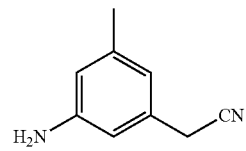

Step 1: 1-(bromomethyl)-3-methyl-5-nitrobenzene

A mixture of 1,3-dimethyl-5-nitrobenzene (1.0 eq), NBS (1.1 eq) and BPO (0.015 eq) in CCl$_4$ (0.5 M) was stirred overnight at 95° C. under Ar. The reaction mixture was filtered, and the filtrate was concentrated. The residue was purified by flash chromatography on silica gel (eluent: petroleum ether) to give the title compound as a yellow oil.

Step 2: 2-(3-methyl-5-nitrophenyl)acetonitrile

A mixture of 1-(bromomethyl)-3-methyl-5-nitrobenzene (1.0 eq), KCN (2.0 eq) in DMSO (0.65 M) was stirred overnight at 40° C. under Ar. After completion, the reaction mixture was diluted with EtOAc, washed with brine, and dried over Na$_2$SO$_4$. The crude product was purified by flash chromatography on silica gel (eluent: petroleum ether:EtOAc=5:1) to give the title compound as a yellow oil.

Step 3: −(3-amino-5-methylphenyl)acetonitrile

A mixture of 2-(3-methyl-5-nitrophenyl)acetonitrile (1.0 eq) and Pd/C (10%, 0.01 eq) in MeOH (0.1 M) was stirred under H$_2$ (balloon) at RT for 2 h. The solid was filtered off, and the filtrate was concentrated. The residue was purified by flash chromatography on silica gel (eluent: petroleum ether:EtOAc=1:1) to give the title compound as a yellow oil. LCMS (m/z): [M+H]$^+$=147.

Intermediate B37: 2-(3-amino-5-methylphenyl)-2-methylpropanenitrile

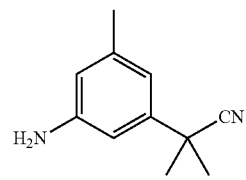

Step 1: 2-methyl-2-(3-methyl-5-nitrophenyl)propanenitrile

At 0° C., to a stirring solution of 2-(3-methyl-5-nitrophenyl)acetonitrile (1.0 eq) in DMF (0.13 M) was added t-BuOK (3.0 eq) portionwise under an Ar atmosphere, and the resulting mixture was stirred at r.t for 16 h. The mixture was quenched with ice-water, extracted with EtOAc three times. The combined organic layer was washed with brine, and then dried over Na$_2$SO$_4$. The crude product was purified by flash chromatography on silica gel (eluent: petroleum ether/EtOAc=25:1 to 10:1) to give the title compound. $^1$H NMR (400 MHz, CDCl$_3$) δ 8.09 (S, 1H), 8.02 (s, 1H), 7.69 (s, 1H), 2.51 (s, 3H), 1.78 (s, 6H).

Step 2:
2-(3-amino-5-methylphenyl)-2-methylpropanenitrile

To a solution of 2-methyl-2-(3-methyl-5-nitrophenyl)propanenitrile (1.0 eq) in MeOH (0.06 M) was added Pd/C (10% wt, 0.04 eq), and the resulting mixture was stirred under H$_2$ at r.t for 6 h. The solid was filtered off, and the filtrate was concentrated and purified by flash chromatography on silica gel (eluent: petroleum ether/EtOAc=20:1 to 8:1) to give the title compound as as an oil. LCMS (m/z): [M+H]$^+$=175.0.

Intermediate B38: methyl
2-(5-amino-2-methylphenyl)acetate

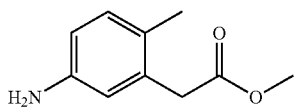

Step 1: 2-(2-methyl-5-nitrophenyl)acetic acid

At 0° C., to a mixture of 2-(o-tolyl)acetic acid (3.5 g, 23.6 mmol, 1.0 eq) in DCM (20 mL) was added a pre-cooled mixture of con. H$_2$SO$_4$ (10 mL) and HNO$_3$ (1.0 mL), and the reaction mixture was stirred at r.t for 2 h before poured into ice-water. The white solid was collected by filtration, and the solid cake was washed with water, and dried under vacuum. The crude product was further purified by flash chromatography on silica gel (DCM/MeOH=10:1) to give the title compound.

Step 2: methyl 2-(2-methyl-5-nitrophenyl)acetate

To a solution of 2-(2-methyl-5-nitrophenyl)acetic acid (1.7 g, 6.52 mmol, 1.0 eq) in MeOH (8.0 mL) was added SOCl$_2$ (5.2 g, 5.0 eq), and the reaction mixture was stirred under Ar at 40° C. for 16 h. The mixture was diluted with EtOAc, washed with brine, dried over Na$_2$SO$_4$. The title compound was obtained as a yellow oil upon removal of solvent.

Step 3: methyl 2-(5-amino-2-methylphenyl)acetate

A mixture of methyl 2-(2-methyl-5-nitrophenyl)acetate (200 mg, 0.96 mmol, 1.0 eq) and Pd/C (10%, 20 mg) in MeOH (20 mL) was stirred under H$_2$ (balloon) at r.t for 2 h. The solid was filtered off, and the filtrate was concentrated. The residue was purified by flash chromatography on silica gel (eluent: petroleum ether:EtOAc=10:1) to give the title compound as a yellow oil. LCMS (m/z): [M+H]$^+$=180.

Intermediate B39:
2-(5-amino-2-methylphenyl)-2-methylpropanenitrile

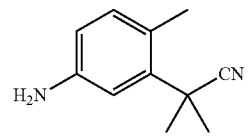

Step 1: (2-methyl-5-nitrophenyl)methanol

To a solution of methyl 2-methyl-5-nitrobenzoate (1.0 eq) in EtOH (0.5 M) at 0° C. was added CeCl$_3$·7H$_2$O (0.2 eq), followed by NaBH$_4$ (2.0 eq) in portions. The resulting mixture was stirred at r.t for 16 h before quenched with ice-water. The mixture was extracted with EtOAc, and the combined organic layer was was dried over Na$_2$SO$_4$. The crude product was purified by flash chromatography on silica gel (eluent: petroleum ether/EtOAc=10:1) to give the title compound as a white solid.

Step 2: 2-(chloromethyl)-1-methyl-4-nitrobenzene

At 0° C., to a solution of (2-methyl-5-nitrophenyl)methanol (1.0 eq) in DCM (0.3 M) was added dropwise SOCl$_2$ (5.0 mL). The resulting mixture was stirred at r.t for 16 before quenched with cold aq. NaHCO$_3$. The mixture was extracted with EtOAc. The organic layer was dried over Na$_2$SO$_4$, filtered, and concentrated to give the compound as a white solid.

Step 3: 2-(2-methyl-5-nitrophenyl)acetonitrile

To a solution of 2-(chloromethyl)-1-methyl-4-nitrobenzene (1.0 eq) in DMSO (0.27 M) was added KCN (2.0 eq). The mixture was stirred at r.t for 16 h before quenched with ice water. The mixture was extracted with EtOAc, and the the combined organic layer was dried over Na$_2$SO$_4$. The crude product was purified by flash chromatography on silica gel (eluent: petroleum ether/EtOAc=5:1-3:1) to give the title compound as a white solid.

Step 4:
2-methyl-2-(2-methyl-5-nitrophenyl)propanenitrile

At 0° C., to a solution of 2-(2-methyl-5-nitrophenyl) acetonitrile (1.0 eq) in DMSO (0.5 M) at was added aq. NaOH (5.0 mL, 30% wt), followed by MeI (10 eq). The mixture was stirred at 0° C. for 5 min, the quenched with aq. NH$_4$Cl. The mixture was worked up, and the crude product was purified by flash chromatography on silica gel (eluent: petroleum ether/EtOAc=20:1-8:1) to give the title compound as a yellow solid.

Step 5:
2-(5-amino-2-methylphenyl)-2-methylpropanenitrile

A mixture of 2-methyl-2-(2-methyl-5-nitrophenyl)propanenitrile (1.0 eq) and Pd/C (10% wt, 0.05 eq) in MeOH (0.04 M) was stirred under H$_2$ at r.t for 1 h. The solid was filtered off, and the filtrate was concentrated to give the title compound. LC-MS (m/z): [M+H]$^+$=175.2.

Intermediate B40: methyl 2-(4-aminophenyl)-2-methylpropanoate

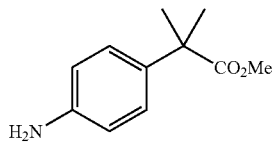

Step 1: methyl 2-methyl-2-(4-nitrophenyl)propanoate

At −5° C., to a solution of methyl 2-(4-nitrophenyl)acetate (1.0 q) in DMF (0.1 M) was added NaH (3.0 eq) in portions. The cooling bath was removed, and the reaction mixture was stirred at r.t for 30 min. The mixture was cooled down to −5° C. again, and MeI (6.0 eq) was added dropwise. The resulting mixture was stirred at r.t. for 1h before quenched with ice water. The mixture was extracted with EtOAc, and the combined organic layer was washed with brine, and then dried over $Na_2SO_4$. The title compound was obtained as a yellow solid upon removal of solvent.

Step 2: methyl 2-(4-aminophenyl)-2-methylpropanoate

A mixture of methyl 2-methyl-2-(4-nitrophenyl)propanoate (1.0 eq), Pd/C (10% wt, 0.03 eq) in MeOH (0.1 M) was stirred under $H_2$ at r.t for 3 h. The solid was filtered off, and the filtrate was concentrated to give the title compound as a colorless oil. LC-MS (m/z): $[M+H]^+$=194.0.

Intermediate B41: methyl 2-(3-aminophenyl)-2,2-difluoroacetate

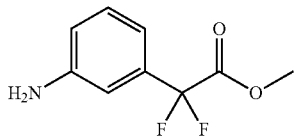

Step 1: methyl 2,2-difluoro-2-(3-nitrophenyl)acetate

At −70° C., to a stirring solution of methyl 2-(3-nitrophenyl)acetate (1.0 eq) in THF (0.13 M) was added dropwise a solution of KHMDS (3.0 eq). The mixture was stirred at −70° C. for 20 min, and then a solution of $FN(SO_2Ph)_2$ (3.0 eq) in THF (1.5 M) was added slowly. The resulting mixture was stirred at −70° C. for 30 min, and was allowed to warm up to −10° C. The reaction was quenched with water, and the mixture was extracted with EtOAc. The combined organic layer was dried over $Na_2SO_4$. The crude product was purified by flash chromatography on silica gel (eluent: petroleum ether/EtOAc=20:1 to 10:1) to give the title compound as an oil.

Step 2: methyl 2-(3-aminophenyl)-2,2-difluoroacetate

A mixture of methyl 2,2-difluoro-2-(3-nitrophenyl)acetate (1 eq) and Pd/C (10%, 0.03 eq) in MeOH (0.2 M) was stirred under $H_2$ (balloon) at r.t for 16 h. The solid was filtered off, and the filtrate was concentrated, and the residue was purified by flash chromatography on silica gel (eluent: petroleum ether/EtOAc=10:1 to 5:1) to give the title compound as a brown oil. LCMS (m/z): $[M+H]^+$=202.

Intermediate B42: 2-(3-aminophenoxy)acetonitrile

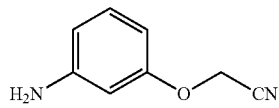

A mixture of 3-nitrophenol (1.0 eq), 2-bromoacetonitrile (1.2 eq) and $K_2CO_3$ (2.0 eq) in $CH_3CN$ (0.5 M) was stirred at RT for 16h. The solid was filtered off, and the filtrate was concentrated to give the crude product of 2-(3-nitrophenoxy)acetonitrile, which was treated with Zn (1.0 eq), sat. $NH_4C_1$/MeOH (5 mL/5 mL) at 65° C. for 3h. The reaction mixture was diluted with EtOAc, washed with water and brine, and dried over $Na_2SO_4$. The crude product was purified by flash chromatography on silica gel (eluent petroleum ether:EtOAc=50:1) to give the title compound as a brown oil. LCMS (m/z): $[M+1]^+$=149.0.

Intermediate B43: 3-(5-amino-2-methoxyphenyl)propanenitrile

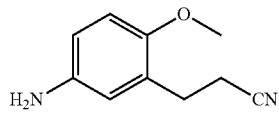

Step 1: (E)-3-(5-amino-2-methoxyphenyl)acrylonitrile

A mixture of 3-bromo-4-methoxyaniline (1 eq), acrylonitrile (5 eq), $Pd_2(dba)_3$ (0.05 eq) and triethyl amine (1.25 eq) in DMF was flushed by Argon, and heated at 100° C. for 1h in a microwave reactor. The mixture was cooled to rt, and filtered. The filtrate was concentrated under reduced pressure. The crude product was purified by flash chromatography on silica (petroleum ether/EtOAc=6:1) to give the title compound as a brown solid.

Step 2: 3-(5-amino-2-methoxyphenyl)propanenitrile

A mixture of (E)-3-(5-amino-2-methoxyphenyl)acrylonitrile (1 eq) and Pd/C (10% wt, 0.05 eq) in MeOH (0.05 M) was stirred under $H_2$ at RT for 16 h. The solid was filtered off, and the filtrate was concentrated. The residue was purified by flash chromatography on silica gel to give the title compound as a brown solid. LCMS (m/z): $[M+H]^+$=177.2; $^1H$ NMR (400 MHz, $CDCl_3$) δ 6.72-6.68 (m, 1H), 6.60-6.56 (m, 2H), 3.76 (s, 3H), 2.87 (t, J=7.4 Hz, 2H), 2.60 (t, J=7.4 Hz, 2H).

Intermediate B44: 3-(4-amino-1H-pyrazol-1-yl)propanenitrile

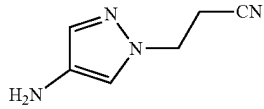

Step 1: 3-(4-nitro-1H-pyrazol-1-yl)propanenitrile

A mixture of 4-nitro-1H-pyrazole (1.0 eq), acrylonitrile (1.0 eq) and $Na_2CO_3$ (2.0 eq) in $H_2O$ (0.9 M) was stirred at 50° C. for 12 h under Ar. The reaction mixture was extracted with DCM/i-PrOH=5:1 (100 mL×3) and $H_2O$ (100 mL). The combined organic layer was washed with brine, and then dried over $Na_2SO_4$. The crude product was purified by flash chromatography on silica gel (elute: petroleum ether/EtOAc=4:1 to 1:1) to give the title compound as a white solid. LC-MS (m/z): $[M+H]^+=167.3$.

Step 2: 3-(4-amino-1H-pyrazol-1-yl)propanenitrile

A mixture of 3-(4-nitro-1H-pyrazol-1-yl)propanenitrile (1.0 eq) and Zn (10.0 eq) in saturated aq. $NH_4Cl$/MeOH (1:2, 0.1 M) was stirred at 80° C. for 1 h. The reaction mixture was filtered, and the solvent was removed under reduced pressure. The residue was purified by flash chromatography on silica gel (elute: DCM/MeOH=10:1) to give the title compound as a brown oil. LC-MS (m/z): $[M+H]^+=137.4$.

Intermediate B45: 3-(3-amino-1H-pyrazol-1-yl)propanenitrile

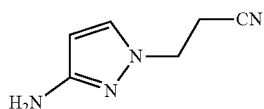

This intermediate was prepared following the procedure described in Intermediate B44 using 3-nitro-1H-pyrazole as the starting material and 1:1 $H_2O$/THF as the solvent in the first step. LC-MS (m/z): $[M+H]^+=137.0$.

EXAMPLES

Example 1: 3-(3-((4-((5,6-dimethyl-[2,2'-bipyridin]-3-yl)oxy)pyridin-2-yl)amino)phenyl)propanoic acid

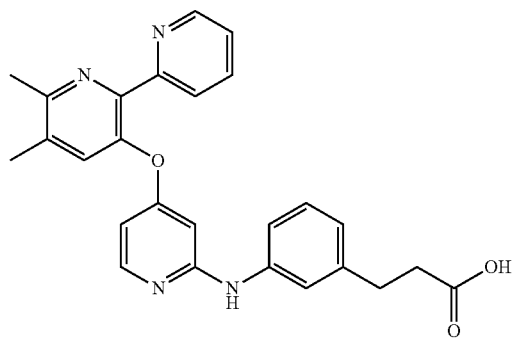 [SMILES: Cc1cc(Oc2ccnc(Nc3cccc(CCC(=O)O)c3)c2)c(-c2ccccn2)nc1C]

Step 1: methyl 3-(3-((4-((5,6-dimethyl-[2,2'-bipyridin]-3-yl)oxy)pyridin-2-yl)amino)phenyl)propanoate A mixture of 3-((2-chloropyridin-4-yl)oxy)-5,6-dimethyl-2,2'-bipyridine (Intermediate A1, 1.0 eq), methyl 3-(3-aminophenyl)propanoate (Intermediate B1, 1.0 eq), $Cs_2CO_3$ (2.0 eq), Xantphos (0.1 eq) and $Pd(OAc)_2$ (0.1 eq) in dioxane (0.064 M) was stirred at 120° C. for 16 h under Ar. The mixture was cooled to rt. The solid was filtered off and the filtrate was concentrated under reduced pressure. The residue was purified by flash chromatography on silica gel (eluent: petroleum ether/EtOAc 5:1 to 0:1) to give the title compound as a yellow solid. LC-MS (m/z): $[M+1]^+=455$.

Step2: 3-(3-((4-((5,6-dimethyl-[2,2'-bipyridin]-3-yl)oxy)pyridin-2-yl)amino)phenyl)propanoic acid To a solution of methyl 3-(3-((4-((5,6-dimethyl-[2,2'-bipyridin]-3-yl)oxy)pyridin-2-yl)amino)phenyl)propanoate (1.0 eq) in THF (0.022 M) was added 1N aq. NaOH (45 eq). The reaction solution was heated to 70° C. and stirred for 2 h. LC-MS showed the reaction was completed. The reaction mixture was concentrated under reduced pressure, and the residue was purified by HPLC (mobile phase: $CH_3CN/H_2O$/0.1% HCOOH). The fractions were collected, and the solvent was removed via lyophilizer to give the title compound as a white solid (formic acid salt). LC-MS (m/z): $[M+1]^+=441.2$; $^1H$ NMR (400 MHz, DMSO) δ 8.83 (s, 1H), 8.50 (ddd, J=4.8, 1.6, 0.8 Hz, 1H), 8.23 (s, 0.4H, HCOOH), 7.97 (d, J=5.6 Hz, 1H), 7.84 (ddd, J=7.2, 4.8, 1.2 Hz, 1H), 7.78 (d, J=8.0 Hz, 1H), 7.57 (s, 1H), 7.46-7.44 (m, 1H), 7.36 (s, 1H), 7.34-7.31 (m, 1H), 7.11 (t, J=8.0 Hz, 1H), 6.71 (d, J=7.6 Hz, 1H), 6.34 (dd, J=5.6, 2.0 Hz, 1H), 6.09 (d, J=2.4 Hz, 1H), 2.74 (t, J=7.6 Hz, 2H), 2.53 (s, 3H), 2.48 (t, J=7.6 Hz, 2H), 2.35 (s, 3H).

The following compounds were prepared according to the procedure described in Example 1, using appropriate intermediates. Compounds without Example Numbers do not fall within Formula (I) or (II).

| Example | Structure | LCMS (m/z) [M + 1]+ | 1H NMR |
|---|---|---|---|
| | Prepared from Intermediates A1 and B3. | 441.3 | 1H NMR (400 MHz, DMSO) δ 8.80 (s, 1H), 8.50 (d, J = 4.4 Hz, 1H), 8.16 (s, 1H, HCOOH), 7.94 (d, J = 5.6 Hz, 1H), 7.84 (td, J = 7.6, 2.0 Hz, 1H), 7.78 (d, J = 7.6 Hz, 1H), 7.57 (s, 1H), 7.47 (d, J = 8.4 Hz, 2H), 7.34-7.31 (m, 1H), 7.06 (d, J = 8.4 Hz, 2H), 6.32 (dd, J = 5.6, 2.0 Hz, 1H), 6.06 (d, J = 2.4 Hz, 1H), 2.73 (t, J = 7.6 Hz, 2H), 2.52 (s, 3H), 2.47 (t, J = 7.6 Hz, 2H), 2.35 (s, 3H). |
| | Prepared from Intermediates A1 and B19. | 442.2 | 1H NMR (400 MHz, DMSO) δ 9.06 (s, 1H), 8.56 (d, J = 2.0 Hz, 1H), 8.49 (d, J = 4.4 Hz, 1H), 8.01 (d, J = 5.6 Hz, 1H), 7.96-7.90 (m, 2H), 7.87-7.78 (m, 2H), 7.59 (s, 1H), 7.35-7.30 (m, 1H), 6.41 (d, J = 5.6, 2.0 Hz, 1H), 6.11 (d, J = 2.0 Hz, 1H), 2.76 (t, J = 7.6 Hz, 2H), 2.53 (s, 3H), 2.47 (t, J = 7.6 Hz, 2H), 2.35 (s, 3H). |
| 4 | Prepared from Intermediates A1 and B10. | 459.2 | 1H NMR (400 MHz, DMSO) δ 8.87 (s, 1H), 8.50 (d, J = 4.0 Hz, 1H), 7.95 (d, J = 5.6 Hz, 1H), 7.84 (td, J = 7.6, 2.0 Hz, 1H), 7.78 (d, J = 7.6 Hz, 1H), 7.57 (s, 1H), 7.52-7.48 (m, 1H), 7.40 (dd, J = 6.8, 2.4 Hz, 1H), 7.34-7.30 (m, 1H), 6.98 (t, J = 9.6 Hz, 1H), 6.34-6.32 (m, 1H), 6.04 (d, J = 2.0 Hz, 1H), 2.76 (t, J = 7.6 Hz, 2H), 2.52 (s, 3H), 2.44 (t, J = 7.6 Hz, 2H), 2.35 (s, 3H). |
| 5 | Prepared from Intermediates A1 and B13. | 475.3 | 1H NMR (400 MHz, DMSO) δ 9.00 (s, 1H), 8.49 (s, 1H), 7.98 (d, J = 5.6 Hz, 1H), 7.85-7.77 (m, 2H), 7.57 (m, 2H), 7.46 (s, 1H), 7.32 (m, 1H), 7.19 (d, J = 9.2 Hz, 1H), 6.37 (d, J = 4.0 Hz, 1H), 6.08 (s, 1H), 2.77 (t, J = 7.6 Hz, 2H), one CH2 and methyl group were covered by solvent, 2.34 (s, 3H). |

-continued

| Example | Structure | LCMS (m/z) [M + 1]+ 1H NMR |
|---|---|---|
| 6 | Prepared from Intermediates A1 and B11. | 459.2 ¹H NMR (400 MHz, CD₃OD) δ 8.57 (d, J = 4.4 Hz, 1H), 7.87-7.83 (m, 2H), 7.73 (d, J = 8.0 Hz, 1H), 7.56 (d, J = 7.2 Hz, 1H), 7.52 (s, 1H), 7.38 (t, J = 5.6 Hz, 1H), 7.01-6.94 (m, 1H), 6.90-6.88 (m, 1H), 6.27 (d, J = 4.4 Hz, 1H), 6.11 (s, 1H), 2.84 (t, J = 7.6 Hz, 2H), 2.58 (s, 3H), 2.47 (t, J = 7.6 Hz, 2H), 2.40 (s, 3H). |
| 7 | Prepared from Intermediates A1 and B17. | 442.4 ¹H NMR (400 MHz, CD₃OD) δ 8.51 (d, J = 4.4 Hz, 1H), 8.31 (s, 1H), 8.14 (d, J = 6.4 Hz, 2H), 7.86 (d, J = 3.6 Hz, 2H), 7.67-7.61 (m, 2H), 7.37-7.35 (m, 1H), 6.94-6.88 (m, 3H), 6.68 (dd, J = 6.4, 2.4 Hz, 1H), 2.99 (t, J = 6.8 Hz, 3H), 2.62-2.57 (s, 3H), 2.59 (t, J = 6.8 Hz, 2H), 2.44 (s, 3H). |
| 8 | Prepared from Intermediates A1 and B18. | 442.4 ¹H NMR (400 MHz, CD₃OD) δ 8.53 (d, J = 4.8Hz, 1H), 8.06 (d, J = 5.2 Hz, 1H), 8.03 (d, J = 6.4 Hz, 1H), 7.86-7.80 (m, 2H), 7.58 (s, 1H), 7.38-7.34 (m, 1H), 7.17 (s, 1H), 6.92 (d, J = 5.2 Hz, 1H), 6.86 (s, 1H), 6.53 (dd, J = 6.0, 2.0 Hz, 1H), 2.91 (t, J = 7.2 Hz, 2H), 2.61 (s, 3H), 2.57 (t, J = 7.2 Hz, 2H), 2.43 (s, 3H). |
| 9 | Prepared from Intermediates A1 and B20. | 442.3 ¹H NMR (400 MHz, DMSO) δ 9.36 (s, 1H), 8.48 (d, J = 4.0 Hz, 1H), 8.24 (s, 1.4H, HCOOH), 8.16 (d, J = 5.2 Hz, 1H), 8.08 (d, J = 6.0 Hz, 1H), 7.84-7.79 (m, 2H), 7.60 (s, 1H), 7.46 (d, J = 5.2 Hz, 1H), 7.44 (s, 1H), 7.35-7.30 (m, 1H), 6.49 (d, J = 5.6 Hz, 1H), 6.18 (s, 1H), 2.84 (t, J = 6.8 Hz, 2H), 2.60 (t, J = 6.8 Hz, 2H), 2.53 (s, 3H), 2.35 (s, 3H). |

-continued

| Example | Structure | LCMS (m/z) [M + 1]+ | 1H NMR |
|---|---|---|---|
| 10 | Prepared from Intermediates A1 and B12. | 459.2 | 1H NMR (400 MHz, CD3OD) δ 8.58 (d, J = 4.8 Hz, 1H), 7.89-7.82 (m, 2H), 7.74 (d, J = 8.0 Hz, 1H), 7.58-7.52 (m, 2H), 7.38 (ddd, J = 7.6, 4.8, 1.2 Hz, 1H), 7.00-6.91 (m, 2H), 6.27 (dd, J = 5.6, 2.0 Hz, 1H), 6.13 (d, J = 2.0 Hz, 1H), 2.92 (t, J = 7.2 Hz, 2H), 2.58 (s, 3H), 2.43 (t, J = 7.2 Hz, 2H), 2.41 (s, 3H). |
| 11 | Prepared from Intermediates A13 and B1. | 375.2 | 1H NMR (400 MHz, DMSO-d6) δ 9.02 (d, J = 3.2 Hz, 1H), 8.13 (t, J = 5.6 Hz, 1H), 7.89-7.85 (m, 1H), 7.75-7.72 (m, 1H), 7.50 (m, 1H), 6.75 (m, 1H), 6.53 (m, 1H), 6.30 (s, 1H), 2.73 (t, J = 6.0 Hz, 2H), 7.39 (s, 1H), 7.15-7.12 (m, 1H), 2.54 (s, 3H), 2.41 (t, J = 6.0 Hz, 2H). |

Example 12: N-(3-(2-(2H-tetrazol-5-yl)ethyl)phenyl)-4-((5,6-dimethyl-[2,2'-bipyridin]-3-yl)oxy)pyridin-2-amine

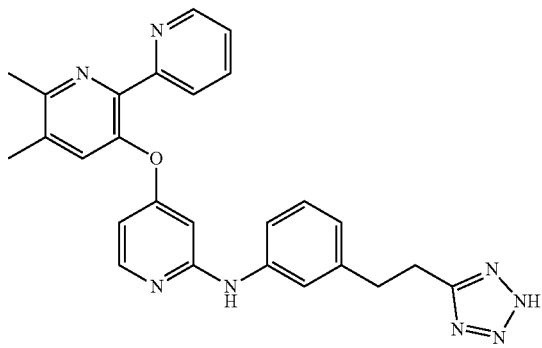 [SMILES: Cc1cc(Oc2ccnc(Nc3cccc(CCc4nn[nH]n4)c3)c2)c(-c2ccccn2)nc1C]

Step 1: 3-(3-((4-((5,6-dimethyl-[2,2'-bipyridin]-3-yl)oxy)pyridin-2-yl)amino)phenyl)propanenitrile A mixture of 3-((2-chloropyridin-4-yl)oxy)-5,6-dimethyl-2,2'-bipyridine (Intermediate A1, 1.0 eq), 3-(3-aminophenyl)propanenitrile (Intermediate B2, 1.0 eq), Cs₂CO₃ (2.0 eq), Xantphos (0.1 eq) and Pd(OAc)₂ (0.1 eq) in dioxane (0.06 M) was stirred at 120° C. for 16 h. The mixture was cooled to r.t. The solid was filtered off and the filtrate was concentrated under reduce pressure. The residue was purified by flash chromatography on silica gel (eluent: Petroleum ether/EtOAc 1:1 to 0:1) to give the title compound as a yellow solid. LC-MS (m/z): [M+1]⁺=422.

Step 2: N-(3-(2-(2H-tetrazol-5-yl)ethyl)phenyl)-4-((5,6-dimethyl-[2,2'-bipyridin]-3-yl)oxy)pyridin-2-amine A mixture of above product (1.0 eq), Bu₂SnO (2.0 eq) and TMSN3 (5.0 eq) in dioxane (0.08 M) was stirred at 120° C. for 16 h under Ar. The mixture was concentrated under reduced pressure. The residue was purified by HPLC (mobile phase: CH₃CN/H₂O/0.1% HCOOH). The fractions were collected, and the solvent was removed via lyophilizer to give the title compound as a yellow solid. LC-MS (m/z): [M+1]⁺=465.2; 1H NMR (400 MHz, DMSO) δ 8.85 (s, 1H), 8.51-8.49 (m, 1H), 8.15 (s, 1H), 7.97 (d, J=6.0 Hz, 1H), 7.84 (td, J=7.6, 1.6 Hz, 1H), 7.79 (d, J=7.6 Hz, 1H), 7.57 (s, 1H), 7.43 (d, J=8.4 Hz, 1H), 7.40H (s, 1H), 7.32 (ddd, J=7.2, 4.8, 1.2 Hz, 1H), 77.11 (t, J=8.0 Hz, 1H), 6.70 (d, J=7.6 Hz, 1H), 6.35 (dd, J=6.0, 2.4 Hz, 1H), 6.09 (d, J=2.0 Hz, 1H), 3.13 (t, J=7.6 Hz, 2H), 2.96 (t, J=7.6 Hz, 2H), 2.52 (s, 3H), 2.35 (s, 3H).

The following compounds were prepared according to the procedure described in Example 12 using appropriate intermediates.

| Example | Structure | LCMS (m/z) [M + 1]+ | 1H NMR |
|---|---|---|---|
| 13 | Prepared from Intermediates A1 and commercially available 3-aminobenzonitrile | 437.3 | 1H NMR (400 MHz, DMSO-d6) δ 9.18 (s, 1H), 8.51 (d, J = 2.4 Hz, 1H), 8.37 (s, 1H), 8.03 (d, J = 6.0 Hz, 1H), 7.86-7.73 (m, 3H), 7.60 (s, 1H), 7.47 (d, J = 7.6 Hz, 1H), 7.41 (t, J = 7.6 Hz, 1H), 7.35-7.33 (m, 1H), 6.42 (d, J = 4.0 Hz, 1H), 6.15 (s, 1H), 2.53 (s, 3H), 2.35 (s, 3H). |
| 14 | Prepared from Intermediates A1 and commercially available 4-aminobenzonitrile | 437.3 | 1H NMR (400 MHz, DMSO-d6) δ 9.24 (s, 1H), 8.50 (d, J = 4.8 Hz, 1H), 8.04 (d, J = 5.6 Hz, 1H), 7.88-7.78 (m, 7H), 7.59 (s, 1H), 7.34-7.31 (m, 1H), 6.45-6.43 (m, 1H), 6.16 (s, 1H), 2.54 (s, 3H), 2.36 (s, 3H). |
| 15 | Prepared from Intermediates A1 and commercially available 2-(4-aminophenyl)acetonitrile | 451.2 | 1H NMR (400 MHz, DMSO-d6) δ 8.85 (s, 1H), 8.50 (d, J = 4.4 Hz, 1H), 8.20 (s, 0.75H, HCOOH), 7.95 (d, J = 5.6 Hz, 1H), 7.84-7.77 (m, 2H), 7.56 (s, 1H), 7.50 (d, J = 8.4 Hz, 2H), 7.33-7.30 (m, 1H), 7.09 (d, J = 8.4 Hz, 2H), 6.33 (dd, J = 6.0, 2.0 Hz, 1H), 6.07 (d, J = 2.0 Hz, 1H), 4.09 (s, 2H), 2.52 (s, 3H), 2.35 (s, 3H). |
| 16 | Prepared from Intermediates A1 and commercially available 2-(3-aminophenyl)acetonitrile | 451.3 | 1H NMR (400 MHz, DMSO-d6) δ 9.59 (br s, 1H), 8.55 (d, J = 4.4 Hz, 1H), 7.98-7.96 (m, 3H), 7.67 (s, 1H), 7.45-7.40 (m, 2H), 7.32 (s, 1H), 7.27 (t, J = 7.6 Hz, 1H), 6.94 (d, J = 5.2 Hz, 1H), 6.55 (d, J = 4.0 Hz, 1H), 6.25 (d, J = 1.6 Hz, 1H), 4.25 (s, 2H), 2.55 (s, 3H), 2.36 (s, 3H). |

-continued

| Example | Structure | LCMS (m/z) [M + 1]+ | 1H NMR |
|---|---|---|---|
| 17 | Prepared from Intermediates A1 and B4. | 465.2 | 1H NMR (400 MHz, DMSO-d6) δ 8.82 (s, 1H), 8.50 (ddd, J = 4.8, 1.6, 0.8 Hz, 1H), 8.15 (s, 0.4H, HCOOH), 7.94 (d, J = 6.0 Hz, 1H), 7.84 (td, J = 7.6, 2.0 Hz, 1H), 7.78 (d, J = 7.6 Hz, 1H), 7.57 (s, 1H), 7.48 (d, J = 8.4 Hz, 2H), 7.32 (ddd, J = 7.6, 4.8, 1.2 Hz, 1H), 7.03 (d, J = 8.4 Hz, 2H), 6.33 (dd, J = 5.6, 2.0 Hz, 1H), 6.05 (d, J = 2.0 Hz, 1H), 3.13 (t, J = 8.0 Hz, 2H), 2.94 (t, J = 8.0 Hz, 2H), 2.52 (s, 3H), 2.35 (s, 3H). |
| 18 | Prepared from Intermediates A1 and B5. | 479.4 | 1H NMR (400 MHz, CD3OD) δ 8.56 (d, J = 4.0 Hz, 1H), 7.87-7.82 (m, 2H), 7.75 (d, J = 7.6Hz, 1H), 7.52 (s, 1H), 7.38-7.35 (m, 1H), 7.23-7.15 (m, 3H), 6.80 (d, J = 8.4 Hz, 1H), 6.25 (dd, J = 6.0, 2.4 Hz, 1H), 6.08 (d, J = 2.0 Hz, 1H), 2.57 (s, 3H), 2.40 (s, 3H), 1.77 (s, 6H). |
| 19 | Prepared from Intermediates A1 and B7. | 483.3 | 1H NMR (400 MHz, DMSO-d6) δ 8.53-8.50 (m, 2H), 7.98 (d, J = 6.4 Hz, 1H), 7.95 (d, J = 5.6 Hz, 1H), 7.84 (td, J = 8.0, 1.6 Hz, 1H), 7.79 (d, J = 8.0 Hz, 1H), 7.56 (s, 1H), 7.33 (t, J = 6.0 Hz, 1H), 7.05 (dd, J = 11.2, 8.4 Hz, 1H), 6.77-6.76 (m, 1H), 6.36 (d, J = 5.6 Hz, 1H), 6.33 (s, 1H), 3.12 (t, J = 7.2 Hz, 2H), 2.96 (t, J = 7.2 Hz, 2H), 2.53 (s, 3H), 2.35 (s, 3H). |
| 20 | Prepared from Intermediates A1 and B9. | 499.4 | 1H NMR (400 MHz, DMSO-d6) δ 9.02 (s, 1H), 8.50 (d, J = 4.4 Hz, 1H), 8.22 (s, 1H, HCOOH), 7.99 (d, J = 6.0 Hz, 1H), 7.85-7.78 (m, 2H), 7.61-7.58 (m, 2H), 7.49 (d, J = 2.4 Hz, 1H), 7.33 (t, J = 5.6 Hz, 1H), 7.25 (d, J = 8.8 Hz, 1H), 6.39 (dd, J = 6.0, 2.0 Hz, 1H), 6.08 (d, J = 2.0 Hz, 1H), 3.06-3.02 (m, 4H), 2.52 (s, 3H), 2.35 (s, 3H). |

-continued

| Example | Structure | LCMS (m/z) [M + 1]+ | 1H NMR |
|---|---|---|---|
| 21 | Prepared from Intermediates A1 and B6. | 483.5 | 1H NMR (400 MHz, DMSO-d6) δ 8.86 (s, 1H), 8.51 (s, 1H), 7.95 (d, J = 5.2 Hz, 1H), 7.86-7.80 (m, 2H), 7.58 (s, 1H), 7.47-7.33 (m, 3H), 7.01 (t, J = 9.6 Hz, 1H), 6.35 (d, J = 4.0 Hz, 1H), 6.04 (s, 1H), 3.13 (t, J = 7.6 Hz, 2H), 3.00 (t, J = 7.6 Hz, 2H), 2.50 (s, 3H), 2.34 (s, 3H). |
| 22 | Prepared from Intermediates A1 and B25. | 533.1 | 1H NMR (400 MHz, CD3OD) δ 8.76 (d, J = 5.2 Hz, 1H), 8.39 (d, J = 8.0 Hz, 1H), 8.36-8.31 (m, 1H), 8.08 (d, J = 6.4 Hz, 1H), 7.77 (t, J = 6.4 Hz, 1H), 7.68 (s, 1H), 7.61 (d, J = 8.8 Hz, 1H), 7.50 (s, 1H), 7.42 (d, J = 8.4 Hz, 1H), 6.67 (dd, J = 6.4, 2.4 Hz, 1H), 6.43 (d, J = 2.4 Hz, 1H), 3.25 (br s, 4H), 2.66 (s, 3H), 2.45 (s, 3H). |
| 23 | Prepared from Intermediates A1 and B16. | 466.2 | 1H NMR (400 MHz, DMSO-d6) δ 9.07 (s, 1H), 8.49-8.54 (m, 2H), 7.9-8.0 (m, 2H), 7.92 (d, J = 2.0 Hz, 1H), 7.78-7.85 (m, 2H), 7.59 (s, 1H), 7.31-7.34 (m, 1H), 6.42 (dd, J = 5.6, 2.4 Hz, 1H), 6.10 (d, J = 2.0 Hz, 1H), 3.11 (t, J = 7.6 Hz, 2H), 2.98 (t, J = 7.6 Hz, 2H), 2.52 (s, 3H), 2.35 (s, 3H). |
| 24 | Prepared from Intermediates A1 and B15. | 466.3 | 1H NMR (400 MHz, CD3OD) δ 8.50 (d, J = 4.8 Hz, 1H), 8.09 (d, J = 6.4 Hz, 2H), 7.86-7.84 (m, 2H), 7.58 (s, 1H), 7.35 (dd, J = 8.4, 4.8 Hz, 1H), 6.96 (d, J = 5.6 Hz, 1H), 6.94 (s, 1H), 6.66 (dd, J = 6.4, 2.0 Hz, 1H), 6.58 (d, J = 2.0 Hz, 1H), 3.19 (t, J = 7.2 Hz, 2H), 3.11 (t, J = 7.2 Hz, 2H), 2.61(s, 3H), 2.42 (s, 3H). |

-continued

| Example | Structure | LCMS (m/z) [M + 1]⁺ | ¹H NMR |
|---|---|---|---|
| 25 | Prepared from Intermediates A1 and B8. | 483.4 | ¹H NMR (400 MHz, DMSO-d6) δ 8.57 (s, 1H), 8.50 (d, J = 4.0 Hz, 1H), 8.04 (dd, J = 8.0, 6.8 Hz, 1H), 7.94 (d, J = 6.4 Hz, 1H), 7.84 (td, J = 7.6, 1.6 Hz, 1H), 7.78 (d, J = 7.6 Hz, 1H), 7.56 (s, 1H), 7.35-7.31 (m, 1H), 6.97 (t, J = 7.6 Hz, 1H), 6.79 (t, J = 7.2 Hz, 1H), 6.38-6.35 (m, 2H), 3.14 (t, J = 7.6 Hz, 2H), 3.03 (t, J = 7.6 Hz, 2H), 2.54 (s, 3H), 2.35 (s, 3H). |
| 26 | Prepared from Intermediates A1 and B14. | 466.3 | ¹H NMR (400 MHz, DMSO-d6) δ 11.28 (s, 1H), 8.44 (d, J = 4.0 Hz, 1H), 8.38 (d, J = 7.2 Hz, 1H), 8.03 (d, J = 8.0 Hz, 1H), 7.94 (td, J = 7.6, 1.6 Hz, 1H), 7.79 (t, J = 8.0 Hz, 1H), 7.76 (s, 1H), 7.39 (dd, J = 6.0, 5.2 Hz, 1H), 7.06 (d, J = 7.2 Hz, 1H), 7.04-7.01 (m, 1H), 6.92 (d, J = 8.0 Hz, 1H), 6.60 (s, 1H), 3.35-3.28 (m, 4H), 2.57 (s, 3H), 2.34 (s, 3H). |
| 27 | Prepared from Intermediates A1 and B24. | 479.4 | ¹H NMR (400 MHz, CD₃OD) δ 8.56 (d, J = 3.6 Hz, 1H), 8.22 (s, 0.7H, HCOOH), 7.87 (td, J = 8.0, 2.0 Hz, 1H), 7.79 (d, J = 8.0 Hz, 1H), 7.73 (d, J = 6.0 Hz, 1H), 7.53 (s, 1H), 7.42-3.36 (m, 1H), 7.09 (t, J = 7.2 Hz, 1H), 7.03 (d, J = 7.2 Hz, 1H), 6.92 (d, J = 7.2 Hz, 1H), 6.31 (dd, J = 6.0, 2.0 Hz, 1H), 5.86 (d, J = 2.0 Hz, 1H), 5.34 (m, 1H), 3.17-3.11 (m, 4H), 2.56 (s, 3H), 2.40 (s, 3H), 2.06 (s, 3H). |
| 28 | Prepared from Intermediates A1 and B21. | 479.5 | ¹H NMR (400 MHz, CD₃OD) δ 8.58 (d, J = 4.4 Hz, 1H), 8.26 (s, 0.6H, HCOOH), 7.90-7.78 (m, 3H), 7.53 (s, 1H), 7.41-3.37 (m, 1H), 7.08-6.99 (m, 3H), 6.92 (d, J = 7.2 Hz, 1H), 6.31 (dd, J = 6.4, 2.4 Hz, 1H), 6.06 (d, J = 2.4 Hz, 1H), 3.16 (t, J = 7.6 Hz, 2H), 3.01 (t, J = 7.6 Hz, 2H), 2.62 (s, 3H), 2.52 (s, 3H), 2.21 (s, 3H). |

| Example | Structure | LCMS (m/z) [M + 1]+ | 1H NMR |
|---|---|---|---|
| 29 | Prepared from Intermediates A1 and B23 | 479.2 | 1H NMR (400 MHz, CDCl3) δ 8.57 (d, J = 4.0 Hz, 1H), 7.90-7.75 (m, 3H), 7.53 (s, 1H), 7.41-3.37 (m, 1H), 7.08-6.99 (m, 3H), 6.96 (s, 1H), 6.94 (s, 1H), 6.60 (s, 1H), 6.31 (dd, J = 5.6, 1.6 Hz, 1H), 6.09 (d, J = 1.6 Hz, 1H), 3.15 (t, J = 7.6 Hz, 2H), 2.96 (t, J = 7.6 Hz, 2H), 2.55 (s, 3H), 2.39 (s, 3H), 2.22 (s, 3H). |
| 30 | Prepared from Intermediates A1 and B22 | 479.2 | 1H NMR (400 MHz, CD3OD) δ 8.56 (d, J = 3.6 Hz, 1H), 7.90-7.78 (m, 3H), 7.53 (s, 1H), 7.41-3.37 (m, 1H), 7.11 (d, J = 7.6 Hz, 1H), 7.07 (s, 1H), 6.84 (d, J = 7.2 Hz, 1H), 6.28 (dd, J = 6.4, 2.4 Hz, 1H), 5.94 (d, J = 2.4 Hz, 1H), 3.12 (t, J = 6.8 Hz, 2H), 2.97 (t, J = 6.8 Hz, 2H), 2.54 (s, 3H), 2.38 (s, 3H), 2.10 (s, 3H). |
| 31 | Prepared from Intermediates A1 and B44. | 455.4 | 1H NMR (400 MHz, CD3OD) δ 8.56 (d, J = 4.4 Hz, 1H), 7.87 (td, J = 7.6, 1.6 Hz, 1H), 7.82-87.77 (m, 2H), 7.64 (s, 1H), 7.52 (s, 1H), 7.41-7.36 (m, 2H), 6.26 (dd, J = 6.4, 2.4 Hz, 1H), 5.97 (d, J = 2.4 Hz, 1H), 4.50 (t, J = 6.8 Hz, 2H), 3.42 (t, J = 6.8 Hz, 2H), 2.58 (s, 3H), 2.41 (s, 3H). |
| 32 | Prepared from Intermediates A1 and B45. | 455.4 | 1H NMR (400 MHz, CD3OD) δ 8.55 (d, J = 3.6 Hz, 1H), 7.90-7.75 (m, 3H), 7.54 (s, 1H), 7.39-7.32 (m, 2H), 6.74 (br s, 1H), 6.33 (d, J = 4.8 Hz, 1H), 5.93 (s, 1H), 4.35 (t, J = 6.8 Hz, 2H), 3.31 (2H, overlapped with MeOH), 2.52 (s, 3H), 2.39 (s, 3H). |

| Example | Structure | LCMS (m/z) [M + 1]+ | 1H NMR |
|---|---|---|---|
| 33 | 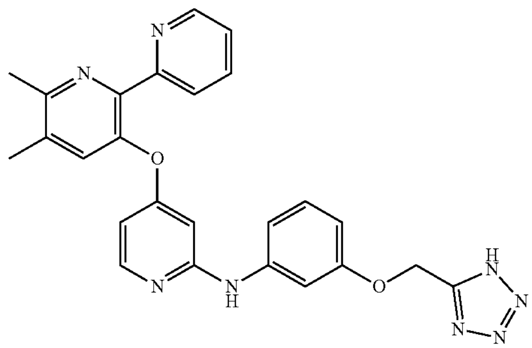 | 467.3 | 1H NMR (400 MHz, CD3OD) δ 8.57 (d, J = 4.8 Hz, 1H), 7.87 (d, J = 5.6 Hz, 1H), 7.85 (td, J = 7.6, 1.6 Hz, 1H), 7.75 (d, J = 8.0 Hz, 1H), 7.53 (s, 1H), 7.39-7.35 (m, 1H), 7.14 (t, J = 8.0 Hz, 1H), 7.10 (t, J = 2.0 Hz, 1H), 6.92 (dd, J = 8.0, 2.0 Hz, 1H), 6.66 (dd, J = 8.0, 2.0 Hz, 1H), 6.28 (dd, J = 6.0, 2.0 Hz, 1H), 6.13 (d, J = 2.0 Hz, 1H), 5.24 (s, 2H), 2.57 (s, 3H), 2.39 (s, 3H). |

Prepared from Intermediates A1 and B42.

Example 34: 2-(5-(3-((4-((5,6-dimethyl-[2,2'-bipyridin]-3-yl)oxy)pyridin-2-yl)amino)benzyl)-2H₁-tetrazol-2-yl)acetic acid (34A) and 2-(5-(3-((4-((5,6-dimethyl-[2,2'-bipyridin]-3-yl)oxy)pyridin-2-yl)amino)benzyl)-1H-tetrazol-1-yl)acetic acid (34B)

Step 1: tert-butyl 2-(5-(3-((4-((5,6-dimethyl-[2,2'-bipyridin]-3-yl)oxy)pyridin-2-yl)amino)benzyl)-2H-tetrazol-2-yl)acetate and tert-butyl 2-(5-(3-((4-((5,6-dimethyl-[2,2'-bipyridin]-3-yl)oxy)pyridin-2-yl)amino)benzyl)-1H-tetrazol-1-yl)acetate To a stirred solution of N-(3-((1H-tetrazol-5-yl)methyl)phenyl)-4-((5,6-dimethyl-[2,2'-bipyridin]-3-yl)oxy)pyridin-2-amine (Example 16, 1.0 eq) in acetone (0.01 M) was added K₂CO₃ (1.5 eq) at 0° C. under Ar. The resulting mixture was stirred at 0° C. for 30 min and tert-butyl 2-bromoacetate (1.5 eq) was added dropwise. The mixture was slowly warmed to rt and stirred for 5 h. The mixture was quenched with sat. NH₄Cl. The mixture was partitioned between DCM/water. The organic phase was dried over Na₂SO₄, concentrated and purified by prep-HPLC (mobile phase: 0.1% TFA/MeCN/H₂O) to give the title compounds A and B as a yellow oil. LC-MS (m/z): [M+1]+=565.

Step 2 for 34A isomer: 2-(5-(3-((4-((5,6-dimethyl-[2,2'-bipyridin]-3-yl)oxy)pyridin-2-yl)amino)benzyl)-2H-tetrazol-2-yl)acetic acid To a stirred solution of above mixture (1.0 eq) in MeCN (0.2 M) was added 4N HCl/dioxane (80 eq). The resulting mixture was stirred at rt for 16 h. The reaction mixture was concentrated under reduced pressure. The residue was purified by HPLC (mobile phase: MeCN/H₂O/0.1% HCOOH). The fractions were collected, and the solvent was removed via lyophilizer to give the title compound. LC-MS (m/z): [M+1]+=509.2; 1H NMR (400 MHz, DMSO-d₆) δ 8.90 (s, 1H), 8.48 (dd, J=4.8, 0.8 Hz, 1H), 7.95 (d, J=5.6 Hz, 1H), 7.82 (td, J=7.6, 2.0 Hz, 1H), 7.77 (d, J=7.6 Hz, 1H), 7.59 (dd, J=8.0, 1.2 Hz, 1H), 7.55 (s, 1H), 7.38 (s, 1H), 7.31 (ddd, J=7.6, 4.8, 1.6 Hz, 1H), 7.14 (t, J=8.0 Hz, 1H), 6.73 (d, J=7.6 Hz, 1H), 6.34 (dd, J=6.0, 2.4 Hz, 1H), 6.08 (d, J=2.4 Hz, 1H), 5.27 (s, 2H), 4.21 (s, 2H), 2.51 (s, 3H), 2.34 (s, 3H).

Step 2 for 34B isomer: 2-(5-(3-((4-((5,6-dimethyl-[2,2'-bipyridin]-3-yl)oxy)pyridin-2-yl)amino)benzyl)-1H-tetrazol-1-yl)acetic acid To a stirred solution of the mixture from step 1 (1.0 eq) in MeCN (0.2 M) was added 4N HCl/dioxane (80 eq). The resulting mixture was stirred at rt for 16 h. The reaction mixture was concentrated under reduced pressure. The residue was purified by HPLC (mobile phase: MeCN/H₂O/0.1% HCOOH). The fractions were collected, and the solvent was removed by lyophilizer to give the title compound. LC-MS (m/z): [M+1]=509.2; ¹H NMR (400 MHz, DMSO-d$_6$) δ8.90 (s, 1H), 8.50 (dd, J=4.8, 0.4 Hz, 1H), 7.96 (d, J=6.0 Hz, 1H), 7.84 (td, J=7.6, 2.0 Hz, 1H), 7.78 (d, J=8.0 Hz, 1H), 7.57 (s, 1H), 7.54 (dd, J=9.2, 0.8 Hz, 1H), 7.47 (s, 1H), 7.32 (ddd, J=7.2, 4.8, 1.2 Hz, 1H), 7.14 (t, J=8.0 Hz, 1H), 6.75 (d, J=7.6 Hz, 1H), 6.34 (dd, J=6.0, 2.0 Hz, 1H), 6.09 (d, J=2.0 Hz, 1H), 5.59 (s, 2H), 4.16 (s, 2H), 2.52 (s, 3H), 2.35 (s, 3H).

The following compounds were prepared according to the procedure described in Example 34.

| Example | Structure | LCMS (m/z) [M + 1]⁺ | ¹H NMR (400 MHz, DMSO) |
|---|---|---|---|
| 35A | Prepared from Example 15. | 509.2 | ¹H NMR (400 MHz, DMSO-d6) δ 8.90 (s, 1H), 8.50 (dd, J = 4.0. 0.8 Hz, 1H), 8.30 (s, 2H, HCOOH), 7.95 (d, J = 6.0 Hz, 1H), 7.84 (td, J = 7.6, 1.6 Hz, 1H), 7.78 (d, J = 7.6 Hz, 1H), 7.57 (s, 1H), 7.53 (d, J = 7.6 Hz, 2H), 7.34-7.30 (m, 1H), 7.09 (d, J = 8.4 Hz, 2H), 6.34 (dd, J = 5.6, 2.4 Hz, 1H), 6.07 (d, J = 2.4 Hz, 1H), 4.62 (s, 2H), 4.10 (s, 2H), 2.52 (s, 3H), 2.35 (s, 3H). |
| 35B | Prepared from Example 15. | 509.2 | ¹H NMR (400 MHz, DMSO-d6) δ 8.86 (s, 1H), 8.50 (d, J = 4.4 Hz, 1H), 8.18 (s, 1H, HCOOH), 7.95 (d, J = 6.0 Hz, 1H), 7.84 (t, J = 6.8 Hz, 1H), 7.78 (d, J = 8.0 Hz, 1H), 7.57 (s, 1H), 7.51 (d, J = 8.0 Hz, 2H), 7.34-7.30 (m, 1H), 7.10 (d, J = 8.4 Hz, 2H), 6.33 (dd, J = 5.6, 1.6 Hz, 1H), 6.06 (d, J = 1.6 Hz, 1H), 4.99 (s, 2H), 4.08 (s, 2H), 2.52 (s, 3H), 2.35 (s, 3H). |

Example 36: 3-(5-((4-((2,6-dimethylpyridin-3-yl)oxy)pyridin-2-yl)amino)-2-fluorophenyl)propanoic acid

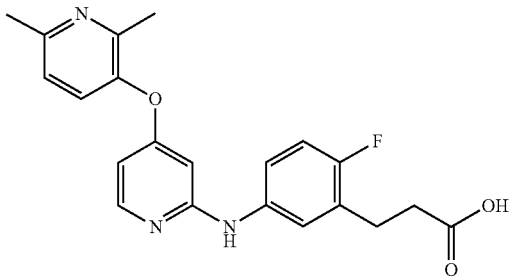 [SMILES: Cc1ccc(Oc2ccnc(Nc3ccc(F)c(CCC(=O)O)c3)c2)c(C)n1]

Step 1: methyl 3-(5-((4-((2,6-dimethylpyridin-3-yl)oxy)pyridin-2-yl)amino)-2-fluorophenyl)propanoate A mixture of 3-((2-chloropyridin-4-yl)oxy)-2,6-dimethylpyridine (Intermediate A2, 1.0 eq), methyl 3-(5-amino-2-fluorophenyl)propanoate (Intermediate B10, 1.3 eq), Pd(OAc)$_2$ (0.1 eq), xantphos (0.1 eq) and Cs$_2$CO$_3$ (2.0 eq) in dioxane (0.29 M) was stirred at 115° C. for 16 h. The reaction was monitored by LC-MS. The reaction mixture was filtered, and the filtrate was concentrated under reduced pressure. The residue was purified by flash chromatography on silica gel (eluent petroleum ether/EtOAc 10:1 to 3:1) to give the title compound as a yellow oil. LC-MS: [M+H]$^+$=396.2.

Step 2: 3-(5-((4-((2,6-dimethylpyridin-3-yl)oxy)pyridin-2-yl)amino)-2-fluorophenyl)propanoic acid A mixture of methyl 3-(5-((4-((2,6-dimethylpyridin-3-yl)oxy)pyridin-2-yl)amino)-2-fluorophenyl)propanoate (1.0 eq) and NaOH (5.0 eq) in MeOH/H$_2$O (v/v 5:1, 0.08 M) was stirred at 50° C. for 2 h. The reaction was monitored by LC-MS. The solid was filter off, and the filtrate was concentrated under reduced pressure. The residue was purified by HPLC (mobile phase: 0.1% NH$_3$·H$_2$O/MeCN/H$_2$O) to give the title compound as a yellow solid. LC-MS (m/z): [M+H]$^+$=382.2; $^1$H NMR (400 MHz, DMSO-d6) δ 8.93 (s, 1H), 8.04 (d, J=6.0 Hz, 1H), 7.55-7.51 (m, 1H), 7.47 (d, J=8.0 Hz, 1H), 7.41 (dd, J=6.4, 2.4 Hz, 1H), 7.21 (d, J=8.4 Hz, 1H), 6.99 (t, J=9.2 Hz, 1H), 6.40 (dd, J=5.6, 2.0 Hz, 1H), 6.02 (d, J=2.0 Hz, 1H), 2.75 (t, J=7.6 Hz, 2H), 2.47 (s, 3H), 2.37 (t, J=7.6 Hz, 2H), 2.28 (s, 3H).

The following compounds were prepared according to the procedure described in Example 36 using appropriate intermediates.

| Example | Structure | LCMS (m/z) [M + 1]$^+$ | $^1$H NMR |
|---|---|---|---|
| 37 | (Prepared from Intermediates A2 and B17.) | 365.1 | $^1$H NMR (400 MHz, DMSO) δ 9.62 (s, 1H), 8.11 (d, J = 2.0 Hz, 1H), 7.53-7.45 (m, 3H), 7.28 (d, J = 8.0 Hz, 1H), 7.20 (d, J = 8.4 Hz, 1H), 6.69 (d, J = 7.2 Hz, 1H), 6.52 (dd, J = 5.6, 2.0 Hz, 1H), 2.66 (t, J = 7.6 Hz, 2H), 2.47 (s, 3H), 2.46 (t, J = 7.6 Hz, 2H), 2.28 (s, 3H). |
| | (Prepared from Intermediates A2 and B19.) | 365.2 | $^1$H NMR (400 MHz, DMSO) δ 9.13 (s, 1H), 8.59 (d, J = 2.0 Hz, 1H), 8.10 (d, J = 5.6 Hz, 1H), 7.97-7.95 (m, 2H), 7.50 (d, J = 8.4 Hz, 1H), 7.23 (d, J = 8.4 Hz, 1H), 6.48 (dd, J = 6.0, 2.4 Hz, 1H), 6.07 (d, J = 2.0 Hz, 1H), 2.76 (t, J = 7.6 Hz, 2H), 2.48 (s, 3H), 2.44 (t, J = 7.6 Hz, 2H), 2.29 (s, 3H). |

| Example | Structure | LCMS (m/z) [M + 1]⁺ | ¹H NMR |
|---|---|---|---|
| 39 | Prepared from Intermediates A2 and B11. | 382.2 | ¹H NMR (400 MHz, CD₃OD) δ 7.97 (d, J = 6.0 Hz, 1H), 7.60 (dd, J = 8.0, 1.6 Hz, 1H), 7.44 (d, J = 8.4 Hz, 1H), 7.22 (d, J = 8.4 Hz, 1H), 7.21 (d, J = 8.4 Hz, 1H), 7.00-6.89 (m, 2H), 6.36 (dd, J = 6.0, 2.0 Hz, 1H), 6.13 (d, J = 2.0 Hz, 1H), 2.85 (t, J = 8.0 Hz, 2H), 2.52 (s, 3H), 2.46 (t, J = 8.0 Hz, 2H), 2.36 (s, 3H). |
| 40 | Prepared from Intermediates A2 and B12. | 382.2 | ¹H NMR (400 MHz, DMSO-d6) δ 8.63 (s, 1H), 8.04 (t, J = 8.0 Hz, 1H), 8.02 (d, J = 5.6 Hz, 1H), 7.47 (d, J = 8.0 Hz, 1H), 7.21 (d, J = 8.0 Hz, 1H), 7.21 (d, J = 8.4 Hz, 1H), 6.98 (t, J = 8.0 Hz, 1H), 6.84 (t, J = 7.2 Hz, 1H), 6.43 (dd, J = 5.6, 2.0 Hz, 1H), 6.30 (d, J = 2.0 Hz, 1H), 2.80 (t, J = 7.6 Hz, 2H), 2.47 (s, 3H), 2.45 (t, J = 7.6 Hz, 2H), 2.28 (s, 3H). |
| 41 | Prepared from Intermediates A2 and B13. | 398.1 | ¹H NMR (400 MHz, CD₃OD) δ 8.01 (d, J = 5.6 Hz, 1H), 7.44 (d, J = 8.4 Hz, 1H), 7.41 (d, J = 2.4 Hz, 1H), 7.35 (dd, J = 8.4, 2.4 Hz, 1H), 7.23 (d, J = 6.8 Hz, 1H), 7.21 (d, J = 8.4 Hz, 1H), 6.37 (dd, J = 6.0, 2.0 Hz, 1H), 6.10 (d, J = 2.0 Hz, 1H), 2.96 (t, J = 8.0 Hz, 2H), 2.56 (t, J = 8.0 Hz, 2H), 2.53 (s, 3H), 2.37 (s, 3H). |
| | Prepared from Intermediates A2 and B18. | 365.3 | ¹H NMR (400 MHz, DMSO) δ 9.61 (s, 1H), 8.10 (d, J = 5.6 Hz, 1H), 8.02 (d, J = 5.2 Hz, 1H), 7.50 (s, 1H), 7.47 (d, J = 8.4 Hz, 1H), 7.36 (d, J = 2.0 Hz, 1H), 7.20 (d, J = 8.4 Hz, 1H), 6.75 (d, J = 4.8 Hz, 1H), 6.35 (dd, J = 5.6, 2.0 Hz, 1H), 2.76 (t, J = 7.6 Hz, 2H), 2.54 (t, J = 7.6 Hz, 2H), 2.48 (s, 3H), 2.29 (s, 3H). |

-continued

| Example | Structure | LCMS (m/z) [M + 1]+ | 1H NMR |
|---|---|---|---|
| 43 | (structure shown) | 375.2 | 1H NMR (400 MHz, DMSO-d6) δ 9.02 (d, J = 3.2 Hz, 1H), 8.13 (t, J = 5.6 Hz, 1H), 7.89-7.85 (m, 1H), 7.75-7.72 (m, 1H), 7.51-7.49 (m, 1H), 7.39 (s, 1H), 7.15-7.12 (m, 1H), 6.76 (m, 1H), 6.53 (m, 1H), 6.30 (s, 1H), 2.73 (m, 2H), 2.54 (s, 3H), 2.41 (m, 2H). |

Prepared from Intermediates A13 and B1.

Example 44: N-(3-(2-(2H-tetrazol-5-yl)ethyl)phenyl)-4-((2,6-dimethylpyridin-3-yl)oxy)pyridin-2-amine

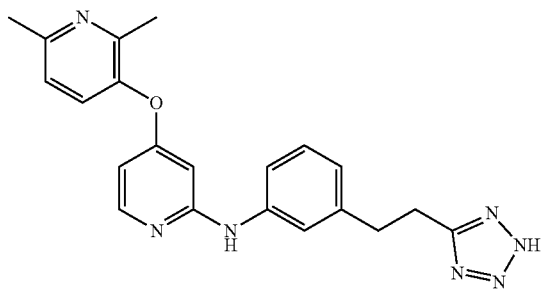 [SMILES: Cc1ccc(Oc2ccnc(Nc3cccc(CCc4nn[nH]n4)c3)c2)c(C)n1]

Step 1: 3-(3-((4-((2,6-dimethylpyridin-3-yl)oxy)pyridin-2-yl)amino)phenyl)propanenitrile A mixture of 3-((2-chloropyridin-4-yl)oxy)-2,6-dimethylpyridine (Intermediate A2, 1.0 eq), 3-(3-aminophenyl)propanenitrile (Intermediate B2, 1.3 eq), $Cs_2CO_3$ (2.0 eq), xantphos (0.1 eq), $Pd(OAc)_2$ (0.1 eq) in dioxane (0.2 M) was stirred at 115° C. for 16h. The reaction was monitored by LC-MS. The solution was cooled down to r.t and diluted with EtOAc (50 mL). The mixture was washed with brine, and then dried over $Na_2SO_4$. The crude product was purified by flash chromatography on silica gel (petroleum ether/EtOAc 3:2) to give title compound as a yellow solid. LC-MS (m/z): [M+H]+=345.

Step 2: N-(3-(2-(2H-tetrazol-5-yl)ethyl)phenyl)-4-((2,6-dimethylpyridin-3-yl)oxy)pyridin-2-amine A mixture of 3-(3-((4-((2,6-dimethylpyridin-3-yl)oxy)pyridin-2-yl)amino)phenyl)propanenitrile (1.0 eq), TMSN3 (5.0 eq) and $Bu_2SnO$ (2.0 eq) in dioxane (0.06 M) was stirred at 120° C. for 16h. The reaction was monitored by LC-MS. The mixture solution was cooled down. The organic phase was concentrated. The residue was purified by HPLC (mobile phase: 0.1% $HCOOH/MeCN/H_2O$). The fractions were collected, and the solvent was removed by lyophilizer to give the title compound as a white solid (formic acid salt). LC-MS (m/z): [M+H]+=388.3; 1H NMR (400 MHz, DMSO) δ 8.93 (s, 1H), 8.17 (s, 0.6H, HCOOH), 8.06 (d, J=5.6 Hz, 1H), 7.50-7.43 (m, 3H), 7.22 (d, J=8.0 Hz, 1H), 7.13 (t, J=8.0 Hz, 1H), 6.72 (d, J=7.2 Hz, 1H), 6.43 (dd, J=5.6, 2.0 Hz, 1H), 6.04 (d, J=1.6 Hz, 1H), 3.15 (t, J=7.6 Hz, 2H), 2.97 (t, J=7.6 Hz, 2H), 2.47 (s, 3H), 2.29 (s, 3H).

The following compounds were prepared according to the procedure described in Example 44 using appropriate intermediates.

| Example | Structure | LCMS (m/z) [M + 1]+ | 1H NMR |
|---|---|---|---|
| 45 | (structure shown) | 406.2 | 1H NMR (400 MHz, DMSO) δ 8.60 (s, 1H), 8.04-8.00 (m, 2H), 7.47 (d,J = 8.0 Hz, 1H), 7.21 (d, J = 8.0 Hz, 1H), 7.06 (dd, J = 11.6, 8.4 Hz, 1H), 6.80-6.76 (m, 1H), 6.44 (dd, J = 5.6, 2.0 Hz, 1H), 6.29 (d, J = 2.0 Hz, 1H), 3.14 (t, J = 7.6 Hz, 2H), 2.98 (t, J = 7.6 Hz, 2H), 2.47 (s, 3H) , 2.28 (s, 3H). |

Prepared from Intermediates A2 and B7.

| Example | Structure | LCMS (m/z) [M + 1]+ | ¹H NMR |
|---|---|---|---|
| 46 | Prepared from Intermediates A2 and B8. | 406.2 | ¹H NMR (400 MHz, DMSO) δ 8.65 (s, 1H), 8.23 (s, 1H), 8.07 (t, J = 8.0 Hz, 1H), 8.03 (d, J = 6.0 Hz, 1H), 7.48 (d, J = 8.0 Hz, 1H), 7.21 (d, J = 8.0 Hz, 1H), 6.98 (t, J = 8.0 Hz, 1H), 6.82 (t, J = 6.4 Hz, 1H), 6.44 (dd, J = 5.6, 2.0 Hz, 1H), 6.32 (d, J = 2.0 Hz, 1H), 3.11-2.95 (m, 4H), 2.47 (s, 3H), 2.29 (s, 3H). |
| 47 | Prepared from Intermediates A2 and B14. | 389.2 | ¹H NMR (400 MHz, DMSO) δ 9.66 (s, 1H), 8.11 (d, J = 5.6 Hz, 1H), 7.51-7.43 (m, 3H), 7.30 (d, J = 8.0 Hz, 1H), 7.16 (d, J = 8.4 Hz, 1H), 6.64 (d, J = 7.2 Hz, 1H), 6.50 (dd, J = 5.6, 2.0 Hz, 1H), 3.01 (t, J = 7.6 Hz, 2H), 2.85 (t, J = 7.6 Hz, 2H), 2.37 (s, 3H), 2.28 (s, 3H). |
| 48 | Prepared from Intermediates A2 and B15. | 389.3 | ¹H NMR (400 MHz, DMSO) δ 9.62 (s, 1H), 8.10 (d, J = 5.6 Hz, 1H), 8.02 (d, J = 4.4 Hz, 1H), 7.50 (s, 1H), 7.46 (d, J = 8.0 Hz, 1H), 7.33 (s, 1H), 7.20 (d, J = 8.0 Hz, 1H), 6.75-6.73 (m, 1H), 6.36 (dd, J = 5.6, 2.0 Hz, 1H), 3.22 (t, J = 7.6 Hz, 2H), 2.95 (t, J = 7.6 Hz, 2H), 2.48 (s, 3H), 2.29 (s, 3H). |
| 49 | Prepared from Intermediates A2 and B16. | 389.2 | ¹H NMR (400 MHz, DMSO-d6) δ 9.13 (s, 1H), 8.56 (d, J = 2.4 Hz, 1H), 8.10 (d, J = 5.6 Hz, 1H), 7.99 (s, 1H), 7.94 (s, 1H), 7.51 (d, J = 8.4 Hz, 1H), 7.24 (d, J = 8.4 Hz, 1H), 6.50 (dd, J = 5.6, 2.0 Hz, 1H), 6.06 (d, J = 2.0 Hz, 1H), 3.10 (t, J = 7.6 Hz, 2H), 2.97 (t, J = 7.6 Hz, 2H), 2.48 (s, 3H), 2.28 (s, 3H). |

| Example | Structure | LCMS (m/z) [M + 1]+ | 1H NMR |
|---|---|---|---|
| 50 | 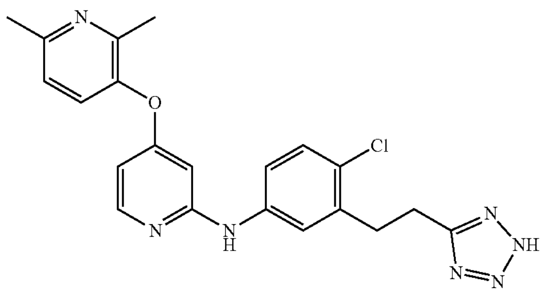 | 422.3 | 1H NMR (400 MHz, CD3OD) δ 8.25 (s, 1H), 8.00 (d,J = 2.0 Hz, 1H), 7.44 (d, J = 8.0 Hz, 1H), 7.39 (d, J = 2.4 Hz, 1H), 7.33 (dd,J = 8.8, 2.4 Hz, 1H), 7.25-7.21 (m, 2H), 6.39 (dd, J = 6.0, 2.0 Hz, 1H), 6.09 (d, J = 2.0 Hz, 1H), 3.23 (t, J = 7.6 Hz, 2H), 3.15 (t, J = 7.6 Hz, 2H), 2.52 (s, 3H) , 2.37 (s, 3H). |
| | Prepared from Intermediates A2 and B9. | | |
| 51 | 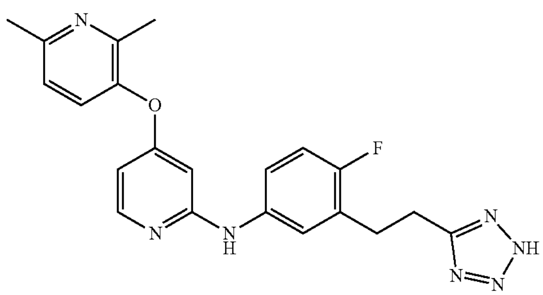 | 406.4 | 1H NMR (400 MHz, CD3OD) δ 8.12 (s, 1H), 7.95 (d,J = 2.0 Hz, 1H), 7.45 (d, J = 8.4 Hz, 1H), 7.30 (dd, J = 6.4, 2.4 Hz, 1H), 7.23 (d,J = 8.4 Hz, 2H), 6.97 (t, J = 9.2 Hz, 1H), 6.38 (dd, J = 6.0, 2.0 Hz, 1H), 6.06 (d,J = 2.0 Hz, 1H), 3.18-3.06 (m, 4H), 2.52 (s, 3H), 2.37 (s, 3H). |
| | Prepared from Intermediates A2 and B6. | | |

Example 52: N-(3-(2-(2H-tetrazol-5-yl)ethyl)phenyl)-4-((6-methyl-2-phenylpyridin-3-yl)oxy)pyridin-2-amine

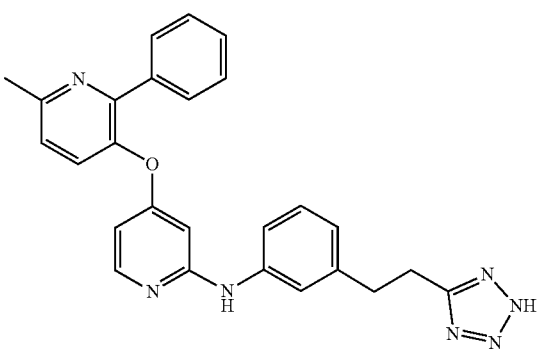 [SMILES: Cc1ccc(Oc2ccnc(Nc3cccc(CCc4nn[nH]n4)c3)c2)c(-c2ccccc2)n1]

Step 1: 3-(3-((4-((6-methyl-2-phenylpyridin-3-yl)oxy)pyridin-2-yl)amino)phenyl)propanenitrile A mixture of 3-((2-chloropyridin-4-yl)oxy)-6-methyl-2-phenylpyridine (Intermediate A6, 1.0 eq), 3-(3-aminophenyl)propanenitrile (Intermediate B2, 1.5 eq), Cs₂CO₃ (2.0 eq), Xantphos (0.1 eq) and Pd(OAc)₂ (0.1 eq) in dioxane (0.25 M) was stirred at 120° C. for 16 h. The reaction mixture was cooled down to r.t, diluted with EtOAc (50 mL), washed with brine and then dried over Na₂SO₄. The organic phase was concentrated to give the title compound as a yellow oil. LC-MS (m/z): [M+H]+=407

Step 2: N-(3-(2-(2H-tetrazol-5-yl)ethyl)phenyl)-4-((6-methyl-2-phenylpyridin-3-yl)oxy)pyridin-2-amine A mixture of 3-(3-((4-((6-methyl-2-phenylpyridin-3-yl)oxy)pyridin-2-yl)amino)phenyl)propanenitrile (1.0 eq), TMSN3 (5.0 eq) and Bu₂SnO (2.0 eq) in dioxane (0.17 M) was stirred at 120° C. for 16 h. The reaction mixture was cooled to RT and concentrated under reduced pressure. The residue was purified by prep-TLC (DCM/MeOH 8:1) to give the title compound as a white solid. LC-MS (m/z): [M+H]=450.4; 1H NMR (400 MHz, DMSO) δ 8.89 (s, 1H), 8.00 (d, J=6.0 Hz, 1H), 7.78 (d, J=8.0 Hz, 2H), 6.66 (d, J=8.4 Hz, 1H), 7.44-7.36 (m, 7H), 7.11 (t, J=7.6 Hz, 1H), 6.71 (d, J=7.6 Hz, 1H), 6.41-6.39 (m, 1H), 6.09 (s, 1H), 3.11 (t, J=7.6 Hz, 2H), 2.95 (t, J=7.6 Hz, 2H), 2.58 (s, 3H).

The following compounds were prepared according to the procedures described in Example 52 using appropriate intermediates.

| Example | Structure | LCMS (m/z) [M + 1]+ | 1H NMR (400 MHz) |
|---|---|---|---|
| 53 | Prepared from Intermediates A7 and B2. | 451.4 | 1H NMR (400 MHz, DMSO) δ 8.95 (dd, J = 2.0, 0.8 Hz, 1H), 8.90 (s, 1H), 8.56 (dd, J = 4.8, 1.6 Hz, 1H), 8.16-8.13 (m, 1H), 8.01 (d, J = 6.0 Hz, 1H), 7.73 (d, J = 8.4 Hz, 1H), 7.47-7.39 (m, 4H), 7.12 (t, J = 7.6 Hz, 1H), 6.71 (d, J = 7.6 Hz, 1H), 6.42 (dd, J = 6.0, 2.0 Hz, 1H), 6.11 (d, J = 2.0 Hz, 1H), 3.12 (t, J = 8.4 Hz, 2H), 2.95 (t, J = 8.4, 2H), 2.60 (s, 3H). |
| 54 | Prepared from Intermediates A8 and B2. | 451.4 | $^1$H NMR (400 MHz, DMSO) δ 8.91 (s, 1H), 8.63 (d, J = 6.0 Hz, 2H), 8.03 (d, J = 6.0 HZ, 1H), 7.77 (d, J = 6.0 Hz, 2H), 7.74 (d, J = 8.4 Hz, 1H), 7.49 (d, J = 8.4 Hz, 1H), 7.43 (d, J = 8.0 Hz, 1H), 7.39 (s, 1H), 7.12 (t, J = 8.0 Hz, 1H), 6.71 (d, J = 7.2 Hz, 1H), 6.44 (dd, J = 6.0, 2.0 Hz, 1H), 6.11 (d, J = 2.0 Hz, 1H), 3.13 (t, J = 8.0 Hz, 2H), 2.96 (t, J = 8.4 Hz, 2H), 2.60 (s, 3H). |
| 55 | Prepared from Intermediates A3 and B2. | 451.3 | $^1$H NMR (400 MHz, CD$_3$OD) δ 8.60 (d, J = 4.0Hz, 1H), 7.89-7.80 (m, 3H), 7.66 (d, J = 8.4 Hz, 1H), 7.47 (d, J = 8.4 Hz, 1H), 7.45-7.40 (m, 1H), 7.20-7.13 (m, 3H), 6.78-6.76 (m, 1H), 6.30 (br, 1H), 6.10 (d, J = 2.0 Hz, 1H), 3.15 (m, 2H), 3.01 (t, J = 8.0 Hz, 2H), 2.60 (s, 3H). |
| 56 | Prepared from Intermediates A15 and B2. | 402.2 | $^1$H NMR (400 MHz, DMSO-d6) δ 8.93 (s, 1H), 8.15 (s, HCOOH, 1H), 8.06 (d, J = 6.0 Hz, 1H), 7.49-7.46 (m, 2H), 7.43 (s, 1H), 7.22 (d, J = 8.4 Hz, 1H), 7.13 (t, J = 7.6 Hz, 1H), 6.72 (d, J = 7.2 Hz, 1H), 6.43 (dd, J = 5.6, 1.6 Hz, 1H), 6.07 (d, J = 1.6 Hz, 1H), 3.15 (t, J = 7.6 Hz, 2H), 2.98 (t, J = 7.6 Hz, 2H), 2.62 (q, J = 7.6 Hz, 2H), 2.49 (s, 3H), 1.14 (t, J = 7.6 Hz, 3H). |

-continued

| Example | Structure | LCMS (m/z) [M + 1]+ | 1H NMR (400 MHz) |
|---|---|---|---|
| 57 | Prepared from Intermediates A16 and B2. | 402.2 | 1H NMR (400 MHz, DMSO-d6) δ 8.93 (s, 1H), 8.30 (s, HCOOH, 1.2H), 8.07 (d, J = 5.6 Hz, 1H), 7.52 (d, J = 8.0 Hz, 1H), 7.48 (d, J = 8.4 Hz, 1H), 7.43 (s, 1H), 7.23 (d, J = 8.4 Hz, 1H), 7.12 (t, J = 7.6 Hz, 1H), 6.74 (d, J = 7.6 Hz, 1H), 6.41 (dd, J = 5.6, 2.0 Hz, 1H), 6.07 (d, J = 2.0 Hz, 1H), 3.00-2.80 (m, 4H), 2.75 (q, J = 7.6 Hz, 2H), 2.31 (s, 3H), 1.25 (t, J = 7.6 Hz, 3H). |
| 58 | Prepared from Intermediates A14 and B2. | 442.2 | 1H NMR (400 MHz, CD3OD) δ 8.02 (d, J = 6.0 Hz, 1H), 7.67 (d, J = 8.4 Hz, 1H), 7.59 (d, J = 8.4 Hz, 1H), 7.33 (s, 1H), 7.24-7.14 (m, 3H), 6.77 (d, J = 6.8 Hz, 1H), 6.41 (dd, J = 6.0, 2.0 Hz, 1H), 6.23 (d, J = 2.0 Hz, 1H), 3.24 (t, J = 7.6 Hz, 2H), 3.05 (t, J = 7.6 Hz, 2H), 2.58 (s, 3H), |
| 59 | Prepared from Intermediates A17 and B2. | 424.4 | 1H NMR (400 MHz, CD3OD) δ 8.17 (s, 1H), 8.02-7.98 (m, 3H), 7.88 (d, J = 8.0 Hz, 1H), 7.72 (t, J = 7.2 Hz, 1H), 7.56 (t, J = 7.2 Hz, 1H), 7.28 (s, 1H), 7.20-7.12 (m, 2H), 6.75 (d, J = 7.2 Hz, 1H), 6.50 (dd, J = 6.0, 2.0 Hz, 1H), 6.23 (d, J = 2.0 Hz, 1H), 3.18 (t, J = 7.6 Hz, 2H), 2.99 (t, J = 7.6 Hz, 2H), 2.61 (s, 3H). |
| 60 | Prepared from Intermediates A6 and B5. | 464.4 | 1H NMR (400 MHz, CD3OD-d4) δ 7.85 (d, J = 6.0 Hz, 1H), 7.68 (dd, J = 8.0, 1.6 Hz, 2H), 7.57 (d, J = 8.4 Hz, 1H), 7.40-7.34 (m, 4H), 7.22-7.19 (m, 3H), 6.89 (dt, J = 7.2, 1.6 Hz, 1H), 6.28 (dd, J = 5.6, 2.0 Hz, 1H), 6.07 (d, J = 2.0 Hz ,1H), 2.60 (s, 3H), 1.78 (s, 6H). |

-continued

| Example | Structure | LCMS (m/z) [M + 1]+ | 1H NMR (400 MHz) |
|---|---|---|---|
| 61 | Prepared from Intermediates A65 and B5. | 464.3 | 1H NMR (400 MHz, DMSO-d6) δ 8.90 (s, 1H), 8.27 (s, 1H, HCOOH), 8.10 (d, J = 7.2 Hz, 2H), 8.05 (d, J = 6.0 Hz, 1H), 7.93 (d, J = 8.4 Hz, 1H), 7.68 (d, J = 8.4 Hz, 2H), 7.51 (t, J = 7.2 Hz, 2H), 7.44 (t, J = 7.2 Hz, 1H), 7.16 (s, 1H), 7.10 (t, J = 8.4 Hz, 1H), 6.72 (d, J = 8.0 Hz, 1H), 6.46 (dd, J = 6.0, 1.6 Hz, 1H), 6.13 (d, J = 1.6 Hz, 1H), 2.42 (s, 3H), 1.66 (s, 6H). |
| 62 | Prepared from Intermediates A66 and B2. | 454.3 | 1H NMR (400 MHz, CD3OD) δ 8.08 (s, 1H), 8.00-7.90 (m, 2H), 7.47 (d, J = 8.0 Hz, 1H), 7.26 (s, 1H), 7.20-7.10 (m, 3H), 6.76 (d, J = 6.4 Hz, 1H), 6.44 (dd, J = 6.0, 2.0 Hz, 1H), 6.17 (d, J = 2.0 Hz, 1H), 3.89 (s, 3H), 3.20 (t, J = 7.6 Hz, 2H), 3.02 (t, J = 7.6 Hz, 2H), 2.55 (s, 3H). |
| 63 | Prepared from Intermediates A4 and B2. | 465.3 | 1H NMR (400 MHz, DMSO-d6) δ 8.83 (s, 1H), 8.22 (s, 1H, HCOOH), 7.98 (d, J = 5.6 Hz, 1H), 7.73 (t, J = 7.6 Hz, 1H), 7.70 (d, J = 8.0 Hz, 1H), 7.60 (d, J = 8.0 Hz, 1H), 7.48-7.40 (m, 3H), 7.19 (d, J = 7.6 Hz, 1H), 7.10 (t, J = 7.6 Hz, 1H), 6.72 (d, J = 7.6 Hz, 1H), 6.33 (dd, J = 6.0, 2.0 Hz, 1H), 6.08 (d, J = 2.0 Hz, 1H), 2.98 (t, J = 8.0 Hz, 1H), 2.87 (t, J = 8.0 Hz, 2H), 2.57 (s, 3H), 2.32 (s, 3H). |

| Example | Structure | LCMS (m/z) [M + 1]+ | 1H NMR (400 MHz) |
|---|---|---|---|
| 64 | Prepared from Intermediates A5 and B2. | 465.3 | 1H NMR (400 MHz, CDCl3) δ 8.32 (d, J = 4.0 Hz, 1H), 7.87 (d, J = 6.0 Hz, 1H), 7.59 (d, J = 8.0 Hz, 1H), 7.51 (d, J = 8.4 Hz, 1H), 7.40 (s, 1H), 7.34 (d, J = 8.4 Hz, 1H), 7.22-7.16 (m, 2H), 6.82 (d, J = 7.6 Hz, 1H), 6.75 (dd, J = 8.0, 1.2 Hz, 1H), 6.37 (dd, J = 6.0, 2.0 Hz, 1H), 6.11 (d, J = 2.0 Hz, 1H), 3.13-3.05 (m, 2H), 3.05-2.97 (m, 2H), 2.45 (s, 3H), 2.35 (s, 3H). |
| 65 | Prepared from Intermediates A3 and B2. | 519.4 | 1H NMR (400 MHz, CD3OD) δ 8.59 (d, J = 4.4 Hz, 1H), 7.97 (d, J = 6.0 Hz, 1H), 7.88 (t, J = 7.2 Hz, 1H), 7.79 (d, J = 7.6 Hz, 1H), 7.67 (d, J = 8.0 Hz, 1H), 7.51-7.38 (m, 5H), 6.37 (d, J = 4.0 Hz, 1H), 6.14 (s, 1H), 3.20 (br s, 4H), 2.63 (s, 3H). |

Example 66: 3-(3-((4-((6-methyl-2-phenylpyridin-3-yl)oxy)-pyridin-2-yl)amino)phenyl)propanoic acid

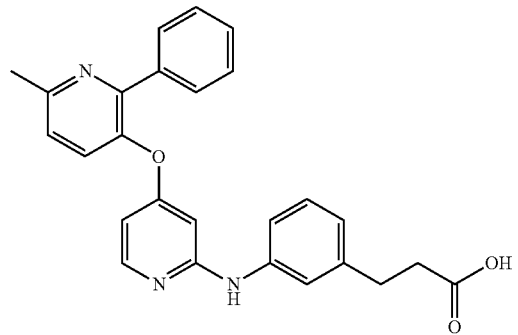 [SMILES: Cc1ccc(Oc2ccnc(Nc3cccc(CCC(=O)O)c3)c2)c(-c2ccccc2)n1]

A mixture of 3-(3-((4-((6-methyl-2-phenylpyridin-3-yl)oxy)pyridin-2-yl)amino)phenyl)propanenitrile (Step 1 of Example 52, 1.0 eq) and KOH (10.0 eq) in dioxane/H2O (5:1, 0.07 M) was stirred at 120° C. for 16 h. The reaction was monitored by LC-MS. The reaction mixture was cooled to r.t. and dioxane was removed. The residue was adjusted to pH 6-7 with 1 N HCl (aq), and the solid was collected by filtration and washed with H2O. The solid was purified by flash chromatography on silica gel (DCM/MeOH 8:1) to give the title compound as a yellow solid. LC-MS (m/z): [M+H]+=426.4; 1H NMR (400 MHz, CDCl3) δ 9.64 (br. s, 1H), 7.76-7.72 (m, 3H), 7.41-7.35 (m, 4H), 7.23-7.17 (m, 2H), 7.14 (s, 1H), 6.99 (dd, J=7.6, 1.6 Hz, 1H), 6.40 (d, J=2.0 Hz, 1H), 6.21 (dd, J=6.0, 2.0 Hz, 1H), 2.95 (t, J=6.8 Hz, 2H), 2.66 (t, J=6.8 Hz, 2H), 2.65 (s, 3H).

Example 67: N-(3-(2-(2H-tetrazol-5-yl)ethyl)phenyl)-4-((1-cyclopropyl-3-(tetrahydro-2H-pyran-4-yl)-1H-pyrazol-4-yl)oxy)pyridin-2-amine

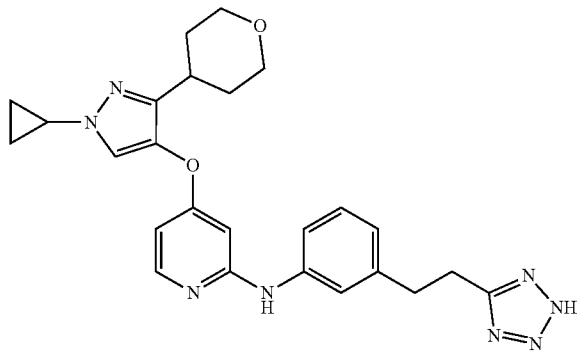 [SMILES: c1cc(CCc2nn[nH]n2)cc(Nc2cc(Oc3cn(C4CC4)nc3C3CCOCC3)ccn2)c1]

Step 1: 3-(3-((4-((1-cyclopropyl-3-(tetrahydro-2H-pyran-4-yl)-1H-pyrazol-4-yl)oxy)pyridin-2-yl)amino)phenyl)propanenitrile To a solution of 2-chloro-4-((1-cyclopropyl-3-(tetrahydro-2H-pyran-4-yl)-1H-pyrazol-4-yl)oxy)pyridine (Intermediate A12, 1.0 eq), 3-(3-aminophenyl)propanenitrile (Intermediate B2, 1.3 eq), Pd(OAc)$_2$ (0.1 eq), xantphos (0.1 eq) and Cs$_2$CO$_3$ (2.0 eq) in dioxane (0.21 M) was stirred at 115° C. for 16 h. The reaction was monitored by LCMS. The reaction mixture was concentrated under reduced pressure. The residue was purified by flash chromatography on silica gel (eluent: petroleum ether/EtOAc 10:1 to 2:1) to give the title compound as a yellow oil. LC-MS (m/z): [M+H]$^+$=430.

Step 2: N-(3-(2-(2H-tetrazol-5-yl)ethyl)phenyl)-4-((1-cyclopropyl-3-(tetrahydro-2H-pyran-4-yl)-1H-pyrazol-4-yl)oxy)pyridin-2-amine A mixture of 3-(3-((4-((1-cyclopropyl-3-(tetrahydro-2H-pyran-4-yl)-1H-pyrazol-4-yl)oxy)pyridin-2-yl)amino)phenyl)propanenitrile (1.0 eq), TMSN3 (5.0 eq) and Bu$_2$SnO (2.0 eq) in dioxane (0.12 M) was stirred at 120° C. for 16 h. The reaction was monitored by LCMS. The reaction mixture was concentrated under reduced pressure. The residue was purified by Prep-TLC (eluent: DCM/MeOH 10:1) to give the title compound as a yellow solid. LC-MS (m/z): [M+H]$^+$=473.5; $^1$H NMR (400 MHz, DMSO-d6) δ 8.96 (s, 1H), 8.02 (d, J=5.6 Hz, 1H), 7.85 (s, 1H), 7.49 (d, J=8.0 Hz, 1H), 7.45 (s, 1H), 7.13 (t, J=7.6 Hz, 1H), 6.72 (d, J=7.6 Hz, 1H), 6.44 (dd, J=5.6, 2.0 Hz, 1H), 6.25 (d, J=2.0 Hz, 1H), 3.84-3.81 (m, 2H), 3.68-3.63 (m, 1H), 3.34-3.30 (m, 2H), 3.15 (t, J=7.6 Hz, 2H), 2.98 (t, J=7.6 Hz, 2H), 2.74-2.69 (m, 1H), 1.67-1.62 (m, 4H), 1.03-0.91 (m, 4H).

Example 68: 3-(3-((4-((1-cyclopropyl-3-(tetrahydro-2H-pyran-4-yl)-1H-pyrazol-4-yl)oxy)pyridin-2-yl)amino)phenyl)propanoic acid

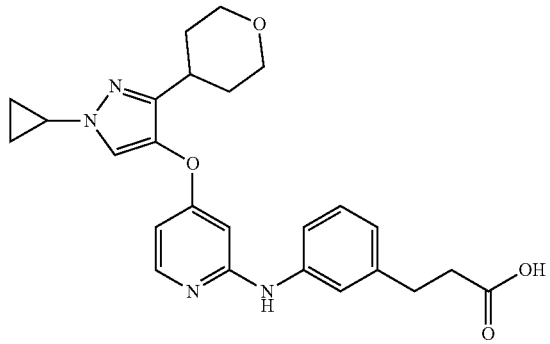 [SMILES: O=C(O)CCc1cccc(Nc2cc(Oc3cn(C4CC4)nc3C3CCOCC3)ccn2)c1]

A mixture of 3-(3-((4-((1-cyclopropyl-3-(tetrahydro-2H-pyran-4-yl)-1H-pyrazol-4-yl)oxy)pyridin-2-yl)amino)phenyl)propanenitrile (Step 1 of Example 67, 1.0 eq) and KOH (5.0 eq) in DMSO/H$_2$O (v/v=1:1, 0.12 M) was stirred at 120° C. for 16 h. The reaction was monitored by LCMS. The reaction mixture was filtered and the filtrate was adjusted pH to 7 with 1.0 M aq. HCl. The precipitated solid was collected by filtration. The filter cake was washed with water and purified by HPLC (mobile phase: 0.1% NH$_3$·H$_2$O/MeCN/H$_2$O). The fractions were collected, and the solvent was removed by lyophilizer to give the title compound as a white solid. LC-MS (m/z): [M+H]$^+$=449.4; $^1$H NMR (400 MHz, DMSO-d6) δ 8.95 (s, 1H), 8.02 (d, J=6.0 Hz, 1H), 7.85 (s, 1H), 7.51 (d, J=8.0 Hz, 1H), 7.39 (s, 1H), 7.11 (t, J=7.6 Hz, 1H), 6.72 (d, J=7.6 Hz, 1H), 6.43 (dd, J=5.6, 2.0 Hz, 1H), 6.25 (d, J=2.0 Hz, 1H), 3.84-3.80 (m, 2H), 3.67-3.63 (m, 1H), 3.34-3.27 (m, 2H), 2.76-2.71 (m, 3H), 2.41 (t, J=8.0 Hz, 2H), 1.67-1.62 (m, 4H), 1.03-0.93 (m, 4H).

The following compound was prepared according to the procedure described in Example 1 using appropriate intermediates.

| Example | Structure | LCMS (m/z) [M + 1]$^+$ | $^1$H NMR (400 MHz) |
|---|---|---|---|
| | | 450.4 | $^1$H NMR (400 MHz, DMSO-d6) δ 9.49 (s, 1H), 8.18 (d, J = 5.2 Hz, 1H), 8.14 (d, J = 5.2 Hz, 1H), 7.87 (s, 1H), 7.52 (d, J = 4.4 Hz, 1H), 7.47 (s, 1H), 6.59 (d, J = 4.4 Hz, 1H), 6.36 (s, 1H), 3.90-3.80 (m, 2H), 3.67-3.63 (m, 1H), 3.38-3.25 (m, 2H), 2.85 (t, J = 7.2 Hz, 2H), 2.71 (m, 1H), 2.56 (t, J = 7.2 Hz, 2H), 1.67-1.62 (m, 4H), 1.03-0.93 (m, 4H). |

Prepared from Intermediates A12 and B20.

Example 70: 2-methyl-2-(3-((4-((6-methyl-2-phenylpyridin-3-yl)oxy)pyridin-2-ylamino)phenylpropanoic acid

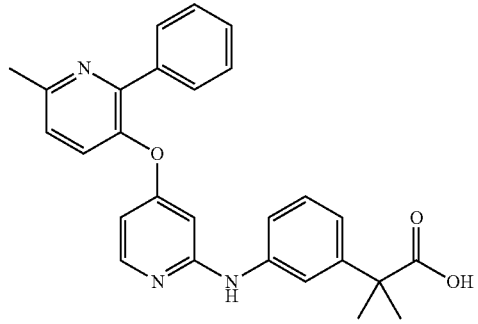 [SMILES: Cc1ccc(Oc2ccnc(Nc3cccc(C(C)(C)C(=O)O)c3)c2)c(-c2ccccc2)n1]

Example 71: 2-(3-((4-((5,6-dimethyl-[2,2'-bipyridin]-3-yl)oxy)pyridin-2-yl)amino)phenyl)-2-methylpropanoic acid

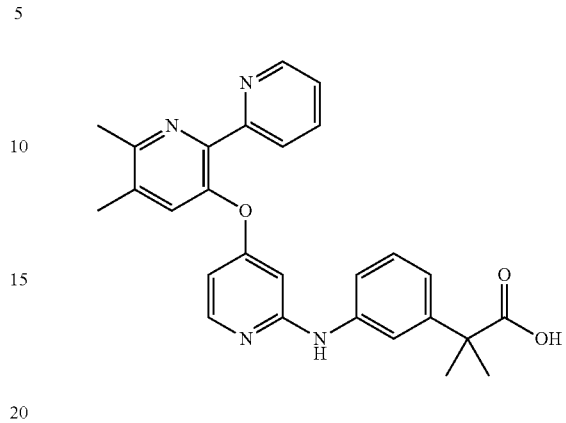

Step 1: 2-methyl-2-(3-((4-((6-methyl-2-phenylpyridin-3-yl)oxy)pyridin-2-yl)amino)phenyl)propanenitrile A solution of 3-((2-chloropyridin-4-yl)oxy)-6-methyl-2-phenylpyridine (Intermediate A6, 1.0 eq), 2-(3-aminophenyl)-2-methylpropanenitrile (Intermediate B5, 1.5 eq), Cs$_2$CO$_3$ (2.0 eq), Xantphos (0.1 eq), Pd(OAc)$_2$ (0.1 eq) in dioxane (0.3 M) was stirred at 120° C. for 16 h. The reaction was monitored by LCMS. The reaction mixture was filtered, and concentrated under reduced pressure. The residue was diluted with EtOAc, washed with water, brine, and then dried over Na$_2$SO$_4$. The crude product was purified by flash chromatography on silica gel (eluent petroleum ether/EtOAc 100:1 to 10/1) to give the title compound. LC-MS (m/z): [M+H]$^+$=421.4; $^1$H NMR (400 MHz, CD$_3$OD) δ 7.94 (d, J=6.0 Hz, 1H), 7.72-7.70 (m, 2H), 7.61 (d, J=8.4 Hz, 2H), 7.42-7.27 (m, 6H), 7.10 (d, J=8.0 Hz, 1H), 6.34 (dd, J=6.0, 2.0 Hz, 1H), 6.13 (d, J=2.0 Hz, 1H), 2.63 (s, 3H), 1.71 (s, 6H).

Step 1: 2-(3-((4-((5,6-dimethyl-[2,2'-bipyridin]-3-yl)oxy)pyridin-2-yl)amino)phenyl)-2-methylpropanenitrile A mixture of 3-((2-chloropyridin-4-yl)oxy)-5,6-dimethyl-2,2'-bipyridine (Intermediate A1, 1.0 eq), 2-(3-aminophenyl)-2-methylpropanenitrile (Intermediate B5, 1.1 eq), Pd(OAc)$_2$ (0.1 eq) and Xantphos (0.1 eq) in dioxane (0.18 M) was stirred at 120° C. for 16 h. The reaction was monitored by LC-MS. The mixture solution was cooled down to r.t and diluted with EtOAc (50 mL). The mixture was washed with brine, and then dried over Na$_2$SO$_4$. The organic phase was concentrated, and the residue was purified by preparation TLC to give the title compound as a pale yellow solid. LC-MS (m/z): [M+H]$^+$=436.3; $^1$H NMR (400 MHz, CDCl$_3$) δ 8.58-8.56 (m, 1H), 7.90 (d, J=5.6 Hz, 1H), 7.71 (d, J=8.0 Hz, 1H), 7.64-7.60 (m, 1H), 7.29 (t, J=1.8 Hz, 1H), 7.25-7.21 (m, 2H), 7.18-7.12 (m, 2H), 7.05-7.02 (m, 1H), 6.76 (s, 1H), 6.23 (dd, J=5.6, 2.0 Hz, 1H), 6.15 (d, J=2.0 Hz, 1H), 2.54 (s, 3H), 2.28 (s, 3H), 1.62 (s, 6H).

Step 2: 2-methyl-2-(3-((4-((6-methyl-2-phenylpyridin-3-yl)oxy)pyridin-2-yl)amino)phenyl)propanoic acid A solution of 2-methyl-2-(3-((4-((6-methyl-2-phenylpyridin-3-yl)oxy)pyridin-2-yl)amino)phenyl)propanenitrile (1.0 eq) in concentrated HCl aqueous solution (0.06 M) was stirred at 110° C. for 16 h in a sealed tube. The reaction was monitored by LCMS. The mixture was purified by HPLC (0.1% NH$_3$·H$_2$O/ACN/H$_2$O) to give the title compound as a white solid. LC-MS (m/z): [M+H]$^+$=440.5; $^1$H NMR (400 MHz, CD$_3$OD) δ 7.86 (d, J=5.6 Hz, 1H), 7.67 (d, J=6.4 Hz, 2H), 7.55 (d, J=8.4 Hz, 1H), 7.39-7.29 (m, 5H), 7.20-7.18 (m, 2H), 7.00-6.99 (m, 1H), 6.26-6.25 (m, 1H), 6.11 (s, 1H), 2.59 (s, 3H), 1.48 (s, 6H).

Step 2: 2-(3-((4-((5,6-dimethyl-[2,2'-bipyridin]-3-yl)oxy)pyridin-2-yl)amino)phenyl)-2-methylpropanoic acid A mixture of above product (1.0 eq) in HCl (aq. 12N) (0.04 M) was stirred at 110° C. in a sealed tube for 16 h. The reaction was monitored by LC-MS. The mixture solution was purified by HPLC (CH$_3$CN/H$_2$O/0.1% HCOOH) to give the title compound as a yellow solid. LC-MS (m/z): [M+H]$^+$=455.4; $^1$H NMR (400 MHz, CD$_3$OD) δ 8.56 (d, J=4.8 Hz, 1H), 8.09 (s, 1H, HCOOH), (m, 1H), 7.92 (td, J=7.6, 1.2 Hz, 1H), 7.87 (d, J=7.6 Hz, 1H), 7.82 (d, J=6.4 Hz, 1H), 7.57 (s, 1H), 7.42 (t, J=5.6 Hz, 1H), 7.33 (t, J=8.0 Hz, 1H), 7.28 (s, 1H), 7.21-7.17 (m, 2H), 6.49 (dd, J=6.4, 2.4 Hz, 1H), 6.19 (d, J=2.4 Hz, 1H), 2.60 (s, 3H), 2.41 (s, 3H), 1.51 (s, 6H).

Example 72: 2-methyl-2-(3-((4-((6-methyl-[2,2'-bipyridin]-3-yl)oxy)pyridin-2-yl)amino)phenyl)propanoic acid

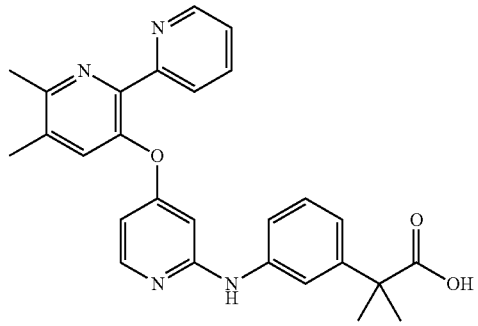 [SMILES: Cc1cc(Oc2ccnc(Nc3cccc(C(C)(C)C(=O)O)c3)c2)c(-c2ccccn2)nc1C]

Step 1: 2-methyl-2-(3-((4-((6-methyl-[2,2'-bipyridin]-3-yl)oxy)pyridin-2-yl)amino)phenyl)propanenitrile A mixture of 3-((2-chloropyridin-4-yl)oxy)-6-methyl-2,2'-bipyridine (Intermediate A3, 1.0 eq), 2-(3-aminophenyl)-2-methylpropanenitrile (Intermediate B5, 1.5 eq), $Cs_2CO_3$ (2.0 eq), Xantphos (0.1 eq), $Pd(OAc)_2$ (0.1 eq) in dioxane (0.033 M) was stirred at 120° C. for 16h. The reaction was monitored by LC-MS. The reaction mixture was cooled down to r.t and diluted with EtOAc, washed with brine, and then dried over $Na_2SO_4$. The organic phase was concentrated under reduced pressure. The residue was purified by HPLC (0.1% $NH_3·H_2O$/ACN/$H_2O$) to give the product as a white solid.

LC-MS (m/z): [M+H]$^+$=422.3; $^1$H NMR (400 MHz, $CD_3OD$) δ 8.59 (s, 1H), 7.91-7.75 (m, 5H), 7.48-7.25 (m, 4H), 7.08-7.06 (m, 1H), 6.30 (s, 1H), 6.12 (s, 1H), 2.63 (s, 3H), 1.68 (s, 6H).

Step2: 2-methyl-2-(3-((4-((6-methyl-[2,2'-bipyridin]-3-yl)oxy)pyridin-2-yl)amino)phenyl)propanoic acid A mixture of 2-methyl-2-(3-((4-((6-methyl-[2,2'-bipyridin]-3-yl)oxy)pyridin-2-yl)amino)phenyl)propanenitrile (1.0 eq), KOH (20 eq) in dioxane-$H_2O$ (1:1, 0.015 M) was stirred at 120° C. for 36h. The reaction was monitored by LC-MS. The mixture solution was cooled down to r.t. and concentrated. The residue was purified by HPLC (0.1% $NH_3·H_2O$/ACN/$H_2O$) to give the the title compound as a yellow solid. LC-MS (m/z): [M+H]$^+$=441.4; $^1$H NMR (400 MHz, DMSO) δ 12.25 (br, 1H), 8.89 (s, 1H), 8.52 (d, J=2.8 Hz, 1H), 7.95 (d, J=5.2 Hz, 1H), 7.86 (t, J=7.6 Hz, 1H), 7.76 (d, J=8.0 Hz, 1H), 7.69 (d, J=8.0 Hz, 1H), 7.65-7.62 (m, 1H), 7.46 (d, J=7.6 Hz, 1H), 7.40-7.34 (m, 2H), 7.15 (s, 1H), 6.86-6.81 (m, 1H), 6.33 (d, J=3.6 Hz, 1H), 6.09 (s, 1H), 2.58 (s, 3H), 1.41 (s, 6H).

The following compounds were prepared according to the procedure described in Example 72 using appropriate intermediates.

| Example | Structure | LCMS (m/z) [M + 1]$^+$ | $^1$H NMR (400 MHz) |
|---|---|---|---|
| 73 | (Prepared from Intermediates A2 and B5.) | 378.2 | $^1$H NMR (400 MHz, DMSO-d6) δ 8.96 (s, 1H), 8.05 (d, J = 5.6 Hz, 1H), 7.67 (d, J = 8.0 Hz, 1H), 7.48 (d, J = 8.4 Hz, 1H), 7.41 (s, 1H), 7.23-7.16 (m, 2H), 6.85 (d, J = 7.6 Hz, 1H), 6.41 (d, J = 3.6 Hz, 1H), 6.05 (s, 1H), 2.47 (s, 3H), 2.28 (s, 3H), 1.42 (s, 6H). |
| 74 | 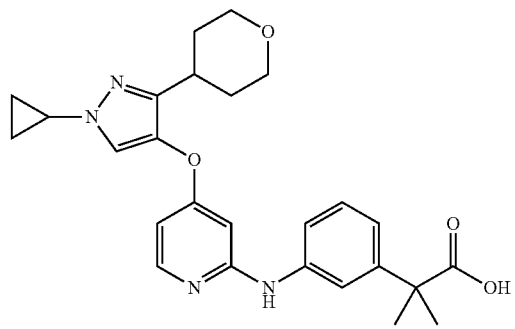 (Prepared from Intermediates A12 and B5.) | 463.4 | $^1$H NMR (400 MHz, $CD_3OD$) δ 8.25 (s, 0.5 H, HCOOH), 7.94 (d, J = 5.6 Hz, 1H), 7.62 (s, 1H), 7.38 (s, 1H), 7.29 (d, J = 7.2 Hz, 1H), 7.24 (t, J = 7.6 Hz, 1H), 7.04 (d, J = 7.6 Hz, 1H), 6.45 (dd, J = 5.6, 2.0 Hz, 1H), 6.31 (d, J = 2.0 Hz, 1H), 3.90-3.80 (m, 2H), 3.58 (sep, 3.6 Hz, 1H), 3.50-3.40 (m, 2H), 2.79 (tt, J = 11.6, 4.0 Hz, 1H), 1.88-1.60 (m, 4H), 1.52 (s, 6H), 1.03-0.93 (m, 4H). |

| Example | Structure | LCMS (m/z) [M + 1]+ | 1H NMR (400 MHz) |
|---|---|---|---|
| 75 | Prepared from Intermediates A65 and B5. | 440.2 | 1H NMR (400 MHz, DMSO-d6) δ 9.65 (br s, 1H), 8.10 (d, J = 7.2 Hz, 2H), 8.06 (d, J = 6.4 Hz, 1H), 7.97 (d, J = 8.4 Hz, 1H), 7.75 (d, J = 8.4 Hz, 1H), 7.52 (t, J = 7.2 Hz, 2H), 7.45 (t, J = 7.2 Hz, 1H), 7.46 (d, J = 7.6 Hz, 1H), 7.34 (s, 1H), 7.29 (t, J = 8.0 Hz, 1H), 7.02 (d, J = 7.6 Hz, 1H), 6.67 (d, J = 5.6 Hz, 1H), 6.20 (d, J = 2.4 Hz, 1H), 2.44 (s, 3H), 1.42 (s, 6H). |
| 76 | Prepared from Intermediates A1 and B42. | 443.2 | 1H NMR (400 MHz, CD3OD) δ 8.58 (d, J = 4.8 Hz, 1H), 7.89-7.84 (m, 2H), 7.75 (d, J = 8.0 Hz, 1H), 7.53 (s, 1H), 7.40-7.37 (m, 1H), 7.10 (t, J = 8.0 Hz, 1H), 6.98 (t, J = 2.0 Hz, 1H), 6.92 (dd, J = 8.0, 2.0 Hz, 1H), 6.66 (dd, J = 8.0, 2.0 Hz, 1H), 6.24 (dd, J = 6.0, 2.0 Hz, 1H), 6.13 (d, J = 2.0 Hz, 1H), 4.34 (s, 2H), 2.58 (s, 3H), 2.41 (s, 3H). |

Example 77: 1-(3-((4-((6-methyl-2-phenylpyridin-3-yl)oxy)pyridin-2-yl)amino)phenyl)cyclopropane-1-carboxylic acid

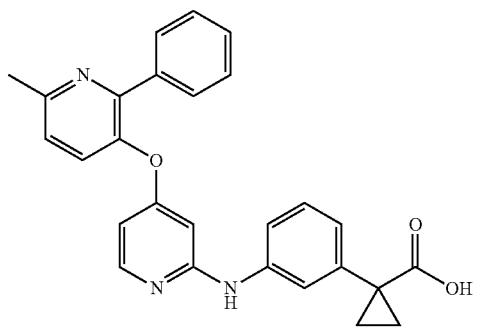 [SMILES: Cc1ccc(Oc2ccnc(Nc3cccc(C4(C(=O)O)CC4)c3)c2)c(-c2ccccc2)n1]

Step 1: methyl 1-(3-((4-((6-methyl-2-phenylpyridin-3-yl)oxy)pyridin-2-yl)amino)phenyl)cyclopropane-1-carboxylate A mixture of 3-((2-chloropyridin-4-yl)oxy)-6-methyl-2-phenylpyridine (Intermediate A6, 1.0 eq), methyl 1-(3-aminophenyl)cyclopropane-1-carboxylate (Intermediate B26, 1.0 eq), Xantphos (0.1 eq), Cs2CO3 (2.0 eq) and Pd(OAc)2 (0.1 eq) in dioxane (0.17 M) was sealed in a tube reactor. The resulting mixture was stirred at 115° C. for 16 h under Ar. The reaction was monitored by LC-MS. The mixture was filtered, the filtrate was concentrated under reduced pressure. The residue was purified by Prep-TLC (eluent: DCM/MeOH 20:1) to give the title compound as a yellow solid. LC-MS (m/z): [M+H]+=452.3.

Step2: 1-(3-((4-((6-methyl-2-phenylpyridin-3-yl)oxy)pyridin-2-yl)amino)phenyl)cyclopropane-1-carboxylic acid A mixture of methyl 1-(3-((4-((6-methyl-2-phenylpyridin-3-yl)oxy)pyridin-2-yl)amino)phenyl)cyclopropane-1-carboxylate (100 mg, 0.22 mmol, 1.0 eq), aq. NaOH (2.0 M, 5.0 eq) in MeOH (0.05 M) was stirred at 50° C. for 2 h. The reaction was monitored by LC-MS. The mixture was concentrated under reduced pressure and the residue was purified by Prep-HPLC (mobile phase: 0.1% HCOOH/MeCN/H2O). The solvent was removed via lyophilizer to give the title compound as a white solid (formic acid salt). LC-MS (m/z): [M+H]+=438.2; 1H NMR (400 MHz, DMSO-d6) δ 8.90 (s, 1H), 8.29 (s, 1H, HCOOH), 8.00 (d, J=6.0 Hz, 1H), 7.78 (d, J=6.8 Hz, 2H), 7.66 (d, J=8.4 Hz, 1H), 7.49 (d, J=8.4 Hz, 1H), 7.45-7.35 (m, 5H), 7.11 (t, J=8.0 Hz, 1H), 6.81 (d, J=7.6 Hz, 1H), 6.38 (dd, J=6.0, 2.0 Hz, 1H), 6.09 (d, J=2.0 Hz, 1H), 2.58 (s, 3H), 1.39 (m, 2H), 1.03 (m, 2H).

The following compounds were prepared according to the procedure described in Example 77 using appropriate intermediates.

| Example | Structure | LCMS (m/z) [M + 1]+ | 1H NMR (400 MHz) |
|---|---|---|---|
| 78 | Prepared from Intermediates A9 and B27. | 474.4 | 1H NMR (400 MHz, CD3OD) δ 7.90 (d, J = 6.0 Hz, 1H), 7.75 (dd, J = 2.4, 2.0 Hz, 1H), 7.68-7.65 (m, 1H), 7.59 (d, J = 8.4 Hz, 1H), 7.39-7.36 (m, 3H), 7.31 (s, 1H), 7.23-7.17 (m, 2H), 7.00 (dt, J = 7.2, 1.6 Hz, 1H), 6.29 (dd, J = 6.0, 2.0 Hz, 1H), 6.12 (d, J = 2.0 Hz, 1H), 2.61 (s, 3H), 1.49 (s, 6H). |
| 79 | Prepared from Intermediates A10 and B27. | 474.3 | 1H NMR (400 MHz, CD3OD) δ 7.90 (d, J = 6.0 Hz, 1H), 7.72 (dt, J = 8.8, 2.0 Hz, 2H), 7.58 (d, J = 8.4 Hz, 1H), 7.40 (dt, J = 8.8, 2.0 Hz, 2H), 7.36 (d, J = 8.4 Hz, 1H), 7.32 (t, J = 1.6 Hz, 1H), 7.24-7.17 (m, 2H), 7.00 (dt, J = 6.8, 1.6 Hz, 1H), 6.29 (dd, J = 6.0, 2.0 Hz, 1H), 6.12 (d, J = 2.0 Hz, 1H), 2.60 (s, 3H), 1.49 (s, 6H). |
| 80 | Prepared from Intermediates A11 and B27. | 474.3 | 1H NMR (400 MHz, CD3OD) δ 7.85 (d, J = 6.0 Hz, 1H), 7.63 (d, J = 8.4 Hz, 1H), 7.46-7.42 (m, 2H), 7.39-7.31 (m, 4H), 7.27-7.18 (m, 2H), 6.99 (d, J = 6.8 Hz, 1H), 6.22 (dd, J = 6.0, 2.0 Hz, 1H), 6.15 (d, J = 2.0 Hz, 1H), 2.59 (s, 3H), 1.50 (s, 6H). |

Example 81: 2-(3-(((4-(((6-ethyl-2-methylpyridin-3-yl)oxy)pyridin-2-yl)amino)phenyl)-2-methylpropanoic acid

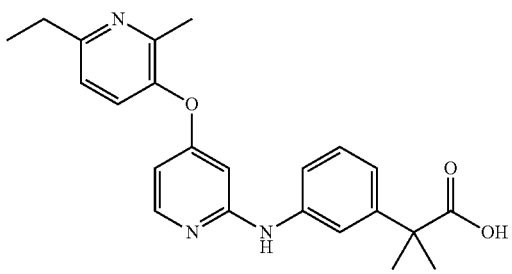 [SMILES: CCc1ccc(Oc2ccnc(Nc3cccc(C(C)(C)C(=O)O)c3)c2)c(C)n1]

Step 1: methyl 2-(3-((4-(((6-ethyl-2-methylpyridin-3-yl)oxy)pyridin-2-yl)amino)phenyl)-2-methylpropanoate A mixture of 3-((2-chloropyridin-4-yl)oxy)-6-ethyl-2-methylpyridine (Intermediate A16, 1.0 eq), methyl 2-(3-aminophenyl)-2-methylpropanoate (Intermediate B27, 1.5 eq), Cs2CO3 (2.0 eq), Xantphos (0.1 eq) and Pd(OAc)2 (0.1 eq) in dioxane (0.1 M) was stirred at 115° C. for 16 h. The reaction mixture was filtered through a pad of celite, and the filtrate was concentrated. The residue was purified by flash chromatography on silica gel (eluent: petroleum ether/EtOAc=10:1 to 1:1) to give the title compound. LC-MS (m/z): [M+H]+=406.2.

Step 2: 2-(3-((4-((6-ethyl-2-methylpyridin-3-yl)oxy)pyridin-2-yl)amino)phenyl)-2-methylpropanoic acid A mixture of methyl 2-(3-((4-((6-ethyl-2-methylpyridin-3-yl)oxy)pyridin-2-yl)amino)phenyl)-2-methylpropanoate (1.0 eq) and KOH (5.0 eq) in MeOH/H₂O (4:1, 0.05 M) was stirred at 50° C. for 16 h. MeOH was removed under reduced pressure, and the aqueous residue was adjusted to pH~7 with 1.0 M aq. HCl. The mixture was extracted with EtOAc, and the combined organic layer was washed with brine, and then dried over Na₂SO₄. The crude product was purified by Prep-HPLC (mobile phase: 0.1% NH₃·H₂O/MeCN/H₂O) to give the title compound as a white solid. LC-MS (m/z): [M+H]N=392.3; ¹H NMR (400 M Hz, DMSO-d6) δ 12.27 (br s, 1H), 8.98 (s, 1H), 8.06 (d, J=6.0 Hz, 1H), 7.69 (dd, J=8.0, 1.2 Hz, 1H), 7.50 (d, J=8.0 Hz, 1H), 7.43 (t, J=1.6 Hz, 1H), 7.22 (d, J=8.4 Hz, 1H), 7.18 (t, J=8.0 Hz, 1H), 6.85 (d, J=8.0 Hz, 1H), 6.42 (dd, J=6.0, 2.0 Hz, 1H), 6.07 (d, J=2.0 Hz, 1H), 2.76 (q, J=7.6 Hz, 2H), 2.46 (s, 3H), 1.44 (s, 6H), 1.26 (t, J=7.6 Hz, 3H).

The following compounds were prepared according to the procedure described in Example 81 using appropriate intermediates.

| Example | Structure | LCMS (m/z) [M + 1]⁺ | ¹H NMR (400 MHz) |
|---|---|---|---|
| 82 | Prepared from Intermediates A49 and B27. | 406.2 | ¹H NMR (400 MHz, CD₃OD) δ 7.96 (d, J = 6.4 Hz, 1H), 7.37 (s, 1H), 7.34 (s, 1H), 7.31-7.21 (m, 2H), 7.04 (d, J = 7.6 Hz, 1H), 6.41 (dd, J = 6.4, 2.0 Hz, 1H), 6.14 (d, J = 2.0 Hz, 1H), 2.82 (q, J = 7.6 Hz, 2H), 2.34 (s, 6H), 1.51 (s, 6H), 1.24 (t, J = 7.6 Hz, 3H). |
| 83 | Prepared from Intermediates A50 and B27. | 426.3 | ¹H NMR (400 MHz, CD₃OD) δ 8.01 (d, J = 6.0 Hz, 1H), 7.59 (s, 1H), 7.41 (s, 1H), 7.32 (d, J = 8.4 Hz, 1H), 7.21 (t, J = 7.6 Hz, 1H), 7.00 (d, J = 7.6 Hz, 1H), 6.38 (dd, J = 6.0, 2.0 Hz, 1H), 6.17 (d, J = 2.0 Hz, 1H), 2.94 (q, J = 7.6 Hz, 2H), 2.37 (s, 3H), 1.51 (s, 6H), 1.28 (t, J = 7.6 Hz, 3H). |
| 84 | Prepared from Intermediates A21 and B27. | 455.3 | ¹H NMR (400 MHz, DMSO-d6) δ 8.90 (s, 1H), 8.52 (d, J = 4.8 Hz, 1H), 7.96 (d, J = 6.0 Hz, 1H), 7.88-7.78 (m, 2H), 7.70 (d, J = 8.4 Hz, 1H), 7.64 (d, J = 8.4 Hz, 1H), 7.47 (d, J = 8.4 Hz, 1H), 7.41 (s, 1H), 7.36-7.33 (m, 1H), 7.15 (t, J = 8.0 Hz, 1H), 6.83 (d, J = 8.0 Hz, 1H), 6.34-6.32 (m, 1H), 6.10 (d, J = 2.4 Hz, 1H), 2.86 (q, J = 7.6 Hz, 2H), 1.31 (t, J = 7.6 Hz, 3H). |

-continued

| Example | Structure | LCMS (m/z) [M + 1]+ | 1H NMR (400 MHz) |
|---|---|---|---|
| 85 | Prepared from Intermediates A23 and B27. | 469.5 | 1H NMR (400 MHz, CD3OD) δ 8.55 (s, 1H), 7.87-7.81 (m, 2H), 7.77 (d, J = 7.6 Hz, 1H), 7.49 (s, 1H), 7.38-7.31 (m, 2H), 7.20-7.17 (m, 2H), 7.00 (d, J = 4.8 Hz, 1H), 6.27 (d, J = 4.4 Hz, 1H), 6.10 (s, 1H), 2.92 (q, J = 7.2 Hz, 2H), 2.43 (s, 3H), 1.50 (s, 6H), 1.32 (t, J = 7.2 Hz, 3H). |
| 86 | Prepared from Intermediates A37 and B27. | 470.2 | 1H NMR (400 MHz, CDCl3) δ 8.24 (s, 1H), 7.83 (d, J = 6.0 Hz, 1H), 7.27-7.21 (m, 4H), 7.08 (d, J = 8.4 Hz, 1H), 7.00-6.90 (m, 3H), 6.77 (d, J = 8.0 Hz, 2H), 6.31 (s, 1H), 6.18 (dd, J = 6.0, 1.6 Hz, 1H), 3.44 (s, 3H), 2.57 (s, 3H), 1.23 (s, 6H). |
| 87 | Prepared from Intermediates A38 and B27. | 470.4 | 1H NMR (400 MHz, CD3OD) δ 7.88 (d, J = 5.6 Hz, 1H), 7.57 (d, J = 8.4 Hz, 1H), 7.35-7.16 (m, 7H), 7.01-6.98 (m, 1H), 6.92 (ddd, J = 7.2, 2.4, 1.6 Hz, 1H), 6.28 (dd, J = 6.0, 2.0 Hz, 1H), 6.12 (d, J = 2.0 Hz, 1H), 3.75 (s, 3H), 2.60 (s, 3H), 1.48 (s, 6H). |
| 88 | Prepared from Intermediates A39 and B27. | 470.4 | 1H NMR (400 MHz, CD3OD) δ 7.87 (d, J = 6.0 Hz, 1H), 7.68-7.64 (m, 2H), 7.53 (d, J = 8.0 Hz, 1H), 7.32-7.26 (m, 2H), 7.24-7.18 (m, 2H), 7.00-6.97 (m, 1H), 6.95-6.92 (m, 2H), 6.28 (dd, J = 6.0, 2.0 Hz, 1H), 6.11 (d, J = 2.0 Hz, 1H), 3.79 (s, 3H), 2.58 (s, 3H), 1.49 (s, 6H). |

-continued

| Example | Structure | LCMS (m/z) [M + 1]+ | 1H NMR (400 MHz) |
|---|---|---|---|
| 89 | Prepared from Intermediates A28 and B27. | 458.3 | 1H NMR (400 MHz, DMSO-d6) δ 12.26 (s, 1H, CO2H), 9.02 (s, 1H), 7.95 (d, J = 5.6 Hz, 1H), 7.69 (d, J = 7.6 Hz, 1H), 7.65-7.60 (m, 1H), 7.49-7.439 (m, 4H), 7.27-7.15 (m, 3H), 6.86 (d, J = 7.2 Hz, 1H), 6.32 (d, J = 4.8 Hz, 1H), 6.14 (d, J = 2.0 Hz, 1H), 2.57 (s, 3H), 1.43 (s, 6H). |
| 90 | Prepared from Intermediates A29 and B27. | 458.3 | 1H NMR (400 MHz, CD3OD) δ 8.10 (d, J = 8.4 Hz, 1H), 7.82 (d, J = 7.2 Hz, 1H), 7.73 (d, J = 8.4 Hz, 1H), 7.63-7.41 (m, 5H), 7.33-7.26 (m, 2H), 7.19 (d, J = 7.2 Hz, 1H), 6.77 (dd, J = 7.2, 2.8 Hz, 1H), 6.38 (d, J = 2.4 Hz, 1H), 2.77 (s, 3H). |
| 91 | Prepared from Intermediates A30 and B27. | 458.4 | 1H NMR (400 MHz, CD3OD) δ 7.87 (d, J = 6.0 Hz, 1H), 7.76-7.73 (m, 2H), 7.56 (d, J = 8.4 Hz, 1H), 7.33 (d, J = 8.4 Hz, 1H), 7.24 (s, 1H), 7.19-7.09 (m, 4H), 7.05-7.02 (m, 1H), 6.26 (dd, J = 6.0, 2.4 Hz, 1H), 6.11 (d, J = 2.0 Hz, 1H), 2.59 (s, 3H), 1.45 (s, 6H). |
| 92 | Prepared from Intermediates A34 and B27. | 454.3 | 1H NMR (400 MHz, CD3OD) δ 7.82 (d, J = 6.0 Hz, 1H), 7.63 (d, J = 8.0 Hz, 1H), 7.41 (d, J = 8.4 Hz, 1H), 7.31 (s, 1H), 7.25-7.14 (m, 6H), 7.02-6.98 (m, 1H), 6.17 (dd, J = 6.0, 2.0 Hz, 1H), 6.07 (d, J = 2.0 Hz, 1H), 2.58 (s, 3H), 2.15 (s, 3H), 1.50 (s, 6H). |

-continued

| Example | Structure | LCMS (m/z) [M + 1]+ | 1H NMR (400 MHz) |
|---|---|---|---|
| 93 | Prepared from Intermediates A35 and B27. | 454.1 | 1H NMR (400 MHz, CD3OD) δ 7.78 (d, J = 6.0 Hz, 1H), 7.47 (d, J = 8.4 Hz, 1H), 7.40 (s, 1H), 7.36 (d, J = 7.6 Hz, 1H), 7.25-7.21 (m, 2H), 7.16 (t, J = 7.6 Hz, 1H), 7.11-7.07 (m, 3H), 6.92-6.90 (m, 1H), 6.17 (dd, J = 6.0, 2.0 Hz, 1H), 6.01 (d, J = 2.0 Hz, 1H), 2.50 (s, 3H), 2.24 (s, 3H), 1.39 (s, 6H). |
| 94 | Prepared from Intermediates A36 and B27. | 454.1 | 1H NMR (400 MHz, CD3OD) δ 7.78 (d, J = 6.0 Hz, 1H), 7.49 (d, J = 8.0 Hz, 2H), 7.45 (d, J = 8.4 Hz, 1H), 7.22 (d, J = 8.0 Hz, 1H), 7.21 (s, 1H), 7.12-7.08 (m, 4H), 6.93-6.89 (m, 1H), 6.17 (dd, J = 6.0, 2.4 Hz, 1H), 6.01 (d, J = 2.0 Hz, 1H), 2.50 (s, 3H), 2.24 (s, 3H), 1.39 (s, 6H). |
| 95 | Prepared from Intermediates A31 and B27. | 465.2 | 1H NMR (400 MHz, CD3OD) δ 7.78 (d, J = 6.0 Hz, 1H), 7.71 (dd, J = 8.0, 0.8 Hz, 1H), 7.59 (td, J = 7.6, 1.2 Hz, 1H), 7.57 (d, J = 8.4 Hz, 1H), 7.51 (dd, J = 7.6, 0.8 Hz, 1H), 7.47 (td, J = 7.6, 1.2 Hz, 1H), 7.38 (d, J = 8.4 Hz, 1H), 7.26 (t, J = 2.0 Hz, 1H), 7.18-7.15 (m, 1H), 7.11 (t, J = 7.6 Hz, 1H), 6.92-6.89 (m, 1H), 6.13 (dd, J = 6.0, 2.4 Hz, 1H), 6.07 (d, J = 2.4 Hz, 1H), 2.53 (s, 3H), 1.41 (s, 6H). |
| 96 | Prepared from Intermediates A32 and B27. | 465.2 | 1H NMR (400 MHz, CD3OD) δ 8.02 (s, 1H), 8.00-7.96 (m, 1H), 7.82 (d, J = 6.0 Hz, 1H), 7.64-7.61 (m, 1H), 7.52-7.46 (m, 2H), 7.31 (d, J = 8.4 Hz, 1H), 7.24 (s, 1H), 7.12-7.09 (m, 2H), 6.94-6.91 (m, 1H), 6.21 (dd, J = 6.0, 2.4 Hz, 1H), 6.03 (d, J = 2.0 Hz, 1H), 2.53 (s, 3H), 1.39 (s, 6H). |

-continued

| Example | Structure | LCMS (m/z) [M + 1]+ | 1H NMR (400 MHz) |
|---|---|---|---|
| 97 | Prepared from Intermediates A33 and B27. | 465.1 | 1H NMR (400 MHz, CD3OD) δ 7.95 (d, J = 8.4 Hz, 2H), 7.92 (d, J = 6.0 Hz, 1H), 7.77 (d, J = 8.4 Hz, 2H), 7.61 (d, J = 8.4 Hz, 1H), 7.41 (d, J = 8.4 Hz, 1H), 7.34 (s, 1H), 7.24-7.20 (m, 2H), 7.03-7.00 (m, 1H), 6.31 (dd, J = 6.0, 2.4 Hz, 1H), 6.15 (d, J = 2.0 Hz, 1H), 2.63 (s, 3H), 1.50 (s, 6H). |
| 98 | Prepared from Intermediates A22 and B27. | 454.2 | 1H NMR (400 MHz, CD3OD) δ 7.85 (d, J = 6.0 Hz, 1H), 7.66 (d, J = 6.4 Hz, 2H), 7.44 (s, 1H), 7.38-7.32 (m, 3H), 7.18-7.13 (m, 3H), 7.07-7.04 (m, 1H), 6.24 (dd, J = 6.0, 2.0 Hz, 1H), 6.10 (d, J = 2.0 Hz, 1H), 2.54 (s, 3H), 2.36 (s, 3H), 1.43 (s, 6H). |
| 99 | Prepared from Intermediates A40 and B27. | 474.1 | 1H NMR (400 MHz, DMSO-d6) δ 8.84 (s, 1H), 8.02 (s, 1H), 7.98 (d, J = 5.6 Hz, 1H), 7.79-7.77 (m, 2H), 7.59 (d, J = 7.2 Hz, 1H), 7.45-7.38 (m, 3H), 7.26 (s, 1H), 7.05 (t, J = 8.0 Hz, 1H), 6.87 (d, J = 8.0 Hz, 1H), 6.37 (dd, J = 6.0, 2.0 Hz, 1.5 Hz, 1H), 6.14 (d, J = 2.0 Hz, 1H), 2.63 (s, 3H), 1.29 (s, 6H). |
| 100 | Prepared from Intermediates A42 and B27. | 468.3 | 1H NMR (400 MHz, CD3OD) δ 7.84 (d, J = 6.0 Hz, 1H), 7.67 (d, J = 6.8 Hz, 2H), 7.44 (s, 1H), 7.39-7.32 (m, 3H), 7.20-7.11 (m, 3H), 7.05 (d, J = 7.2 Hz, 1H), 6.24 (dd, J = 6.0, 1.6 Hz, 1H), 6.10 (d, J = 1.6 Hz, 1H), 2.73 (q, J = 7.6 Hz, 2H), 2.58 (s, 3H), 1.43 (s, 6H), 1.26 (t, J = 7.6 Hz, 3H). |

-continued

| Example | Structure | LCMS (m/z) [M + 1]+ | 1H NMR (400 MHz) |
|---|---|---|---|
| 101 | Prepared from Intermediates A41 and B27. | 480.1 | 1H NMR (400 MHz, CD3OD) δ 7.84 (d, J = 4.8 Hz, 1H), 7.65 (d, J = 6.8 Hz, 2H), 7.38-7.28 (m, 4H), 7.23-7.18 (m, 3H), 7.00 (d, J = 6.4 Hz, 1H), 6.27-6.24 (m, 1H), 6.06 (s, 1H), 2.69 (s, 3H), 2.05-1.97 (m, 1H), 1.49 (s, 6H), 1.07-1.02 (m, 2H), 0.70-0.66 (m, 2H). |
| 102 | Prepared from Intermediates A43 and B27. | 482.2 | 1H NMR (400 MHz, CDCl3) δ 9.62 (s, 1H), 7.69 (d, J = 6.4 Hz, 1H), 7.66 (d, J = 7.2 Hz, 2H), 7.32-7.14 (m, 5H), 7.11 (t, J = 8.0 Hz, 1H), 7.02 (d, J = 8.0 Hz, 1H), 6.89 (d, J = 8.0 Hz, 1H), 6.36 (d, J = 2.0 Hz, 1H), 6.13 (dd, J = 6.0, 2.0 Hz, 1H), 3.06 (quin, J = 7.6 Hz, 1H), 2.56 (s, 3H), 1.54 (s, 6H), 1.17 (d, J = 6.8 Hz, 6H) |
| 103 | Prepared from Intermediates A44 and B27. | 498.2 | 1H NMR (400 MHz, DMSO-d6) δ 8.95 (s, 1H), 8.20 (s, 1H), 7.99 (d, J = 6.0 Hz, 1H), 7.81 (d, J = 7.2 Hz, 2H), 7.66-7.63 (m, 2H), 7.44-7.30 (m, 4H), 7.16 (t, J = 8.4 Hz, 1H), 6.84 (d, J = 8.0 Hz, 1H), 6.37 (dd, J = 5.6, 2.0 Hz, 1H), 6.08 (d, J = 2.0 Hz, 2H), 2.77 (s, 3H), 1.56 (s, 6H), 1.42 (s, 6H). |
| 104 | Prepared from Intermediates A45 and B27. | 454.1 | 1H NMR (400 MHz, CD3OD) δ 7.85 (d, J = 6.0 Hz, 1H), 7.71 (dd, J = 8.0, 1.6 Hz, 2H), 7.58 (d, J = 8.4 Hz, 1H), 7.41-7.33 (m, 4H), 7.22-7.12 (m, 3H), 7.05 (d, J = 7.2 Hz, 1H), 6.25 (dd, J = 6.0, 2.4 Hz, 1H), 6.11 (d, J = 2.4 Hz, 1H), 2.88 (q, J = 7.6 Hz, 2H), 1.44 (s, 6H), 1.35 (t, J = 7.6 Hz, 3H). |

| Example | Structure | LCMS (m/z) [M + 1]+ | 1H NMR (400 MHz) |
|---|---|---|---|
| 105 | Prepared from Intermediates A48 and B27. | 466.3 | 1H NMR (400 MHz, CD3OD) δ 7.85 (d, J = 5.6 Hz, 1H), 7.75 (d, J = 6.8 Hz, 2H), 7.47 (d, J = 8.4 Hz, 1H), 7.36-7.31 (m, 3H), 7.25-7.14 (m, 4H), 7.04 (d, J = 6.4 Hz, 1H), 6.26-6.24 (m, 1H), 6.09 (d, J = 1.6 Hz, 1H), 2.16-2.14 (m, 1H), 1.45 (s, 6H), 1.04-1.01 (m, 4H). |
| 106 | Prepared from Intermediates A47 and B27. | 468.4 | 1H NMR (400 MHz, CD3OD) δ 7.87 (d, J = 6.0 Hz, 1H), 7.71-7.69 (m, 2H), 7.57 (d, J = 8.0 Hz, 1H), 7.40-7.32 (m, 4H), 7.27 (s, 1H), 7.19-7.16 (m, 2H), 7.03-7.00 (m, 1H), 6.26 (dd, J = 6.0, 2.0 Hz, 1H), 6.10 (d, J = 2.0 Hz, 1H), 2.84 (t, J = 7.6 Hz, 2H), 1.81 (sext, J = 7.6 Hz, 2H), 1.47 (s, 6H), 1.01 (t, J = 7.6 Hz, 3H). |
| 107 | Prepared from Intermediates A46 and B27. | 468.4 | 1H NMR (400 MHz, DMSO-d6) δ 10.26 (br s, 1H), 7.96 (d, J = 6.8 Hz, 1H), 7.79 (d, J = 8.4 Hz, 3H), 7.46-7.41 (m, 4H), 7.38-7.34 (m, 1H), 7.26-7.16 (m, 3H), 6.72-6.69 (m, 1H), 6.21 (d, J = 2.4 Hz, 1H), 3.15 (sept, J = 6.8 Hz, 1H), 1.43 (s, 6H), 1.31 (d, J = 6.8 Hz, 6H). |
| 108 | Prepared from Intermediates A25 and B27. | 448.3 | 1H NMR (400 MHz, CDCl3) δ 7.89 (d, J = 6.4 Hz, 1H), 7.37 (s, 1H), 7.21-7.11 (m, 4H), 7.03 (d, J = 8.0 Hz, 1H), 6.49 (d, J = 1.6 Hz, 1H), 6.19 (dd, J = 6.4, 2.4 Hz, 1H), 4.07 (dd, J = 11.2, 3.6 Hz, 2H), 3.46 (t, J = 11.6 Hz, 2H), 3.10-3.02 (m, 1H), 2.54 (s, 3H), 2.11-1.93 (m, 4H), 1.60 (s, 6H). |

| Example | Structure | LCMS (m/z) [M + 1]+ | 1H NMR (400 MHz) |
|---|---|---|---|
| 109 | Prepared from Intermediates A1 and B34. | 469.3 | 1H NMR (400 MHz, DMSO-d6) δ 8.83 (s, 1H), 8.51-8.49 (m, 1H), 7.96 (d, J = 5.6 Hz, 1H), 7.85-7.76 (m, 2H), 7.58-7.55 (m, 2H), 7.39-7.36 (m, 1H), 7.34-7.30 (m, 1H), 7.12 (t, J = 8.0 Hz, 1H), 6.87 (d, J = 7.6 Hz, 1H), 6.33 (dd, J = 6.0, 2.0 Hz, 1H), 6.09 (d, J = 2.0 Hz, 1H), 2.52 (s, 3H), 2.51 (s, 2H), 2.35 (s, 3H), 1.32 (s, 6H). |
| 110 | 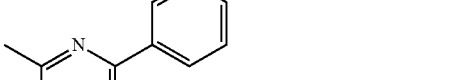Prepared from Intermediates A6 and B34. | 454.3 | 1H NMR (400 MHz, DMSO-d6) δ 8.87 (s, 1H), 8.31 (s, 1H), 7.99 (d, J = 5.6 Hz, 1H), 7.80-7.77 (m, 2H), 7.65 (d, J = 8.0 Hz, 1H), 7.56 (dd, J = 8.0, 1.2 Hz, 1H), 7.41-7.35 (m, 4H), 7.12 (t, J = 8.0 Hz, 1H), 6.88 (d, J = 8.4 Hz, 1H), 6.38 (dd, J = 6.0, 2.4 Hz, 1H), 6.08 (d, J = 2.4 Hz, 1H), 2.58 (s, 3H), 1.33 (s, 6H) missing CH2 overlaped with solvent peak. |
| | Prepared from Intermediates A12 and commercially available methyl 3-aminobenzoate. | 421.4 | 1H NMR (400 MHz, CD3OD) δ 7.95 (d, J = 6.0 Hz, 1H), 7.81 (s, 1H), 7.63-7.55 (m, 3H), 7.25 (t, J = 8.0 Hz, 1H), 6.40 (dd, J = 6.0, 2.0 Hz, 1H), 6.28 (d, J = 2.0 Hz, 1H), 3.95-3.91 (m, 2H), 3.61-3.58 (m, 1H), 3.43 (td, J = 11.6, 2.0 Hz, 2H), 2.84-2.77 (m, 1H), 1.89-1.69 (m, 4H), 1.14-1.00 (m, 4H). |

| Example | Structure | LCMS (m/z) [M + 1]+ | 1H NMR (400 MHz) |
|---------|-----------|---------------------|------------------|
| | Prepared from Intermediates A12 and commercially available methyl 3-amino-5-methylbenzoate. | 435.2 | 1H NMR (400 MHz, CD3OD) δ 7.95 (d, J = 6.0 Hz, 1H), 7.63 (s, 1H), 7.62 (s, 1H), 7.43 (s, 1H), 7.42 (s, 1H), 6.40 (dd, J = 6.0, 2.4 Hz, 1H), 6.28 (d, J = 2.4 Hz, 1H), 3.95-3.91 (m, 2H), 3.59-3.56 (m, 1H), 3.43 (td, J = 11.6, 2.0 Hz, 2H), 2.82-2.78 (m, 1H), 2.33 (s, 3H), 1.85-1.80 (m, 2H), 1.72-1.69 (m, 2H), 1.06-1.00 (m, 4H). |
| | Prepared from Intermediates A12 and B40. | 463.5 | 1H NMR (400 MHz, DMSO-d6) δ 8.89 (s, 1H), 7.99 (d, J = 6.0 Hz, 1H), 7.84 (s, 1H), 7.47 (d, J = 8.8 Hz, 2H), 7.22 (d, J = 8.8 Hz, 2H), 6.40-6.38 (m, 1H), 6.23 (d, J = 2.4 Hz, 1H), 3.83-3.80 (m, 2H), 3.66-3.63 (m, 1H), 3.33-3.28 (m, 2H), 2.73-2.67 (m, 1H), 1.67-1.63 (m, 4H), 1.37 (s, 6H), 1.04-0.93 (m, 4H). |
| 115 | Prepared from Intermediates A12 and commercially available methyl 3-amino-6-methylbenzoate. | 435.4 | 1H NMR (400 MHz, DMSO-d6) δ 8.90 (s, 1H), 8.00 (d, J = 6.0 Hz, 1H), 7.83 (s, 1H), 7.76 (s, 1H), 7.58 (d, J = 7.6 Hz, 1H), 6.98 (d, J = 8.4 Hz, 1H), 6.38 (dd, J = 6.0, 2.0 Hz, 1H), 6.23 (d, J = 2.0 Hz, 1H), 3.83-3.80 (m, 2H), 3.67-3.63 (m, 1H), 3.33-3.27 (m, 2H), 2.73-2.69 (m, 1H), 2.37 (s, 3H), 1.66-1.62 (m, 4H), 1.02-0.92 (m, 4H). |
| | Prepared from Intermediates A12 and B38. | 449.3 | 1H NMR (400 MHz, DMSO-d6) δ 8.73 (s, 1H), 7.97 (d, J = 5.6 Hz, 1H), 7.84 (s, 1H), 7.36 (dd, J = 8.0, 2.0 Hz, 1H), 7.14 (d, J = 2.4 Hz, 1H), 6.87 (d, J = 8.0 Hz, 1H), 6.34 (dd, J = 5.6, 2.4 Hz, 1H), 6.23 (d, J = 2.4 Hz, 1H), 3.85-3.79 (m, 2H), 3.68-3.62 (m, 1H), 3.31-3.21 (m, 2H), 3.07 (s, 2H), 2.71-2.70 (m, 1H), 2.14 (s, 3H), 1.69-1.61 (m, 4H), 1.04-0.91 (m, 4H). |

| Example | Structure | LCMS (m/z) [M + 1]+ | 1H NMR (400 MHz) |
|---|---|---|---|
| | Prepared from Intermediates A12 and commercially available methyl 4-aminopicolinate | 422.1 | 1H NMR (400 MHz, CD3OD) δ 8.24 (d, J = 6.4 Hz, 1H), 8.19 (d, J = 5.6 Hz, 1H), 8.06 (s, 2H), 7.67 (s, 1H), 6.65 (dd, J = 6.0, 2.0 Hz, 1H), 6.45 (d, J = 1.6 Hz, 1H), 3.94-3.91 (m, 2H), 3.62-3.58 (m, 1H), 3.43 (td, J = 12.0, 2.0 Hz, 2H), 2.84-2.78 (m, 1H), 1.89-1.78 (m, 2H), 1.74-1.70 (m, 2H), 1.11-1.00 (m, 4H). |
| 118 | Prepared from Intermediates A63 and B27. | 477.3 | 1H NMR (400 MHz, CD3OD) δ 7.95 (d, J = 5.6 Hz, 1H), 7.68 (s, 1H), 7.38 (s, 1H), 7.30 (d, J = 8.0 Hz, 1H), 7.21 (t, J = 8.0 Hz, 1H), 7.00 (d, J = 7.6 Hz, 1H), 6.43 (dd, J = 6.0, 2.4 Hz, 1H), 6.30 (d, J = 2.4 Hz, 1H), 4.73 (quin, J = 8.4 Hz, 1H), 3.96-3.92 (m, 2H), 3.44 (td, J = 12.0, 2.0 Hz, 2H), 2.83-2.81 (m, 1H), 2.53-2.42 (m, 4H), 1.90-1.80 (m, 4H), 1.74-1.69 (m, 2H), 1.51 (s, 6H). |
| 119 | Prepared from Intermediates A12 and commercially available methyl 3-amino-6-methylbenzoate. | 455.2 | 1H NMR (400 MHz, DMSO-d6) δ 12.26 (br s, 1H), 9.08 (br s, 1H), 8.10 (s, 1H), 8.03 (d, J = 6.0 Hz, 1H), 7.70 (d, J = 7.2 Hz, 2H), 7.64 (d, J = 7.6 Hz, 1H), 7.42 (s, 1H), 7.37 (t, J = 7.6 Hz, 2H), 7.28 (t, J = 7.6 Hz, 1H), 6.87 (d, J = 7.6 Hz, 1H), 6.36 (dd, J = 6.0, 2.0 Hz, 1H), 6.23 (d, J = 2.0 Hz, 1H), 3.85-3.78 (m, 1H), 1.48 (s, 6H), 1.18-1.13 (m, 2H), 1.08-1.00 (m, 2H). |
| 120 | Prepared from Intermediates A57 and B27. | 429.2 | 1H NMR (400 MHz, CD3OD) δ 8.21 (br, 1H, HCO2H), 7.92 (d, J = 6.0 Hz, 1H), 7.72-7.68 (m, 3H), 7.37-7.30 (m, 3H), 7.28-7.24 (m, 1H), 7.21 (t, J = 7.6 Hz, 1H), 7.16 (d, J = 8.4 Hz, 1H), 7.01 (d, J = 7.6 Hz, 1H), 6.49 (dd, J = 6.0, 2.4 Hz, 1H), 6.36 (d, J = 2.0 Hz, 1H), 3.92 (s, 3H), 1.50 (s, 6H). |

| Example | Structure | LCMS (m/z) [M + 1]⁺ | ¹H NMR (400 MHz) |
|---|---|---|---|
| 121 | Prepared from Intermediates A64 and B27. | 465.2 | ¹H NMR (400 MHz, DMSO-d6) δ 8.92 (s, 1H), 8.84 (s, 1H), 8.23 (t, J = 59.2 Hz, 1H), 8.04 (d, J = 6.0 Hz, 1H), 7.77 (d, J = 7.2 Hz, 2H), 7.44 (t, J = 7.2 Hz, 2H), 7.40-7.32 (m, 3H), 7.04 (t, J = 7.6 Hz, 1H), 6.89 (d, J = 8.0 Hz, 1H), 6.52 (dd, J = 6.0, 2.0 Hz, 1H), 6.40 (d, J = 2.0 Hz, 1H), 1.29 (s, 6H). |
| 122 | Prepared from Intermediates A58 and B27. | 443.2 | ¹H NMR (400 MHz, CD₃OD) δ 7.92 (s, 1H), 7.73 (s, 1H), 7.71 (dd, J = 7.2, 1.2 Hz, 2H), 7.36-7.30 (m, 3H), 7.28 (t, J = 7.2 Hz, 1H), 7.20-7.18 (m, 2H), 7.02-6.99 (m, 1H), 6.47 (d, J = 4.0 Hz, 1H), 6.35 (s, 1H), 4.20 (q, J = 7.2 Hz, 2H), 1.57-1.43 (m, 9H). |
| 123 | Prepared from Intermediates A59 and B27. | 479.1 | ¹H NMR (400 MHz, CD₃OD) δ 7.93 (br, 1H), 7.80 (s, 1H), 7.74 (d, J = 7.2 Hz, 2H), 7.35-7.26 (m, 4H), 7.20-7.18 (m, 2H), 7.01-6.99 (m, 1H), 6.47-6.45 (m, 1H), 6.35 (s, 1H), 6.25 (tt, J = 55.2, 4.0 Hz, 1H), 4.57 (dt, J = 14.0, 4.0 Hz, 2H), 1.50 (s, 6H). |
| 124 | Prepared from Intermediates A60 and B27. | 457.2 | ¹H NMR (400 MHz, DMSO-d6) δ 8.97 (s, 1H), 8.05 (s, 1H), 8.02 (d, J = 5.6 Hz, 1H), 7.71 (d, J = 8.4 Hz, 2H), 7.65 (d, J = 8.0 Hz, 1H), 7.40 (s, 1H), 7.36 (t, J = 7.6 Hz, 2H), 7.26 (t, J = 7.6 Hz, 1H), 7.14 (t, J = 7.6 Hz, 1H), 6.86 (d, J = 7.6 Hz, 1H), 6.50 (dd, J = 6.0, 2.0 Hz, 1H), 6.30 (d, J = 2.0 Hz, 1H), 4.52 (sept, J = 6.8 Hz, 1H), 1.49 (d, J = 6.8 Hz, 6H), 1.42 (s, 6H). |

-continued

| Example | Structure | LCMS (m/z) [M + 1]+ | 1H NMR (400 MHz) |
|---|---|---|---|
| 125 | Prepared from Intermediates A56 and B27. | 469.3 | 1H NMR (400 MHz, CD3OD) δ 7.92 (d, J = 5.6 Hz, 1H), 7.82 (s, 1H), 7.72 (d, J = 7.2 Hz, 2H), 7.35-7.26 (m, 4H), 7.19 (d, J = 4.8 Hz, 2H), 7.01-6.98 (m, 1H), 6.47 (dd, J = 6.0, 2.0 Hz, 1H), 6.33 (d, J = 2.4 Hz, 1H), 4.86-4.80 (m, 1H), 2.63-2.48 (m, 4H), 1.94-1.87 (m, 2H), 1.50 (s, 6H). |
| 126 | Prepared from Intermediates A61 and B27. | 471.2 | 1H NMR (400 MHz, CD3OD) δ 7.94 (d, J = 6.0 Hz, 1H), 7.89 (s, 1H), 7.80-7.77 (m, 2H), 7.37-7.25 (m, 4H), 7.19-7.10 (m, 2H), 7.00-6.97 (m, 1H), 6.48 (dd, J = 6.0, 2.4 Hz, 1H), 6.34 (d, J = 2.0 Hz, 1H), 5.57-5.51 (m, 1H), 5.12 (t, J = 6.4 Hz, 2H), 5.06 (t, J = 7.2 Hz, 2H), 1.49 (s, 6H). |
| 127 | Prepared from Intermediates A52 and B27. | 461.4 | 1H NMR (400 MHz, CD3OD) δ 7.94 (d, J = 5.2 Hz, 1H), 7.56 (s, 1H), 7.37 (s, 1H), 7.30-7.19 (m, 2H), 7.02 (d, J = 8.0 Hz, 1H), 6.41 (d, J = 4.8 Hz, 1H), 6.28 (s, 1H), 3.56-3.53 (m, 1H), 2.53-2.51 (m, 1H), 1.79-1.65 (m, 4H), 1.52-1.44 (m, 8H), 1.30-1.187 (m, 4H), 1.04-0.97 (m, 4H). |
| 128 | Prepared from Intermediates A53 and B27. | 447.6 | 1H NMR (400 MHz, CD3OD) δ 7.85 (dd, J = 7.2, 2.8 Hz, 1H), 7.80 (s, 1H), 7.49 (t, J = 8.0 Hz, 1H), 7.45-7.42 (m, 1H), 7.32 (s, 1H), 7.23 (d, J = 7.6 Hz, 1H), 6.81 (dd, J = 7.2, 2.4 Hz, 1H), 6.46 (d, J = 2.4 Hz, 1H), 3.65-3.60 (m, 1H), 2.96-2.91 (m, 1H), 1.97-1.93 (m, 2H), 1.75-1.56 (m, 6H), 1.56 (s, 6H), 1.14-1.00 (m, 4H). |

| Example | Structure | LCMS (m/z) [M + 1]⁺ | ¹H NMR (400 MHz) |
|---|---|---|---|
| 129 | Prepared from Intermediates A54 and B27. | 433.3 | ¹H NMR (400 MHz, CD₃OD) δ 7.93 (d, J = 6.0 Hz, 1H), 7.58 (s, 1H), 7.39-7.36 (m, 1H), 7.29-7.24 (m, 1H), 7.22 (t, J = 7.6 Hz, 1H), 7.02 (d, J = 7.6 Hz, 1H), 6.40 (dd, J = 6.0, 2.0 Hz, 1H), 6.26 (d, J = 2.0 Hz, 1H), 3.58-3.56 (m, 1H), 3.41-3.31 (m, 1H), 2.31-1.82 (m, 6H), 1.52 (s, 6H), 1.07-1.00 (m, 4H). |
| 130 | Prepared from Intermediates A55 and B27. | 456.1 | ¹H NMR (400 MHz, CD₃OD) δ 8.69-8.67 (m, 1H), 7.90-7.85 (m, 2H), 7.59 (d, J = 8.0 Hz, 1H), 7.48 (s, 1H), 7.39 (ddd, J = 7.6, 4.8, 1.2 Hz, 1H), 7.35 (s, 1H), 7.24-7.21 (m, 2H), 7.01 (d, J = 7.2 Hz, 1H), 6.40 (dd, J = 6.0, 2.4 Hz, 1H), 6.31 (d, J = 2.0 Hz, 1H), 4.10-4.07 (m, 1H), 1.51 (s, 6H), 1.03-0.90 (m, 4H). |

Example 131: 2,2-difluoro-2-(3-((4-((6-methyl-2-phenylpyridin-3-yl)oxy)pyridin-2-yl)amino)phenyl) acetic acid

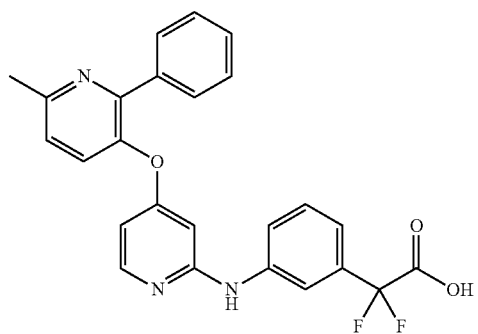 [SMILES: Cc1ccc(Oc2ccnc(Nc3cccc(C(F)(F)C(=O)O)c3)c2)c(-c2ccccc2)n1]

A mixture of 3-((2-chloropyridin-4-yl)oxy)-6-methyl-2-phenylpyridine (Intermediate A6, 1.0 eq), methyl 2-(3-aminophenyl)-2,2-difluoroacetate (Intermediate B41, 2.2 eq), Cs₂CO₃ (2.0 eq), Xantphos (0.10 eq), Pd(OAc)₂ (0.10 eq) in dioxane (0.23 M) was stirred at 110° C. for 16 h under an Ar atmosphere. The mixture was filtered, and the filtrate was concentrated. The residue was purified by Prep-HPLC (mobile phase: 0.1% HCOOH/CH₃CN/H₂O to give the title compound as a solid. LC-MS (m/z): [M+H]⁺=448.2; ¹H NMR (400 MHz, DMSO-d6) δ 9.15 (s, 1H), 8.24 (s, 0.4H, HCO2H), 8.03 (d, J=5.6 Hz, 1H), 7.82-7.76 (m, 4H), 7.67 (d, J=8.4 Hz, 1H), 7.43-7.28 (m, 5H), 7.02 (d, J=7.6 Hz, 1H), 6.44 (dd, J=6.0, 2.0 Hz, 1H), 6.11 (d, J=2.0 Hz, 1H), 2.59 (s, 3H).

Example 132: 2-(3-((4-((1-cyclopropyl-3-phenyl-1H-pyrazol-4-yl)oxy)pyridin-2-yl)amino)phenyl)-2, 2-difluoroacetic acid

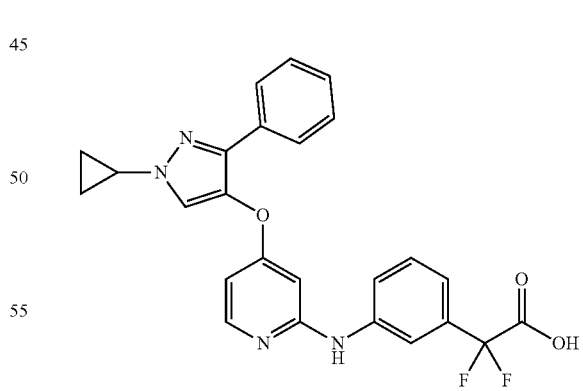

This compound was prepared by following the procedure described in Example 131 using Intermediate A51 and Intermediate B41. LC-MS (m/z): [M+H]⁺=463.2; ¹H NMR (400 MHz, DMSO-d6) δ 9.12 (s, 1H), 8.09 (s, 1H), 8.05 (d, J=5.6 Hz, 1H), 7.78 (d, J=8.8 Hz, 1H), 7.71-7.68 (m, 3H), 7.36 (t, J=7.6 Hz, 2H), 7.29-7.23 (m, 2H), 6.99 (d, J=7.6 Hz, 1H), 6.53 (dd, J=5.6, 2.4 Hz, 1H), 6.32 (d, J=2.4 Hz, 1H), 3.84-3.77 (m, 1H), 1.17-1.13 (m, 2H), 1.04-1.00 (m, 2H).

Example 133: 3-(3-((4-((6-ethyl-2-methylpyridin-3-yl)oxy)pyridin-2-yl)amino)phenyl)-2,2-dimethylpropanoic acid

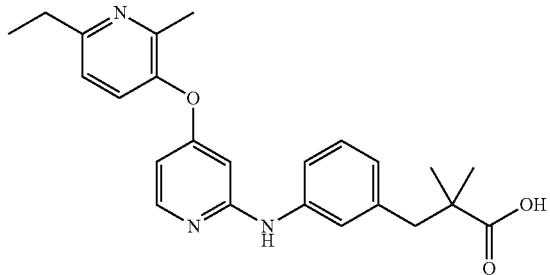 [SMILES: CCc1ccc(Oc2ccnc(Nc3cccc(CC(C)(C)C(=O)O)c3)c2)c(C)n1]

Step 1: 3-(3-((4-((6-ethyl-2-methylpyridin-3-yl)oxy)pyridin-2-yl)amino)phenyl)-2,2-dimethylpropanenitrile A mixture of 3-((2-chloropyridin-4-yl)oxy)-6-ethyl-2-methylpyridine (Intermediate A16, 1.0 eq), 3-(3-aminophenyl)-2,2-dimethylpropanenitrile (Intermediate B31, 1.1 eq), Pd(OAc)$_2$ (0.1 eq), Xantphos (0.1 eq) and Cs$_2$CO$_3$ (2.0 eq) in dioxane (0.1 M) was stirred at 110° C. for 16 h under an Ar atmosphere. The mixture was cooled to RT, and diluted with DCM/H$_2$O. The organic layer was separated, and dried over Na$_2$SO$_4$. The crude product was purified by prep-TLC (petroleum ether/EtOAc=2:1) to give the title compound as a white solid. LC-MS (m/z): [M+H]$^+$=387.4.

Step 2: 3-(3-((4-((6-ethyl-2-methylpyridin-3-yl)oxy)pyridin-2-yl)amino)phenyl)-2,2-dimethylpropanoic acid A mixture of 3-(3-((4-((6-ethyl-2-methylpyridin-3-yl)oxy)pyridin-2-yl)amino)phenyl)-2,2-dimethylpropanenitrile (1.0 eq) in conc. HCl (0.04 M) was stirred at 115° C. for 16 h. The mixture was concentrated, and the residue was purified by Prep-HPLC (mobile phase: 0.1% HCOOH/MeCN/H$_2$O) to give the title compound as a white solid. LC-MS (m/z): [M+H]$^+$=406.3; $^1$H NMR (400 MHz, CD$_3$OD) δ 7.97 (d, J=6.0 Hz, 1H), 7.46 (d, J=8.0 Hz, 1H), 7.26-7.22 (m, 2H), 7.17-7.13 (m, 2H), 6.81 (d, J=7.2 Hz, 1H), 6.36 (dd, J=6.0, 2.4 Hz, 1H), 6.11 (d, J=2.0 Hz, 1H), 2.81 (s, 2H), 2.80 (q, J=7.6 Hz, 2H), 2.38 (s, 3H), 1.29 (d, J=7.6 Hz, 3H), 1.14 (s, 6H).

The following compounds were prepared according to the procedure described in Example 133 using corresponding intermediates.

| Example | Structure | LCMS (m/z) [M + 1]$^+$ | $^1$H NMR (400 MHz) |
|---|---|---|---|
| 134 | Prepared from Intermediates A1 and B37. | 469.2 | $^1$H NMR (400 MHz, DMSO-d$_6$) δ 8.58 (d, J = 4.8 Hz, 1H), 7.87-7.83 (m, 2H), 7.75 (d, J = 8.0 Hz, 1H), 7.51 (s, 1H), 7.38 (dd, J = 6.8, 5.6 Hz, 1H), 7.07 (s, 1H), 7.03 (s, 1H), 6.81 (s, 1H), 6.27 (dd, J = 5.6, 1.6 Hz, 1H), 6.11 (s, 1H), 2.57 (s, 3H), 2.40 (s, 3H), 2.27 (s, 3H), 1.47 (s, 6H). |
| 135 | Prepared from Intermediates A1 and B32. | 483.3 | $^1$H NMR (400 MHz, DMSO-d6) δ 8.58 (d, J = 4.4 Hz, 1H), 7.87-7.82 (m, 2H), 7.75 (d, J = 7.6 Hz, 1H), 7.51 (s, 1H), 7.40-7.35 (m, 1H), 6.99 (s, 1H), 6.88 (s, 1H), 6.63 (s, 1H), 6.25 (dd, J = 6.0, 2.4 Hz, 1H), 6.10 (d, J = 2.0 Hz, 1H), 2.75 (s, 2H), 2.58 (s, 3H), 2.40 (s, 3H), 2.24 (s, 3H), 1.12 (s, 6H). |

| Example | Structure | LCMS (m/z) [M + 1]+ | 1H NMR (400 MHz) |
|---|---|---|---|
| 136 | Prepared from Intermediates A1 and B39. | 469.5 | 1H NMR (400 MHz, MeOD-d4) δ 8.57 (d, J = 3.6 Hz, 1H), 7.87-7.81 (m, 2H), 7.76-7.74 (m, 1H), 7.52 (s, 1H), 7.39-7.36 (m, 1H), 7.28 (s, 1H), 7.10-7.02 (m, 2H), 6.28 (d, J = 6.0 Hz, 1H), 6.11 (s, 1H), 2.57 (s, 3H), 2.40 (s, 3H), 2.23 (s, 3H), 1.48 (s, 6H). |
| 137 | Prepared from Intermediates A1 and B31. | 469.3 | 1H NMR (400 MHz, DMSO-d6) δ 8.82 (s, 1H), 8.50 (d, J = 4.0 Hz, 1H), 7.95 (d, J = 6.0 Hz, 1H), 7.85 (td, J = 8.0, 1.2 Hz, 1H), 7.78 (d, J = 8.0 Hz, 1H), 7.56 (s, 1H), 7.51 (d, J = 8.0 Hz, 1H), 7.35-7.30 (m, 1H), 7.28 (s, 1H), 7.09 (t, J = 7.6 Hz, 1H), 6.64 (d, J = 7.2 Hz, 1H), 6.33 (dd, J = 5.6, 2.0 Hz, 1H), 6.09 (d, J = 2.4 Hz, 1H), 2.67 (s, 2H), 2.53 (s, 3H), 2.33 (s, 3H), 1.06 (s, 6H). |
| 138 | Prepared from Intermediates A21 and B2. | 441.3 | 1H NMR (400 MHz, CD3OD) δ 8.58-8.57 (m, 1H), 7.90-7.84 (m, 2H), 7.79 (d, J = 7.6 Hz, 1H), 7.67 (d, J = 8.4 Hz, 1H), 7.48 (d, J = 8.4 Hz, 1H), 7.41-7.38 (m, 1H), 7.18-7.14 (m, 3H), 6.86-6.83 (m, 1H), 6.29 (dd, J = 6.0, 2.0 Hz, 1H), 6.11 (d, J = 2.4 Hz, 1H), 2.93 (q, J = 7.6 Hz, 2H), 2.85 (t, J = 7.6 Hz, 2H), 2.56 (t, J = 7.6 Hz, 2H), 1.36 (t, J = 7.6 Hz, 3H). |
| 139 | Prepared from Intermediates A23 and B2. | 455.4 | 1H NMR (400 MHz, CD3OD) δ 8.56 (d, J = 4.0 Hz, 1H), 8.34 (s, 1H, HCO2H), 7.89-7.80 (m, 2H), 7.79 (d, J = 8.0 Hz, 1H), 7.51 (s, 1H), 7.37 (ddd, J = 7.2, 4.8, 1.2 Hz, 1H), 7.19-7.11 (m, 3H), 6.86-6.82 (m, 1H), 6.27 (dd, J = 6.0, 2.0 Hz, 1H), 6.09 (d, J = 2.0 Hz, 1H), 2.93 (q, J = 7.6 Hz, 2H), 2.84 (t, J = 7.6 Hz, 2H), 2.55 (t, J = 7.6 Hz, 2H), 2.43 (s, 3H), 1.32 (t, J = 7.6 Hz, 3H). |

-continued

| Example | Structure | LCMS (m/z) [M + 1]+ | 1H NMR (400 MHz) |
|---|---|---|---|
| 140 | Prepared from Intermediates A6 and B31. | 454.3 | 1H NMR (400 MHz, CDCl3) δ 13.63 (br s, 1H), 10.29 (s, 1H), 8.59 (s, 1H), 7.75-7.40 (m, 7H), 7.09-7.00 (m, 2H), 6.92 (m, 1H), 6.47 (m, 1H), 6.17 (s, 1H), 3.07 (s, 3H), 2.73 (s, 2H), 1.20 (s, 6H). |
| 141 | Prepared from Intermediates A6 and B32. | 468.2 | 1H NMR (400 MHz, DMSO-d6) δ 7.85 (d, J = 6.0 Hz, 1H), 7.70-7.67 (m, 2H), 7.56 (d, J = 8.0 Hz, 1H), 7.39-7.33 (m, 4H), 6.98 (s, 1H), 6.87 (s, 1H), 6.64 (s, 1H), 6.27 (dd, J = 6.0, 2.0 Hz, 1H), 6.08 (d, J = 2.0 Hz, 1H), 2.75 (s, 2H), 2.60 (s, 3H), 2.24 (s, 3H), 1.12 (s, 6H). |
| 142 | Prepared from Intermediates A6 and B37. | 454.3 | 1H NMR (400 MHz, DMSO-d6) δ 8.85 (s, 1H), 7.99 (d, J = 5.6 Hz, 1H), 7.79-7.76 (m, 2H), 7.65 (d, J = 8.4 Hz, 1H), 7.43-7.35 (m, 5H), 7.17 (s, 1H), 6.66 (s, 1H), 6.38 (dd, J = 6.0, 2.0 Hz, 1H), 6.08 (d, J = 2.0 Hz, 1H), 2.58 (s, 3H), 2.23 (s, 3H), 1.39 (s, 6H). |
| 143 | Prepared from Intermediates A24 and B37. | 476.3 | 1H NMR (400 MHz, DMSO-d6) δ 8.90 (s, 1H), 8.06 (d, J = 5.6 Hz, 1H), 7.50 (s, 1H), 7.35 (s, 1H), 7.20 (s, 1H), 6.66 (s, 1H), 6.44 (dd, J = 6.0, 2.4 Hz, 1H), 6.06 (d, J = 2.4 Hz, 1H), 3.69-3.66 (m, 2H), 3.34-3.28 (m, 2H), 3.00-2.98 (m, 1H), 2.45 (s, 3H), 2.23 (s, 6H), 1.89-1.85 (m, 2H), 1.50-1.47 (m, 2H), 1.42 (s, 6H). |

| Example | Structure | LCMS (m/z) [M + 1]+ | 1H NMR (400 MHz) |
|---|---|---|---|
| 144 | Prepared from Intermediates A16 and B37. | 406.3 | 1H NMR (400 MHz, CD3OD) δ 7.98 (d, J = 5.6 Hz, 1H), 7.46 (d, J = 8.4 Hz, 1H), 7.23 (d, J = 8.4 Hz, 1H), 7.17 (s, 1H), 7.05 (s, 1H), 6.84 (s, 1H), 6.37 (dd, J = 6.0, 2.4 Hz, 1H), 6.12 (d, J = 1.6 Hz, 1H), 2.80 (q, J = 7.6 Hz, 2H), 2.38 (s, 3H), 2.27 (s, 3H), 1.47 (s, 6H), 1.29 (d, J = 7.6 Hz, 3H). |
| 145 | Prepared from Intermediates A16 and B32. | 420.3 | 1H NMR (400 MHz, CD3OD) δ 8.26 (d, J = 8.4 Hz, 1H), 7.93 (d, J = 7.2 Hz, 1H), 7.79 (d, J = 8.8 Hz, 1H), 7.05 (s, 2H), 6.92 (s, 1H), 6.85 (dd, J = 7.2, 2.4 Hz, 1H), 6.47 (d, J = 2.4 Hz,1H), 3.05 (q, J = 7.6 Hz, 2H), 2.85 (s, 2H), 2.65 (s, 3H), 2.36 (s, 3H), 1.42 (t, J = 7.6 Hz, 3H) , 1.15 (s, 6H). |
| 146 | Prepared from Intermediates A16 and B2. | 378.2 | 1H NMR (400 MHz, CD3OD) δ 7.98 (d, J = 6.0 Hz, 1H), 7.47 (d, J = 8.0 Hz, 1H), 7.25-7.20 (m, 3H), 7.16 (t, J = 7.6 Hz, 1H), 6.85 (d, J = 7.2 Hz, 1H), 6.37 (dd, J = 5.6, 2.4 Hz, 1H), 6.12 (d, J = 2.4 Hz, 1H), 2.86 (t, J = 7.6 Hz, 2H), 2.81 (q, J = 7.6 Hz, 2H), 2.57 (t, J = 7.6 Hz, 2H), 2.38 (s, 3H), 1.29 (t, J = 7.6 Hz, 3H). |
| 147 | Prepared from Intermediates A16 and B23. | 392.2 | 1H NMR (400 MHz, DMSO-d6) δ 8.85 (s, 1H), 8.06 (d, J = 6.0 Hz, 1H), 7.52 (d, J = 8.4 Hz, 1H), 7.28 (s, 1H), 7.26 (d, J = 10.4 Hz, 1H), 7.17 (s, 1H), 6.55 (s, 1H), 6.41 (dd, J = 6.0, 1.6 Hz, 1H), 6.05 (d, J = 1.6 Hz, 1H), 2.79-2.68 (m, 4H), 2.45 (t, J = 7.6 Hz, 2H), 2.30 (s, 3H), 2.20 (s, 3H), 1.25 (t, J = 7.6 Hz, 3H). |

-continued

| Example | Structure | LCMS (m/z) [M + 1]+ | 1H NMR (400 MHz) |
|---|---|---|---|
| 148 | Prepared from Intermediates A49 and B37. | 420.3 | 1H NMR (400 MHz, CD3OD) δ 7.95 (d, J = 6.0 Hz, 1H), 7.34 (s, 1H), 7.13 (s, 1H), 7.08 (s, 1H), 6.88 (s, 1H), 6.43 (dd, J = 6.0, 2.4 Hz, 1H), 6.13 (d, J = 2.4 Hz, 1H), 2.82 (q, J = 7.6 Hz, 2H), 2.34 (s, 6H), 2.29 (s, 3H), 1.49 (s, 6H), 1.24 (t, J = 7.6 Hz, 3H). |
| 149 | Prepared from Intermediates A49 and B2. | 392.2 | 1H NMR (400 MHz, CD3OD) δ 7.97 (d, J = 6.0 Hz, 1H), 7.32 (s, 1H), 7.25-7.20 (m, 2H), 7.16 (t, J = 7.6 Hz, 1H), 6.85 (d, J = 7.2 Hz, 1H), 6.37 (dd, J = 6.0, 2.0 Hz, 1H), 6.10 (d, J = 2.0 Hz, 1H), 2.88-2.76 (m, 4H), 2.57 (t, J = 7.6 Hz, 2H), 2.34 (s, 3H), 2.33 (s, 3H), 1.24 (t, J = 7.6 Hz, 3H). |
| 150 | Prepared from Intermediates A49 and B23. | 406.2 | 1H NMR (400 MHz, CD3OD) δ 7.96 (d, J = 6.0 Hz, 1H), 7.32 (s, 1H), 7.02 (s, 1H), 7.01 (s, 1H), 6.68 (s, 1H), 6.37 (dd, J = 6.0, 2.0 Hz, 1H), 6.09 (d, J = 2.0 Hz, 1H), 2.85-2.78 (m, 4H), 2.54 (t, J = 7.6 Hz, 2H), 2.34 (s, 3H), 2.33 (s, 3H), 2.25 (s, 3H), 1.24 (t, J = 7.6 Hz, 3H). |
| 151 | Prepared from Intermediates A49 and B31. | 420.3 | 1H NMR (400 MHz, CD3OD) δ 7.97 (d, J = 4.8 Hz, 1H), 7.31 (s, 1H), 7.25 (d, J = 8.0 Hz, 1H), 7.17 (s, 1H), 7.14 (t, J = 8.0 Hz, 1H), 6.81 (d, J = 7.6 Hz, 1H), 6.35-6.33 (m, 1H), 6.10 (s, 1H), 2.85-2.78 (m, 4H), 2.34 (s, 3H), 2.33 (s, 3H), 1.24 (t, J = 7.6 Hz, 3H), 1.13 (s, 6H). |

| Example | Structure | LCMS (m/z) [M + 1]+ | 1H NMR (400 MHz) |
|---|---|---|---|
| 152 | Prepared from Intermediates A49 and B32. | 434.2 | 1H NMR (400 MHz, CD3OD) δ 7.95 (d, J = 6.0 Hz, 1H), 7.31 (s, 1H), 7.05 (s, 1H), 6.94 (s, 1H), 6.63 (s, 1H), 6.34 (dd, J = 6.0, 2.0 Hz, 1H), 6.08 (d, J = 2.0 Hz, 1H), 2.81 (q, J = 7.6 Hz, 2H), 2.76 (s, 2H), 2.34 (s, 3H), 2.33 (s, 3H), 2.24 (s, 3H), 1.24 (t, J = 7.6 Hz, 3H), 1.13 (s, 6H). |
| 153 | Prepared from Intermediates A50 and B37. | 440.1 | 1H NMR (400 MHz, CD3OD) δ 7.95 (d, J = 6.4 Hz, 1H), 7.65 (s, 1H), 7.15 (s, 1H), 7.10 (s, 1H), 6.96 (s, 1H), 6.52 (dd, J = 6.4, 2.0 Hz, 1H), 6.18 (d, J = 2.4 Hz, 1H), 2.95 (q, J = 7.6 Hz, 2H), 2.38 (s, 3H), 2.32 (s, 3H), 1.50 (s, 6H), 1.28 (t, J = 7.6 Hz, 3H). |
| 154 | Prepared from Intermediates A50 and B2. | 412.1 | 1H NMR (400 MHz, CD3OD) δ 8.00 (d, J = 5.6 Hz, 1H), 7.60 (s, 1H), 7.28-7.23 (m, 2H), 7.17 (t, J = 7.6 Hz, 1H), 6.85 (d, J = 7.2 Hz, 1H), 6.38 (dd, J = 5.6, 2.0 Hz, 1H), 6.15 (d, J = 2.0 Hz, 1H), 2.94 (q, J = 7.6 Hz, 2H), 2.86 (t, J = 8.0 Hz, 2H), 2.58 (t, J = 7.6 Hz, 2H), 2.37 (s, 3H), 1.28 (t, J = 7.6 Hz, 3H). |
| 155 | Prepared from Intermediates A50 and B31. | 440.1 | 1H NMR (400 MHz, CD3OD) δ 7.99 (d, J = 6.0 Hz, 1H), 7.59 (s, 1H), 7.27 (d, J = 8.0 Hz, 1H), 7.20 (s, 1H), 7.15 (t, J = 8.0 Hz, 1H), 6.81 (d, J = 7.6 Hz, 1H), 6.37 (dd, J = 6.0, 2.4 Hz, 1H), 6.14 (d, J = 2.0 Hz, 1H), 2.94 (q, J = 7.6 Hz, 2H), 2.81 (s, 2H), 2.37 (s, 3H), 1.28 (t, J = 7.6 Hz, 3H), 1.14 (s, 6 H). |

| Example | Structure | LCMS (m/z) [M + 1]+ | 1H NMR (400 MHz) |
|---|---|---|---|
| 156 | Prepared from Intermediates A50 and B32. | 454.1 | 1H NMR (400 MHz, CD3OD) δ 7.87 (d, J = 6.8 Hz, 1H), 7.74 (s, 1H), 7.03 (s, 1H), 6.98 (s, 1H), 6.90 (s, 1H), 6.71 (dd, J = 6.8, 2.4 Hz, 1H), 6.19 (d, J = 2.4 Hz, 1H), 2.96 (q, J = 7.6 Hz, 2H), 2.84 (s, 2H), 2.39 (s, 3H), 2.33 (s, 3H), 1.29 (t, J = 7.6 Hz, 3H), 1.15 (s, 6H). |
| 157 | Prepared from Intermediates A26 and B37. | 426.1 | 1H NMR (400 MHz, CD3OD) δ 7.89 (d, J = 6.8 Hz, 1H), 7.74 (s, 1H), 7.12-7.07 (m, 3H), 6.68 (dd, J = 6.8, 2.4 Hz, 1H), 6.23 (d, J = 2.4 Hz, 1H), 2.60 (s, 3H), 2.37 (s, 3H), 2.35 (s, 3H), 1.51 (s, 6H). |
| 158 | Prepared from Intermediates A26 and B32. | 440.2 | 1H NMR (400 MHz, CD3OD) δ 8.14 (s, 1H), 7.89 (d, J = 6.0 Hz, 1H), 7.06 (s, 2H), 6.91 (s, 1H), 6.83-6.80 (m, 1H), 6.37 (s, 1H), 2.86 (s, 2H), 2.70 (s, 3H), 2.50 (s, 3H), 2.36 (s, 3H), 1.15 (s, 6H). |
| 116 | Prepared from Intermediates A12 and B39. | 477.3 | 1H NMR (400 MHz, CD3OD) δ 7.92 (d, J = 5.6 Hz, 1H), 7.61 (s, 1H), 7.28 (d, J = 8.4 Hz, 1H), 7.17 (d, J = 8.4 Hz, 1H), 7.13 (s, 1H), 6.41 (d, J = 6.0 Hz, 1H), 6.28 (s, 1H), 3.94-3.91 (m, 2H), 3.59-3.55 (m, 1H), 3.47-3.37 (m, 2H), 2.82-2.78 (m, 1H), 2.25 (s, 3H), 1.84-1.78 (m, 2H), 1.71-1.68 (m, 2H), 1.53 (s, 6H), 1.05-0.98 (m, 4H). |

| Example | Structure | LCMS (m/z) [M + 1]⁺ | ¹H NMR (400 MHz) |
|---|---|---|---|
| 159 | Prepared from Intermediates A12 and B35. | 477.3 | ¹H NMR (400 MHz, DMSO-d6) δ 8.39 (br s, 1H, HCO2H), 7.94 (d, J = 5.2 Hz, 1H), 7.61 (s, 1H), 7.36 (s, 1H), 7.32-7.30 (m, 1H), 7.22-7.20 (m, 2H), 7.07-7.04 (m, 1H), 6.42 (dd, J = 6.0, 2.0 Hz, 1H), 6.31 (d, J = 2.0 Hz, 1H), 3.95-3.91 (m, 2H), 3.60-3.56 (m, 1H), 3.43 (td, J = 12.0, 2.0 Hz, 2H), 2.83-2.75 (m, 1H), 2.59 (s, 2H), 1.87-1.77 (m, 2H), 1.72-1.67 (m, 2H), 1.42 (s, 6H), 1.08-1.00 (m, 4H). |
| 160 | Prepared from Intermediates A12 and B39. | 477.4 | ¹H NMR (400 MHz, DMSO-d6) δ 7.93 (d, J = 6.0 Hz, 1H), 7.61 (s, 1H), 7.24 (d, J = 8.4 Hz, 1H) 7.19-7.14 (m, 2H), 6.84 (d, J = 7.6 Hz, 1H), 6.42 (dd, J = 6.0, 2.0 Hz, 1H), 6.27 (d, J = 1.6 Hz, 1H), 3.96-3.91 (m, 2H), 3.60-3.56 (m, 1H), 3.43 (td, J = 11.6, 2.0 Hz, 2H), 2.82 (s, 2H), 2.82-2.80 (m, 1H), 1.84-1.80 (m, 2H), 1.72-1.69 (m, 2H), 1.05 (s, 6H), 1.04-1.00 (m, 4H). |
| 161 | Prepared from Intermediates A12 and B37. | 477.3 | ¹H NMR (400 MHz, CD₃OD) δ 7.94 (d, J = 6.0 Hz, 1H), 7.61 (s, 1H), 7.14 (s, 1H), 7.10 (s, 1H), 6.84 (s, 1H), 6.42 (dd, J = 6.0, 2.4 Hz, 1H), 6.29 (d, J = 2.0 Hz, 1H), 3.95-3.90 (m, 2H), 3.59-3.56 (m, 1H), 3.42 (td, J = 11.6, 2.0 Hz, 2H), 2.82-2.78 (m, 1H), 2.29 (s, 3H), 1.84-1.78 (m, 2H), 1.72-1.68 (m, 2H), 1.49 (s, 6H), 1.07-0.99 (m, 4H). |
| 162 | Prepared from Intermediates A12 and B32. | 491.2 | ¹H NMR (400 MHz, CD₃OD) δ 7.92 (d, J = 1.6 Hz, 1H), 7.60 (s, 1H), 7.06 (s, 1H), 6.94 (s, 1H), 6.66 (s, 1H), 6.40 (d, J = 4.0 Hz, 1H), 6.26 (s, 1H), 3.95-3.91 (m, 2H), 3.60-3.56 (m, 1H), 3.43 (td, J = 11.6, 2.0 Hz, 2H), 2.83-2.77 (m, 3H), 2.26 (s, 3H), 1.85-1.68 (m, 4H), 1.28 (s, 6H), 1.14-0.98 (m, 4H). |

| Example | Structure | LCMS (m/z) [M + 1]+ | 1H NMR (400 MHz) |
|---|---|---|---|
| 163 | Prepared from Intermediates A12 and commercially available 2-(3-aminophenyl)acetonitrile | 435.4 | 1H NMR (400 MHz, CD3OD) δ 7.94 (d, J = 5.6 Hz, 1H), 7.62 (s, 1H), 7.33-7.28 (m, 2H), 7.19 (t, J = 7.6 Hz, 1H), 6.92 (d, J = 7.6 Hz, 1H), 6.41 (dd, J = 6.0, 2.0 Hz, 1H), 6.29 (d, J = 2.0 Hz, 1H), 3.95-3.91 (m, 2H), 3.59-3.55 (m, 1H), 3.51 (s, 2H), 3.43 (td, J = 12.0, 2.0 Hz, 2H), 2.84-2.77 (m, 1H), 1.89-1.69 (m, 4H), 1.09-1.00 (m, 4H). |
| 164 | Prepared from Intermediates A12 and B36. | 449.2 | 1H NMR (400 MHz, DMSO-d6) δ 8.92 (s, 1H), 8.02 (d, J = 6.0 Hz, 1H), 7.85 (s, 1H), 7.37 (s, 1H), 7.26 (s, 1H), 6.59 (s, 1H), 6.42 (dd, J = 6.0, 2.4 Hz, 1H), 6.26 (d, J = 2.0 Hz, 1H), 3.85-3.80 (m, 2H), 3.68-3.63 (m, 1H), 3.39 (s, 2H), 3.30-3.27 (m, 2H), 2.72-2.69 (m, 1H), 2.22 (s, 3H), 1.67-1.62 (m, 4H), 1.05-0.93 (m, 4H). |
| 165 | Prepared from Intermediates A63 and B37. | 491.4 | 1H NMR (400 MHz, CD3OD) δ 7.94 (d, J = 6.0 Hz, 1H), 7.68 (s, 1H), 7.15 (s, 1H), 7.10 (s, 1H), 6.83 (s, 1H), 6.43 (dd, J = 6.0, 2.0 Hz, 1H), 6.29 (d, J = 2.0 Hz, 1H), 4.75-4.70 (m, 1H), 3.96-3.92 (m, 2H), 3.44 (td, J = 12.0, 2.0 Hz, 2H), 2.83-2.81 (m, 1H), 2.52-2.42 (m, 4H), 1.90-1.80 (m, 4H), 1.74-1.69 (m, 2H), 1.49 (s, 6H). |
| 166 | Prepared from Intermediates A63 and B39. | 491.3 | 1H NMR (400 MHz, CD3OD) δ 8.38 (br s, 1H, HCO2H), 7.92 (d, J = 5.6 Hz, 1H), 7.68 (s, 1H), 7.35 (d, J = 2.0 Hz, 1H), 7.18-7.14 (m, 1H), 7.05 (d, J = 8.4 Hz, 1H), 6.42 (dd, J = 6.0, 2.4 Hz, 1H), 6.29 (d, J = 2.0 Hz, 1H), 4.72 (quin, J = 8.4 Hz, 1H), 3.95-3.91 (m, 2H), 3.44 (td, J = 12.0, 2.0 Hz, 2H), 2.85-2.78 (m, 1H), 2.52-2.40 (m, 4H), 2.24 (m, 3H), 1.90-1.78 (m, 4H), 1.74-1.69 (m, 2H), 1.50 (s, 6H). |

-continued

| Example | Structure | LCMS (m/z) [M + 1]+ | 1H NMR (400 MHz) |
|---|---|---|---|
| 167 | Prepared from Intermediates A62 and B37. | 479.3 | 1H NMR (400 MHz, CD3OD) δ 7.90 (d, J = 6.4 Hz, 1H), 7.64 (s, 1H), 7.13 (s, 1H), 7.09 (s, 1H), 6.95 (s, 1H), 6.53 (dd, J = 6.0, 2.0 Hz, 1H), 6.31 (d, J = 2.0 Hz, 1H), 4.45-4.39 (m, 1H), 3.96-3.92 (m, 2H), 3.45 (td, J = 12.0, 2.0 Hz, 2H), 2.85-2.79 (m, 1H), 2.31 (s, 3H), 1.88-1.78 (m, 2H), 1.73-1.69 (m, 2H), 1.51 (s, 6H), 1.46 (d, J = 6.8 Hz, 6H). |
| 168 | Prepared from Intermediates A51 and B31. | 469.3 | 1H NMR (400 MHz, DMSO-d6) δ 12.16 (br s, 1H), 8.91 (s, 1H), 8.07 (s, 1H), 8.02 (d, J = 5.6 Hz, 1H), 7.70 (d, J = 7.2 Hz, 2H), 7.53 (d, J = 7.6 Hz, 1H), 7.36 (t, J = 7.6 Hz, 2H), 7.28-7.24 (m, 2H), 7.10 (t, J = 7.6 Hz, 1H), 6.66 (d, J = 8.0 Hz, 1H), 6.51 (dd, J = 6.0, 2.4 Hz, 1H), 6.29 (d, J = 2.4 Hz, 1H), 3.82-3.78 (m, 1H), 2.70 (s, 2H), 1.17-1.13 (m, 2H), 1.06 (s, 6H), 1.03-1.01 (m, 2H). |
| 169 | Prepared from Intermediates A51 and B37. | 469.2 | 1H NMR (400 MHz, CD3OD) δ 7.92 (d, J = 6.0 Hz, 1H), 7.77 (s, 1H), 7.70 (d, J = 7.2 Hz, 2H), 7.34-7.25 (m, 3H), 7.11 (s, 1H), 7.03 (s, 1H), 6.82 (s, 1H), 6.46 (dd, J = 6.0, 2.0 Hz, 1H), 6.32 (d, J = 2.0 Hz, 1H), 3.73-3.67 (m, 1H), 2.27 (s, 3H), 1.48 (s, 6H), 1.19-1.14 (m, 2H), 1.10-1.05 (m, 2H). |
| 170 | Prepared from Intermediates A51 and B32. | 483.2 | 1H NMR (400 MHz, CD3OD) δ 7.91 (d, J = 6.0 Hz, 1H), 7.76 (s, 1H), 7.72-7.69 (m, 2H), 7.33 (t, J = 7.6 Hz, 2H), 7.28-7.26 (m, 1H), 6.99 (s, 1H), 6.89 (s, 1H), 6.64 (s, 1H), 6.44 (dd, J = 6.0, 2.0 Hz, 1H), 6.29 (d, J = 2.0 Hz, 1H), 3.72-3.68 (m, 1H), 2.75 (s, 2H), 2.24 (s, 3H), 1.12 (s, 6H), 1.18-1.05 (m, 4H). |

-continued

| Example | Structure | LCMS (m/z) [M + 1]+ | 1H NMR (400 MHz) |
|---|---|---|---|
| 171 | Prepared from Intermediates A51 and B2. | 441.2 | 1H NMR (400 MHz, CD3OD) δ 7.91 (d, J = 5.6 Hz, 1H), 7.79 (s, 1H), 7.71 (d, J = 8.0 Hz, 2H), 7.36-7.25 (m, 3H), 7.22-7.10 (m, 3H), 6.89 (d, J = 7.2 Hz, 1H), 6.51 (d, J = 5.6 Hz, 1H), 6.31 (s, 1H), 3.73-3.69 (m, 1H), 2.85 (t, J = 7.6 Hz, 2H), 2.57 (t, J = 7.6 Hz, 2H), 1.17-1.01 (m, 4H). |
| 172 | Prepared from Intermediates A56 and B37. | 483.3 | 1H NMR (400 MHz, CD3OD) δ 7.89 (d, J = 6.0 Hz, 1H), 7.84 (s, 1H), 7.72 (d, J = 7.2 Hz, 2H), 7.34 (t, J = 7.6 Hz, 2H), 7.27 (t, J = 7.6 Hz, 1H), 7.09 (s, 1H), 7.02 (s, 1H), 6.90 (s, 1H), 6.54 (dd, J = 6.0, 2.4 Hz, 1H), 6.34 (d, J = 2.4 Hz, 1H), 4.81-4.78 (m, 1H), 2.63-2.46 (m, 4H), 2.28 (s, 3H), 1.94-1.87 (m, 2H), 1.49 (s, 6H). |
| 173 | Prepared from Intermediates A56 and B2. | 455.3 | 1H NMR (400 MHz, DMSO-d6) δ 12.16 (br s, 1H), 8.92 (s, 1H), 8.13 (s, 1H), 8.04 (d, J = 6.0 Hz, 1H), 7.72 (d, J = 7.2 Hz, 2H), 7.46 (d, J = 8.8 Hz, 1H), 7.30-7.25 (m, 3H), 7.27 (t, J = 7.6 Hz, 1H), 7.11 (t, J = 7.6 Hz, 1H), 6.72 (d, J = 7.2 Hz, 1H), 6.52-6.50 (m, 1H), 6.28 (s, 1H), 4.88-4.83 (m, 1H), 2.74 (t, J = 7.6 Hz, 2H), 2.66-2.45 (m, 6H), 1.83-1.79 (m, 2H). |

Example 174: 3-(3-((4-((6-ethyl-2,5-dimethylpyridin-3-yl)oxy)pyridin-2-yl)amino)benzyl)oxetane-3-carboxylic acid

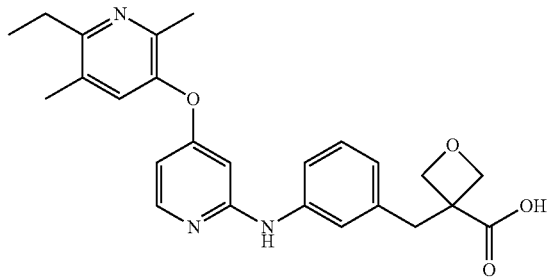 [SMILES: CCc1nc(C)c(Oc2ccnc(Nc3cccc(CC4(C(=O)O)COC4)c3)c2)cc1C]

Step 1: 3-(3-((4-((6-ethyl-2,5-dimethylpyridin-3-yl)oxy)pyridin-2-yl)amino)benzyl)oxetane-3-carbonitrile A mixture of 3-((2-chloropyridin-4-yl)oxy)-6-ethyl-2,5-dimethylpyridine (Intermediate A49, 1.0 eq), 3-(3-aminobenzyl)oxetane-3-carbonitrile (Intermediate B33, 1.0 eq), Cs$_2$CO$_3$ (2.0 eq), Xantphos (0.2 eq) and Pd(OAc)$_2$ (0.2 eq) in dioxane (0.06 M) was stirred at 110° C. for 16 h under Ar. The mixture was filtered through a pad of celite, and the filtrate was concentrated. The residue was redissolved in EtOAc, washed with water, brine, and then dried over Na$_2$SO$_4$. The crude product was purified by flash chromatography on silica gel (eluent: petroleum ether/EtOAc=10:1 to 2:1) to give the title compound as a yellow solid. LC-MS (m/z): [M+H]$^+$=415.2.

Step 2: 3-(3-((4-((6-ethyl-2,5-dimethylpyridin-3-yl)oxy)pyridin-2-yl)amino)benzyl)oxetane-3-carboxylic acid A mixture of 3-(3-((4-((6-ethyl-2,5-dimethylpyridin-3-yl)oxy)pyridin-2-yl)amino)benzyl)oxetane-3-carbonitrile (1.0 eq) and KOH (5.0 eq) in ethylene glycol/H$_2$O (v/v=4:1, 0.02 M) was stirred at 130° C. for 2 h. The mixture was cooled to RT, washed with EtOAc.

The aqueous layer was adjusted to pH ~7 with 1.0 M aq. HCl, and the solvent was removed under reduced pressure. The residue was purified by Prep-HPLC (mobile phase: 0.1% HCOOH/MeCN/H$_2$O) to give the title compound as a white solid. LC-MS (m/z): [M+H]$^+$=434.2; $^1$H NMR (400 MHz, CD$_3$OD) δ 7.97 (d, J=6.0 Hz, 1H), 7.33 (s, 1H), 7.27-7.25 (m, 2H), 7.17 (t, J=7.6 Hz, 1H), 6.83 (d, J=7.6 Hz, 1H), 6.38 (dd, J=6.0, 2.0 Hz, 1H), 6.10 (d, J=1.6 Hz, 1H), 4.84 (d, J=6.4 Hz, 2H), 4.60 (d, J=6.0 Hz, 2H), 3.27 (s, 2H), 2.82 (q, J=7.6 Hz, 2H), 2.34 (s, 6H), 1.24 (t, J=7.6 Hz, 3H).

Example 175: N-(3-(2-(2H-tetrazol-5-yl)ethyl)phenyl)-4-((6-ethyl-[2,2'-bipyridin]-3-yl)oxy)pyridin-2-amine

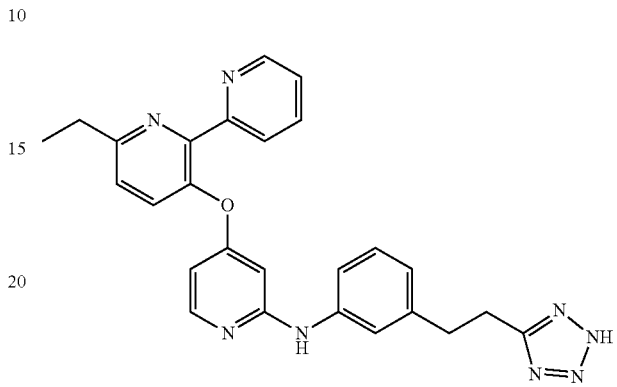

Step 1: 3-(3-((4-((6-ethyl-[2,2'-bipyridin]-3-yl)oxy)pyridin-2-yl)amino)phenyl)propanenitrile A mixture of 3-((2-chloropyridin-4-yl)oxy)-6-ethyl-2,2'-bipyridine (Intermediate A21, 1.0 eq), 3-(3-aminophenyl)propanenitrile (Intermediate B2, 1.0 eq), Cs$_2$CO$_3$ (2.0 eq), Xantphos (0.10 eq), Pd(OAc)$_2$ (0.1 eq) in dioxane (0.1 M) was stirred at 110° C. for 16 h under an Ar atmosphere. The solid was filtered off, and the filtrate was concentrated. The residue was purified by flash chromatography on silica gel (eluent: petroleum ether/EtOAc=20:1) to give the title compound as a yellow solid. LC-MS (m/z): [M+1]$^+$=422.3.

Step 2: N-(3-(2-(2H-tetrazol-5-yl)ethyl)phenyl)-4-((6-ethyl-[2,2'-bipyridin]-3-yl)oxy)pyridin-2-amine A mixture of 3-(3-((4-((6-ethyl-[2,2'-bipyridin]-3-yl)oxy)pyridin-2-yl)amino)phenyl)propanenitrile (1.0 eq), TMSN3 (5.0 eq) and Bu$_2$SnO (2.0 eq) in dioxane (0.04 M) was stirred at 100° C. for 16 h under an Ar atmosphere. The solvent was removed, and the residue was purified by the Prep-HPLC (mobile phase: 0.1% HCOOH/MeCN/H$_2$O) to give the title compound as a white solid. LC-MS (m/z): [M+H]$^+$=465.2; $^1$H NMR (400 MHz, CD$_3$OD) δ 8.58 (d, J=4.8 Hz, 1H), 7.89 (td, J=8.0, 1.6 Hz, 1H), 7.86 (d, J=6.0 Hz, 1H), 7.82 (d, J=8.0 Hz, 1H), 7.68 (d, J=8.4 Hz, 1H), 7.49 (d, J=8.0 Hz, 1H), 7.43-7.38 (m, 1H), 7.22 (s, 1H), 7.17-7.10 (m, 2H), 6.76 (d, J=6.8 Hz, 1H), 6.32 (dd, J=6.0, 2.0 Hz, 1H), 6.09 (d, J=2.0 Hz, 1H), 3.18 (t, J=7.6 Hz, 2H), 3.02 (t, J=7.6 Hz, 2H), 2.90 (q, J=7.6 Hz, 2H), 1.34 (t, J=7.6 Hz, 3H).

The following compounds were prepared according to the procedure described in Example 175 using corresponding intermediates.

| Example | Structure | LCMS (m/z) [M + 1]+ | 1H NMR (400 MHz) |
|---|---|---|---|
| 176 | Prepared from Intermediates A1 and B31. | 493.4 | 1H NMR (400 MHz, CD3OD) δ 8.49 (d, J = 4.0 Hz, 1H), 7.78-7.68 (m, 3H), 7.44-7.30 (m, 2H), 7.04-6.93 (m, 2H), 6.80 (s, 1H), 6.30-6.18 (m, 2H), 5.96 (s, 1H), 2.86 (s, 2H), 2.49 (s, 3H), 2.32 (s, 3H), 1.35 (s, 6H). |
| 177 | Prepared from Intermediates A1 and B43. | 495.4 | 1H NMR (400 MHz, DMSO-d6) δ 8.62 (s, 1H), 8.51 (d, J = 4.0 Hz, 1H), 8.18 (s, 1H), 7.91 (d, J = 6.0 Hz, 1H), 7.83 (m, 1H), 7.77 (d, J = 7.6 Hz, 1H), 7.56 (s, 1H), 7.41-7.38 (m, 1H), 7.34-7.31 (m, 1H), 7.22 (s, 1H), 6.84 (d, J = 8.8 Hz, 1H), 6.27 (dd, J = 6.0, 2.4 Hz, 1H), 6.00 (d, J = 2.4 Hz, 1H), 3.72 (s, 3H), 3.00-2.98 (m, 2H), 2.90-2.78 (m, 2H), 2.47 (s, 3H), 2.34 (s, 3H). |
| 178 | Prepared from Intermediates A1 and B28. | 495.3 | 1H NMR (400 MHz, CD3OD) δ 8.57 (d, J = 4.8 Hz, 1H), 7.87-7.76 (m, 3H), 7.52 (s, 1H), 7.40-7.36 (m, 1H), 6.80 (s, 1H), 6.70 (s, 1H), 6.31 (s, 2H), 6.10 (s, 1H), 3.69 (s, 3H), 3.16 (t, J = 7.6 Hz, 2H), 2.96 (t, J = 7.6 Hz, 2H), 2.55 (s, 3H), 2.39 (s, 3H). |
| 179 | Prepared from Intermediates A1 and B29. | 483.4 | 1H NMR (400 MHz, CD3OD) δ 8.57 (d, J = 4.0 Hz, 1H), 7.91 (d, J = 5.6 Hz, 1H), 7.85 (t, J = 7.6 Hz, 1H), 7.77 (d, J = 8.0 Hz, 1H), 7.52 (s, 1H), 7.37 (t, J = 5.2 Hz, 1H), 7.23 (d, J = 11.2 Hz, 1H), 6.92 (s, 1H), 6.46 (dd, J = 5.6, 4.0 Hz, 1H), 6.32 (d, J = 4.0 Hz, 1H), 6.09 (s, 1H), 3.17 (t, J = 7.6 Hz, 2H), 3.00 (t, J = 7.6 Hz, 2H), 2.57 (s, 3H), 2.40 (s, 3H). |

-continued

| Example | Structure | LCMS (m/z) [M + 1]+ | 1H NMR (400 MHz) |
|---|---|---|---|
| 180 | Prepared from Intermediates A1 and B30. | 499.3 | 1H NMR (400 MHz, CD$_3$OD) δ 8.58 (d, J = 4.8 Hz, 1H), 7.92 (d, J = 5.6 Hz, 1H), 7.86 (td, J = 7.6, 1.2 Hz, 1H), 7.78 (d, J = 7.2 Hz, 1H), 7.53 (s, 1H), 7.42-7.37 (m, 2H), 7.10 (s, 1H), 6.74 (s, 1H), 6.33 (dd, J = 6.0, 2.4 Hz, 1H), 6.07 (d, J = 2.4 Hz, 1H), 3.18 (t, J = 8.0 Hz, 2H), 3.00 (d, J = 8.0 Hz, 2H), 2.58 (s, 3H), 2.41 (s, 3H). |
| 181 | Prepared from Intermediates A18 and B2. | 479.2 | 1H NMR (400 MHz, CD$_3$OD) δ 8.59 (s, 1H), 7.86-7.79 (m, 3H), 7.54 (s, 1H), 7.40-7.39 (m, 1H), 7.18-7.10 (m, 3H), 6.77 (d, J = 6.8 Hz, 1H), 6.31 (m, 1H), 6.09 (m, 1H), 3.15-3.12 (m, 2H), 3.02-2.98 (m, 2H), 2.78-2.73 (m, 2H), 2.58 (s, 3H), 1.27 (t, J = 6.8 Hz, 3H). |
| 182 | Prepared from Intermediates A19 and B2. | 491.4 | 1H NMR (400 MHz, CD$_3$OD) δ 8.70 (d, J = 5.2 Hz, 1H), 8.25 (s, 2H), 7.85 (d, J = 7.2 Hz, 1H), 7.69-7.67 (m, 1H), 7.45 (s, 1H), 7.39 (t, J = 7.6 Hz, 1H), 7.18-7.11 (m, 3H), 6.74 (dd, J = 7.2, 2.4 Hz, 1H), 6.31 (d, J = 2.4 Hz, 1H), 3.27 (t, J = 7.6 Hz, 2H), 3.11 (t, J = 7.6 Hz, 2H), 2.79 (s, 3H), 2.14-2.10 (m, 1H), 1.19-1.14 (m, 2H), 0.81-0.77 (m, 2H). |
| 183 | Prepared from Intermediates A20 and B2. | 493.2 | 1H NMR (400 MHz, DMSO-d6) δ 8.84 (s, 1H), 8.50 (d, J = 4.2 Hz, 1H), 8.29 (s, 2H, HCO2H), 7.96 (d, J = 6.0 Hz, 1H), 7.84 (td, J = 7.6, 1.6 Hz, 1H), 7.79 (d, J = 7.6 Hz, 1H), 7.59 (s, 1H), 7.45 (d, J = 8.4 Hz, 1H), 7.39 (s, 1H), 7.35-7.27 (m, 1H), 7.10 (t, J = 8.0 Hz, 1H), 6.72 (d, J = 7.6 Hz, 1H), 6.31 (dd, J = 6.0, 2.4 Hz, 1H), 6.07 (d, J = 2.4 Hz, 1H), 3.17 (sept, J = 6.8 Hz, 1H), 3.00-2.95 (m, 2H), 2.90-2.85 (m, 2H), 2.61 (s, 3H), 1.25 (d, J = 6.8 Hz, 6H). |

| Example | Structure | LCMS (m/z) [M + 1]+ | 1H NMR (400 MHz) |
|---------|-----------|---------------------|------------------|
| 184 | Prepared from Intermediates A3 and B43. | 481.4 | 1H NMR (400 MHz, DMSO-d6) 8.51 (d, J = 5.8 Hz, 1H), 7.95-7.92 (m, 2H), 7.84 (d, J = 6.8 Hz, 1H), 7.78-7.76 (m, 1H), 7.53 (d, J = 7.8 Hz, 1H), 7.44-7.41 (m, 1H), 7.21-7.19 (m,1H), 7.10 (s,1H), 7.02-6.99 (m, 1H), 6.60-6.58 (m, 1H), 6.12 (s, 1H), 3.78 (s, 3H), 3.12 (t, J = 7.6 Hz, 2H), 2.97 (t, J = 7.6 Hz, 2H), 2.59 (s, 3H). |
| 185 | Prepared from Intermediates A23 and B2. | 479.2 | 1H NMR (400 MHz, CD3OD) δ 8.56 (d, J = 4.8 Hz, 1H), 7.88-7.81 (m, 3H), 7.52 (s, 1H), 7.40-7.36 (m, 1H), 7.21 (s, 1H), 7.17-7.10 (m, 2H), 6.76 (d, J = 6.8 Hz, 1H), 6.33 (dd, J = 6.0, 2.0 Hz, 1H), 6.08 (d, J = 2.0 Hz, 1H), 3.19 (t, J = 7.6 Hz, 2H), 3.02 (t, J = 7.6 Hz, 2H), 2.91 (q, J = 7.6 Hz, 2H), 2.44 (s, 3H), 1.30 (t, J = 7.6 Hz, 3H). |
| 186 | Prepared from Intermediates A50 and B23. | 450.2 | 1H NMR (400 MHz, CD3OD) δ 7.99 (d, J = 6.0 Hz, 1H), 7.61 (s, 1H), 7.07 (s, 1H), 7.03 (s, 1H), 6.61 (s, 1H), 6.40 (dd, J = 6.0, 2.0 Hz, 1H), 6.12 (d, J = 2.4 Hz, 1H), 3.21 (t, J = 7.6 Hz, 2H), 2.99 (t, J = 7.6 Hz, 2H), 2.94 (q, J = 7.6 Hz, 2H), 2.37 (s, 3H), 2.24 (s, 3H), 1.28 (t, J = 7.6 Hz, 3H). |
| 187 | Prepared from Intermediates A16 and B23 | 416.3 | 1H NMR (400 MHz, CD3OD) δ 7.97 (d, J = 5.6 Hz,1H), 7.48 (d, J = 8.4 Hz,1H), 7.24 (d, J = 8.4 Hz, 1H), 7.05 (s, 1H), 6.99 (s, 1H), 6.62 (s, 1H), 6.41 (dd, J = 6.0, 1.6 Hz, 1H), 6.10 (d, J = 1.6 Hz,1H), 3.21 (t, J = 7.6 Hz, 2H), 2.99 (t, J = 7.6 Hz, 2H), 2.80 (q, J = 7.6 Hz, 2H), 2.39 (s, 3H), 2.23 (s, 3H), 1.29 (t, J = 7.6 Hz, 3H). |

-continued

| Example | Structure | LCMS (m/z) [M + 1]+ | 1H NMR (400 MHz) |
|---|---|---|---|
| 188 | Prepared from Intermediates A27 and B2. | 402.2 | 1H NMR (400 MHz, DMSO-d6) δ 9.30 (br s, 1H), 8.06 (d, J = 6.0 Hz, 1H), 7.64 (s, 1H), 7.43-7.39 (m, 2H), 7.19 (t, J = 8.0 Hz, 1H), 6.82 (d, J = 7.6 Hz, 1H), 6.52-6.50 (m, 1H), 6.18 (s, 1H), 3.17 (t, J = 7.6 Hz, 2H), 3.01 (t, J = 7.6 Hz, 2H), 2.49 (s, 3H), 2.35 (s, 3H), 2.29 (s, 3H). |
| 189 | Prepared from Intermediates A26 and B23. | 436.1 | 1H NMR (400 MHz, DMSO-d6) δ 8.85 (s, 1H), 8.16 (s, 0.6H, HCO2H), 8.08 (d, J = 6.0 Hz, 1H), 7.85 (s, 1H), 7.28 (s, 1H), 7.22 (s, 1H), 6.57 (s, 1H), 6.44 (dd, J = 6.0, 2.0 Hz, 1H), 6.08 (d, J = 2.0 Hz, 1H), 3.07 (t, J = 7.6 Hz, 2H), 2.89 (t, J = 7.6 Hz, 2H), 2.54 (s, 3H), 2.28 (s, 3H), 2.20 (s, 3H). |
| 190 | Prepared from Intermediates A49 and B23. | 430.2 | 1H NMR (400 MHz, CD3OD) δ 8.38 (s, 2H, HCO2H), 7.96 (d, J = 6.0 Hz, 1H), 7.33 (s, 1H), 7.04 (s, 1H), 7.01 (s, 1H), 6.62 (s, 1H), 6.39 (dd, J = 6.0, 2.0 Hz, 1H), 6.08 (d, J = 2.0 Hz, 1H), 3.18 (t, J = 7.6 Hz, 2H), 2.97 (t, J = 7.6 Hz, 2H), 2.81 (q, J = 7.6 Hz, 2H), 2.34 (s, 6H), 2.23 (s, 3H), 1.23 (t, J = 7.6 Hz, 3H). |
| 191 | Prepared from Intermediates A25 and B2. | 458.3 | 1H NMR (400 MHz, CDCl3) δ 8.05 (d, J = 6.0 Hz, 1H), 7.58 (s, 1H), 7.26-7.19 (m, 2H), 7.08 (d, J = 8.0 Hz, 1H), 6.83 (d, J = 7.6 Hz, 1H), 6.78 (d, J = 7.6 Hz, 1H), 6.41 (dd, J = 6.0, 2.0 Hz, 1H), 6.12 (d, J = 2.4 Hz, 1H), 5.36-5.33 (m, 1H), 4.07 (dd, J = 11.2, 3.6 Hz, 2H), 3.53-3.46 (m, 2H), 3.38 (t, J = 7.2 Hz, 2H), 3.17-3.08 (m, 2H), 2.56 (s, 3H), 2.24-2.13 (m, 2H), 2.12-2.05 (m, 2H). |

-continued

| Example | Structure | LCMS (m/z) [M + 1]⁺ | ¹H NMR (400 MHz) |
|---|---|---|---|
| 192 | Prepared from Intermediates A6 and B31. | 478.4 | ¹H NMR (400 MHz, CDCl₃) δ 7.88 (s, 1H), 7.78 (d, J = 6.8 Hz, 2H), 7.42-7.34 (m, 4H), 7.20 (d, J = 8.0 Hz, 1H), 7.07 (t, J = 7.6 Hz, 1H), 6.90 (d, J = 7.2 Hz, 1H), 6.77 (s, 1H), 6.51 (d, J = 7.6 Hz, 1H), 6.30 (d, J = 4.4 Hz, 1H), 6.09 (s, 1H), 2.91 (s, 2H), 2.65 (s, 3H), 1.51 (s, 6H). |
| 193 | Prepared from Intermediates A12 and commercially available 2-(3-aminophenyl)acetonitrile. | 459.3 | ¹H NMR (400 MHz, DMSO-d6) δ 9.03 (s, 1H), 8.16 (s, 0.6 H, HCO2H), 8.01 (d, J = 6.0 Hz, 1H), 7.84 (s, 1H), 7.63 (d, J = 8.0 Hz, 1H), 7.40 (s, 1H), 7.17 (t, J = 7.6 Hz, 1H), 6.76 (d, J = 7.6 Hz, 1H), 6.44 (dd, J = 6.0, 2.4 Hz, 1H), 6.24 (d, J = 2.4 Hz, 1H), 4.18 (s, 2H), 3.82 (dt, J = 11.2, 3.2 Hz, 2H), 3.69-3.63 (m, 1H), 3.34-3.27 (m, 2H), 2.72-2.69 (m, 1H), 1.69-1.62 (m, 4H), 1.05-0.93 (m, 4H). |
| 194 | Prepared from Intermediates A12 and B36. | 473.4 | ¹H NMR (400 MHz, DMSO-d6) δ 8.91 (s, 1H), 8.01 (d, J = 6.0 Hz, 1H), 7.84 (s, 1H), 7.42 (s, 1H), 7.18 (s, 1H), 6.58 (s, 1H), 6.42 (dd, J = 6.0, 2.0 Hz, 1H), 6.24 (d, J = 2.0 Hz, 1H), 4.08 (s, 2H), 3.84-3.79 (m, 2H), 3.67-3.63 (m, 1H), 3.33-3.26 (m, 2H), 2.75-2.65 (m, 1H), 2.21 (s, 3H), 1.67-1.61 (m, 4H), 1.04-0.99 (m, 2H), 0.97-0.92 (m, 2H). |
| 195 | Prepared from Intermediates A12 and B5. | 487.4 | ¹H NMR (400 MHz, DMSO-d6) δ 9.06 (br s, 1H), 8.14 (s, 0.6 H, HCO2H), 7.98 (d, J = 6.0 Hz, 1H), 7.85 (s, 1H), 7.72-7.70 (m, 1H), 7.23-7.17 (m, 2H), 6.78-6.73 (m, 1H), 6.47-6.44 (m, 1H), 6.22 (s, 1H), 3.84-3.83 (m, 2H), 3.68-3.62 (m, 2H), 2.73-2.67 (m, 1H), 2.44-2.33 (m, 1H), 1.75 (s, 6H), 1.71-1.58 (m, 4H), 1.07-0.85 (m, 4H). |

-continued

| Example | Structure | LCMS (m/z) [M + 1]+ | 1H NMR (400 MHz) |
|---|---|---|---|
| 196 | Prepared from Intermediates A12 and B37. | 501.2 | 1H NMR (400 MHz, CD3OD) δ 8.21 (s, 0.6 H, HCO2H), 7.92 (d, J = 6.0 Hz, 1H), 7.63 (s, 1H), 7.11 (s, 1H), 7.07 (s, 1H), 6.68 (s, 1H), 6.45 (dd, J = 6.0, 2.4 Hz, 1H), 6.26 (d, J = 2.4 Hz, 1H), 3.96-3.91 (m, 2H), 3.61-3.56 (m, 1H), 3.43 (td, J = 7.6, 2.0 Hz, 2H), 2.84-2.76 (m, 1H), 2.27 (s, 3H), 1.80 (s, 6H), 1.87-1.66 (m, 2H), 1.73-1.69 (m, 2H), 1.09-0.91 (m, 4H). |
| 197 | Prepared from Intermediates A51 and B2. | 465.2 | 1H NMR (400 MHz, CD3OD) δ 8.14 (br s, 0.4 H, HCO2H), 7.93-7.90 (m, 1H), 7.80-7.78 (m, 1H), 7.72-7.70 (m, 2H), 7.33-7.11 (m, 6H), 6.76 (s, 1H), 6.51-6.49 (m, 1H), 6.30-6.29 (m, 1H), 3.72-3.69 (m, 1H), 3.21-3.19 (m, 2H), 3.03-3.01 (m, 2H), 1.18-1.06 (m, 4H). |
| 198 | Prepared from Intermediates A51 and commercially available 2-(3-aminophenyl)acetonitrile. | 451.2 | 1H NMR (400 MHz, DMSO-d6) δ 8.98 (s, 1H), 8.08 (s, 1H), 8.02 (d, J = 5.6 Hz, 1H), 7.70-7.67 (m, 2H), 7.59-7.56 (m, 1H), 7.38-7.33 (m, 3H), 7.28-7.26 (m, 1H), 7.15 (t, J = 8.0 Hz, 1H), 6.74 (d, J = 7.6 Hz, 1H), 6.52 (dd, J = 6.0, 2.4 Hz, 1H), 6.29 (d, J = 2.4 Hz, 1H), 4.16 (s, 2H), 3.83-3.78 (m, 1H), 1.16-1.12 (m, 2H), 1.04-1.00 (m, 2H). |
| 199 | Prepared from Intermediates A51 and B36. | 465.2 | 1H NMR (400 MHz, CD3OD) δ 7.95 (s, 1H), 7.80 (d, J = 7.2 Hz, 1H), 7.67 (d, J = 6.8 Hz, 2H), 7.38-7.31 (m, 3H), 7.14 (s, 1H), 7.02 (s, 2H), 6.85 (dd, J = 7.2, 2.4 Hz, 1H), 6.45 (d, J = 2.4 Hz, 1H), 4.29 (s, 2H), 3.76-3.74 (m, 1H), 2.35 (s, 3H), 1.19-1.16 (m, 2H), 1.11-1.08 (m, 2H). |

| Example | Structure | LCMS (m/z) [M + 1]⁺ | ¹H NMR (400 MHz) |
|---|---|---|---|
| 200 | Prepared from Intermediates A56 and B2. | 479.5 | ¹H NMR (400 MHz, CD₃OD) δ 7.92 (d, J = 6.0 Hz, 1H), 7.83 (s, 1H), 7.73 (d, J = 6.8 Hz, 2H), 7.35-7.30 (m, 2H), 7.30-7.22 (m, 2H), 7.16-7.09 (m, 2H), 6.76 (d, J = 6.0 Hz, 1H), 6.50-6.49 (m, 1H), 6.30 (s, 1H), 4.85-4.77 (m, 1H), 3.20 (t, J = 7.2 Hz, 2H), 3.01 (t, J = 7.2 Hz, 2H), 2.62-2.57 (m, 2H), 2.55-2.50 (m, 2H), 1.91-1.88 (m, 2H). |
| 201 | Prepared from Intermediates A56 and commercially available 2-(3-aminophenyl)acetonitrile. | 465.2 | ¹H NMR (400 MHz, CD₃OD) δ 7.91 (d, J = 6.0 Hz, 1H), 7.84 (s, 1H), 7.73 (d, J = 7.6 Hz, 2H), 7.36-7.20 (m, 6H), 6.89-6.86 (m, 1H), 6.52 (dd, J = 6.0, 2.0 Hz, 1H), 6.31 (d, J = 2.0 Hz, 1H), 4.81-4.79 (m, 1H), 4.23 (s, 2H), 2.64-2.54 (m, 2H), 2.54-2.48 (m, 2H), 1.95-1.87 (m, 2H). |
| 202 | Prepared from Intermediates A56 and B36. | 479.4 | ¹H NMR (400 MHz, CD₃OD) δ 7.90 (d, J = 6.0 Hz, 1H), 7.84 (s, 1H), 7.73 (d, J = 7.2 Hz, 2H), 7.33 (t, J = 7.6 Hz, 2H), 7.26 (t, J = 7.2 Hz, 1H), 7.11 (s, 1H), 7.03 (s, 1H), 6.73 (s, 1H), 6.52 (dd, J = 6.0, 2.4 Hz, 1H), 6.31 (d, J = 2.4 Hz, 1H), 4.84-4.79 (m, 1H), 4.18 (s, 2H), 2.63-2.46 (m, 4H), 2.24 (s, 3H), 1.94-1.87 (m, 2H). |

The following compounds can be prepared using the reaction schemes and methods herein.
| Additional Examples | Structure |
|---|---|
| 203 | 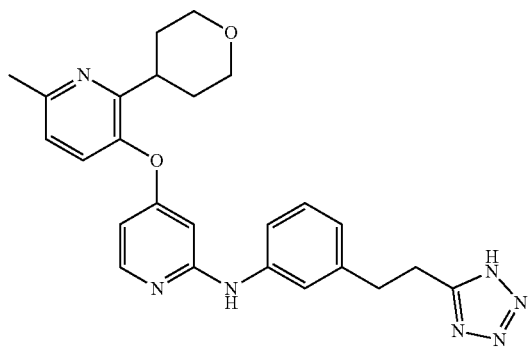 [SMILES: Cc1ccc(Oc2ccnc(Nc3cccc(CCc4nnn[nH]4)c3)c2)c(C2CCOCC2)n1] |
| 204 | 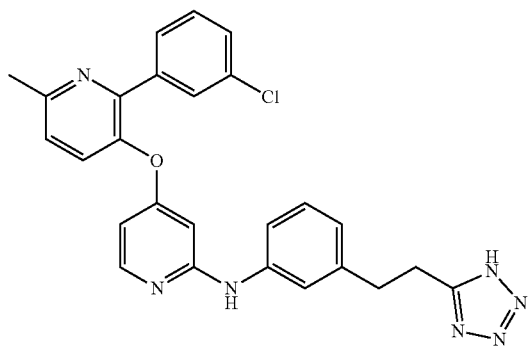 [SMILES: Cc1ccc(Oc2ccnc(Nc3cccc(CCc4nnn[nH]4)c3)c2)c(-c2cccc(Cl)c2)n1] |
| 205 | 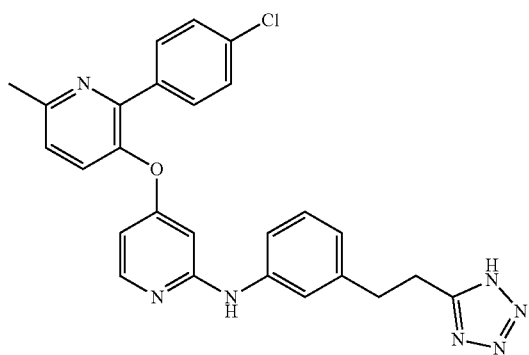 [SMILES: Cc1ccc(Oc2ccnc(Nc3cccc(CCc4nnn[nH]4)c3)c2)c(-c2ccc(Cl)cc2)n1] |
| 206 | 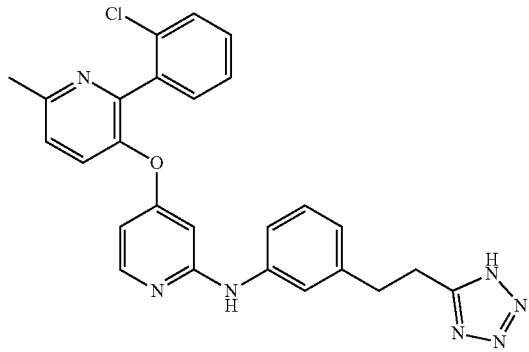 [SMILES: Cc1ccc(Oc2ccnc(Nc3cccc(CCc4nnn[nH]4)c3)c2)c(-c2ccccc2Cl)n1] |

-continued
| Additional Examples | Structure |
|---|---|
| 207 | 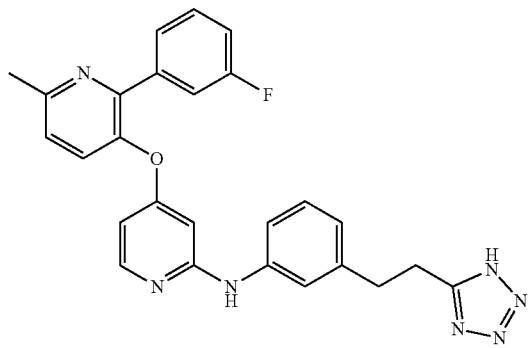 [SMILES: Cc1ccc(Oc2ccnc(Nc3cccc(CCc4nnn[nH]4)c3)c2)c(-c2cccc(F)c2)n1] |
| 208 | 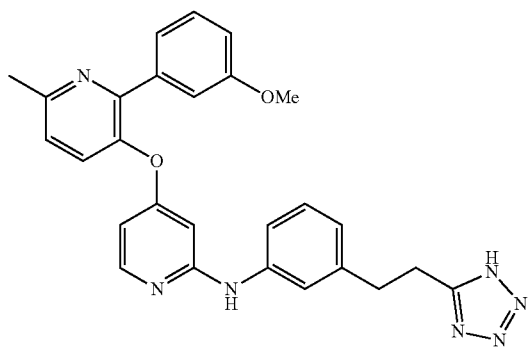 [SMILES: COc1cccc(-c2nc(C)ccc2Oc2ccnc(Nc3cccc(CCc4nnn[nH]4)c3)c2)c1] |
| 209 | 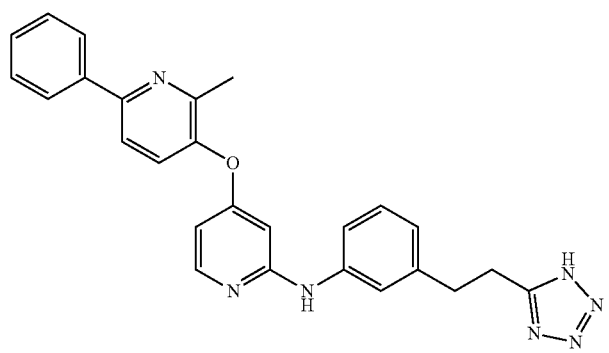 [SMILES: Cc1nc(-c2ccccc2)ccc1Oc1ccnc(Nc2cccc(CCc3nnn[nH]3)c2)c1] |
| 210 | 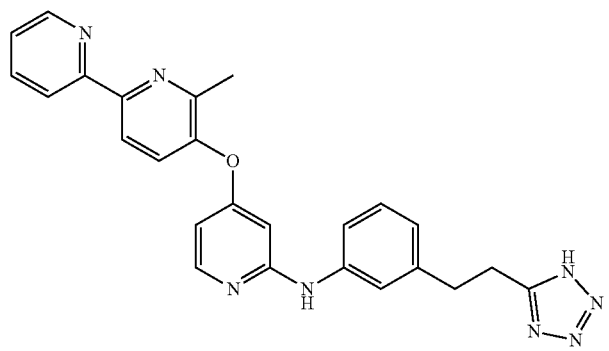 [SMILES: Cc1nc(-c2ccccn2)ccc1Oc1ccnc(Nc2cccc(CCc3nnn[nH]3)c2)c1] |

-continued
| Additional Examples | Structure |
|---|---|
| 211 | 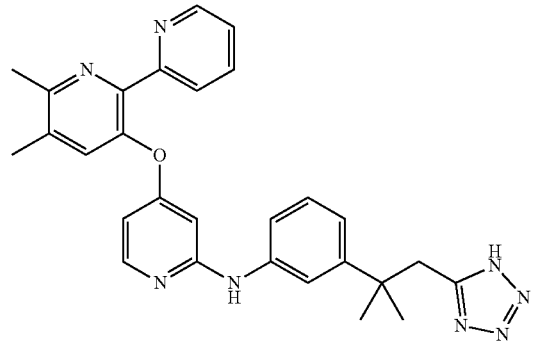 |
| 212 | 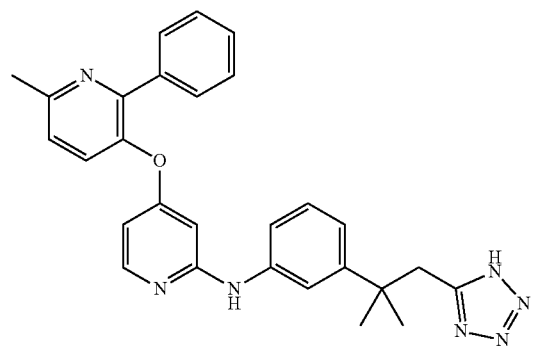 [SMILES: Cc1ccc(Oc2ccnc(Nc3cccc(C(C)(C)Cc4nnn[nH]4)c3)c2)c(-c2ccccc2)n1] |
| 213 | 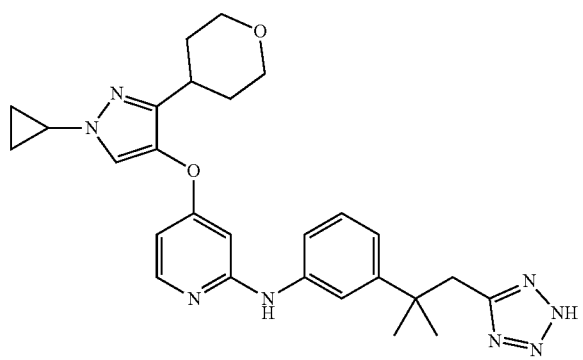 [SMILES: CC(C)(Cc1nn[nH]n1)c1cccc(Nc2cc(Oc3cn(C4CC4)nc3C3CCOCC3)ccn2)c1] |
| 214 | 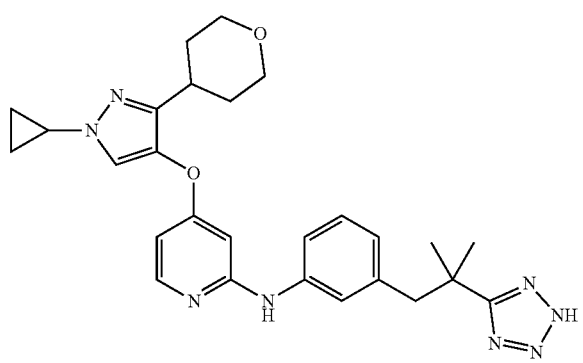 [SMILES: CC(C)(Cc1cccc(Nc2cc(Oc3cn(C4CC4)nc3C3CCOCC3)ccn2)c1)c1nn[nH]n1] |

| Additional Examples | Structure |
|---|---|
| 215 | *(structure: 5,6-dimethyl-2,2'-bipyridine linked via O to a pyridine, which is linked via NH to a phenyl bearing a CF2-tetrazole group)* |
| 216 | *(structure: 5,6-dimethyl-2,2'-bipyridine linked via O to a pyridine, which is linked via NH to a phenyl bearing a CH2-CF2-tetrazole group)* |
| 217 | *(structure: 6-cyclopropyl-2-(tetrahydropyran-4-yl)pyridine linked via O to a pyridine, which is linked via NH to a phenyl bearing a 2-methylpropanoic acid group)* |

In some embodiments, the present disclosure provides for a compound selected from the group consisting of the the Example Compounds described herein.

Assays:

HEK-Blue TGFβ Cellular Reporter Gene Assay:

HEK-Blue TGFβ cell was purchased from Invivogen. Cell suspension of $2.5 \times 10^5$ cells/ml was prepared using Test Medium (DMEM containing 0.5% v/v heat-inactivated FBS). TGF-β working solution (6 ng/ml) was obtained through diluting TGF-β stock solution (10 μg/ml) by Test Medium before use. Eight different concentrations of all compounds were obtained by 3× gradient dilution method using TGF-β working solution. Add 100 μl of Test Medium (Vehicle) or test article or TGF-β working solution per well of a flat-bottom 96-well plate. Add 100 μl of HEK-Blue TGF-β cell suspension per well. Incubate the plate at 37° C. in a $CO_2$ incubator for 22~23 h. Add 150 μl of resuspended QUANTI-Blue per well of a new flat-bottom 96-well plate. Add 30 μl of induced HEK-Blue TGF-β cells supernatant. Avoid pipetting at the bottom of wells. Incubate the plate at 37° C. incubator for 30~40 min. Determine secreted embryonic alkaline phosphatase (SEAP) levels using a spectrophotometer at 630 nm.

The inhibition was calculated using the equation:

$$\text{Inhibition rate}(\%) = \frac{(TGF\beta - \text{Vehicle}) - (\text{Compound} - \text{Vehicle})}{TGF\beta - \text{Vehicle}} \times 100\%$$

Activity Data:
HEK-Blue TGFβ Cellular Reporter Gene Assay:

| Example | HEK-Blue TGFβ reporter IC50 (μM) | Example | HEK-Blue TGFβ reporter IC50 (μM) | Example | HEK-Blue TGFβ reporter IC50 (μM) |
|---|---|---|---|---|---|
| 1 | 0.18 | 2 | 0.23 | 3 | >10 |
| 4 | 0.20 | 5 | 0.15 | 6 | 0.16 |
| 7 | 0.17 | 8 | 0.59 | 9 | >10 |

-continued

| Example | HEK-Blue TGFβ reporter IC50 (μM) | Example | HEK-Blue TGFβ reporter IC50 (μM) | Example | HEK-Blue TGFβ reporter IC50 (μM) |
|---|---|---|---|---|---|
| 10 | 0.22 | 11 | 3.81 | 12 | 0.13 |
| 13 | 1.08 | 14 | >10 | 15 | 1.84 |
| 16 | 0.39 | 17 | 0.65 | 18 | 0.18 |
| 19 | 0.16 | 20 | 0.12 | 21 | 0.16 |
| 22 | 0.23 | 23 | >10 | 24 | 4.53 |
| 25 | 0.64 | 26 | 0.35 | 27 | 0.25 |
| 28 | 0.05 | 29 | 0.038 | 30 | 0.11 |
| 31 | >10 | 32 | 3.71 | 33 | 7.31 |
| 34A | 12.7 | 34B | >10 | 35A | >10 |
| 35B | >10 | 36 | 0.18 | 37 | 0.20 |
| 38 | >10 | 39 | 0.26 | 40 | 0.22 |
| 41 | 0.10 | 42 | 0.14 | 43 | 3.81 |
| 44 | 0.12 | 45 | 0.42 | 46 | 0.52 |
| 47 | 0.31 | 48 | 3.03 | 49 | >10 |
| 50 | 0.63 | 51 | 0.27 | 52 | 0.037 |
| 53 | 2.95 | 54 | 6.39 | 55 | 0.20 |
| 56 | 0.16 | 57 | 0.13 | 58 | 0.15 |
| 59 | 0.45 | 60 | 0.079 | 61 | 0.19 |
| 62 | 2.11 | 63 | 0.72 | 64 | 2.60 |
| 65 | 0.52 | 66 | 0.024 | 67 | 2.65 |
| 68 | 0.74 | 69 | >10 | 70 | 0.007 |
| 71 | 0.14 | 72 | 0.18 | 73 | 0.14 |
| 74 | 0.23 | 75 | 8.12 | 76 | >10 |
| 77 | 0.080 | 78 | 0.11 | 79 | 0.18 |
| 80 | 0.11 | 81 | 0.031 | 82 | 0.018 |
| 83 | 0.035 | 84 | 0.055 | 85 | 0.044 |
| 86 | 0.24 | 87 | 0.094 | 88 | 0.039 |
| 89 | 0.027 | 90 | 0.024 | 91 | 0.018 |
| 92 | 0.080 | 93 | 0.12 | 94 | 0.064 |
| 95 | 0.29 | 96 | 0.19 | 97 | 0.20 |
| 98 | 0.051 | 99 | 0.023 | 100 | 2.59 |
| 101 | 3.31 | 102 | 2.71 | 103 | >10 |
| 104 | 0.022 | 105 | 0.13 | 106 | 0.12 |
| 107 | 0.18 | 108 | 0.90 | 109 | 0.051 |
| 110 | 0.030 | 111 | 6.20 | 112 | 1.67 |
| 113 | 0.51 | 114 | 2.54 | 115 | 1.10 |
| 116 | 1.02 | 117 | >10 | 118 | 0.31 |
| 119 | 0.013 | 120 | 0.050 | 121 | 0.078 |
| 122 | 0.029 | 123 | 0.18 | 124 | 0.19 |
| 125 | 0.066 | 126 | 0.20 | 127 | 0.012 |
| 128 | 0.022 | 129 | 0.029 | 130 | >10 |
| 131 | 1.73 | 132 | >10 | 133 | 0.028 |
| 134 | 0.078 | 135 | 0.043 | 136 | 0.10 |
| 137 | 0.071 | 138 | 0.049 | 139 | 0.042 |
| 140 | 0.035 | 141 | 0.012 | 142 | 0.007 |
| 143 | 0.13 | 144 | 0.075 | 145 | 0.033 |
| 146 | 0.021 | 147 | 0.025 | 148 | 0.034 |
| 149 | 0.021 | 150 | 0.027 | 151 | 0.030 |
| 152 | 0.020 | 153 | 0.070 | 154 | 0.016 |
| 155 | 0.030 | 156 | 0.023 | 157 | 0.027 |
| 158 | 0.037 | 159 | 0.14 | 160 | 0.21 |
| 161 | 0.18 | 162 | 0.12 | 163 | 3.60 |
| 164 | 1.11 | 165 | 0.25 | 166 | 0.48 |
| 167 | 0.62 | 168 | 0.21 | 169 | 0.007 |
| 170 | 0.014 | 171 | 0.016 | 172 | 0.12 |
| 173 | 0.026 | 174 | 0.057 | 175 | 0.044 |
| 176 | 0.15 | 177 | 0.15 | 178 | 0.21 |
| 179 | 0.17 | 180 | 0.079 | 181 | 0.21 |
| 182 | 0.64 | 183 | 0.24 | 184 | 0.33 |
| 185 | 0.039 | 186 | 0.051 | 187 | 0.027 |
| 188 | 0.073 | 189 | 0.024 | 190 | 0.006 |
| 191 | 3.69 | 192 | 0.065 | 193 | >10 |
| 194 | 4.14 | 195 | 2.23 | 196 | 0.27 |
| 197 | 0.035 | 198 | 0.11 | 199 | 0.060 |
| 200 | 0.086 | 201 | 0.089 | 202 | 0.12 |

Comparing $AUC_{liver}/AUC_{heart}$ ratio of selected Examples with clinic compounds Galunisertib and LY3200882. Tissue exposure was measured in Balb/c mouse with PO dosing at 10 mpk. Note that cardiac toxicity was identified as the most relevant for LY3200882 and as a limiting factor for galunisertib. See Stauber, et al., J. Clin. Pract., 2014, 4(3), 196.

General PK Protocol:

The Balb/c mice were fasted overnight with free access to drinking water prior to treatment. Compounds were formulated in 0.5% CMC/0.5% Tween 80 with or without 1 eq. of NaOH, and administrated intragastrically at 10 mg/Kg. The liver and heart tissues of mice were collected at time points 0.5, 1, 3, 5, 7, 24h (2 mice per time point) post dose by first sacrificing the animal by $CO_2$ inhalation. After flushing with ice saline and removal of excess water on its surface, the liver and heart tissues were weighed and homogenized in 1:5 volumes (w/v) of water with 20% methanol. Tissue samples were kept at −40~−20° C. prior to analysis. Concentrations of compounds in the liver and hearts were determined using an established liquid chromatography-tandem mass spectrometry (LC-MS/MS) method. Tissue concentration-time data were processed by linear regression analysis. All pharmacokinetic parameters were calculated using non-compartment model of Pharsight Phoenix 8.0.

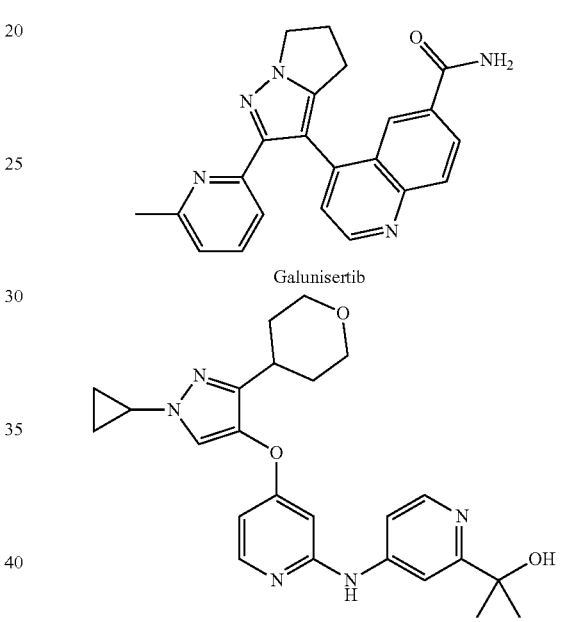

Galunisertib

LY3200882

| Example | $AUC_{liver}/AUC_{heart}$ |
|---|---|
| Galunisertib | 2.9 |
| LY3200882 | 1.3 |
| 1 | 13.2 |
| 12 | 60.9 |
| 16 | 142 |
| 44 | 29.9 |
| 52 | 70.6 |
| 70 | 67.7 |
| 74 | 266 |
| 81 | 124 |
| 104 | 27.8 |
| 161 | 464 |
| 175 | 183 |

As the data shows, the compounds of the invention are much more prone to concentrate in the liver than in cardiac tissue when compared to galunisertib or LY3200882, and are thus better able to provide a useful safety margin and therapeutic index than the known compounds. Since cardiotoxicity is a major concern when developing a new drug, the compound s of the invention, which exhibit potent in vitro activity on the target site and significantly better pharmacokinetic properties to promote safety, are shown to be superior to the compounds known in the art.

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any apparent alternative or additional embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

The invention claimed is:

1. A compound of Formula (I):

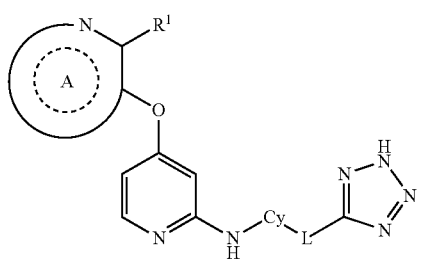

(I)

wherein:

Ring A is a 5 or 6 membered heteroaromatic ring optionally containing an additional nitrogen atom as a ring member and is optionally fused to a phenyl or pyridinyl ring, and Ring A is optionally substituted by one or two groups independently selected from halo, $C_1$-$C_4$ alkyl, $C_1$-$C_4$ haloalkyl, $C_1$-$C_4$ alkoxy, $C_1$-$C_4$ haloalkoxy, phenyl, pyridinyl, a 4-6 membered cyclic ether, and $C_3$-$C_6$ cycloalkyl;

$R^1$ is selected from H, halo, CN, $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, 5-6 membered heterocyclyl containing N, O or S as a ring member, phenyl, and 5-6 membered heteroaryl containing one or two nitrogen atoms as ring members, wherein said $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, phenyl, 5-6 membered heterocyclyl, and 5-6 membered heteroaryl are each optionally substituted with one or two groups selected from $R^2$; wherein $R^2$ is independently selected at each occurrence from halo, CN, —OH, $C_1$-$C_4$ alkyl, $C_1$-$C_4$ haloalkyl, $C_1$-$C_4$ alkoxy, $C_1$-$C_4$ haloalkoxy, and $C_3$-$C_6$ cycloalkyl;

Cy is a ring selected from $C_3$-$C_6$ cycloalkyl, phenyl, and 5-6 membered heteroaryl containing one or two nitrogen atoms as ring members, and is optionally further substituted with one or two groups selected from halo, $C_1$-$C_4$ alkyl, $C_1$-$C_4$ haloalkyl, $C_1$-$C_4$ alkoxy, and $C_1$-$C_4$ haloalkoxy; and L is a divalent linker selected from a bond, $CR_2$, —$(CR_2)_{2-4}$—, —O—$(CR_2)_{1-3}$—, and —$(CR_2)_m$—X—$(CR_2)_n$—, wherein R is independently selected at each occurrence from H, F, and $C_1$-$C_4$ alkyl; or two R groups on the same carbon can be taken together with the carbon to which they are attached to form a 3-6 membered cycloalkyl ring or 3-6 membered cyclic ether;

m is 0, 1, or 2;

n is 0, 1 or 2; and

X is a 5-membered heteroaromatic ring containing one to four heteroatoms selected from N, O and S as ring members; or a pharmaceutically acceptable salt thereof.

2. The compound of claim 1, wherein $R^1$ is selected from $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, 5-6 membered heterocyclyl containing N, O or S as a ring member, phenyl, and 5-6 membered heteroaryl containing one or two nitrogen atoms as ring members, wherein said $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl, 5-6 membered heterocyclyl containing N, O or S as a ring member, phenyl, and 5-6 membered heteroaryl are each optionally substituted with one or two groups selected from $R^2$;

or a pharmaceutically acceptable salt thereof.

3. The compound of claim 1, wherein $R^1$ is methyl, phenyl, or 2-pyridinyl; or a pharmaceutically acceptable salt thereof.

4. The compound of claim 1, wherein Cy is a ring selected from phenyl and pyridinyl, and is optionally further substituted with a group selected from halo, $C_1$-$C_4$ alkyl, $C_1$-$C_4$ haloalkyl, $C_1$-$C_4$ alkoxy, and $C_1$-$C_4$ haloalkoxy; or a pharmaceutically acceptable salt thereof.

5. The compound of claim 1, wherein L is selected from $CH_2$, —$CH_2CH_2$—, $C(Me)_2$, —CHMe-, —$OCH_2$—, —$CH_2CF_2$—, —$CF_2CH_2$—, —$CMe_2CH_2$—, and —$CH_2CMe_2$-; or a pharmaceutically acceptable salt thereof.

6. The compound of claim 1, which is a compound of formula (Ia):

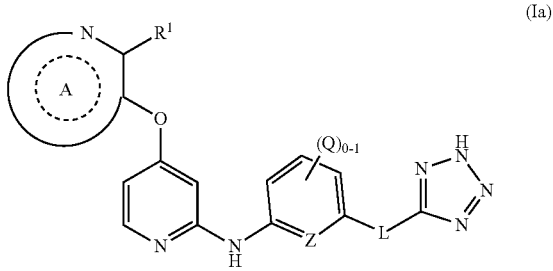

(Ia)

wherein Q is independently selected at each occurrence from halo, $C_1$-$C_4$ alkyl, $C_1$-$C_4$ haloalkyl, and $C_1$-$C_4$ alkoxy; and Z is CH, CQ or N;

or a pharmaceutically acceptable salt thereof.

7. The compound of claim 1, which is a compound of formula (Ib):

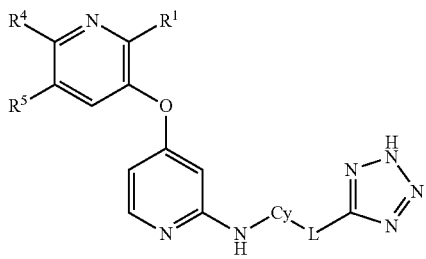

wherein $R^4$ and $R^5$ are independently selected from H, halo, $C_1$-$C_4$ alkyl, $C_1$-$C_4$ haloalkyl, $C_1$-$C_4$ alkoxy, $C_1$-$C_4$ haloalkoxy, phenyl and pyridinyl; or $R^4$ and $R^5$ can be taken together with the carbon atoms to which they are attached to form a phenyl ring fused to the pyridinyl ring to which $R^4$ and $R^5$ are attached;

or a pharmaceutically acceptable salt thereof.

8. The compound of claim 1, wherein the compound is selected from the following list of compounds:

-continued

| No. | Structure |
|---|---|
| 21 | |
| 22 | |
| 23 | |
| 24 | |
| 25 | |

-continued

| No. | Structure |
|---|---|
| 26 | 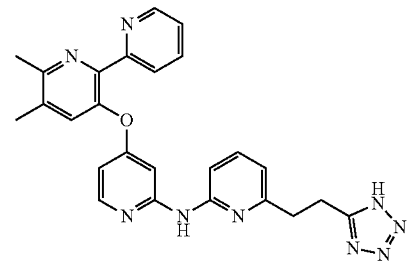 [SMILES: Cc1cc(Oc2ccnc(Nc3cccc(CCc4nnn[nH]4)n3)c2)c(-c2ccccn2)nc1C] |
| 27 | 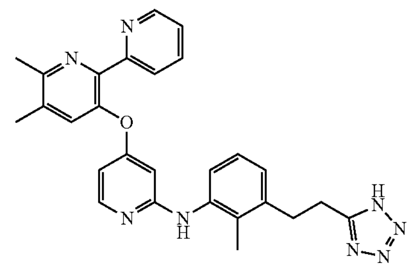 [SMILES: Cc1cc(Oc2ccnc(Nc3cccc(CCc4nnn[nH]4)c3C)c2)c(-c2ccccn2)nc1C] |
| 28 | 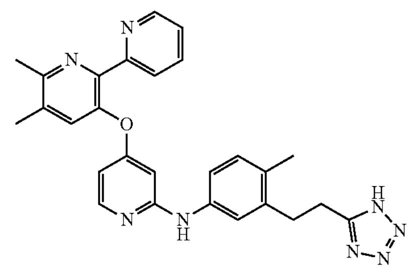 [SMILES: Cc1ccc(Nc2cc(Oc3cc(C)c(C)nc3-c3ccccn3)ccn2)cc1CCc1nnn[nH]1] |
| 29 | 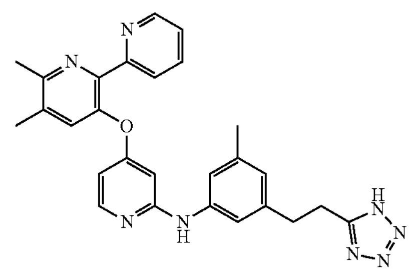 [SMILES: Cc1cc(CCc2nnn[nH]2)cc(Nc2cc(Oc3cc(C)c(C)nc3-c3ccccn3)ccn2)c1] |
| 30 | 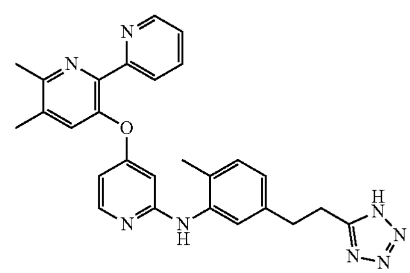 [SMILES: Cc1ccc(CCc2nnn[nH]2)cc1Nc1cc(Oc2cc(C)c(C)nc2-c2ccccn2)ccn1] |
| 31 | 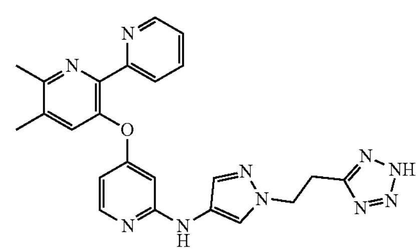 [SMILES: Cc1cc(Oc2ccnc(Nc3cnn(CCc4nn[nH]n4)c3)c2)c(-c2ccccn2)nc1C] |

| No. | Structure |
|---|---|
| 32 | 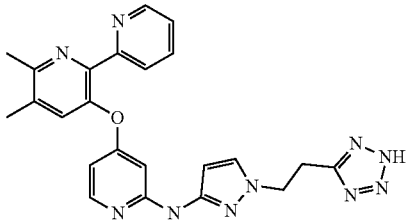 |
| 33 | 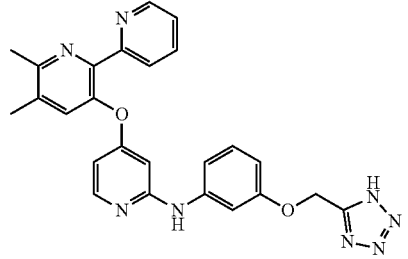 [SMILES: Cc1cc(Oc2ccnc(Nc3cccc(OCc4nnn[nH]4)c3)c2)c(-c2ccccn2)nc1C] |
| 44 | 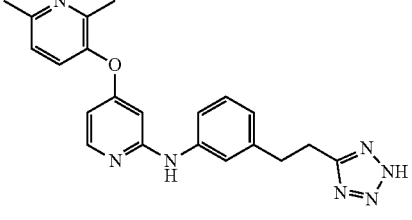 |
| 45 | 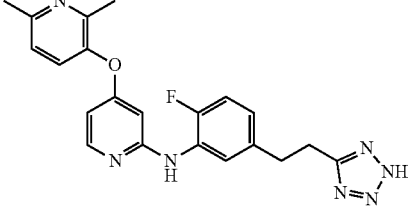 |
| 46 | 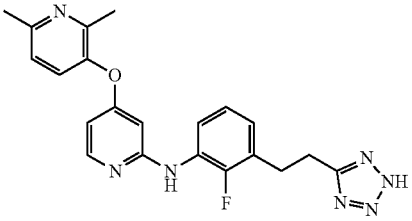 [SMILES: Cc1ccc(Oc2ccnc(Nc3cccc(CCc4nn[nH]n4)c3F)c2)c(C)n1] |
| 47 | 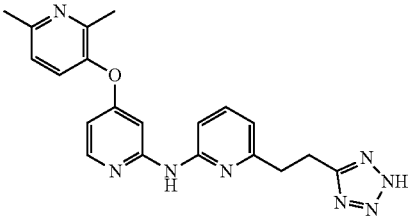 [SMILES: Cc1ccc(Oc2ccnc(Nc3cccc(CCc4nn[nH]n4)n3)c2)c(C)n1] |
| No. | Structure |
|---|---|
| 48 | 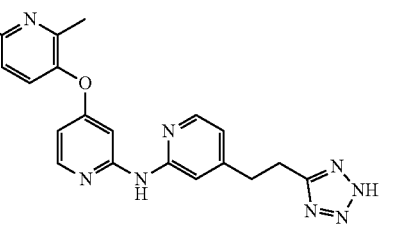 |
| 49 | 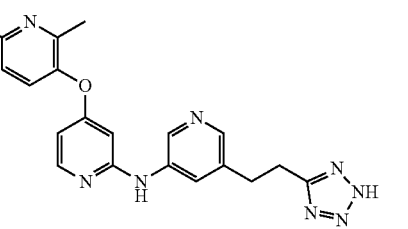 |
| 50 | 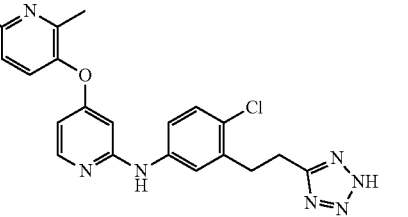 |
| 51 | 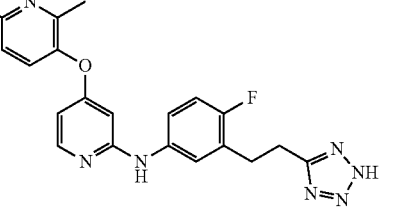 |
| 52 | 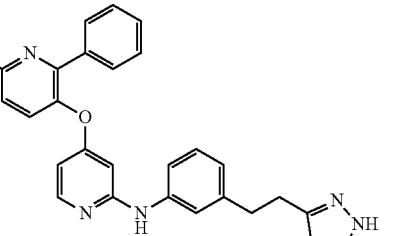 |
| 53 | 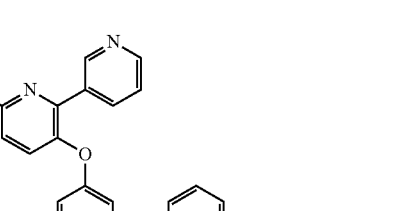 |

-continued

| No. | Structure |
|---|---|
| 54 | 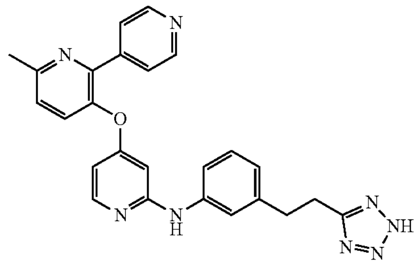 [SMILES: Cc1ccc(Oc2ccnc(Nc3cccc(CCc4nn[nH]n4)c3)c2)c(-c2ccncc2)n1] |
| 55 | 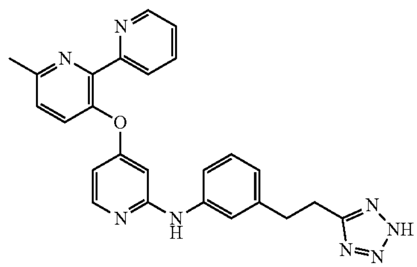 [SMILES: Cc1ccc(Oc2ccnc(Nc3cccc(CCc4nn[nH]n4)c3)c2)c(-c2ccccn2)n1] |
| 56 | 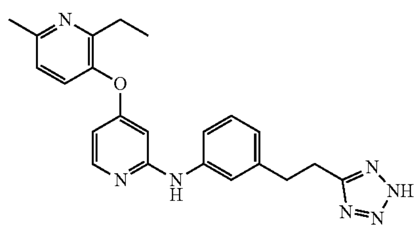 [SMILES: CCc1nc(C)ccc1Oc1ccnc(Nc2cccc(CCc3nn[nH]n3)c2)c1] |
| 57 | 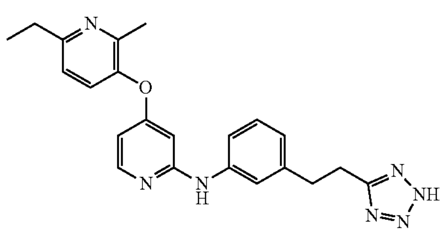 [SMILES: CCc1ccc(Oc2ccnc(Nc3cccc(CCc4nn[nH]n4)c3)c2)c(C)n1] |
| 58 | 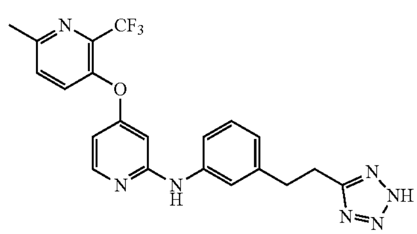 [SMILES: Cc1ccc(Oc2ccnc(Nc3cccc(CCc4nn[nH]n4)c3)c2)c(C(F)(F)F)n1] |
| 59 | 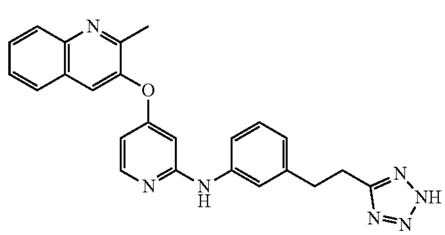 [SMILES: Cc1nc2ccccc2cc1Oc1ccnc(Nc2cccc(CCc3nn[nH]n3)c2)c1] |

-continued

| No. | Structure |
|---|---|
| 60 | 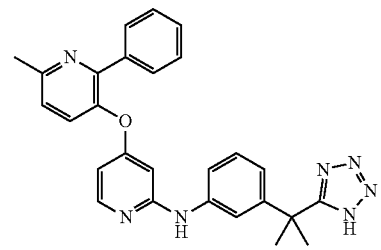 [SMILES: Cc1ccc(Oc2ccnc(Nc3cccc(C(C)(C)c4nnn[nH]4)c3)c2)c(-c2ccccc2)n1] |
| 61 | 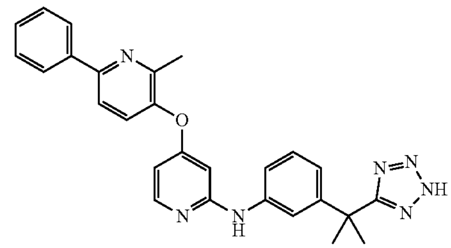 [SMILES: Cc1nc(-c2ccccc2)ccc1Oc1ccnc(Nc2cccc(C(C)(C)c3nn[nH]n3)c2)c1] |
| 62 | 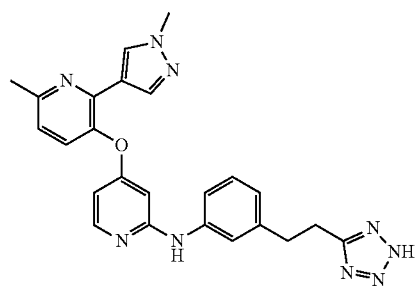 [SMILES: Cc1ccc(Oc2ccnc(Nc3cccc(CCc4nn[nH]n4)c3)c2)c(-c2cnn(C)c2)n1] |
| 63 | 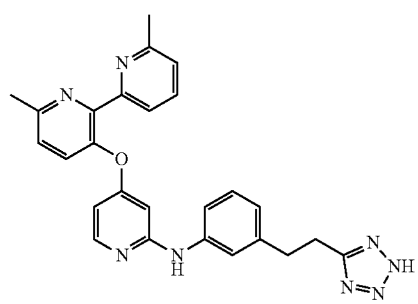 [SMILES: Cc1cccc(-c2nc(C)ccc2Oc2ccnc(Nc3cccc(CCc4nn[nH]n4)c3)c2)n1] |
| 64 | 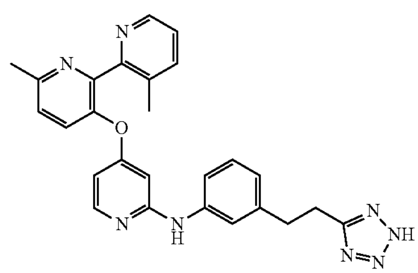 [SMILES: Cc1ccc(Oc2ccnc(Nc3cccc(CCc4nn[nH]n4)c3)c2)c(-c2ncccc2C)n1] |

| No. | Structure |
|---|---|
| 65 | 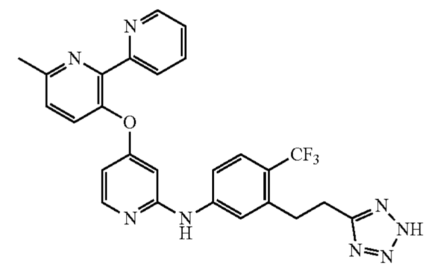 [SMILES: Cc1ccc(Oc2ccnc(Nc3ccc(C(F)(F)F)c(CCc4nn[nH]n4)c3)c2)c(-c2ccccn2)n1] |
| 67 | 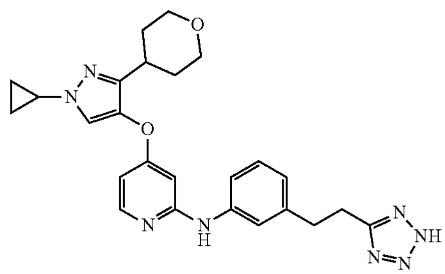 [SMILES: c1cc(CCc2nn[nH]n2)cc(Nc2cc(Oc3cn(C4CC4)nc3C3CCOCC3)ccn2)c1] |
| 175 | 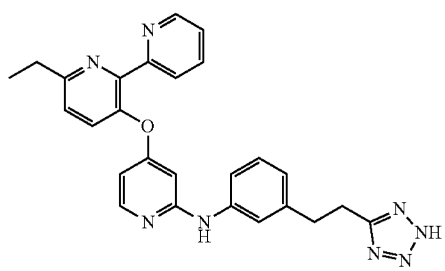 [SMILES: CCc1ccc(Oc2ccnc(Nc3cccc(CCc4nn[nH]n4)c3)c2)c(-c2ccccn2)n1] |
| 176 | 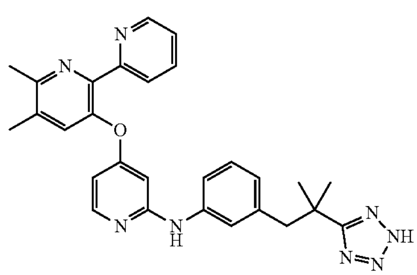 [SMILES: Cc1cc(Oc2ccnc(Nc3cccc(CC(C)(C)c4nn[nH]n4)c3)c2)c(-c2ccccn2)nc1C] |
| 177 | 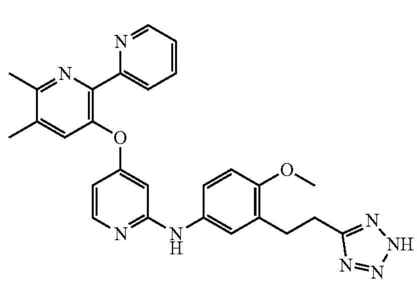 [SMILES: COc1ccc(Nc2cc(Oc3cc(C)c(C)nc3-c3ccccn3)ccn2)cc1CCc1nn[nH]n1] |

| No. | Structure |
|---|---|
| 178 | 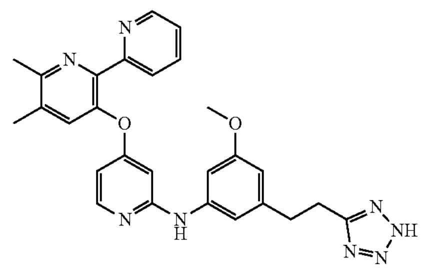 [SMILES: COc1cc(CCc2nn[nH]n2)cc(Nc2cc(Oc3cc(C)c(C)nc3-c3ccccn3)ccn2)c1] |
| 179 | 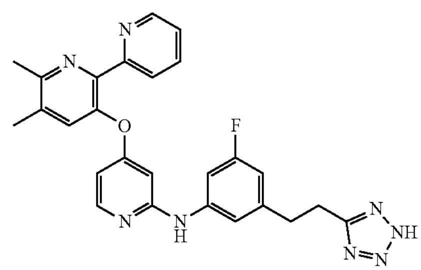 [SMILES: Cc1cc(Oc2ccnc(Nc3cc(F)cc(CCc4nn[nH]n4)c3)c2)c(-c2ccccn2)nc1C] |
| 180 | 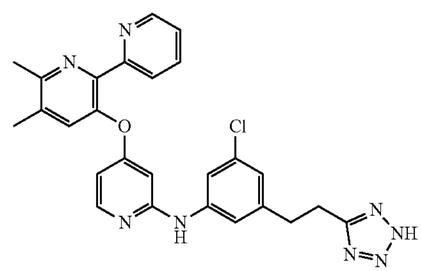 [SMILES: Cc1cc(Oc2ccnc(Nc3cc(Cl)cc(CCc4nn[nH]n4)c3)c2)c(-c2ccccn2)nc1C] |
| 181 | 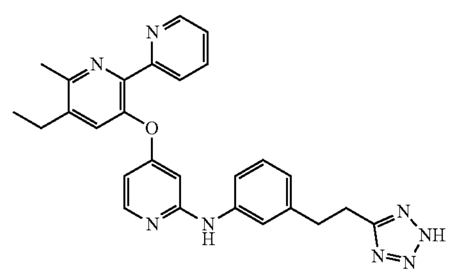 [SMILES: CCc1cc(Oc2ccnc(Nc3cccc(CCc4nn[nH]n4)c3)c2)c(-c2ccccn2)nc1C] |
| 182 | 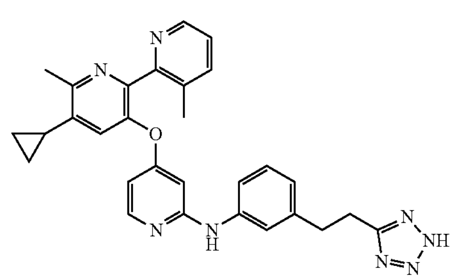 [SMILES: Cc1cccnc1-c1nc(C)c(C2CC2)cc1Oc1ccnc(Nc2cccc(CCc3nn[nH]n3)c2)c1] |

| No. | Structure |
|---|---|
| 183 | 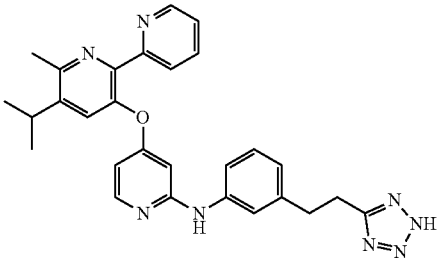 |
| 184 | 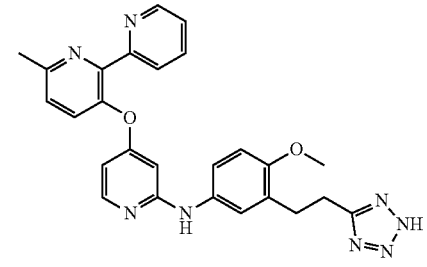 [SMILES: COc1ccc(Nc2cc(Oc3ccc(C)nc3-c3ccccn3)ccn2)cc1CCc1nn[nH]n1] |
| 185 | 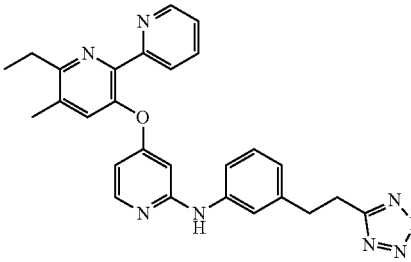 |
| 186 | 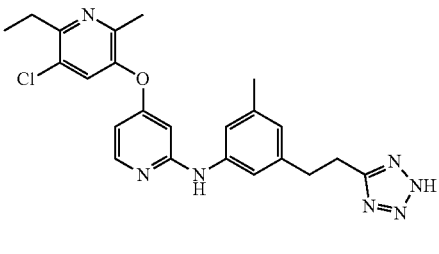 [SMILES: CCc1nc(C)c(Oc2ccnc(Nc3cc(C)cc(CCc4nn[nH]n4)c3)c2)cc1Cl] |
| 187 | 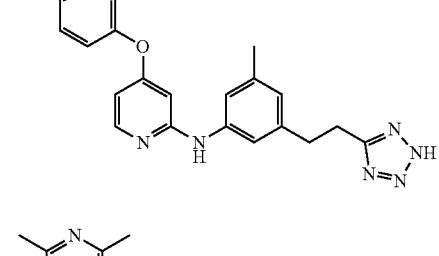 |
| 188 | 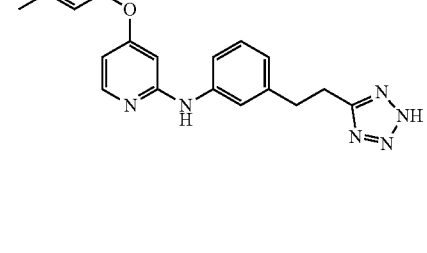 |
| No. | Structure |
|---|---|
| 189 | 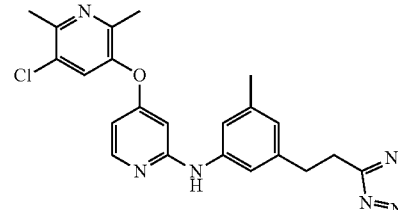 |
| 190 | 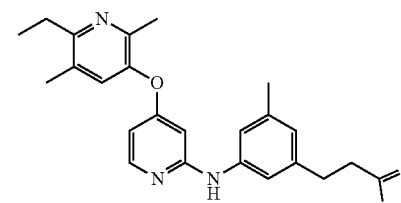 |
| 191 | 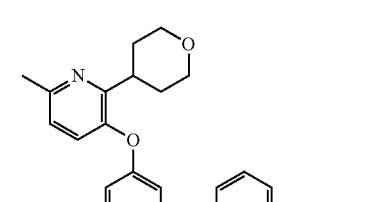 |
| 192 | 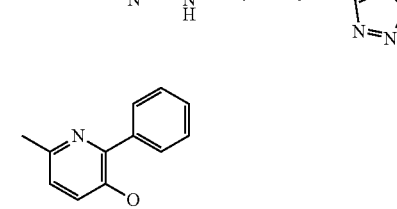 |
| 193 | 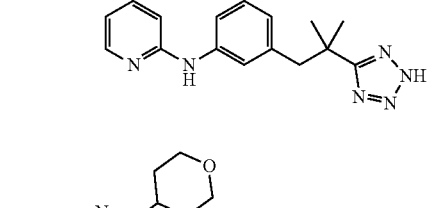 |
| 194 | 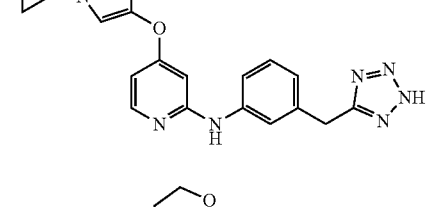 |

| No. | Structure |
|---|---|
| 195 | 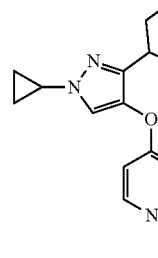 |
| 196 | 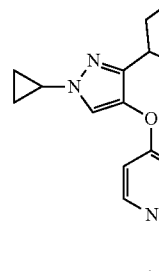 |
| 197 | 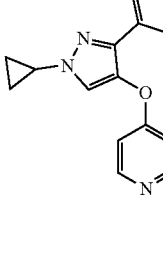 |
| 198 | 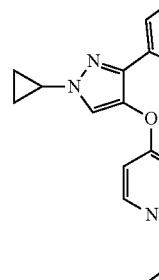 |
| 199 | 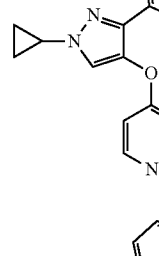 |
| 200 | 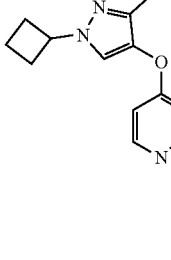 |
| 201 | 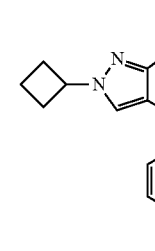 |
| 202 | 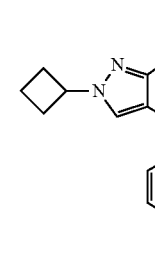 |
| 203 | 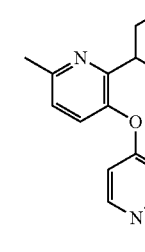 |
| 204 | 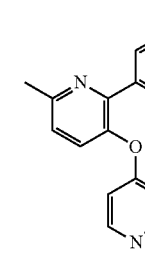 |
| 205 | 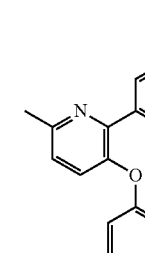 |
| 206 | 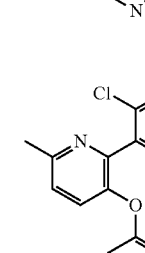 |

| No. | Structure |
|---|---|
| 207 | 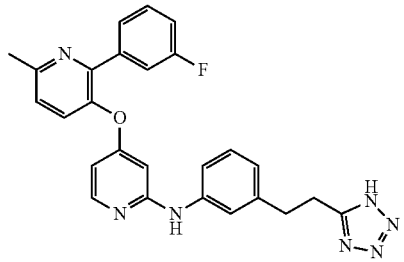 [SMILES: Cc1ccc(Oc2ccnc(Nc3cccc(CCc4nnn[nH]4)c3)c2)c(-c2cccc(F)c2)n1] |
| 208 | 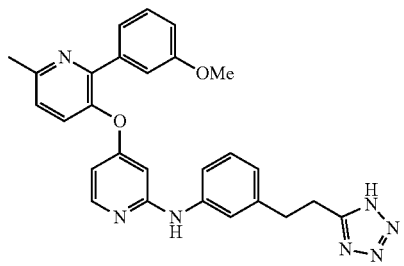 [SMILES: COc1cccc(-c2nc(C)ccc2Oc2ccnc(Nc3cccc(CCc4nnn[nH]4)c3)c2)c1] |
| 209 | 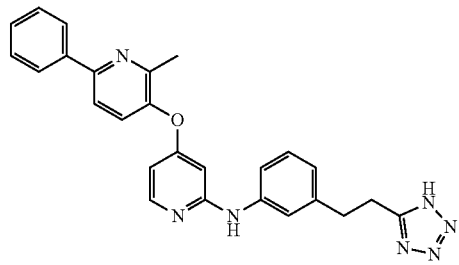 [SMILES: Cc1nc(-c2ccccc2)ccc1Oc1ccnc(Nc2cccc(CCc3nnn[nH]3)c2)c1] |
| 210 | 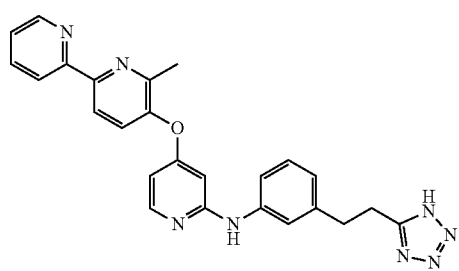 [SMILES: Cc1nc(-c2ccccn2)ccc1Oc1ccnc(Nc2cccc(CCc3nnn[nH]3)c2)c1] |
| 211 | 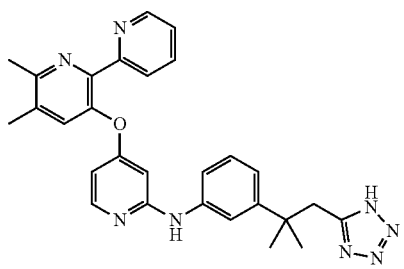 |

| No. | Structure |
|---|---|
| 212 | 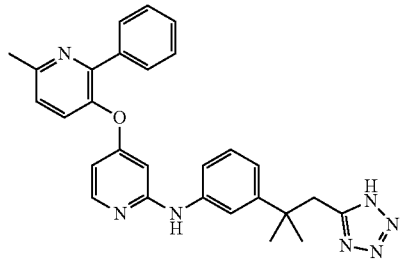 [SMILES: Cc1ccc(Oc2ccnc(Nc3cccc(C(C)(C)Cc4nnn[nH]4)c3)c2)c(-c2ccccc2)n1] |
| 213 | 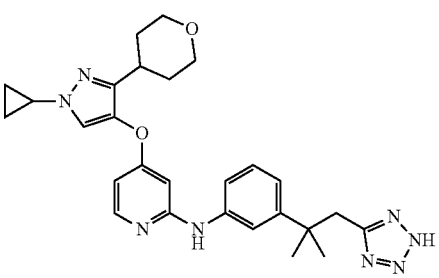 [SMILES: CC(C)(Cc1nn[nH]n1)c1cccc(Nc2cc(Oc3cn(C4CC4)nc3C3CCOCC3)ccn2)c1] |
| 214 | 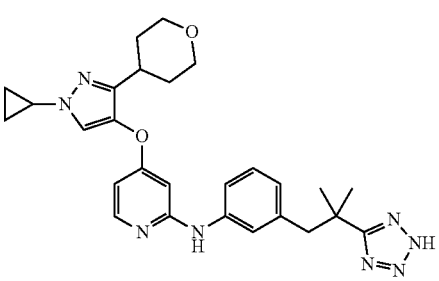 [SMILES: CC(C)(Cc1cccc(Nc2cc(Oc3cn(C4CC4)nc3C3CCOCC3)ccn2)c1)c1nn[nH]n1] |
| 215 | 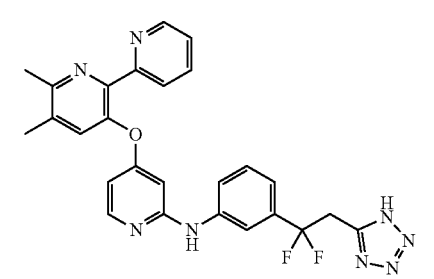 [SMILES: Cc1cc(Oc2ccnc(Nc3cccc(C(F)(F)Cc4nnn[nH]4)c3)c2)c(-c2ccccn2)nc1C] |
| 216 | 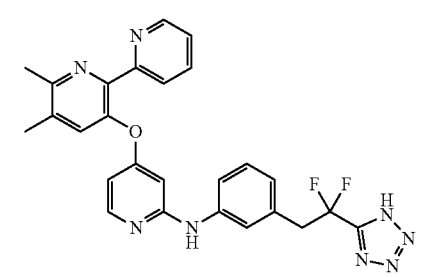 [SMILES: Cc1cc(Oc2ccnc(Nc3cccc(CC(F)(F)c4nnn[nH]4)c3)c2)c(-c2ccccn2)nc1C] | or a pharmaceutically acceptable salt thereof.

9. A pharmaceutical composition comprising a compound of claim 1 admixed with at least one pharmaceutically acceptable carrier or excipient.

10. A method to treat colon cancer, hepatocellular carcinoma (HCC), renal cancer, pancreatic cancer, liver cancer, gastric cancer, or fibrosis in the liver or kidney, which comprises administering to a subject in need thereof an effective amount of a compound of claim 1.

11. A pharmaceutical combination comprising an effective amount of a compound according to claim 1, and an additional therapeutic agent.

12. The compound of claim 4, which is of the formula

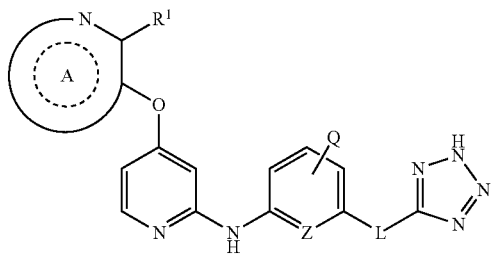

wherein
Z is CH or N, and Q is selected from H, Me, $CF_3$, OMe and halo;
or a pharmaceutically acceptable salt thereof.

13. The compound of claim 1, wherein L is a divalent linker selected from $CR_2$, $-(CR_2)_{2-4}-$, $-O-(CR_2)_{1-3}-$, and $-(CR_2)_m-X-(CR_2)_n-$; or a pharmaceutically acceptable salt thereof.

14. The compound of claim 13, wherein R is independently selected at each occurrence from H, F and Me; or a pharmaceutically acceptable salt thereof.

15. The compound of claim 1, wherein Ring A is pyridinyl or pyrazolyl, and is optionally substituted by one or two groups independently selected from halo, $C_1$-$C_4$ alkyl, $C_1$-$C_4$ haloalkyl, $C_1$-$C_4$ alkoxy, $C_1$-$C_4$ haloalkoxy, and $C_3$-$C_6$ cycloalkyl; or a pharmaceutically acceptable salt thereof.

16. The compound of claim 1, wherein $R^1$ is pyridinyl, phenyl, tetrahydrofuranyl, or tetrahydropyranyl, and is optionally substituted with one or two groups selected from $R^2$; or a pharmaceutically acceptable salt thereof.

17. The compound of claim 1, wherein L is [Cy]-$(CR_2)_m-X-(CR_2)_n-$, where
[Cy] indicates where L is attached to the group Cy;
m is 1 or 2;
n is 0, 1 or 2; and
X is a tetrazolyl ring;
or a pharmaceutically acceptable salt thereof.

18. The compound of claim 1, wherein L is $CH_2$, $C(Me)_2$, $-OCH_2$-[T], $-CH_2CH_2-$, $-C(Me)_2CH_2$-[T], $-CH_2C(Me)_2$-[T], or $-CF_2CH_2$-[T], wherein [T] indicates which end of L is attached to the tetrazole ring in Formula (I); or a pharmaceutically acceptable salt thereof.

19. A method to treat colon cancer, hepatocellular carcinoma (HCC), renal cancer, pancreatic cancer, liver cancer, gastric cancer, or fibrosis in the liver or kidney, which comprises administering to a subject in need thereof an effective amount of a pharmaceutical composition of claim 9.

* * * * *